United States Patent
Zeng et al.

(10) Patent No.: US 11,522,140 B2
(45) Date of Patent: Dec. 6, 2022

(54) ORGANIC ELECTROLUMINESCENT MATERIALS AND DEVICES

(71) Applicant: Universal Display Corporation, Ewing, NJ (US)

(72) Inventors: Lichang Zeng, Lawrenceville, NJ (US); Ting-Chih Wang, Lawrenceville, NJ (US); Alexey Borisovich Dyatkin, Ambler, PA (US); Chuanjun Xia, Lawrenceville, NJ (US)

(73) Assignee: UNIVERSAL DISPLAY CORPORATION, Ewing, NJ (US)

(*) Notice: Subject to any disclaimer, the term of this patent is extended or adjusted under 35 U.S.C. 154(b) by 0 days.

(21) Appl. No.: 15/207,853

(22) Filed: Jul. 12, 2016

(65) Prior Publication Data

US 2017/0054087 A1 Feb. 23, 2017

Related U.S. Application Data

(60) Provisional application No. 62/205,919, filed on Aug. 17, 2015.

(51) Int. Cl.

| | |
|---|---|
| *H01L 51/00* | (2006.01) |
| *C09K 11/02* | (2006.01) |
| *C09K 11/06* | (2006.01) |
| *H05B 33/20* | (2006.01) |
| *H01L 51/50* | (2006.01) |
| *H01L 51/56* | (2006.01) |

(52) U.S. Cl.
CPC ........ *H01L 51/0074* (2013.01); *C09K 11/025* (2013.01); *C09K 11/06* (2013.01); *H01L 51/0052* (2013.01); *H01L 51/0067* (2013.01); *H01L 51/0073* (2013.01); *H05B 33/20* (2013.01); *H01L 51/001* (2013.01); *H01L 51/0054* (2013.01); *H01L 51/0072* (2013.01); *H01L 51/0085* (2013.01); *H01L 51/5016* (2013.01); *H01L 51/56* (2013.01); *H01L 2251/5384* (2013.01)

(58) Field of Classification Search
CPC combination set(s) only.
See application file for complete search history.

(56) References Cited

U.S. PATENT DOCUMENTS

| 4,769,292 A | 9/1988 | Tang et al. |
| 5,061,569 A | 10/1991 | VanSlyke et al. |

(Continued)

FOREIGN PATENT DOCUMENTS

| CN | 102850329 | 1/2013 |
| EP | 0650955 | 5/1995 |

(Continued)

OTHER PUBLICATIONS

Ye, Hua et al., "Conjugated polymers containing trifluoren-2-ylamine, trifluoren-2-ylbenzene and trifluoren-2-yltriazine tor electroluminescence" Polymer 54 (2013) 162-173.

(Continued)

*Primary Examiner* — Sean M DeGuire
(74) *Attorney, Agent, or Firm* — Duane Morris LLP

(57) ABSTRACT

A mixture of carbazole and triazine derivatives that can be thermally evaporated from one crucible to fabricate thin films for electroluminescent devices is disclosed.

16 Claims, 2 Drawing Sheets

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 5,981,092 A | 11/1999 | Arai et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,821,643 B1 | 11/2004 | Hu et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,252,859 B2 | 8/2007 | Ng et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 8,679,647 B2 | 3/2014 | Pflumm et al. |
| 9,831,437 B2 | 11/2017 | Zeng et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0016907 A1* | 1/2004 | Shi ............... H01L 51/0008 |
| | | 252/301.16 |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0134317 A1 | 6/2006 | Yang et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0249148 A1 | 10/2007 | Werner et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0072887 A1* | 3/2010 | Kwong ............... H01L 51/0072 |
| | | 548/440 |
| 2010/0187984 A1 | 7/2010 | Lin et al. |
| 2011/0037057 A1 | 2/2011 | Lecloux et al. |
| 2011/0227049 A1 | 9/2011 | Xia et al. |
| 2011/0260138 A1 | 10/2011 | Xia et al. |
| 2012/0126208 A1 | 5/2012 | Kawamura et al. |
| 2012/0216208 A1 | 8/2012 | Takemura et al. |
| 2013/0075716 A1* | 3/2013 | Nishimura ............ H01L 51/5004 |
| | | 257/40 |
| 2013/0112952 A1 | 5/2013 | Adamovich et al. |
| 2013/0264560 A1 | 10/2013 | Dobbs et al. |
| 2014/0001456 A1 | 1/2014 | Mizutani et al. |
| 2014/0231769 A1* | 8/2014 | Nishimura ............ H01L 51/0073 |
| | | 257/40 |
| 2014/0264292 A1 | 9/2014 | Xia et al. |
| 2014/0299192 A1 | 10/2014 | Lee et al. |
| 2014/0312338 A1 | 10/2014 | Mizutani et al. |
| 2015/0001524 A1 | 1/2015 | Brooks et al. |
| 2015/0014649 A1 | 1/2015 | Ma et al. |
| 2015/0025239 A1 | 1/2015 | Ahn et al. |
| 2015/0053938 A1 | 2/2015 | Zeng et al. |
| 2015/0053939 A1 | 2/2015 | Adamovich et al. |
| 2016/0141505 A1 | 5/2016 | Park et al. |
| 2016/0149139 A1 | 5/2016 | Xia et al. |
| 2016/0276596 A1* | 9/2016 | Jang ..................... H01B 1/04 |
| 2017/0170407 A1* | 6/2017 | Park ..................... C07D 403/04 |

FOREIGN PATENT DOCUMENTS

| | | |
|---|---|---|
| EP | 1156536 | 11/2001 |
| EP | 1725079 | 11/2006 |
| EP | 2034538 | 3/2009 |
| JP | 2004022334 | 1/2004 |
| JP | 200511610 | 1/2005 |
| JP | 2007123392 | 5/2007 |
| JP | 2007254297 | 10/2007 |
| JP | 2008074939 | 4/2008 |
| JP | 2011-63584 | 3/2011 |
| JP | 2014125449 | 7/2014 |
| JP | 2015-134743 | 7/2015 |
| KR | 20120078301 | 7/2012 |
| KR | 20120129733 | 11/2012 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004070787 | 8/2004 |
| WO | 2004093207 | 10/2004 |
| WO | 04107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |

(56) References Cited

FOREIGN PATENT DOCUMENTS

| WO | 2008132085 | 11/2008 |
|---|---|---|
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2011136755 | 11/2011 |
| WO | 2012023947 | 2/2012 |
| WO | 2012033061 | 3/2012 |
| WO | 2012133644 | 10/2012 |
| WO | 2013032297 | 3/2013 |
| WO | 2013191177 | 12/2013 |
| WO | 2014015931 | 1/2014 |
| WO | 2014104515 | 7/2014 |
| WO | 2015053459 | 4/2015 |
| WO | 2015111848 | 7/2015 |

OTHER PUBLICATIONS

Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90:183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1:15-20 (2000).
Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4'4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91:209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

(56) References Cited

OTHER PUBLICATIONS

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 16(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

Abstract of U.S. Appl. No. 14/624,097, filed Feb. 27, 2015, entitled "Organic Electroluminescent Materials and Devices," Applicant Universal Display Corporation.

Abstract of U.S. Appl. No. 14/194,689, filed Mar. 1, 2014, entitled "Organic Electroluminescent Materials and Devices," Applicant Universal Display Corporation.

Harton et al., "Carbon-13 Labeling for Improved Tracer Depth Profiling of Organic Materials Using Secondary Ion Mass Spectrometry" J. Am. Soc. Mass Spectrom, (2006), vol. 17, pp. 1142-1145.

Harton et al., "Carbon-13 Labeling for Quantitative Analysis of Molecular Movement in Heterogeneous Organic Materials Using Secondary Ion Mass Spectrometry" Anal. Chem., (2007), vol. 79, pp. 5358-5363.

Extended European Search Report dated Jan. 1, 2016 for corresponding EP Application No. 15175686.3.

Notice of Reasons for Rejection dated Dec. 11, 2018 for corresponding Japanese Patent Application No. JP 2015-136658.

\* cited by examiner

ORGANIC ELECTROLUMINESCENT MATERIALS AND DEVICES

CROSS-REFERENCE TO RELATED APPLICATIONS

This application is a non-provisional application of U.S. Provisional Application Ser. No. 62/205,919, filed Aug. 17, 2015, the entire contents of which is incorporated herein by reference.

PARTIES TO A JOINT RESEARCH AGREEMENT

The claimed invention was made by, on behalf of, and/or in connection with one or more of the following parties to a joint university corporation research agreement: The Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD

The present invention relates to compounds for use as host materials in the emissive layers in electroluminescent devices such as organic light emitting diodes and the devices including the compounds.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

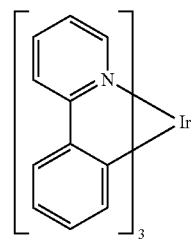

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

According to an embodiment, a composition of materials comprising a mixture of organic materials consisting of carbazole and triazine derivatives is disclosed. The mixture comprises a first compound and a second compound, wherein the first compound has a formula:

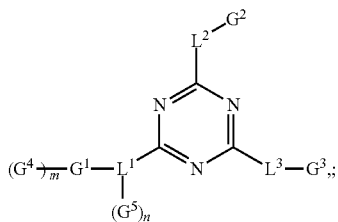

Formula I wherein $G^1$ is selected from the group consisting of dibenzofuran, dibenzothiophene, dibenzoselenophene, and fluorene;

wherein $L^1$, $L^2$ and $L^3$ are each independently selected from the group consisting of direct bond, phenyl, biphenyl, terphenyl, pyridine, pyrimidine, and combinations thereof;

wherein $G^4$ is selected from the group consisting of phenyl, biphenyl, terphenyl, naphthalene, phenanthrene, pyridine, pyrimidine, pyrazine, quinoline, isoquinoline, phenanthroline, fluorene, and combinations thereof;

wherein $G^2$, $G^3$, and $G^5$ are each independently selected from the group consisting of phenyl, biphenyl, terphenyl, fluorene, naphthalene, phenanthrene, pyridine, pyrimidine, pyrazine, quinoline, isoquinoline, phenanthroline, aza-fluorene, and combinations thereof;

wherein $G^2$, $G^3$, $G^4$, and $G^5$ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof;

wherein m is an integer from 0 to 7,
wherein n is an integer from 0 to 4;
wherein, when m or n is larger than 1, each $G^4$ or $G^5$ can be same or different;
wherein when n is 0 and m is equal to or greater than 1, then each $G^4$ is selected from the group consisting of phenyl, and biphenyl;
wherein when n is equal to or greater than 1, $L^1$ is not a direct bond;
wherein when m and n are both 0, $L^1$ is biphenyl;
wherein when $G^4$ is present and is fluorene, $L^1$ is not a direct bond;
wherein the second compound has a formula:

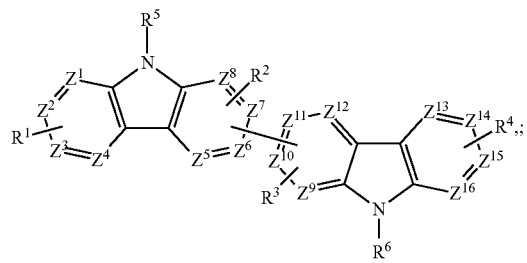

Formula II wherein each $Z^1$ to $Z^{16}$ is C or N;
wherein one of $Z^5$ to $Z^8$ bonds to one of $Z^9$ to $Z^{12}$ through a C—C bond;
wherein $R^1$, and $R^4$ each independently represent mono, di, tri, or tetra substitution, or no substitution;
wherein $R^2$, and $R^3$ each independently represent mono, di, or tri substitution, or no substitution; and
wherein $R^1$ to $R^6$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and any two adjacent substituents are optionally joined or fused into a ring.

According to another embodiment, a first organic light emitting device is also provided. The organic light emitting device can include an anode, a cathode, and an organic layer, disposed between the anode and the cathode, wherein the organic layer can include a composition of materials comprising a mixture of a first compound and a second compound, wherein the first compound has a formula:

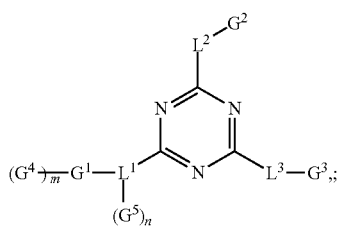

Formula I wherein $G^1$ is selected from the group consisting of dibenzofuran, dibenzothiophene, dibenzoselenophene, and fluorene;

wherein $L^1$, $L^2$ and $L^3$ are each independently selected from the group consisting of direct bond, phenyl, biphenyl, terphenyl, pyridine, pyrimidine, and combinations thereof;

wherein G⁴ is selected from the group consisting of phenyl, biphenyl, terphenyl, naphthalene, phenanthrene, pyridine, pyrimidine, pyrazine, quinoline, isoquinoline, phenanthroline, fluorene, and combinations thereof;

wherein G², G³, and G⁵ are each independently selected from the group consisting of phenyl, biphenyl, terphenyl, fluorene, naphthalene, phenanthrene, pyridine, pyrimidine, pyrazine, quinoline, isoquinoline, phenanthroline, aza-fluorene, and combinations thereof;

wherein G², G³, G⁴, and G⁵ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof;

wherein m is an integer from 0 to 7, wherein n is an integer from 0 to 4;

wherein, when m or n is larger than 1, each G⁴ or G⁵ can be same or different;

wherein when n is 0 and m is equal to or greater than 1, then each G⁴ is selected from the group consisting of phenyl, and biphenyl;

wherein when n is equal to or greater than 1, L¹ is not a direct bond;

wherein when m and n are both 0, L¹ is biphenyl;

wherein when G⁴ is present and is fluorene, L¹ is not a direct bond;

wherein the second compound has a formula:

Formula II

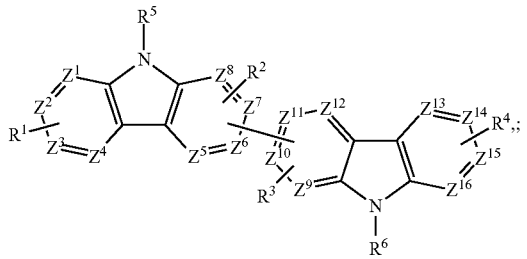

wherein each Z¹ to Z¹⁶ is C or N;

wherein one of Z⁵ to Z⁸ bonds to one of Z⁹ to Z¹² through a C—C bond;

wherein R¹, R⁴ each independently represents mono, di, tri, or tetra substitution, or no substitution;

wherein R², R³ each independently represents mono, di, or tri substitution, or no substitution; and wherein R¹ to R⁶ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and any two adjacent substituents are optionally joined or fused into a ring.

The first organic light emitting device can be incorporated into one or more of a consumer product, an electronic component module, an organic light-emitting device, and/or a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
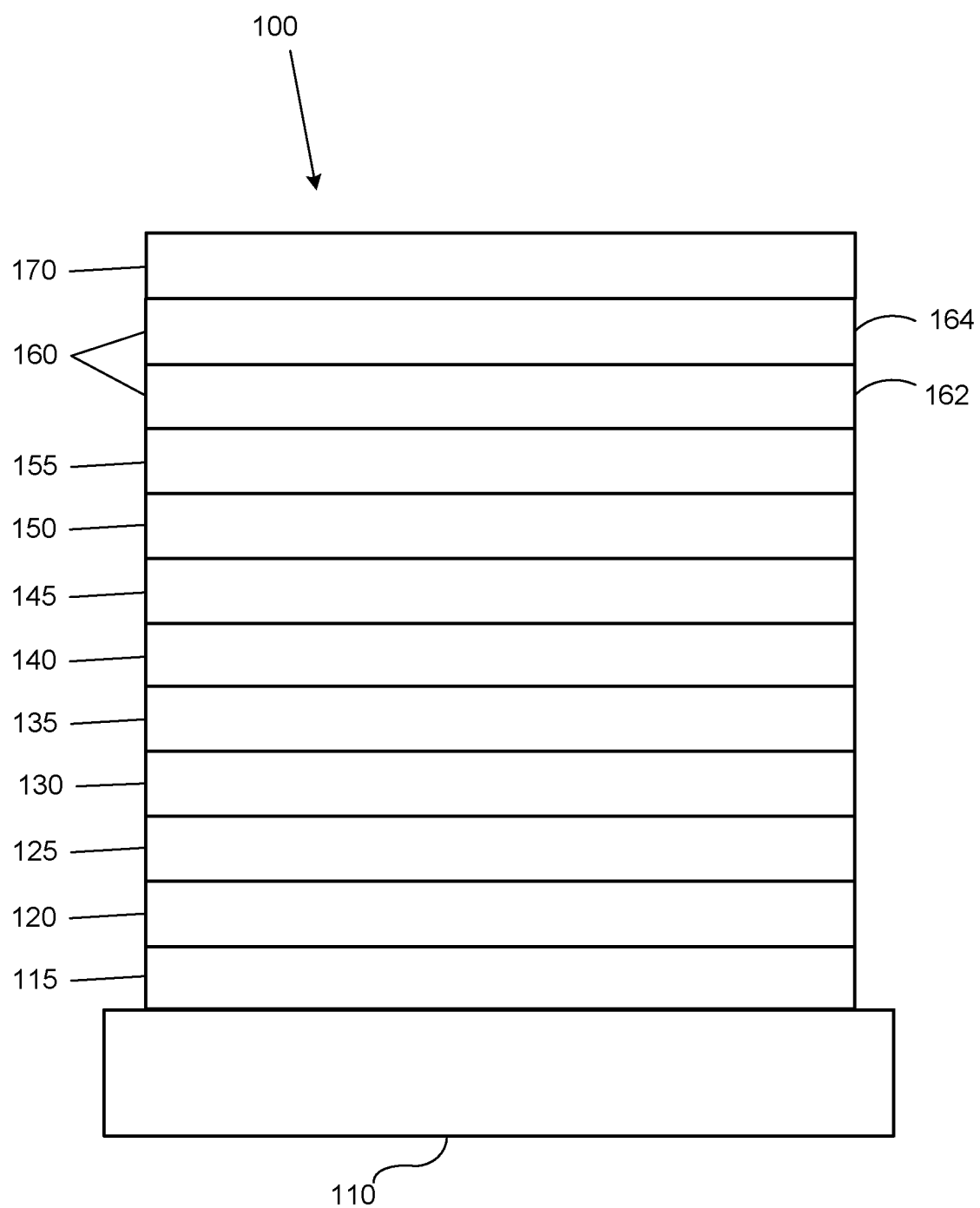
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F₄-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
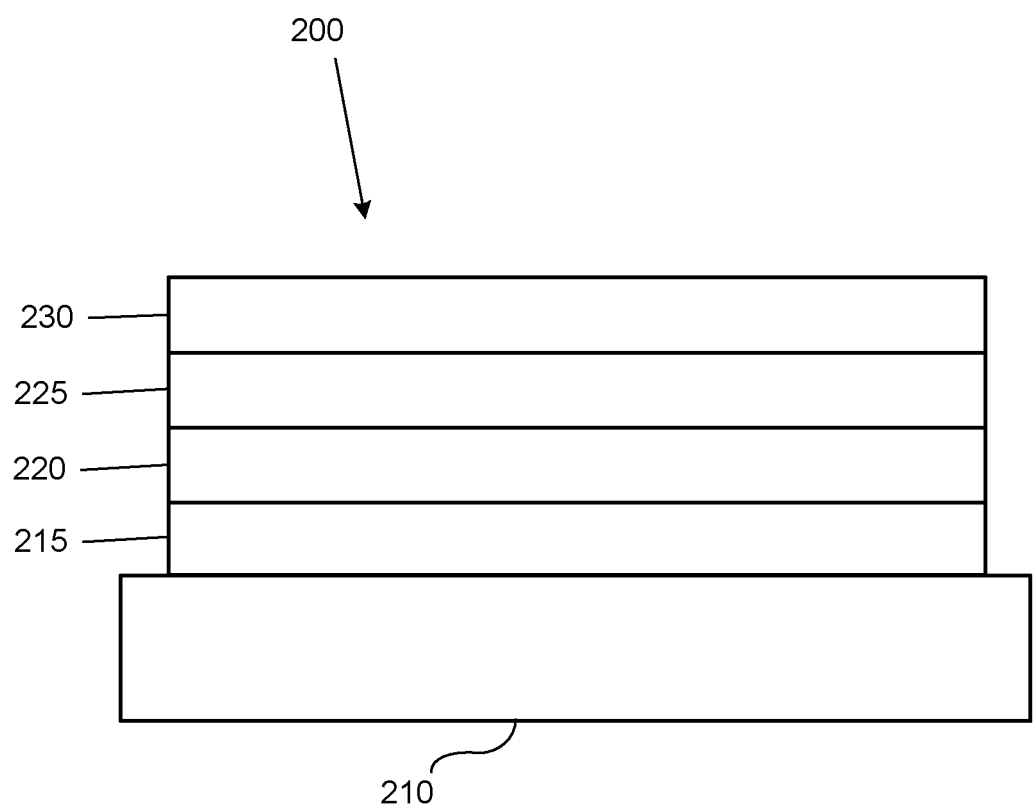
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable device, laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Hetero-aromatic cyclic radicals also means heteroaryl. Preferred hetero-non-aromatic cyclic groups are those containing 3 to 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the state of the art OLED devices, the emissive layer (EML) may consist of three or more components. In one example, the EML can consist of a combination of two host-type compounds and an emitter compound (e.g. a hole transporting cohost (h-host), an electron transporting cohost (e-host), and a compound capable of functioning as an emitter in an OLED at room temperature). In another example, the EML can consist of one host-type compound and two emitter-type compounds (e.g., a host compound and two compounds each capable of functioning as an emitter in an OLED at room temperature). Conventionally, in order to fabricate such EMLs having three or more components using VTE process, three or more evaporation sources are required, one for each of the components. Because the concentration of the components are important for the device performance, typically, the rate of deposition of each component is measured individually during the deposition process. This makes the VTE process complicated and costly compared to a standard two-component EML with a single host and an emitter, which requires only two evaporation sources.

Premixing two or more materials and evaporating them from one VTE sublimation crucible can reduce the number of VTE evaporation sources and simplify the fabrication process. In order for materials to be premixable into an evaporation source, they should co-evaporate and deposit uniformly without changing the ratio. The ratio of the components in the mixture should be the same as the ratio of the components in the evaporation deposited films from these premixed materials. Therefore, the concentration of the two components in the deposited film is controlled by their concentration in the premixed evaporation source. Variations in the film's composition may adversely affect the device performance. In order to obtain a stable co-evaporation from a mixture of compounds under vacuum, one would assume that the materials must have the same evaporation temperature under the same condition. However, this may not be the only parameter one has to consider. When two compounds are mixed together, they may interact with each other and the evaporation property of the mixture may differ from their individual properties. On the other hand, materials with slightly different evaporation temperatures may form a stable co-evaporation mixture. Therefore, it is extremely difficult to achieve a stable co-evaporation mixture. So far, there have been very few stable co-evaporation mixture examples. "Evaporation temperature" of a material is measured in a vacuum deposition tool at a constant pressure, normally between $1 \times 10^{-7}$ Torr to $1 \times 10^{-8}$ Torr, at a 2 Å/sec deposition rate on a surface positioned at a set distance away from the evaporation source of the material being evaporated, e.g. sublimation crucible in a VTE tool. The various measured values such as temperature, pressure, deposition rate, etc. disclosed herein are expected to have nominal variations because of the expected tolerances in the measurements that produced these quantitative values as understood by one of ordinary skill in the art.

Many factors other than temperature can contribute to the ability to achieve stable co-evaporation, such as the miscibility of the different materials and the phase transition temperatures of the different materials. The inventors found that when two materials have similar evaporation temperatures, and similar mass loss rate or similar vapor pressures, the two materials can co-evaporate consistently. "Mass loss rate" of a material is defined as the percentage of mass lost over time ("percentage/minute" or "%/min") and is determined by measuring the time it takes to lose the first 10% of the mass of a sample of the material as measured by thermal gravity analysis (TGA) under a given experimental condition at a given constant temperature for a given material after the a steady evaporation state is reached. The given constant temperature is one temperature point that is chosen so that the value of mass loss rate is between about 0.05 to 0.50%/min. A skilled person in this field should appreciate that in order to compare two parameters, the experimental condition should be consistent. The method of measuring mass loss rate and vapor pressure is well known in the art and can be found, for example, in Bull. et al. Mater. Sci. 2011, 34, 7.

This disclosure describes a new class of h- and e-hosts that can be premixed and stably co-evaporated from a single source.

According to an aspect of the present disclosure, a composition of materials comprising a mixture of a first compound and a second compound is disclosed, wherein the first compound has a formula:

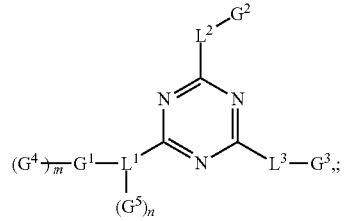

Formula I wherein $G^1$ is selected from the group consisting of dibenzofuran, dibenzothiophene, dibenzoselenophene, and fluorene;

wherein $L^1$, $L^2$ and $L^3$ are each independently selected from the group consisting of direct bond, phenyl, biphenyl, terphenyl, pyridine, pyrimidine, and combinations thereof;

wherein $G^4$ is selected from the group consisting of phenyl, biphenyl, terphenyl, naphthalene, phenanthrene, pyridine, pyrimidine, pyrazine, quinoline, isoquinoline, phenanthroline, fluorene, and combinations thereof;

wherein $G^2$, $G^3$, and $G^5$ are each independently selected from the group consisting of phenyl, biphenyl, terphenyl, fluorene, naphthalene, phenanthrene, pyridine, pyrimidine, pyrazine, quinoline, isoquinoline, phenanthroline, aza-fluorene, and combinations thereof;

wherein $G^2$, $G^3$, $G^4$, and $G^5$ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof;

wherein m is an integer from 0 to 7,
wherein n is an integer from 0 to 4;
wherein, when m or n is larger than 1, each $G^4$ or $G^5$ can be same or different;
wherein when n is 0 and m is equal to or greater than 1, then $G^4$ is selected from the group consisting of phenyl, and biphenyl;
wherein when n is equal to or greater than 1, $L^1$ is not a direct bond;
wherein when m and n are both 0, $L^1$ is biphenyl;
wherein when $G^4$ is present and is fluorene, $L^1$ is not a direct bond;
wherein the second compound has a formula:

Formula II

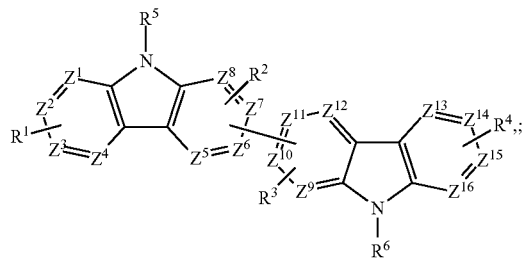

wherein each $Z^1$ to $Z^{16}$ is C or N;
wherein one of $Z^5$ to $Z^8$ bonds to one of $Z^9$ to $Z^{12}$ through a C—C bond;
wherein $R^1$, and $R^4$ each independently represent mono, di, tri, or tetra substitution, or no substitution;
wherein $R^2$, and $R^3$ each independently represent mono, di, or tri substitution, or no substitution;
wherein $R^1$ to $R^6$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and
wherein any two adjacent substituents are optionally joined or fused into a ring.

The composition of materials is useful as an evaporation source in a VTE process for depositing a host material in an OLED.

In one embodiment of the composition, n is 0.
In one embodiment of the composition, n is equal to or greater than 1.
In some embodiments of the composition, the fragment $G^4$ has the structure selected from the group consisting of:

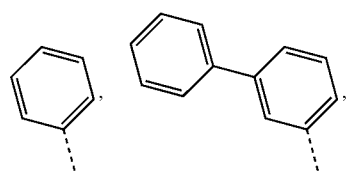

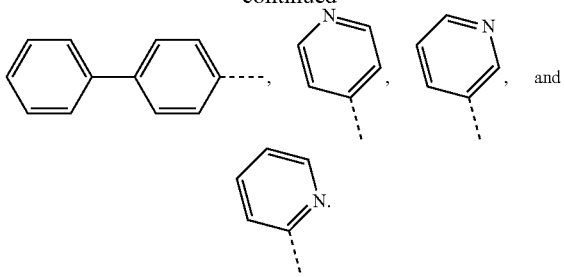

In some embodiments of the composition, $L^1$ is selected from the group consisting of:

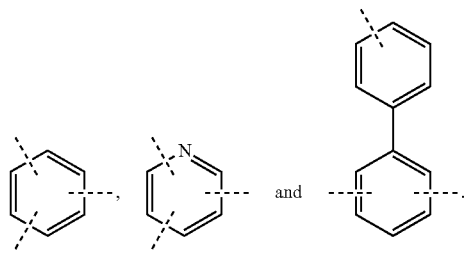

In some embodiments of the composition, $G^2$, $G^3$ and $G^5$ are independently selected from the group consisting of:

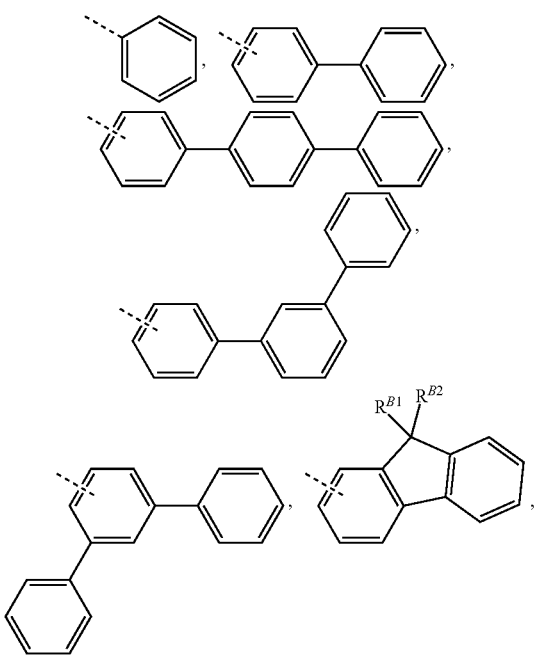
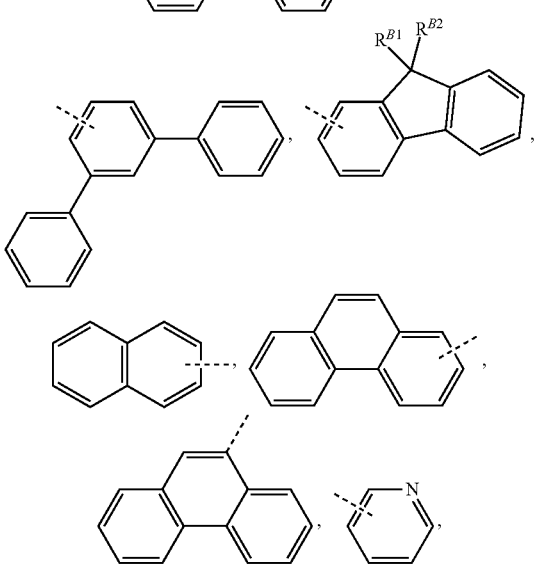

-continued

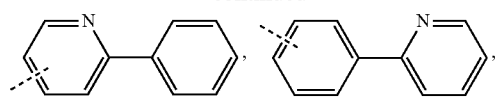

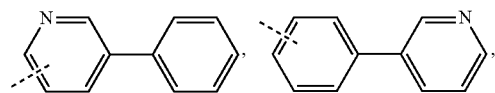

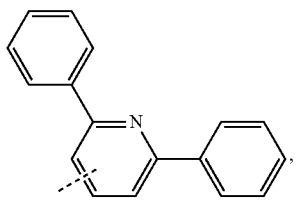

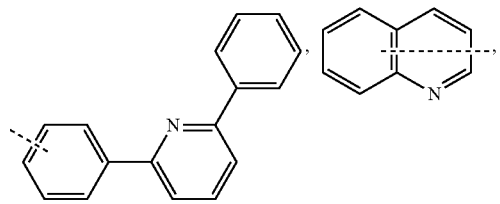

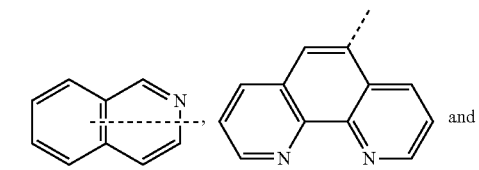 and

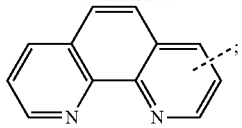

wherein $R^{B1}$ and $R^{B2}$ are independently selected from the group consisting of hydrogen, deuterium, alkyl, cycloalkyl, alkoxyl, aryl, heteraryl, halogen, and combinations thereof; and wherein $R^{B1}$ and $R^{B2}$ are optionally jointed to form a ring.

In some embodiments of the composition, the first compound has the formula:

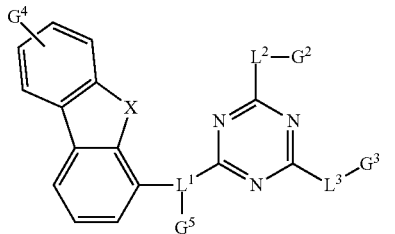 or

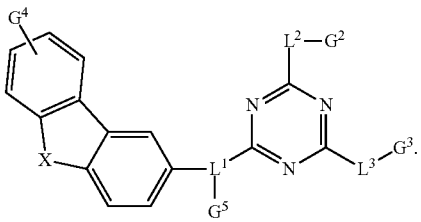

In some embodiments of the composition, the first compound is selected from the group consisting of:

Compound A1 through A3, each represented by the formula

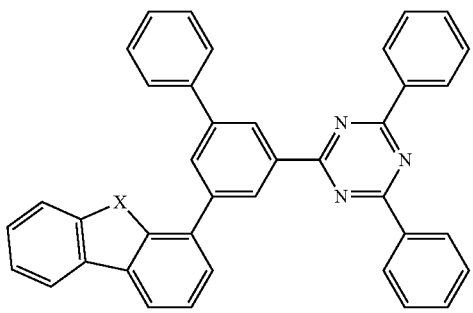

wherein in Compound A1: X = O, in Compound A2: X = S, in Compound A3: X = Se

Compound A4 through A6, each represented by the formula

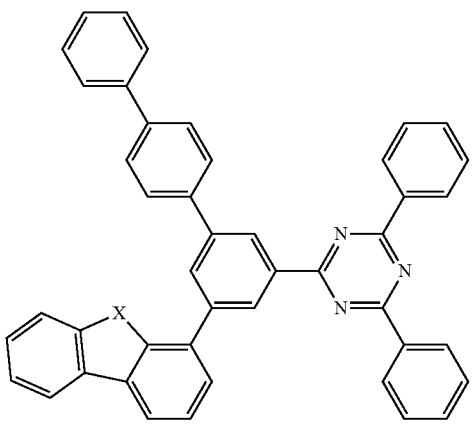
wherein in Compound A4: X = O, in Compound A5: X = S, in Compound A6: X = Se
Compound A7 through A9, each represented by the formula
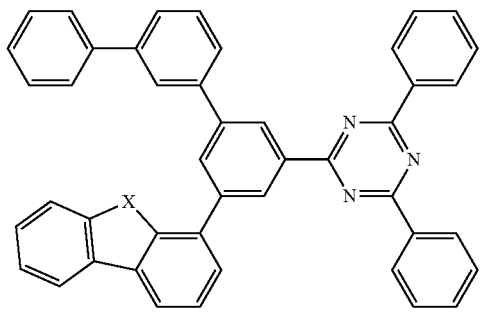
wherein in Compound A7: X = O, in Compound A8: X = S, in Compound A9: X = Se
Compound A10 through A12, each represented by the formula
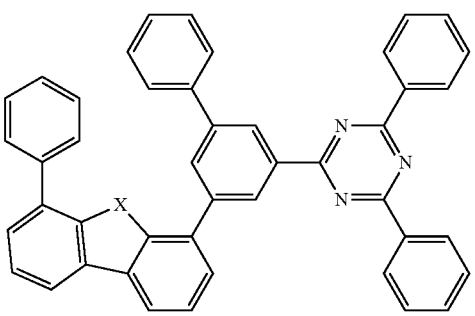
wherein in Compound A10: X = O, in Compound A11: X = S, in Compound A12: X = Se
Compound A13 through A15, each represented by the formula

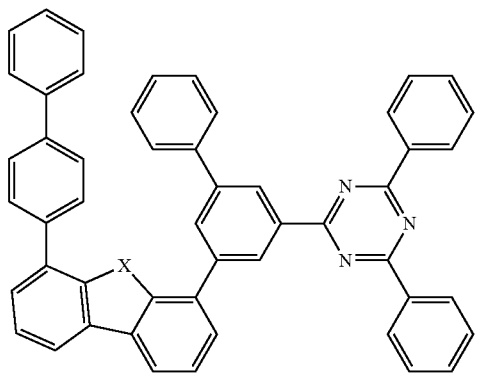
wherein in Compound A13: X = O, in Compound A14: X = S, in Compound A15: X = Se
Compound A16 through A18, each represented by the formula
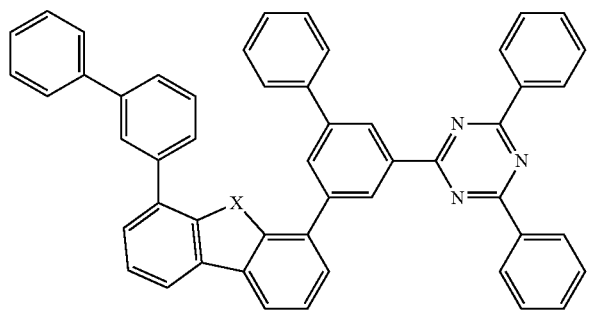
wherein in Compound A16: X = O, in Compound A17: X = S, in Compound A18: X = Se
Compound A19 through A21, each represented by the formula
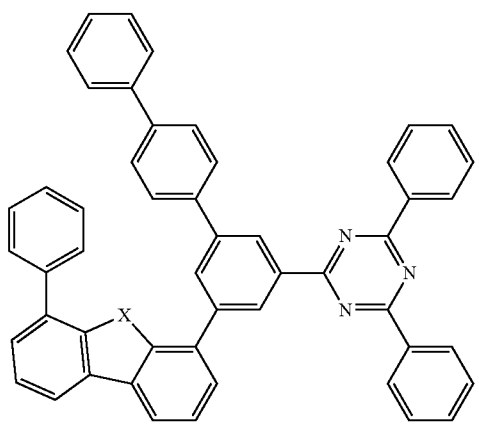
wherein in Compound A19: X = O, in Compound A20: X = S, in Compound A21: X = Se
Compound A22 through A24, each represented by the formula

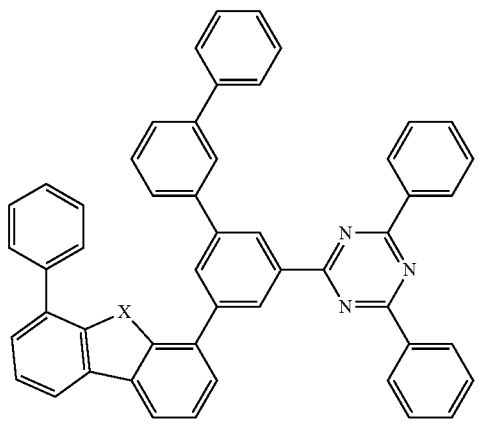
wherein in Compound A22: X = O, in Compound A23: X = S, in Compound A24: X = Se
Compound A25 through A27, each represented by the formula
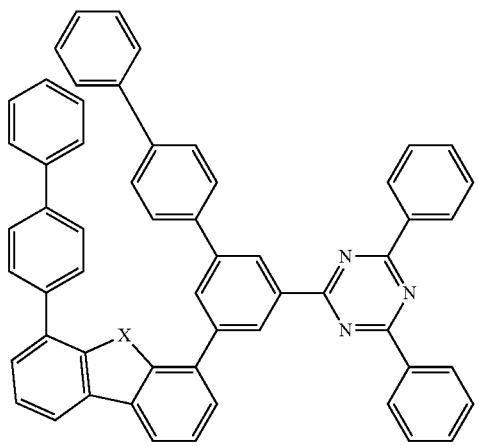
wherein in Compound A25: X = O, in Compound A26: X = S, in Compound A27: X = Se
Compound A28 through A30, each represented by the formula
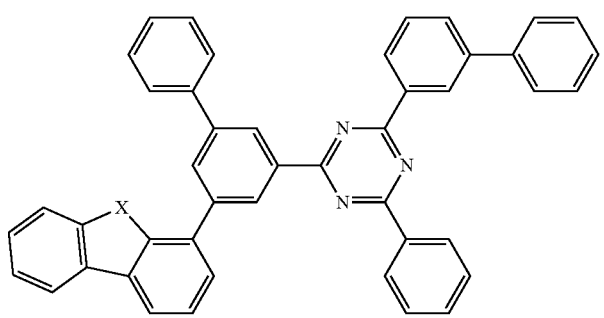
wherein in Compound A28: X = O, in Compound A29: X = S, in Compound A30: X = Se
Compound A31 through A33, each represented by the formula

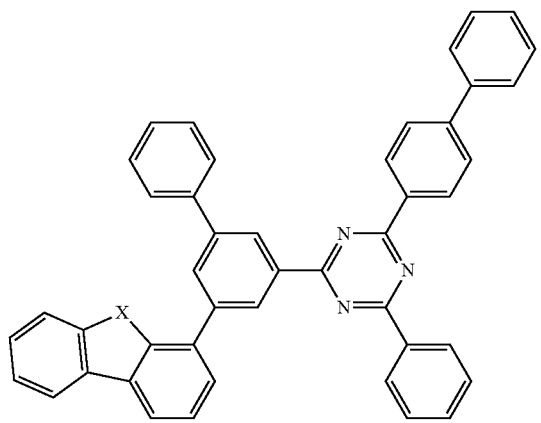
wherein in Compound A31: X = O, in Compound A32: X = S, in Compound A33: X = Se
Compound A34 through A36, each represented by the formula
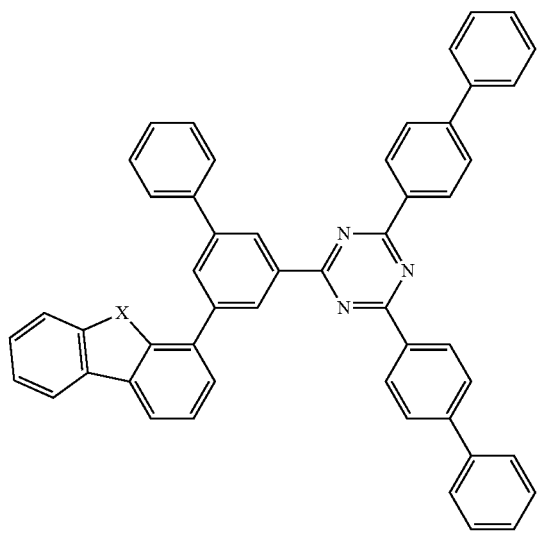
wherein in Compound A34: X = O, in Compound A35: X = S, in Compound A36: X = Se
Compound A37 through A39, each represented by the formula
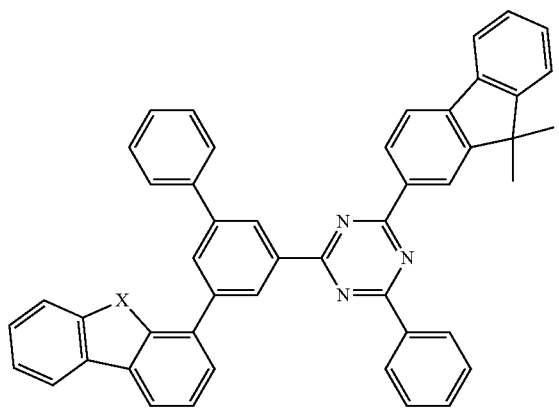
wherein in Compound A37: X = O, in Compound A38: X = S, in Compound A39: X = Se
Compound A40 through A42, each represented by the formula

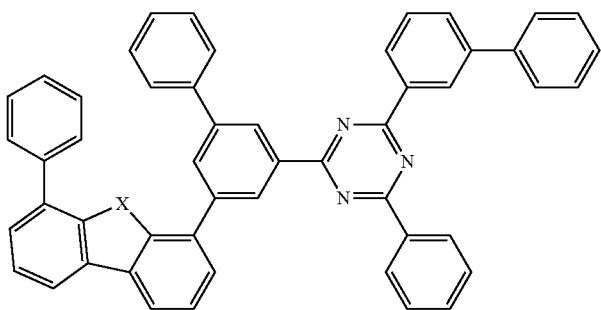
wherein in Compound A40: X = O, in Compound A41: X = S, in Compound A42: X = Se
Compound A43 through A45, each represented by the formula
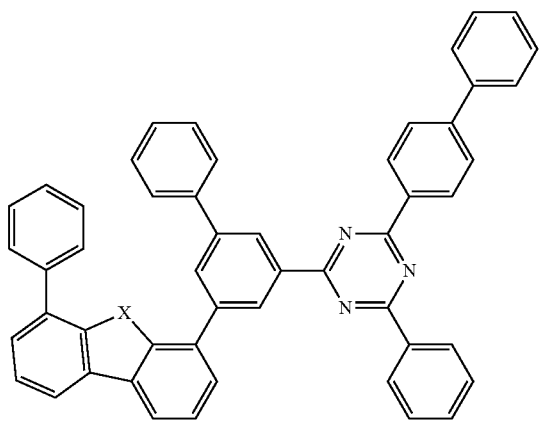
wherein in Compound A43: X = O, in Compound A44: X = S, in Compound A45: X = Se
Compound A46 through A48, each represented by the formula
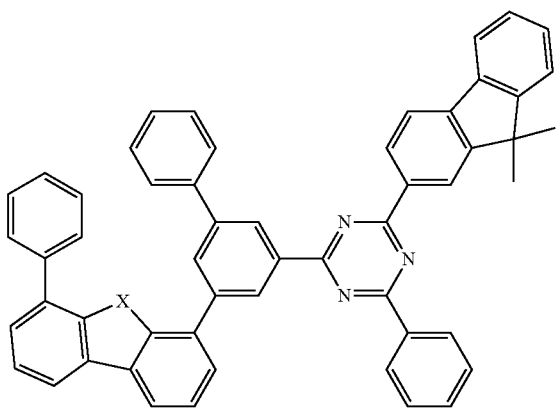
wherein in Compound A46: X = O, in Compound A47: X = S, in Compound A48: X = Se
Compound A49 through A51, each represented by the formula

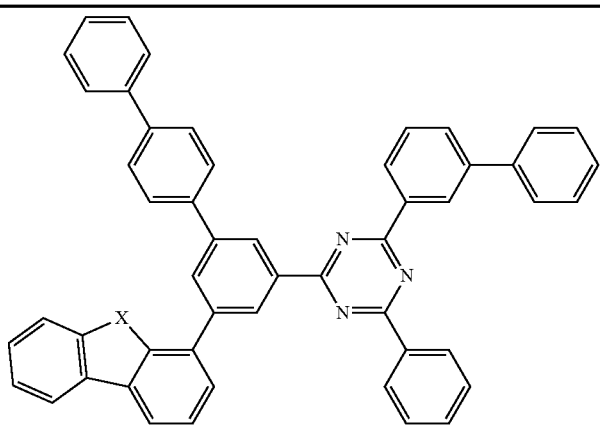
wherein in Compound A49: X = O, in Compound A50: X = S, in Compound A51: X = Se
Compound A52 through A54, each represented by the formula
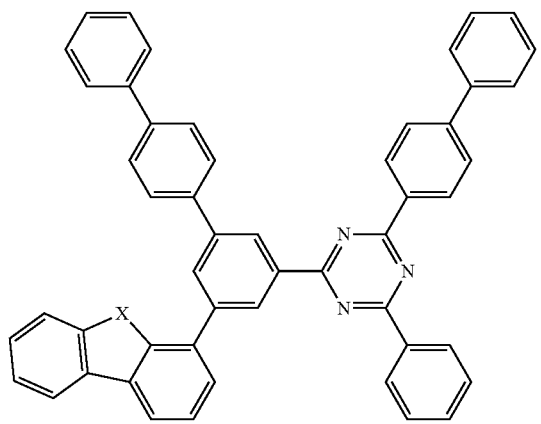
wherein in Compound A52: X = O, in Compound A53: X = S, in Compound A54: X = Se
Compound A55 through A57, each represented by the formula
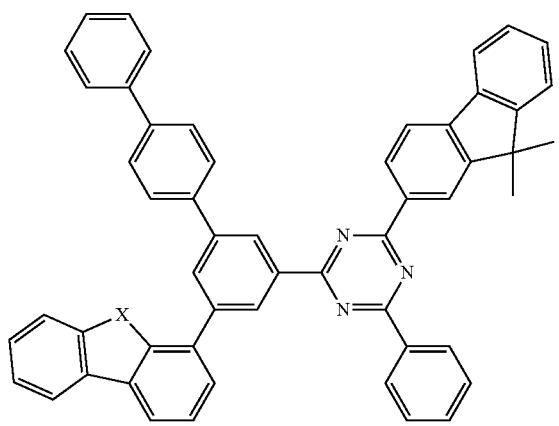
wherein in Compound A55: X = O, in Compound A56: X = S, in Compound A57: X = Se
Compound A58 through A60, each represented by the formula

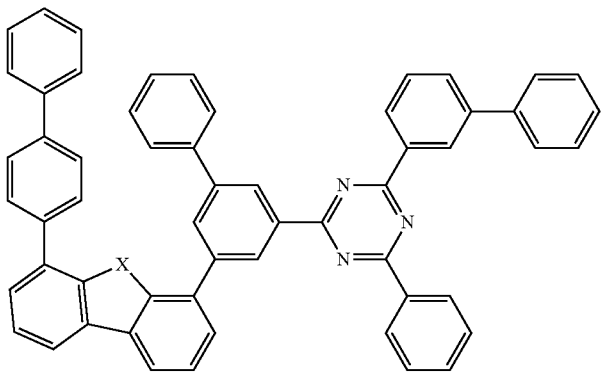
wherein in Compound A58: X = O, in Compound A59: X = S, in Compound A60: X = Se
Compound A61 through A63, each represented by the formula
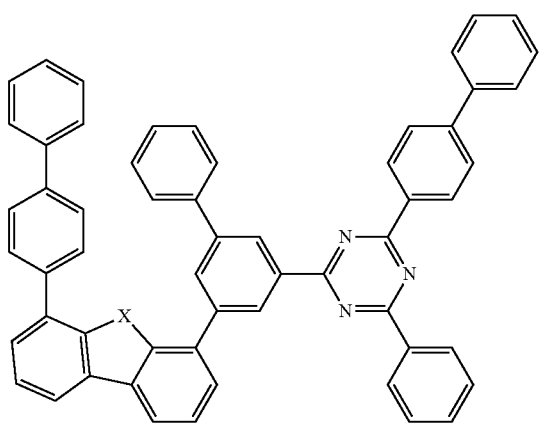
wherein in Compound A61: X = O, in Compound A62: X = S, in Compound A63: X = Se
Compound A64 through A66, each represented by the formula
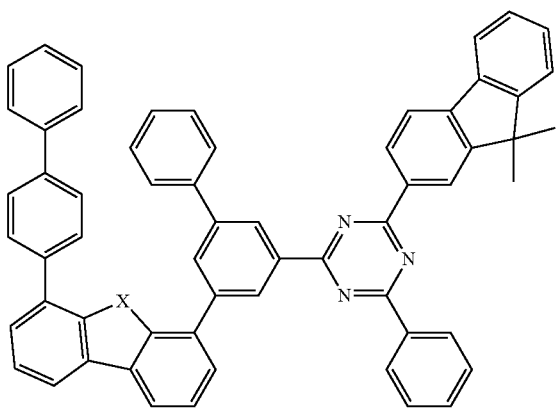
wherein in Compound A64: X = O, in Compound A65: X = S, in Compound A66: X = Se
Compound A67 through A69, each represented by the formula

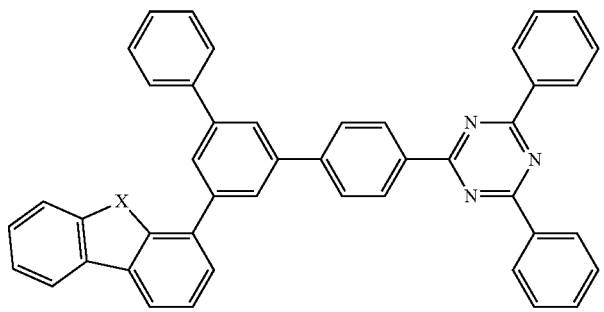
wherein in Compound A67: X = O, in Compound A68: X = S, in Compound A69: X = Se
Compound A70 through A72, each represented by the formula
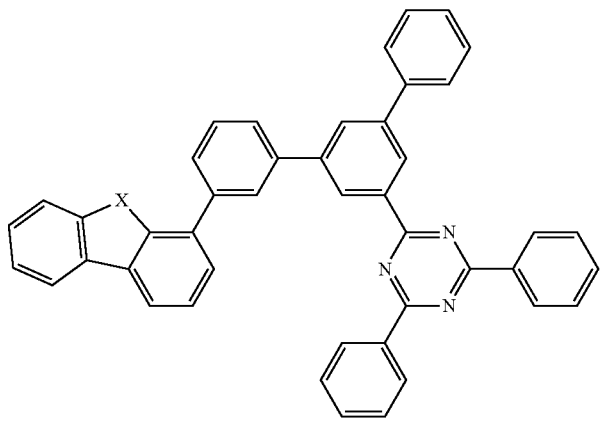
wherein in Compound A70: X = O, in Compound A71: X = S, in Compound A72: X = Se
Compound A73 through A75, each represented by the formula
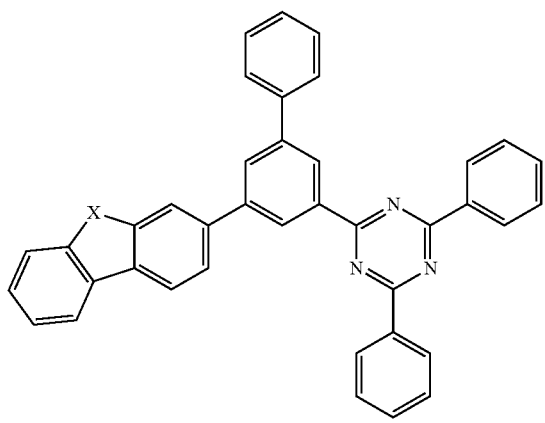
wherein in Compound A73: X = O, in Compound A74: X = S, in Compound A75: X = Se
Compound A76 through A78, each represented by the formula

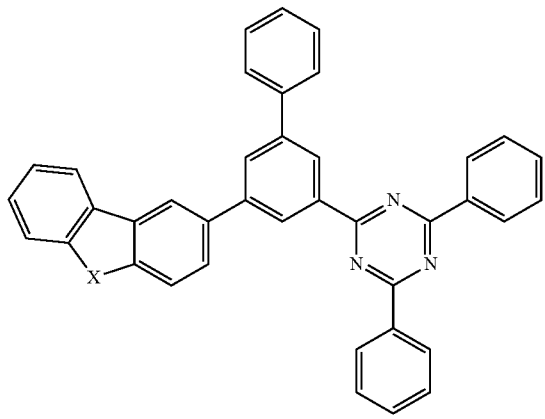
wherein in Compound A76: X = O, in Compound A77: X = S, in Compound A78: X = Se
Compound A79 through A81, each represented by the formula
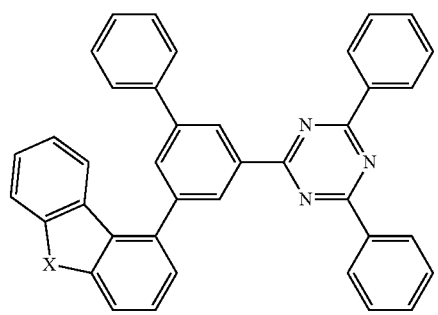
wherein in Compound A79: X = O, in Compound A80: X = S, in Compound A81: X = Se
Compound A82 through A84, each represented by the formula
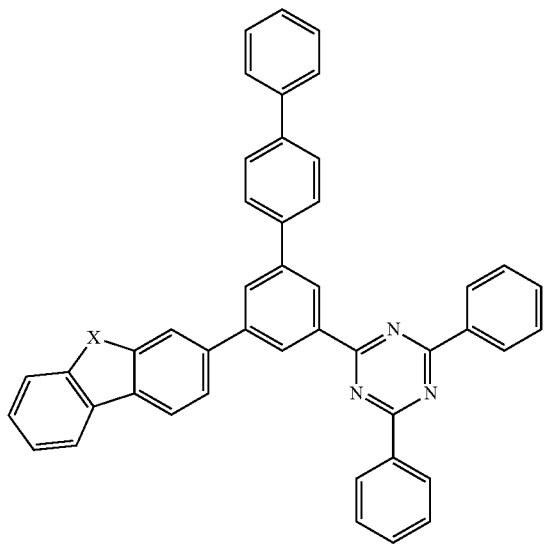
wherein in Compound A82: X = O, in Compound A83: X = S, in Compound A84: X = Se
Compound A85 through A87, each represented by the formula

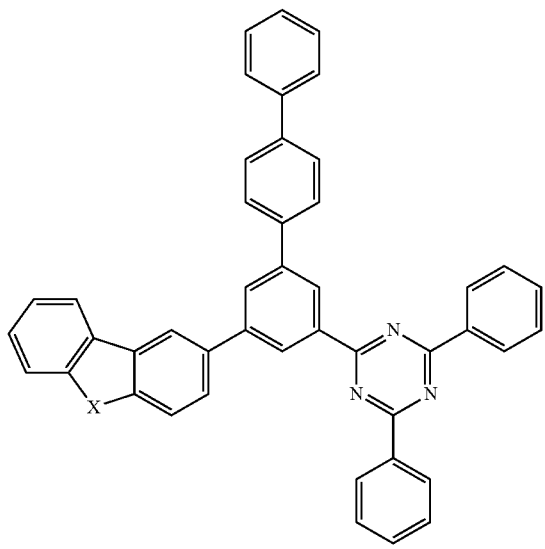
wherein in Compound A85: X = O, in Compound A86: X = S, in Compound A87: X = Se
Compound A88 through A90, each represented by the formula
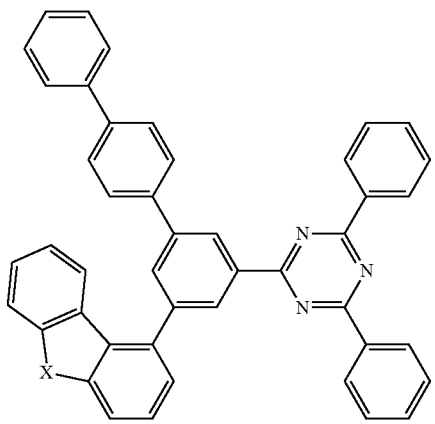
wherein in Compound A88: X = O, in Compound A89: X = S, in Compound A90: X = Se
Compound A91 through A93, each represented by the formula
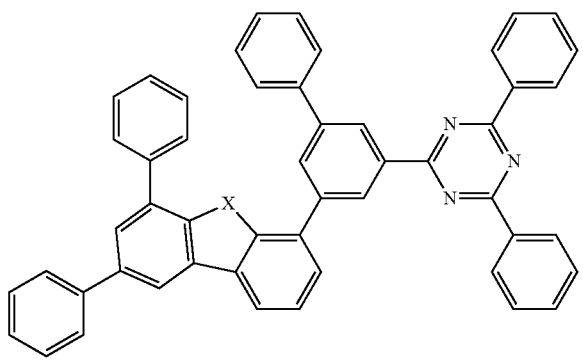
wherein in Compound A91: X = O, in Compound A92: X = S, in Compound A93: X = Se
Compound A94 through A96, each represented by the formula

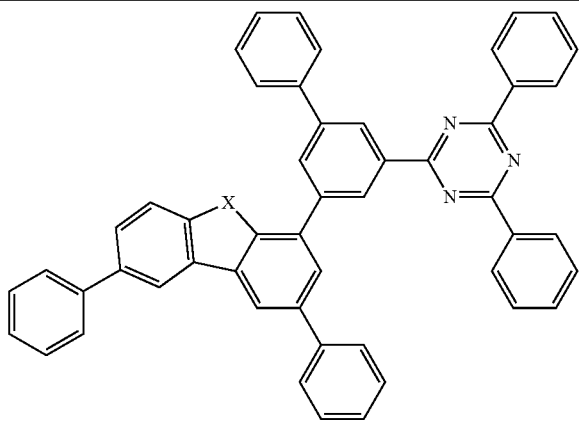
wherein in Compound A94: X = O, in Compound A95: X = S, in Compound A96: X = Se
Compound A97 through A99, each represented by the formula
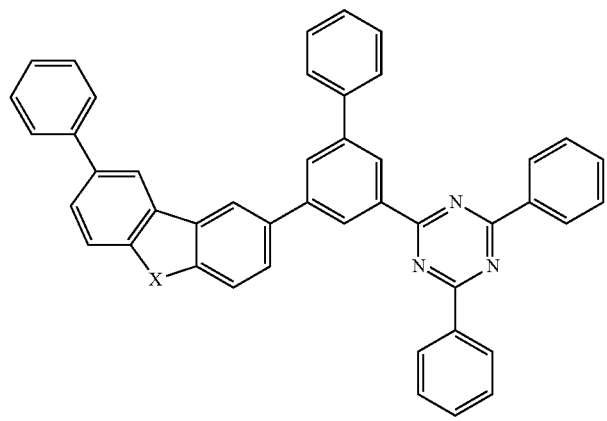
wherein in Compound A97: X = O, in Compound A98: X = S, in Compound A99: X = Se
Compound A100 through A102, each represented by the formula
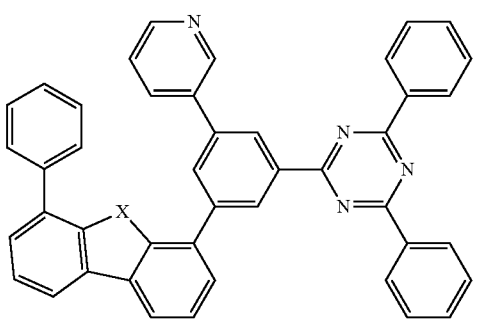
wherein in Compound A100: X = O, in Compound A101: X = S, in Compound A102: X = Se
Compound A103 through A105, each represented by the formula

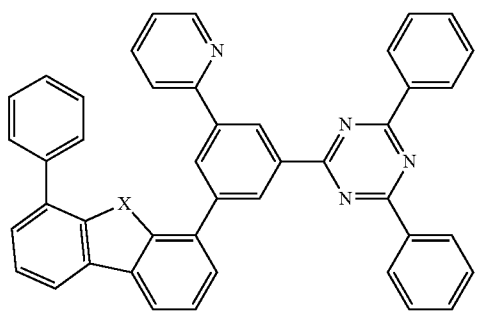
wherein in Compound A103: X = O, in Compound A104: X = S, in Compound A105: X = Se
Compound A106 through A108, each represented by the formula
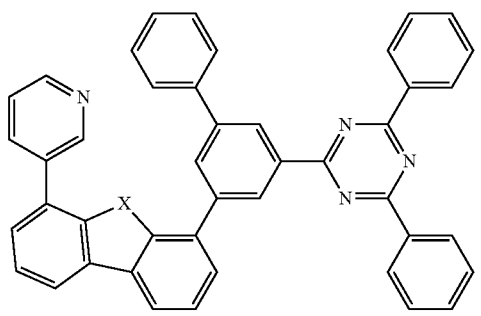
wherein in Compound A106: X = O, in Compound A107: X = S, in Compound A108: X = Se
Compound A109 through A111, each represented by the formula
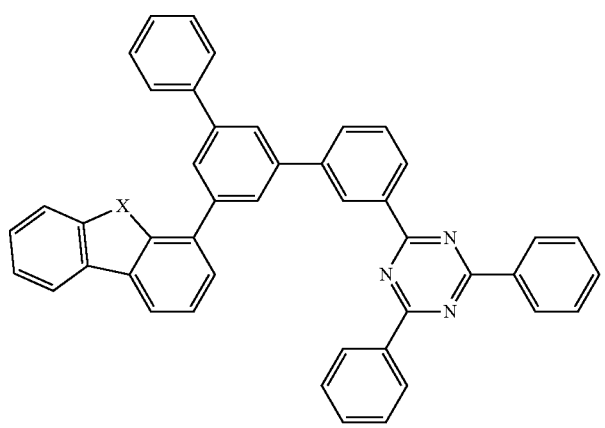
wherein in Compound A109: X = O, in Compound A110: X = S, in Compound A111: X = Se
Compound A112 through A114, each represented by the formula

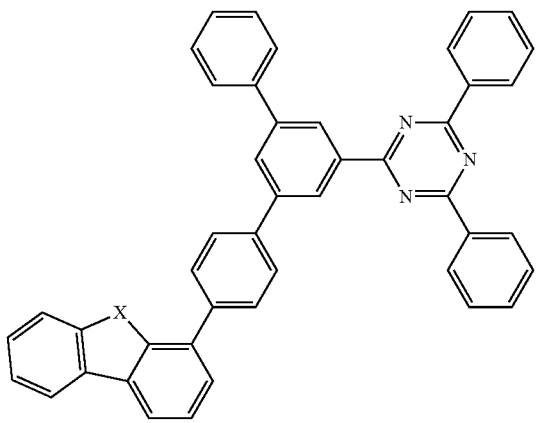
wherein in Compound A112: X = O, in Compound A113: X = S, in Compound A114: X = Se
Compound A115 through A117, each represented by the formula
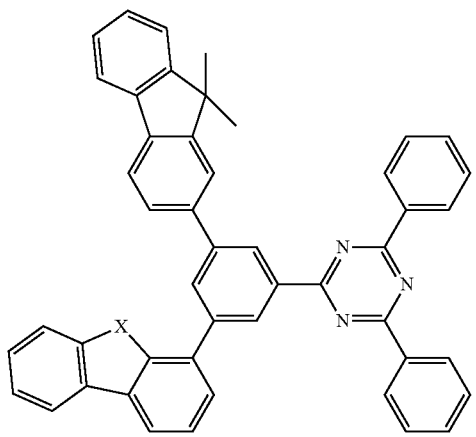
wherein in Compound A115: X = O, in Compound A116: X = S, in Compound A117: X = Se
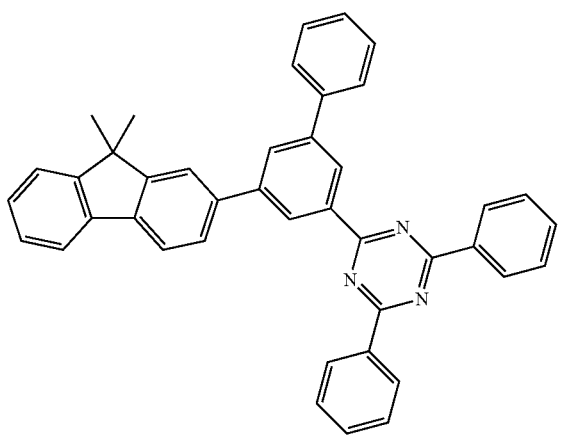 [SMILES: CC1(C)c2ccccc2-c2ccc(-c3cc(-c4ccccc4)cc(-c4nc(-c5ccccc5)nc(-c5ccccc5)n4)c3)cc21]
Compound B1

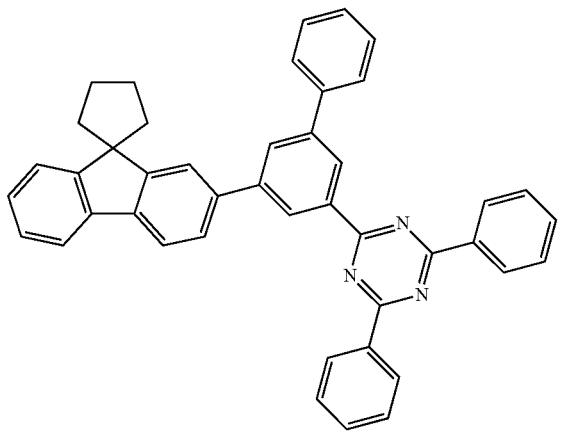 [SMILES: c1ccc(-c2cc(-c3ccc4c(c3)C3(CCCC3)c3ccccc3-4)cc(-c3nc(-c4ccccc4)nc(-c4ccccc4)n3)c2)cc1]
Compound B2
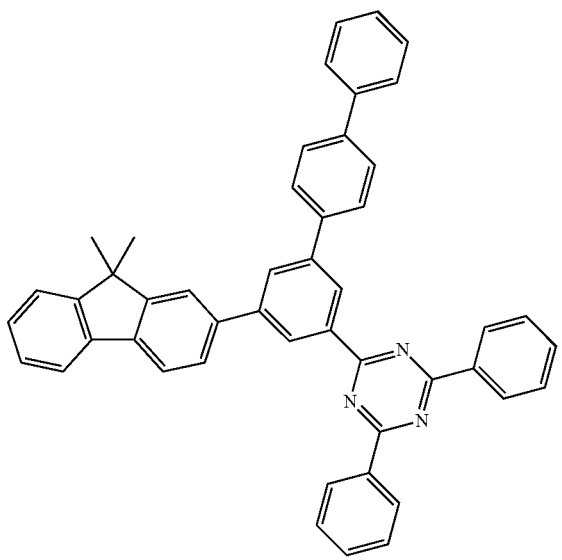 [SMILES: CC1(C)c2ccccc2-c2ccc(-c3cc(-c4ccc(-c5ccccc5)cc4)cc(-c4nc(-c5ccccc5)nc(-c5ccccc5)n4)c3)cc21]
Compound B3
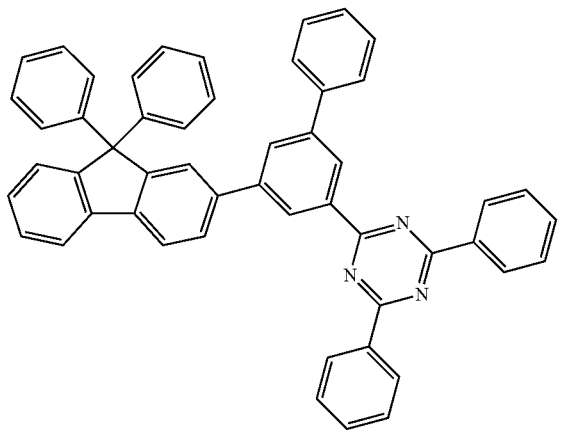 [SMILES: c1ccc(-c2cc(-c3ccc4c(c3)C(c3ccccc3)(c3ccccc3)c3ccccc3-4)cc(-c3nc(-c4ccccc4)nc(-c4ccccc4)n3)c2)cc1]
Compound B4

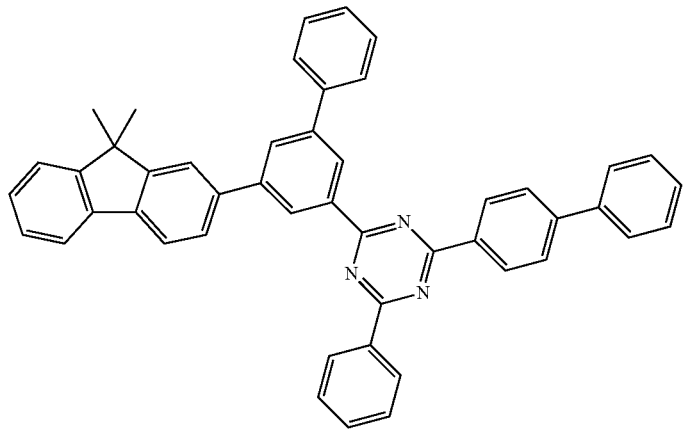 [SMILES: CC1(C)c2ccccc2-c2ccc(-c3cc(-c4ccccc4)cc(-c4nc(-c5ccccc5)nc(-c5ccc(-c6ccccc6)cc5)n4)c3)cc21]
Compound B5
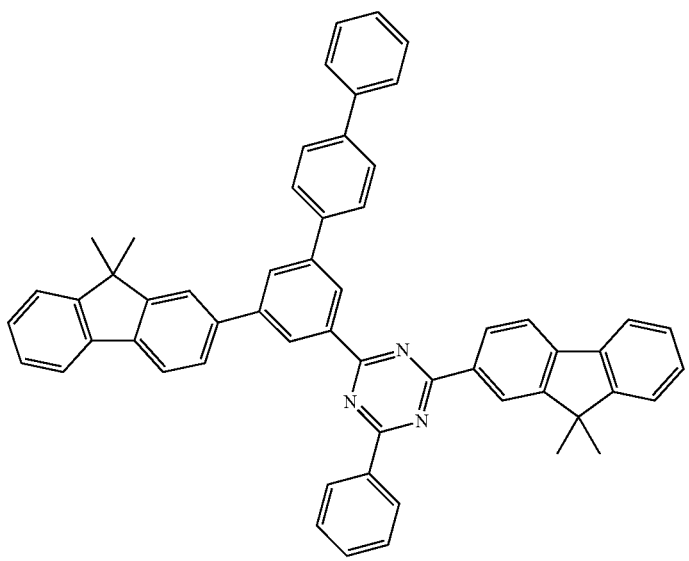 [SMILES: CC1(C)c2ccccc2-c2ccc(-c3cc(-c4ccc(-c5ccccc5)cc4)cc(-c4nc(-c5ccccc5)nc(-c5ccc6c(c5)C(C)(C)c5ccccc5-6)n4)c3)cc21]
Compound B6
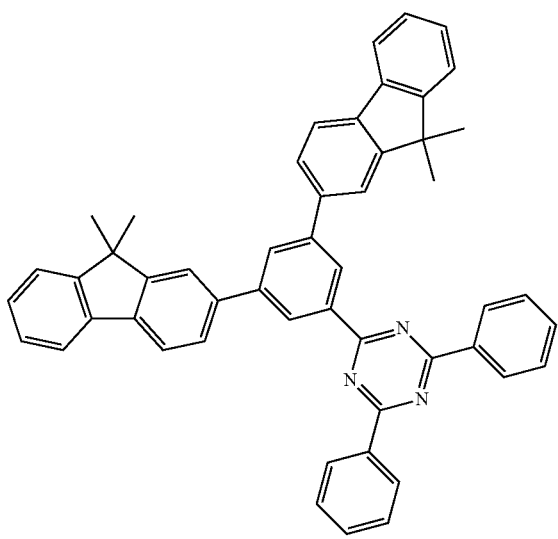 [SMILES: CC1(C)c2ccccc2-c2ccc(-c3cc(-c4ccc5c(c4)C(C)(C)c4ccccc4-5)cc(-c4nc(-c5ccccc5)nc(-c5ccccc5)n4)c3)cc21]
Compound B7

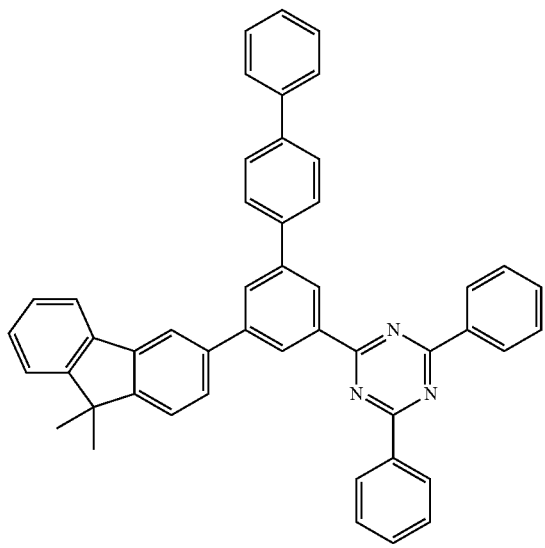 [SMILES: CC1(C)c2ccccc2-c2cc(-c3cc(-c4ccc(-c5ccccc5)cc4)cc(-c4nc(-c5ccccc5)nc(-c5ccccc5)n4)c3)ccc21]
Compound B8
Compound C1 through C3, each represented by the formula
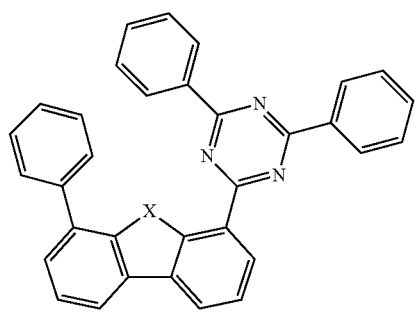
wherein in Compound C1: X = O, in Compound C2: X = S, in Compound C3: X = Se
Compound C4 through C6, each represented by the formula
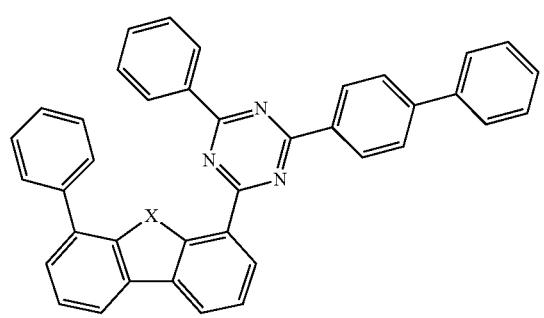
wherein in Compound C4: X = O, in Compound C5: X = S, in Compound C6: X = Se
Compound C7 through C9, each represented by the formula

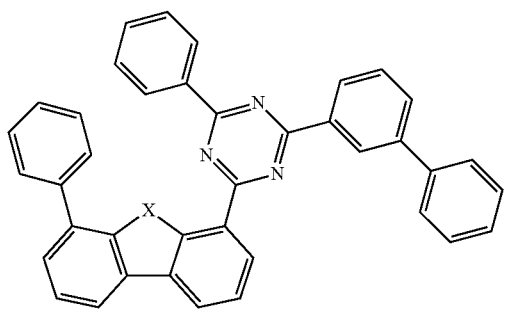
wherein in Compound C7: X = O, in Compound C8: X = S, in Compound C9: X = Se
Compound C10 through C12, each represented by the formula
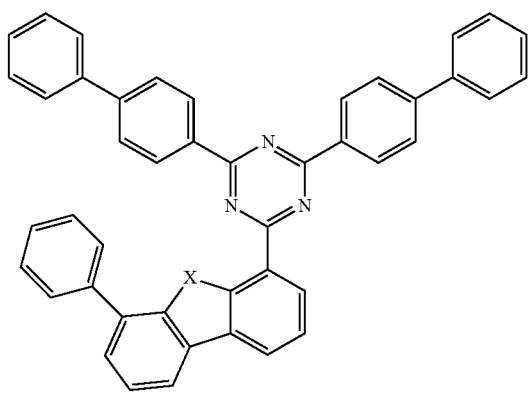
wherein in Compound C10: X = O, in Compound C11: X = S, in Compound C12: X = Se
Compound C13 through C15, each represented by the formula
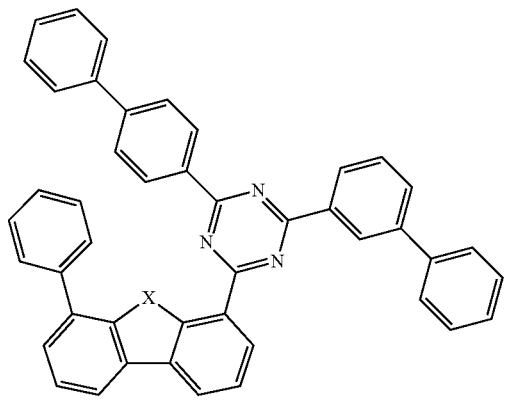
wherein in Compound C13: X = O, in Compound C14: X = S, in Compound C15: X = Se
Compound C16 through C18, each represented by the formula

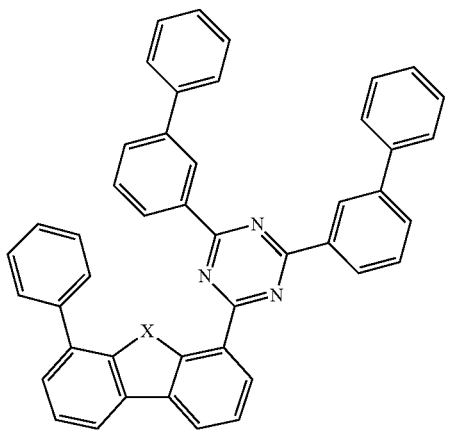
wherein in Compound C16: X = O, in Compound C17: X = S, in Compound C18: X = Se
Compound C19 through C21, each represented by the formula
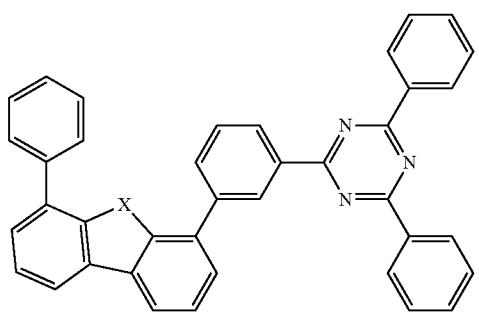
wherein in Compound C19: X = O, in Compound C20: X = S, in Compound C21: X = Se
Compound C22 through C24, each represented by the formula
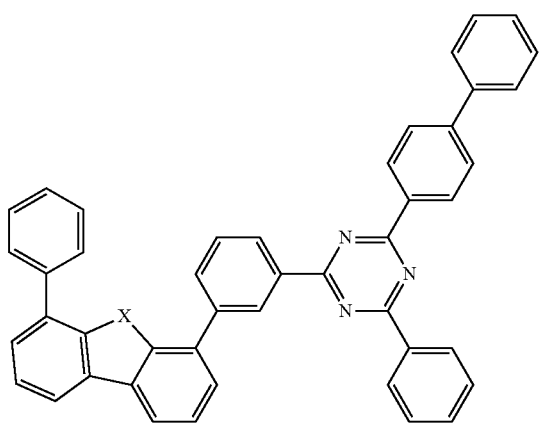
wherein in Compound C22: X = O, in Compound C23: X = S, in Compound C24: X = Se
Compound C25 through C27, each represented by the formula

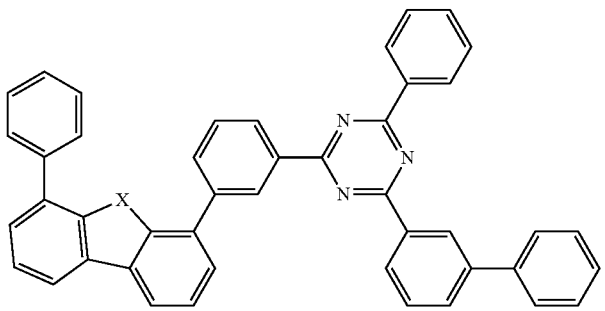
wherein in Compound C25: X = O, in Compound C26: X = S, in Compound C27: X = Se
Compound C28 through C30, each represented by the formula
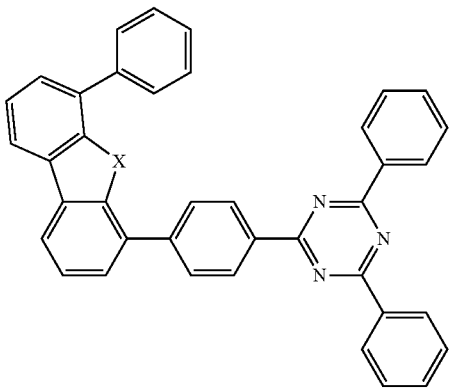
wherein in Compound C28: X = O, in Compound C29: X = S, in Compound C30: X = Se
Compound C31 through C33, each represented by the formula
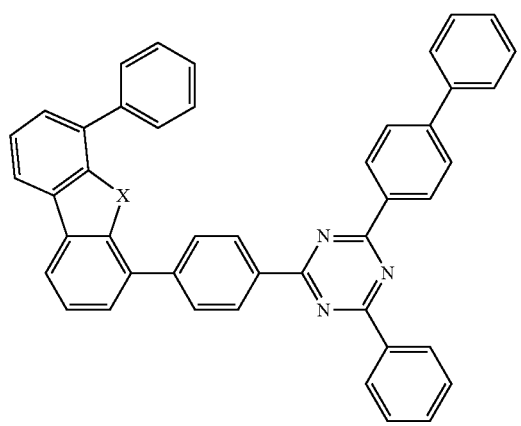
wherein in Compound C31: X = O, in Compound C32: X = S, in Compound C33: X = Se
Compound C34 through C36, each represented by the formula

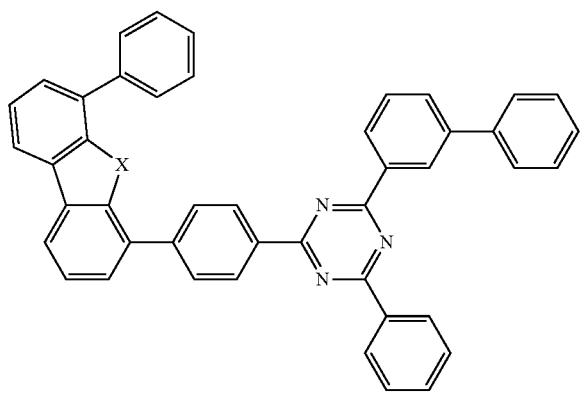
wherein in Compound C34: X = O, in Compound C35: X = S, in Compound C36: X = Se
Compound C37 through C39, each represented by the formula
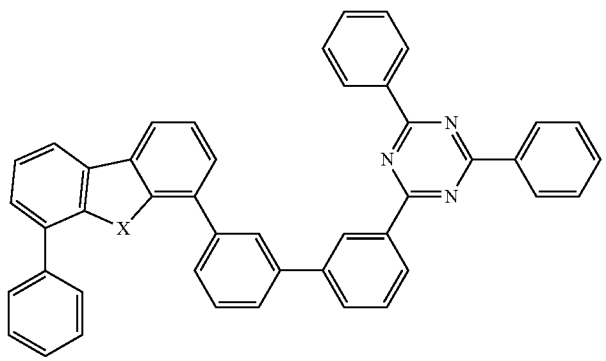
wherein in Compound C37: X = O, in Compound C38: X = S, in Compound C39: X = Se
Compound C40 through C42, each represented by the formula
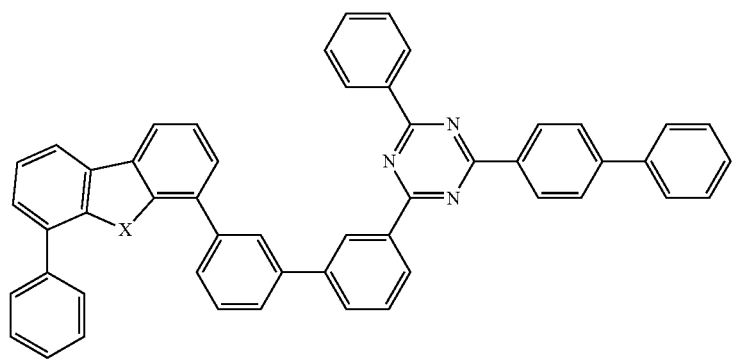
wherein in Compound C40: X = O, in Compound C41: X = S, in Compound C42: X = Se
Compound C43 through C45, each represented by the formula

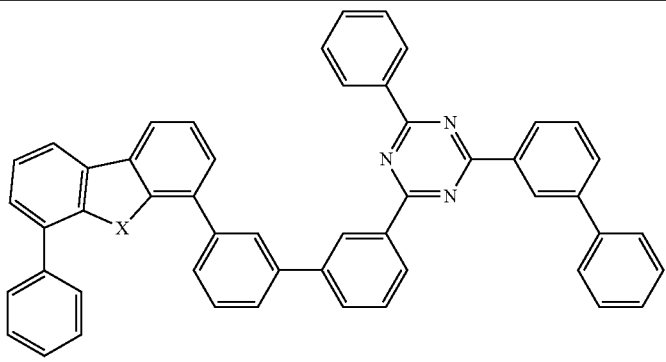

wherein in Compound C43: X = O, in Compound C44: X = S, in Compound C45: X = Se
Compound C46 through C48, each represented by the formula

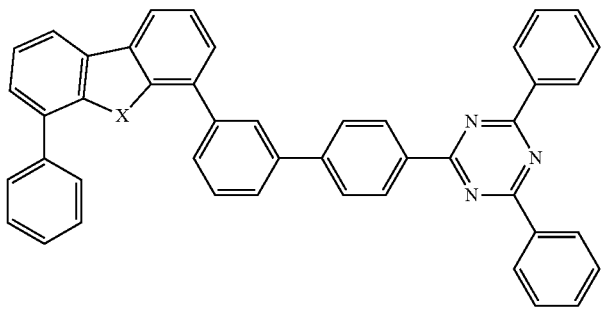

wherein in Compound C46: X = O, in Compound C47: X = S, in Compound C48: X = Se
Compound C49 through C51, each represented by the formula

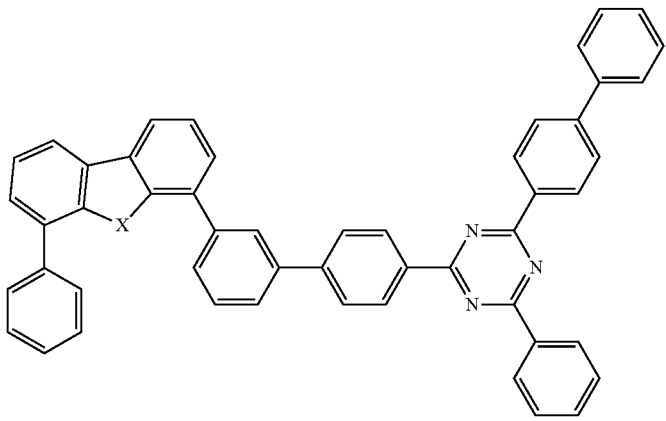

wherein in Compound C49: X = O, in Compound C50: X = S, in Compound C51: X = Se
Compound C52 through C54, each represented by the formula

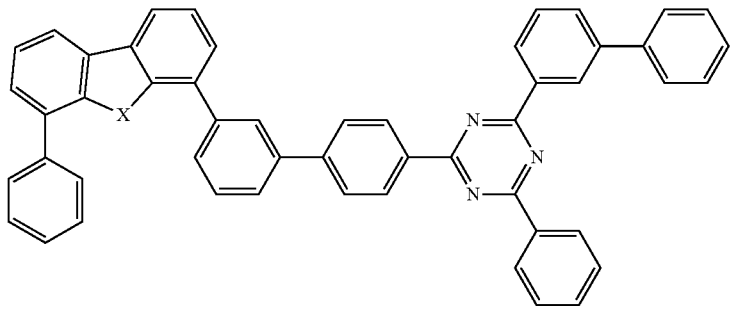

wherein in Compound C52: X = O, in Compound C53: X = S, in Compound C54: X = Se
Compound C55 through C57, each represented by the formula

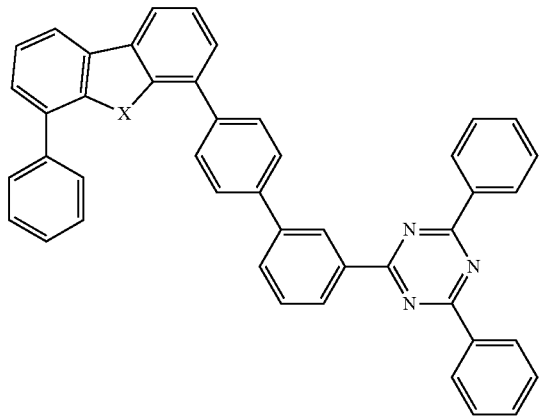
wherein in Compound C55: X = O, in Compound C56: X = S, in Compound C57: X = Se
Compound C58 through C60, each represented by the formula
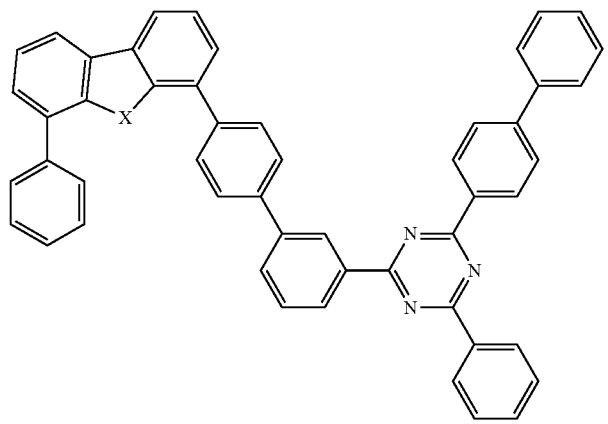
wherein in Compound C58: X = O, in Compound C59: X = S, in Compound C60: X = Se
Compound C61 through C63, each represented by the formula
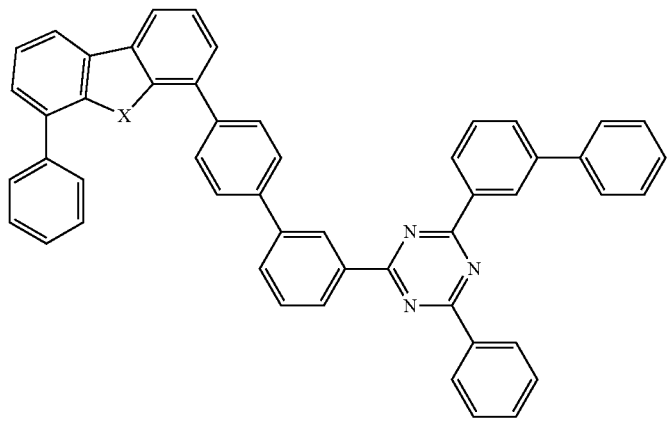
wherein in Compound C61: X = O, in Compound C62: X = S, in Compound C63: X = Se
Compound C64 through C66, each represented by the formula

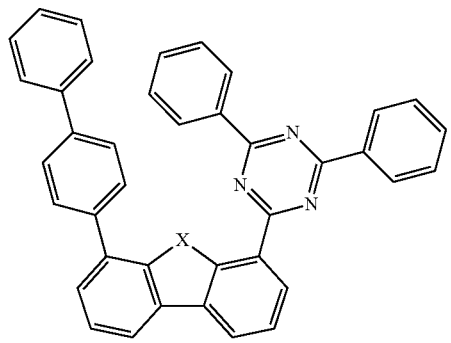
wherein in Compound C64: X = O, in Compound C65: X = S, in Compound C66: X = Se
Compound C67 through C69, each represented by the formula
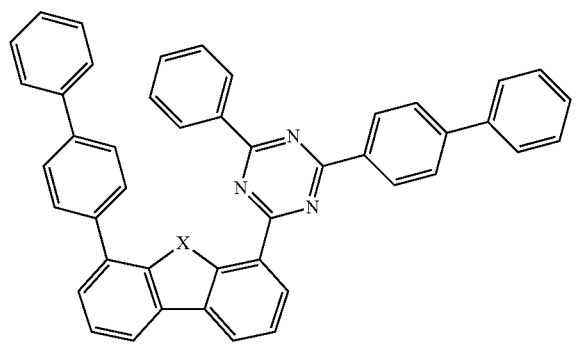
wherein in Compound C67: X = O, in Compound C68: X = S, in Compound C69: X = Se
Compound C70 through C72, each represented by the formula
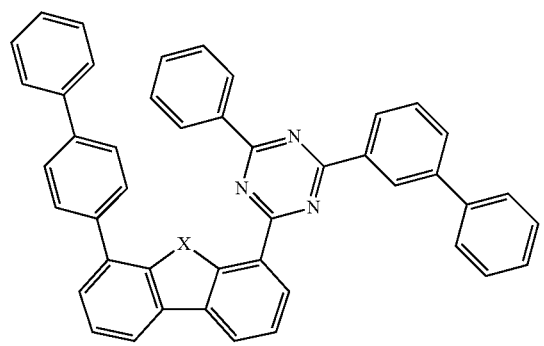
wherein in Compound C70: X = O, in Compound C71: X = S, in Compound C72: X = Se
Compound C73 through C75, each represented by the formula

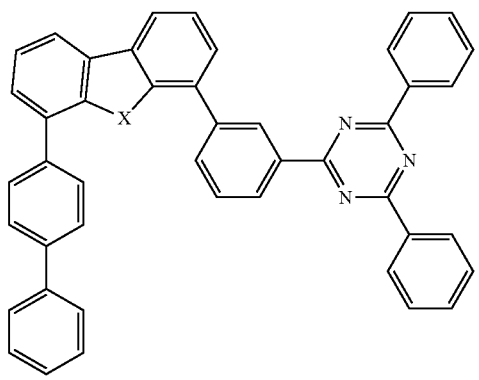
wherein in Compound C73: X = O, in Compound C74: X = S, in Compound C75: X = Se
Compound C76 through C78, each represented by the formula
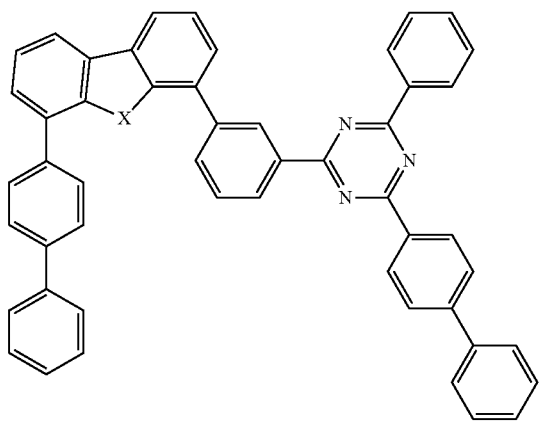
wherein in Compound C76: X = O, in Compound C77: X = S, in Compound C78: X = Se
Compound C79 through C81, each represented by the formula
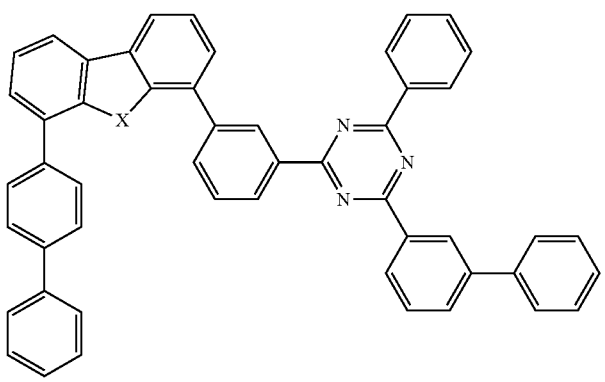
wherein in Compound C79: X = O, in Compound C80: X = S, in Compound C81: X = Se
Compound C82 through C84, each represented by the formula

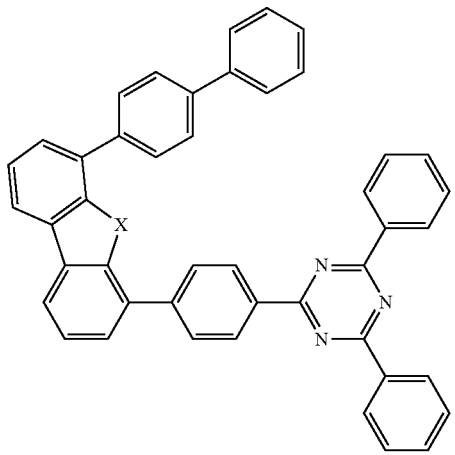
wherein in Compound C82: X = O, in Compound C83: X = S, in Compound C84: X = Se
Compound C85 through C87, each represented by the formula
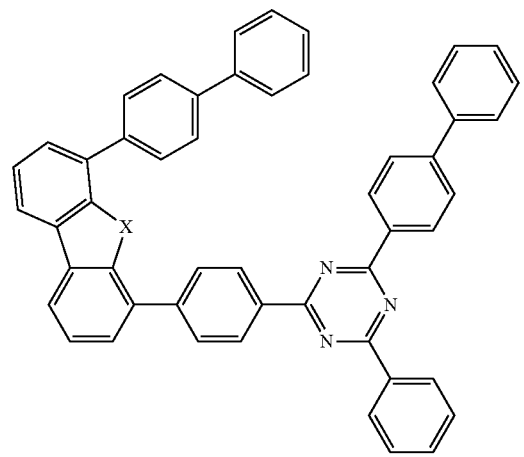
wherein in Compound C85: X = O, in Compound C86: X = S, in Compound C87: X = Se
Compound C88 through C90, each represented by the formula
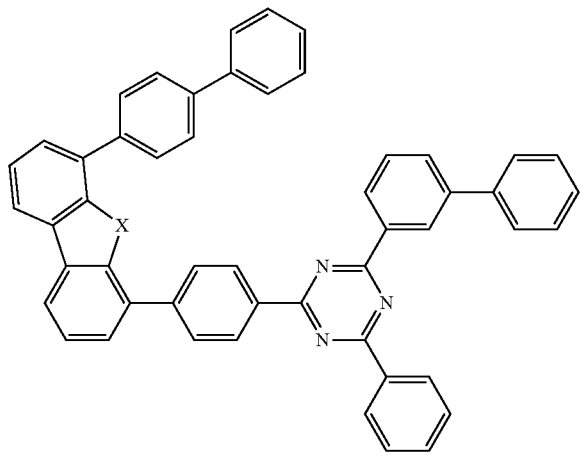
wherein in Compound C88: X = O, in Compound C89: X = S, in Compound C90: X = Se
Compound C91 through C93, each represented by the formula

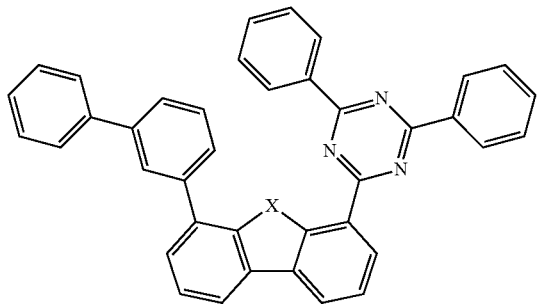

wherein in Compound C91: X = O, in Compound C92: X = S, in Compound C93: X = Se
Compound C94 through C96, each represented by the formula

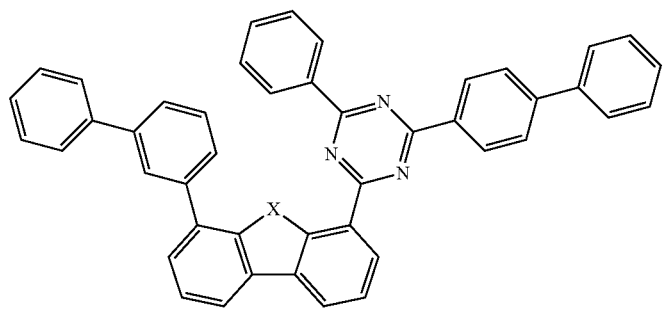

wherein in Compound C94: X = O, in Compound C95: X = S, in Compound C96: X = Se
Compound C97 through C99, each represented by the formula

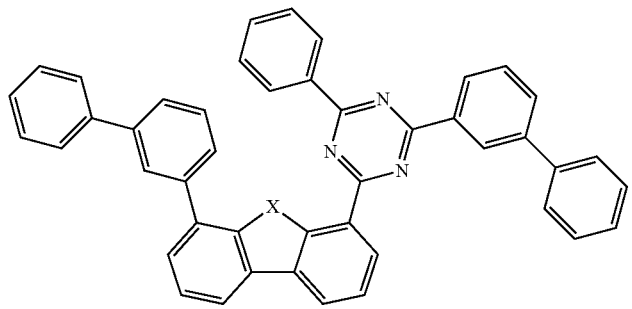

wherein in Compound C97: X = O, in Compound C98: X = S, in Compound C99: X = Se
Compound C100 through C102, each represented by the formula

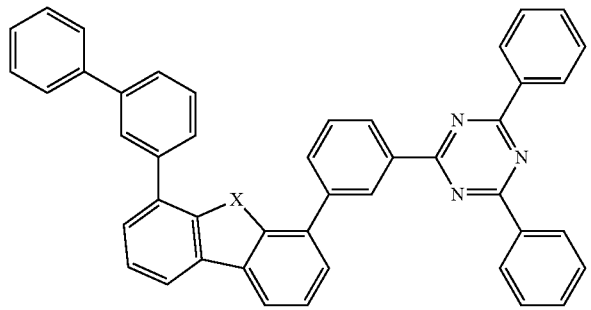

wherein in Compound C100: X = O, in Compound C101: X = S, in Compound C102: X = Se
Compound C103 through C105, each represented by the formula

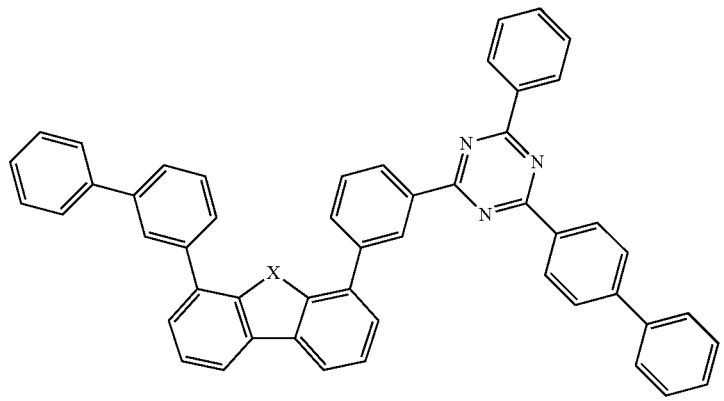
wherein in Compound C103: X = O, in Compound C104: X = S, in Compound C105: X = Se
Compound C106 through C108, each represented by the formula
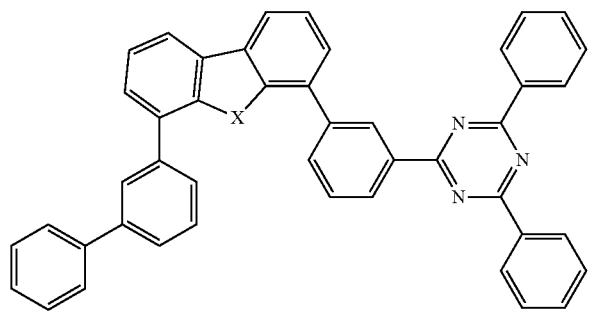
wherein in Compound C106: X = O, in Compound C107: X = S, in Compound C108: X = Se
Compound C109 through C111, each represented by the formula
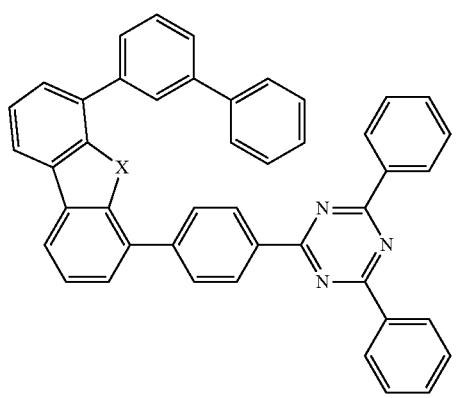
wherein in Compound C109: X = O, in Compound C110: X = S, in Compound C111: X = Se
Compound C112 through C114, each represented by the formula

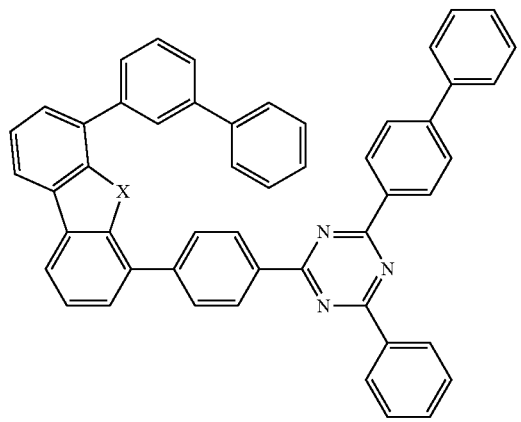
wherein in Compound C112: X = O, in Compound C113: X = S, in Compound C114: X = Se
Compound C115 through C117, each represented by the formula
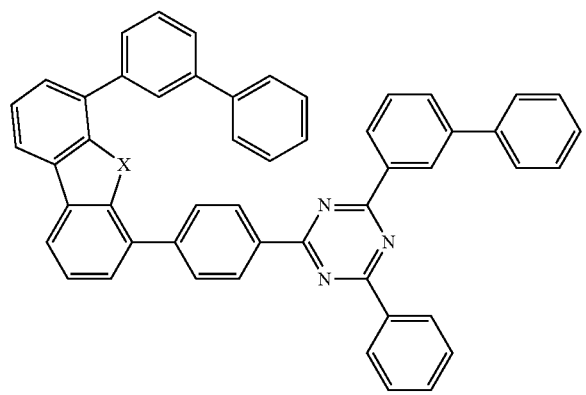
wherein in Compound C115: X = O, in Compound C116: X = S, in Compound C117: X = Se
Compound C118 through C120 each represented by the formula
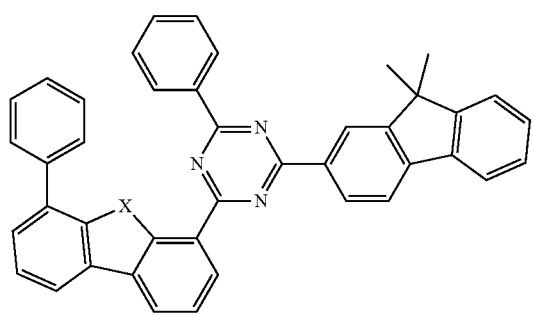
wherein in Compound C118: X = O, in Compound C119: X = S, in Compound C120: X = Se
Compound C121 through C123, each represented by the formula

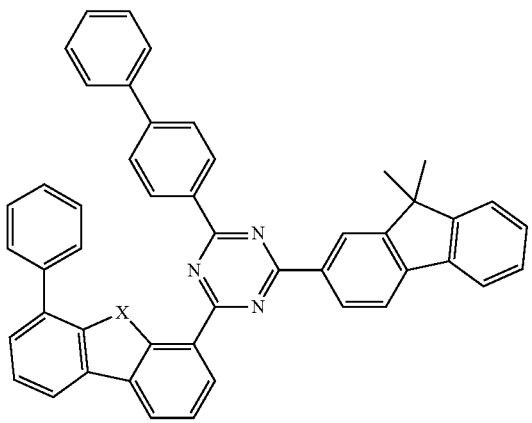
wherein in Compound C121: X = O, in Compound C122: X = S, in Compound C123: X = Se
Compound C124 through C126, each represented by the formula
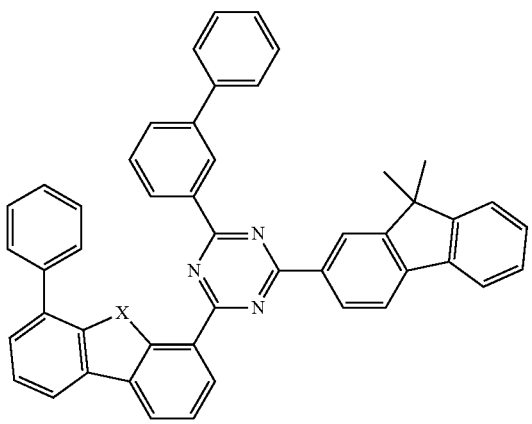
wherein in Compound C124: X = O, in Compound C125: X = S, in Compound C126: X = Se
Compound C127 through C129, each represented by the formula
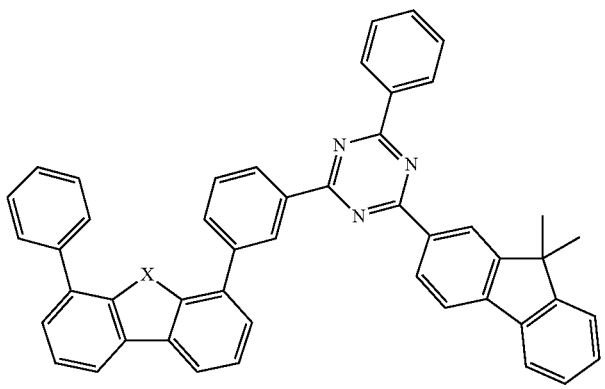
wherein in Compound C127: X = O, in Compound C128: X = S, in Compound C129: X = Se
Compound C130 through C132, each represented by the formula

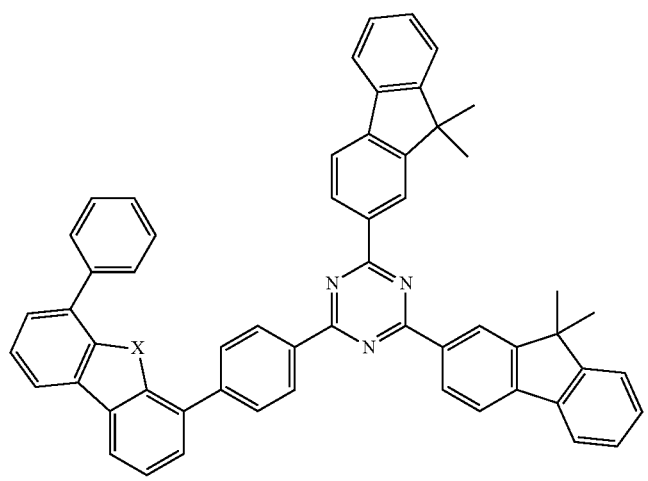
wherein in Compound C130: X = O, in Compound C131: X = S, in Compound C132: X = Se
Compound C133 through C135, each represented by the formula
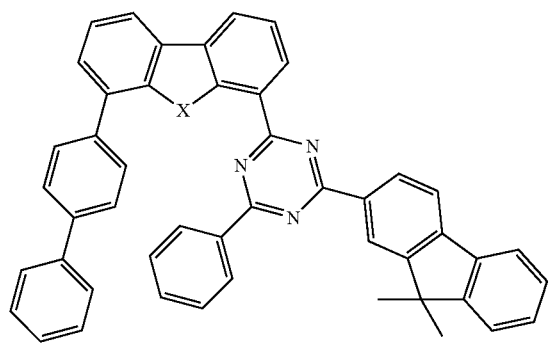
wherein in Compound C133: X = O, in Compound C134: X = S, in Compound C135: X = Se
Compound C136 through C138, each represented by the formula
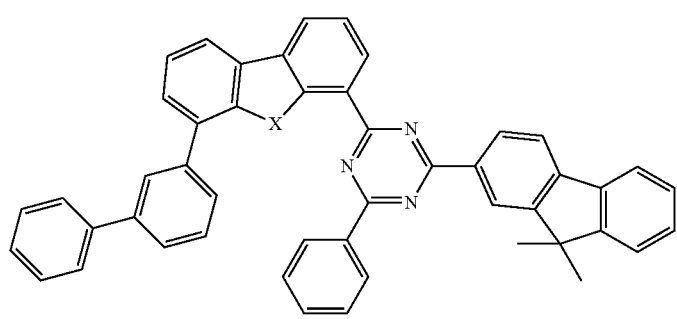
wherein in Compound C136: X = O, in Compound C137: X = S, in Compound C138: X = Se
Compound C139 through C141, each represented by the formula

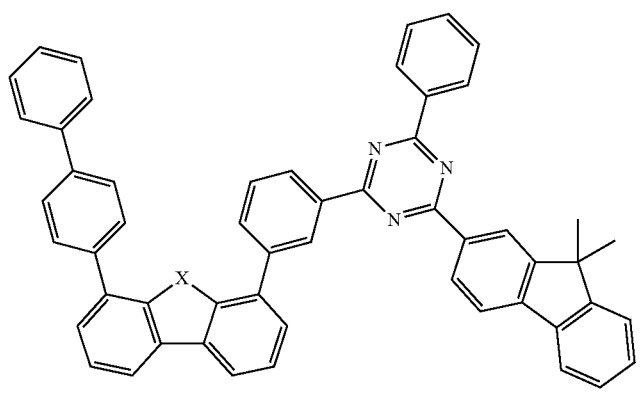
wherein in Compound C139: X = O, in Compound C140: X = S, in Compound C141: X = Se
Compound C142 through C144, each represented by the formula
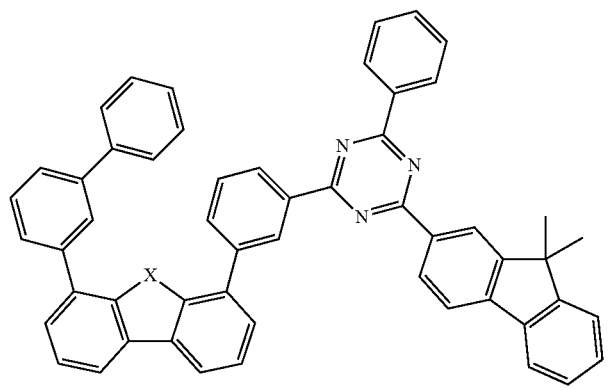
wherein in Compound C142: X = O, in Compound C143: X = S, in Compound C144: X = Se
Compound C145 through C147, each represented by the formula
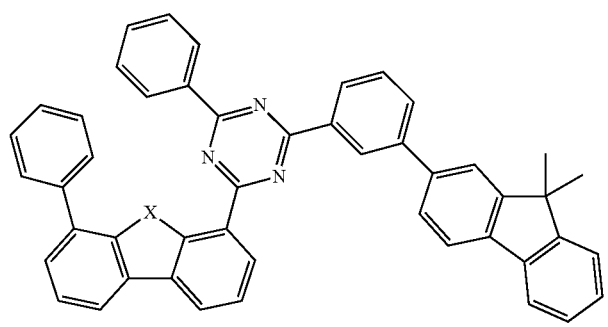
wherein in Compound C145: X = O, in Compound C146: X = S, in Compound C147: X = Se
Compound C148 through C150, each represented by the formula

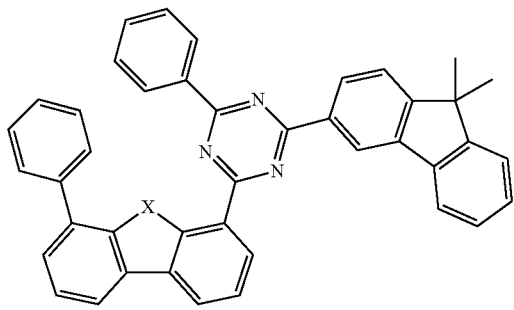

wherein in Compound C148: X = O, in Compound C149: X = S, in Compound C150: X = Se
Compound C151 through C153, each represented by the formula

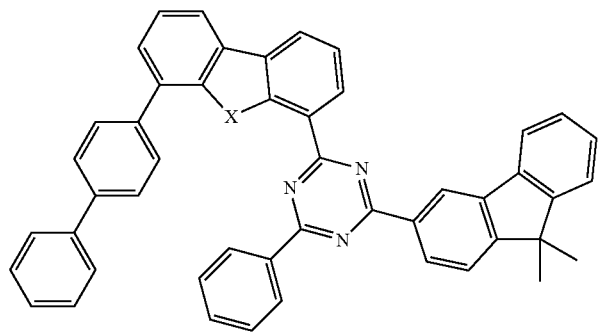

wherein in Compound C151: X = O, in Compound C152: X = S, in Compound C153: X = Se
Compound C154 through C156, each represented by the formula

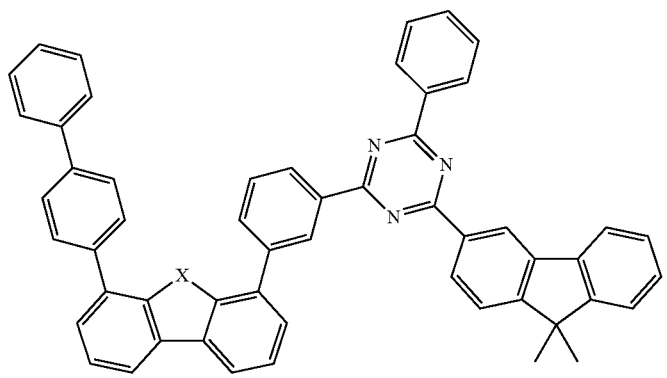

wherein in Compound C154: X = O, in Compound C155: X = S, in Compound C156: X = Se
Compound C157 through C159, each represented by the formula

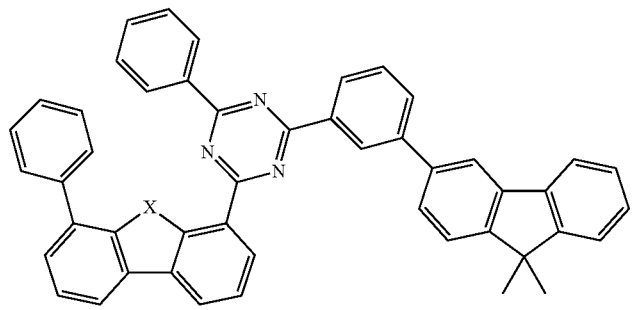

wherein in Compound C157: X = O, in Compound C158: X = S, in Compound C159: X = Se
Compound C160 through C162, each represented by the formula

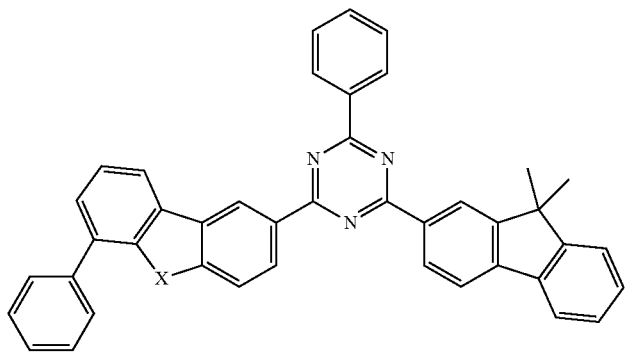
wherein in Compound C160: X = O, in Compound C161: X = S, in Compound C162: X = Se
Compound C163 through C165, each represented by the formula
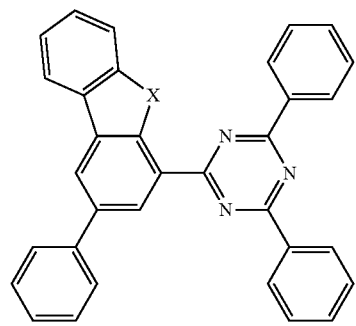
wherein in Compound C163: X = O, in Compound C164: X = S, in Compound C165: X = Se
Compound C166 through C168, each represented by the formula
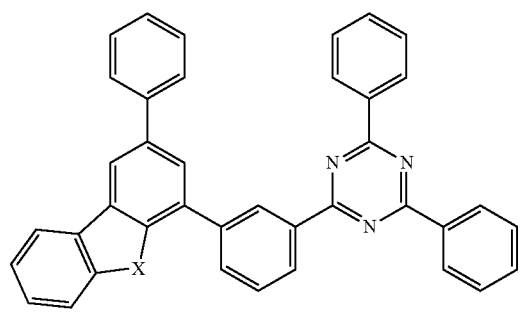
wherein in Compound C166: X = O, in Compound C167: X = S, in Compound C168: X = Se
Compound C169 through C171, each represented by the formula

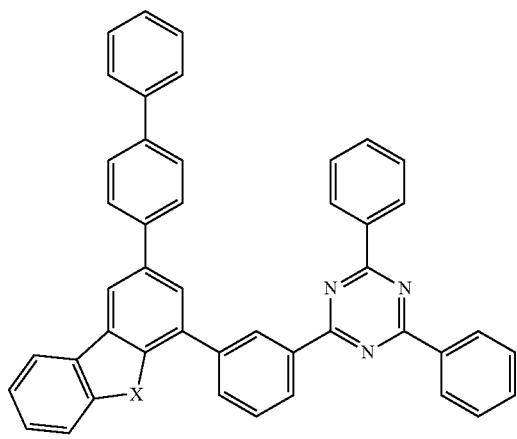
wherein in Compound C169: X = O, in Compound C170: X = S, in Compound C171: X = Se
Compound C172 through C174, each represented by the formula
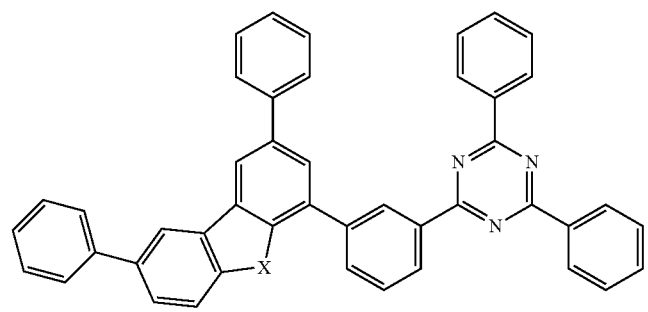
wherein in Compound C172: X = O, in Compound C173: X = S, in Compound C174: X = Se
Compound C175 through C177, each represented by the formula
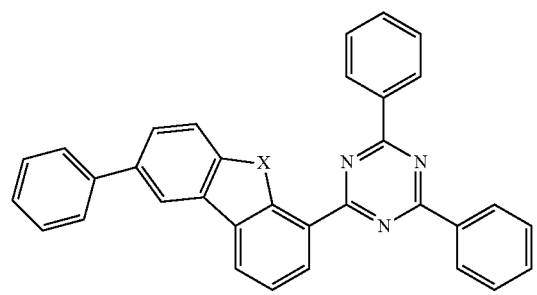
wherein in Compound C175: X = O, in Compound C176: X = S, in Compound C177: X = Se
Compound C178 through C180, each represented by the formula

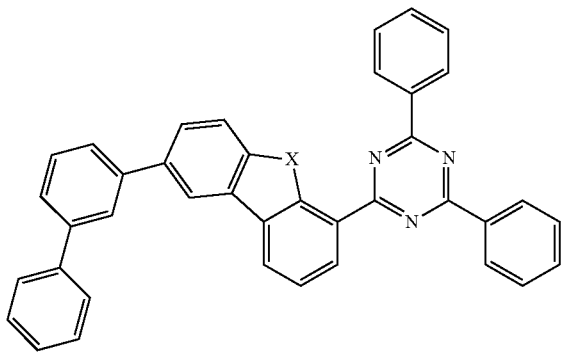

wherein in Compound C178: X = O, in Compound C179: X = S, in Compound C180: X = Se
Compound C181 through C183, each represented by the formula

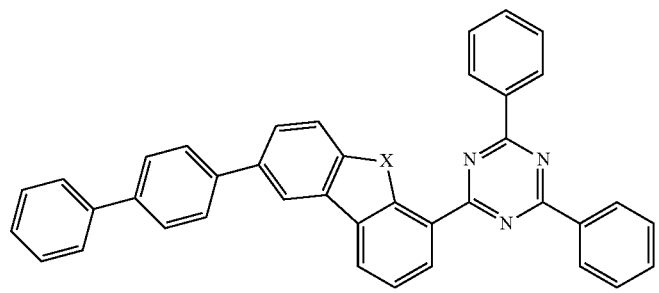

wherein in Compound C181: X = O, in Compound C182: X = S, in Compound C183: X = Se
Compound C184 through C186, each represented by the formula

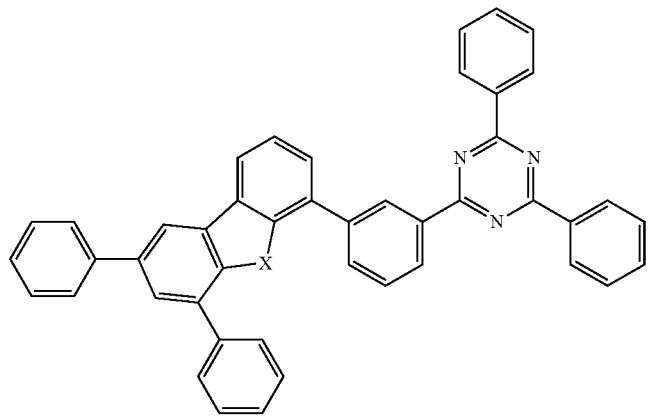

wherein in Compound C184: X = O, in Compound C185: X = S, in Compound C186: X = Se
Compound C187 through C189, each represented by the formula

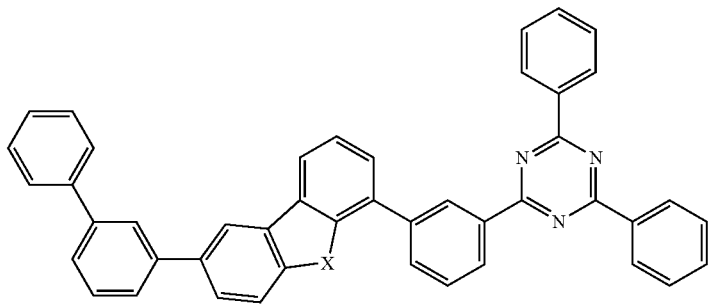

wherein in Compound C187: X = O, in Compound C188: X = S, in Compound C189: X = Se
Compound C190 through C192, each represented by the formula

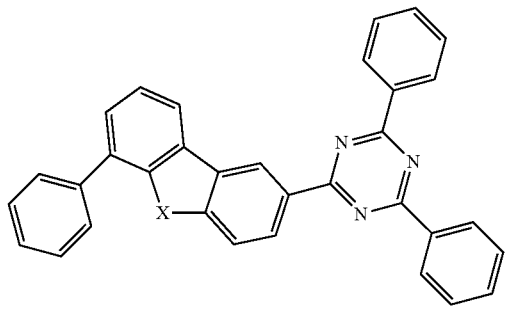

wherein in Compound C190: X = O, in Compound C191: X = S, in Compound C192: X = Se
Compound C193 through C195, each represented by the formula

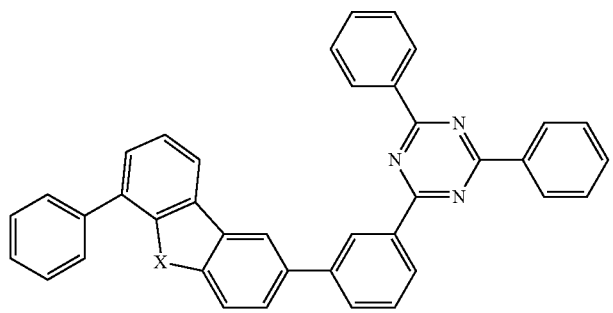

wherein in Compound C193: X = O, in Compound C194: X = S, in Compound C195: X = Se
Compound C196 through C198, each represented by the formula

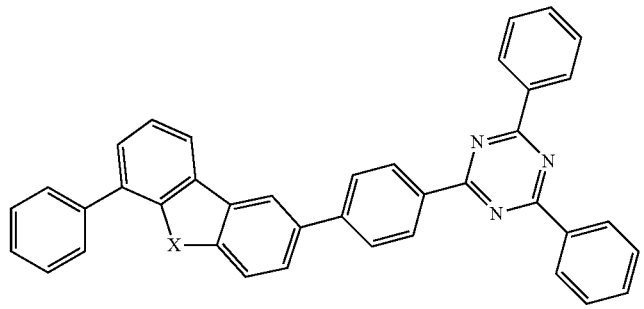

wherein in Compound C196: X = O, in Compound C197: X = S, in Compound C198: X = Se
Compound C199 through C201, each represented by the formula

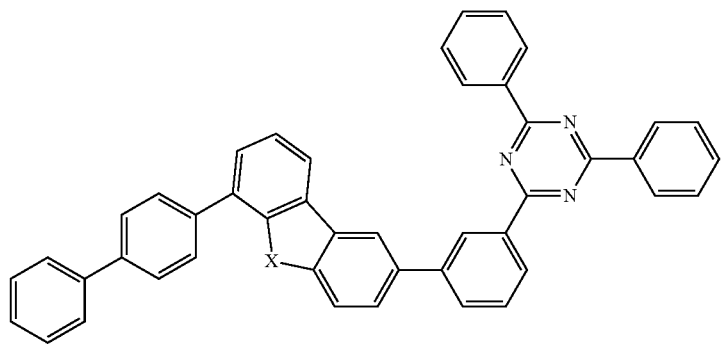

wherein in Compound C199: X = O, in Compound C200: X = S, in Compound C201: X = Se
Compound C202 through C204, each represented by the formula

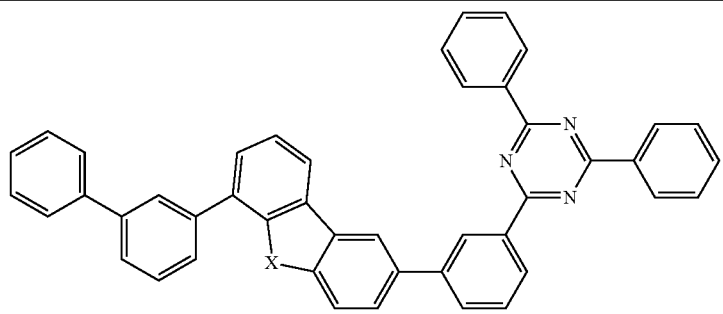

wherein in Compound C202: X = O, in Compound C203: X = S, in Compound C204: X = Se
Compound C205 through C207, each represented by the formula

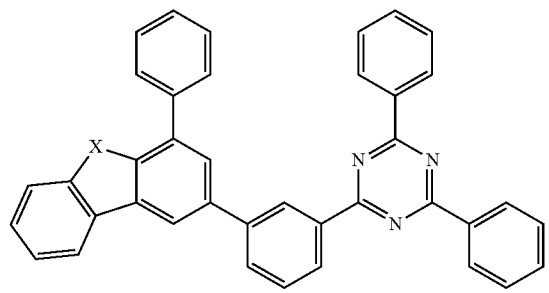

wherein in Compound C205: X = O, in Compound C206: X = S, in Compound C207: X = Se
Compound C208 through C210, each represented by the formula

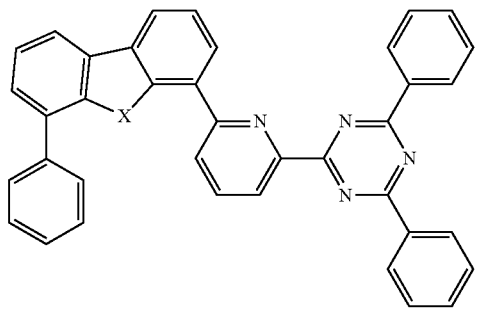

wherein in Compound C208: X = O, in Compound C209: X = S, in Compound C210: X = Se
Compound C211 through C213, each represented by the formula

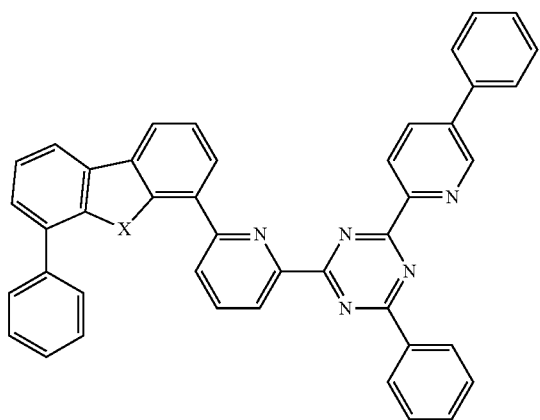

wherein in Compound C211: X = O, in Compound C212: X = S, in Compound C213: X = Se
Compound C214 through C216, each represented by the formula

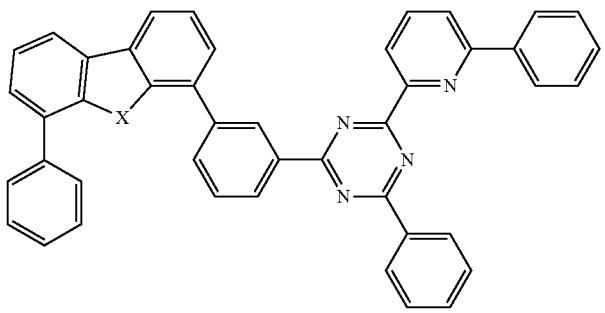
wherein in Compound C214: X = O, in Compound C215: X = S, in Compound C216: X = Se
Compound C217 through C219, each represented by the formula
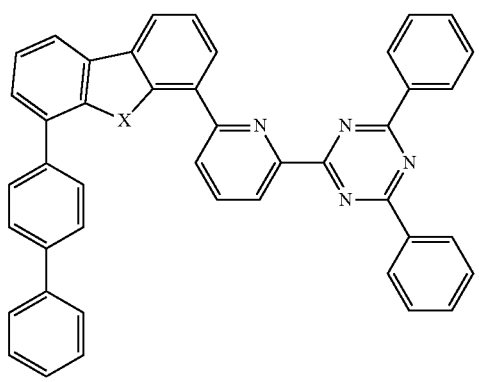
wherein in Compound C217: X = O, in Compound C218: X = S, in Compound C219: X = Se
Compound C220 through C222, each represented by the formula
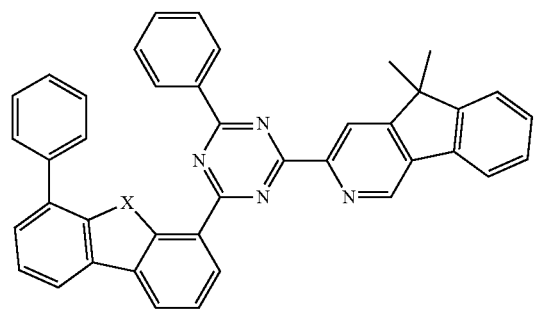
wherein in Compound C220: X = O, in Compound C221: X = S, in Compound C222: X = Se
Compound C223 through C225, each represented by the formula

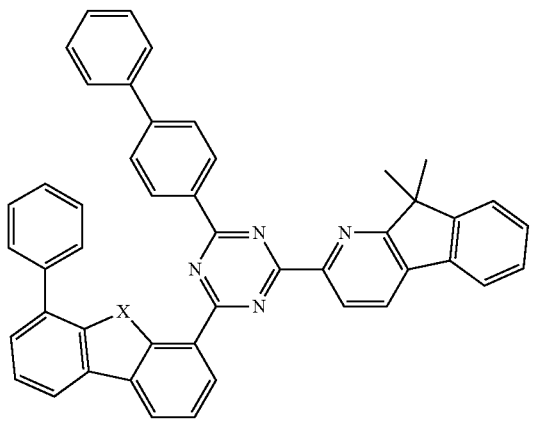

wherein in Compound C223: X = O, in Compound C224: X = S, in Compound C225: X = Se
Compound C226 through C228, each represented by the formula

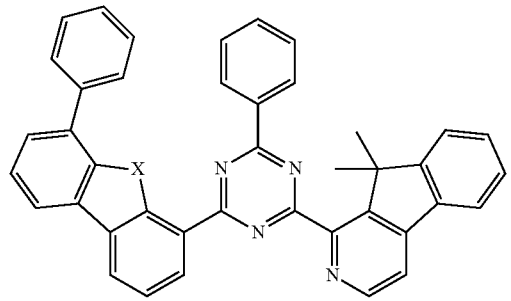

wherein in Compound C226: X = O, in Compound C227: X = S, in Compound C228: X = Se
Compound C229 through C231, each represented by the formula

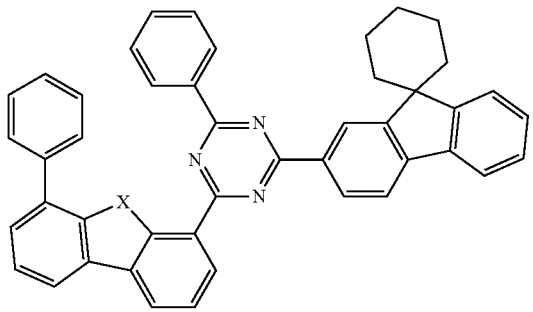

wherein in Compound C229: X = O, in Compound C230: X = S, in Compound C231: X = Se
Compound C232 through C234, each represented by the formula

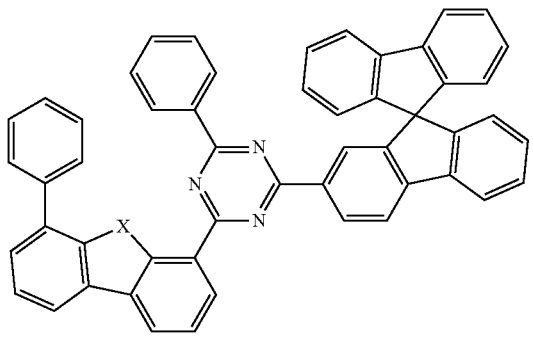

wherein in Compound C232: X = O, in Compound C233: X = S, in Compound C234: X = Se
Compound C235 through C237, each represented by the formula

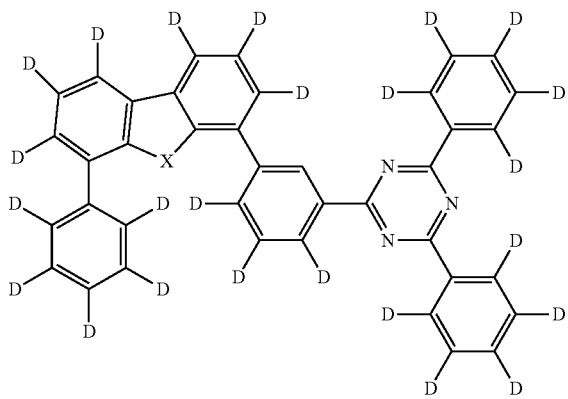
wherein in Compound C235: X = O, in Compound C236: X = S, in Compound C237: X = Se
Compound C238 through C240, each represented by the formula
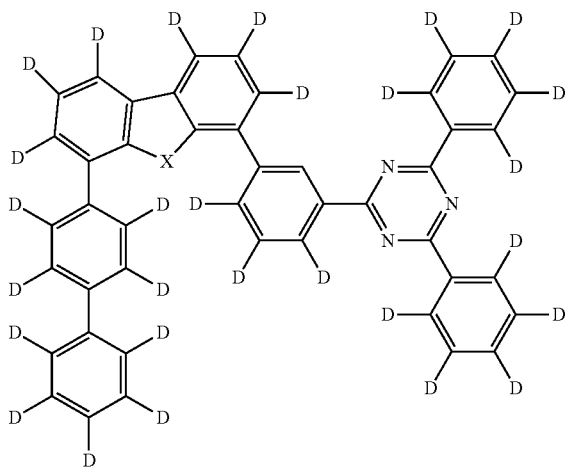
wherein in Compound C238: X = O, in Compound C239: X = S, in Compound C240: X = Se
Compound C241 through C243, each represented by the formula
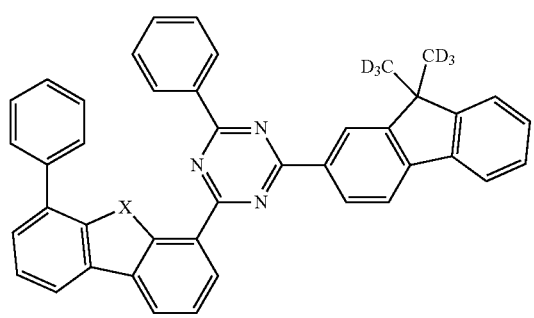
wherein in Compound C241: X = O, in Compound C242: X = S, in Compound C243: X = Se
Compound C244 through C246, each represented by the formula

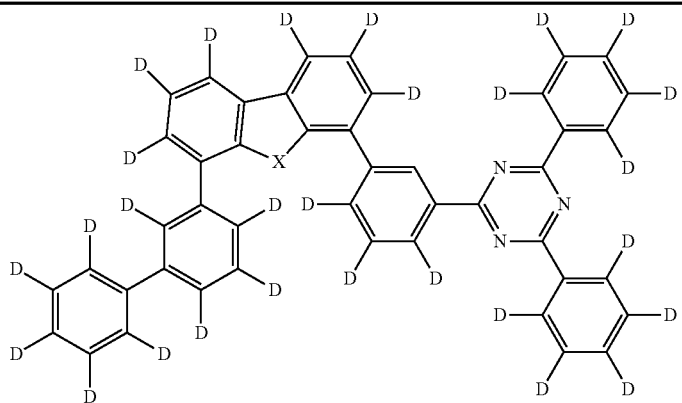
wherein in Compound C244: X = O, in Compound C245: X = S, in Compound C246: X = Se
Compound C247 through C249, each represented by the formula
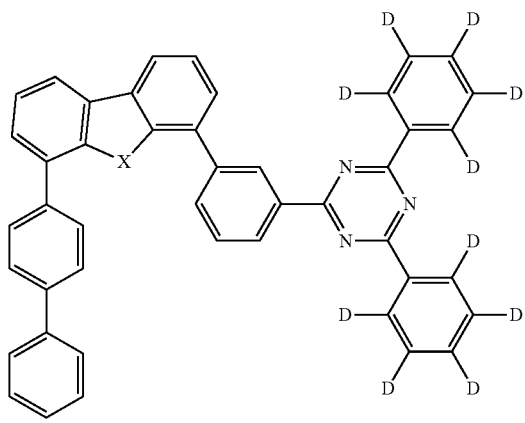
wherein in Compound C247: X = O, in Compound C248: X = S, in Compound C249: X = Se
Compound C250 through C252, each represented by the formula
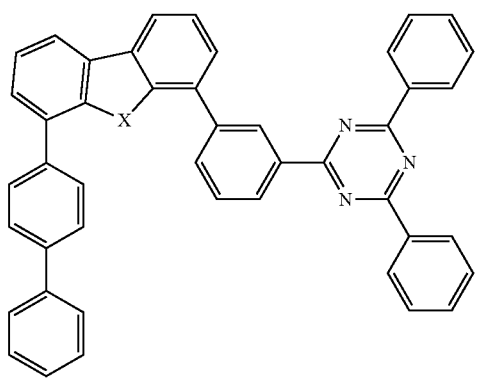
wherein in Compound C250: X = O, in Compound C251: X = S, in Compound C252: X = Se
Compound C253 through C255, each represented by the formula

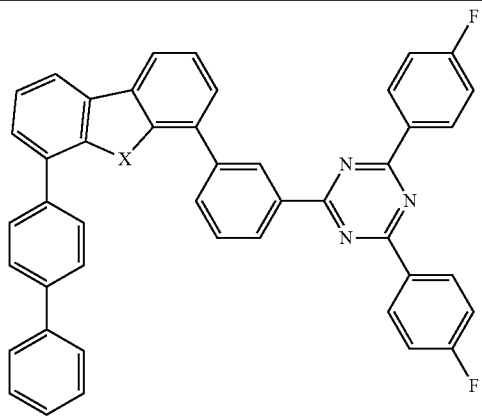
wherein in Compound C253: X = O, in Compound C254: X = S, in Compound C255: X = Se
Compound D1 through D3, each represented by the formula
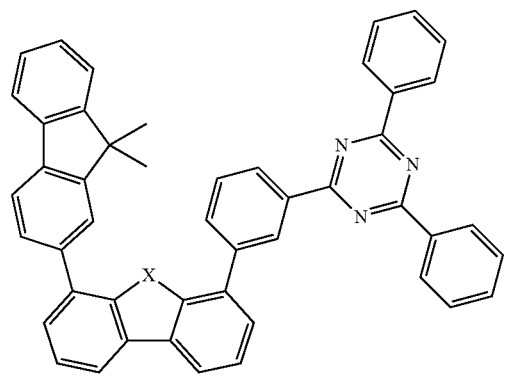
wherein in Compound D1: X = O, in Compound D2, X = S, and in Compound D3, X = Se
Compound D4 through D6, each represented by the formula
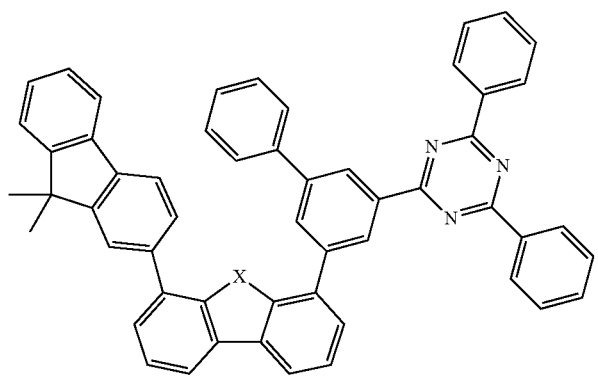
wherein in Compound D4: X = O, in Compound D5, X = S, and in Compound D6, X = Se
Compound D7 through D9, each represented by the formula

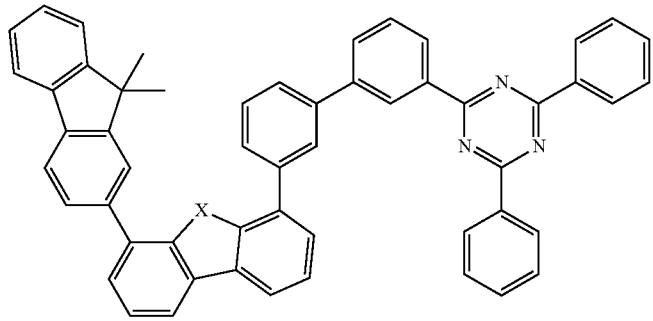
wherein in Compound D7: X = O, in Compound D8, X = S, and in Compound D9, X = Se
Compound D10 through D12, each represented by the formula
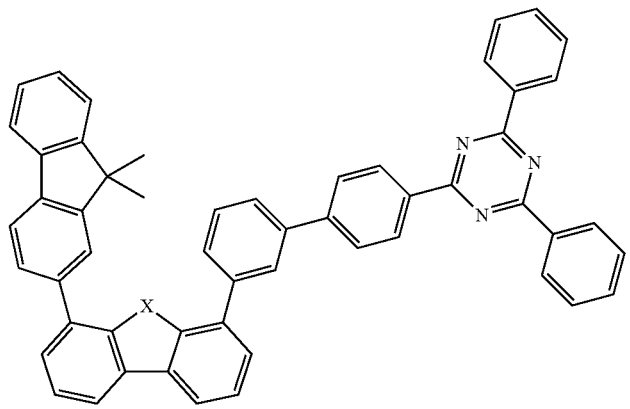
wherein in Compound D10: X = O, in Compound D11, X = S, and in Compound D12, X = Se
Compound D13 through D15, each represented by the formula
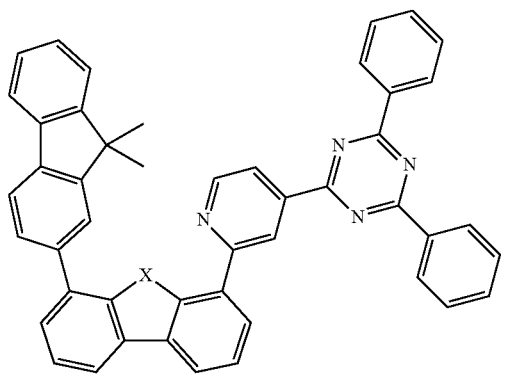
wherein in Compound D13: X = O, in Compound D14, X = S, and in Compound D15, X = Se
Compound D16 through D18, each represented by the formula

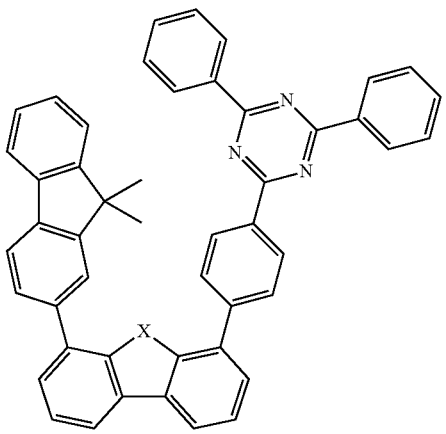
wherein in Compound D16: X = O, in Compound D17, X = S, and in Compound D18, X = Se
Compound D19 through D21, each represented by the formula
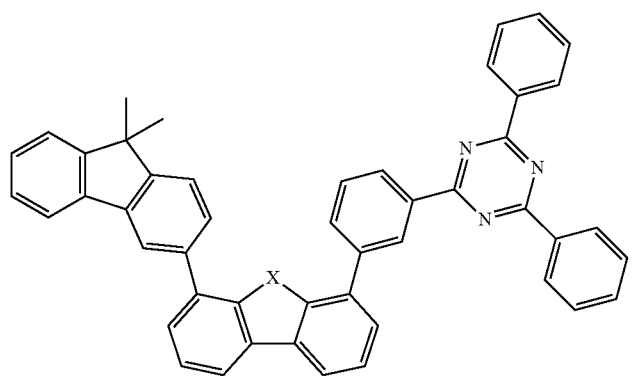
wherein in Compound D19: X = O, in Compound D20, X = S, and in Compound D21, X = Se
Compound D22 through D24, each represented by the formula
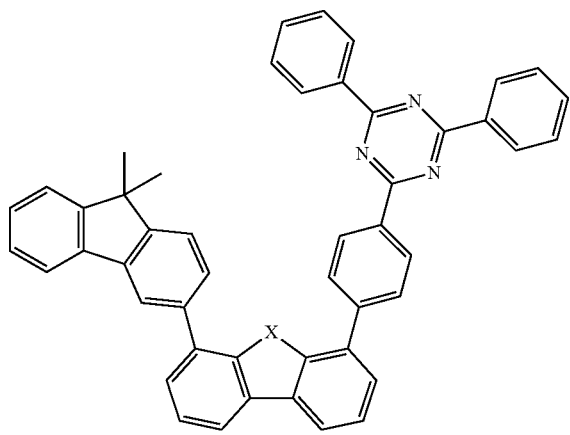
wherein in Compound D22: X = O, in Compound D23, X = S, and in Compound D24, X = Se
Compound D25 through D27, each represented by the formula

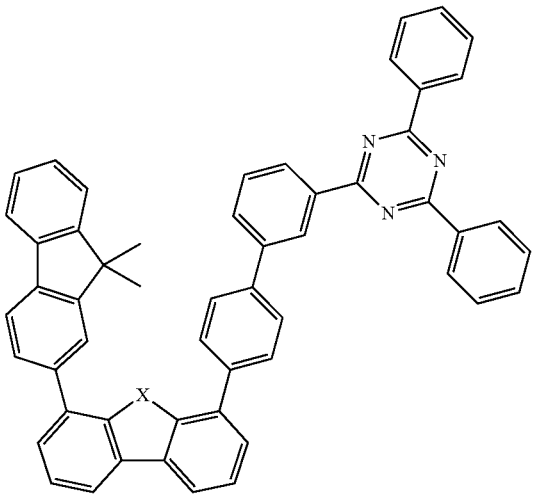
wherein in Compound D25: X = O, in Compound D26, X = S, and in Compound D27, X = Se
Compound D28 through D30, each represented by the formula
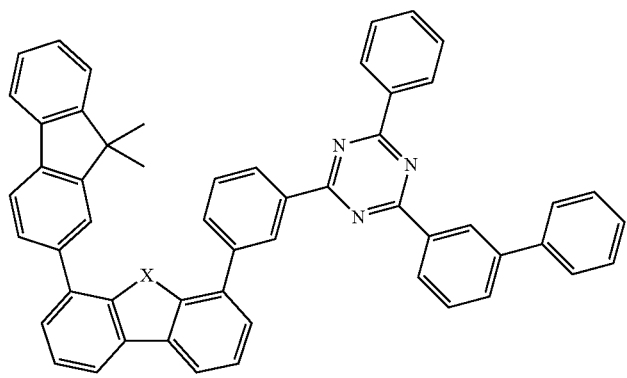
wherein in Compound D28: X = O, in Compound D29, X = S, and in Compound D30, X = Se
Compound D31 through D33, each represented by the formula
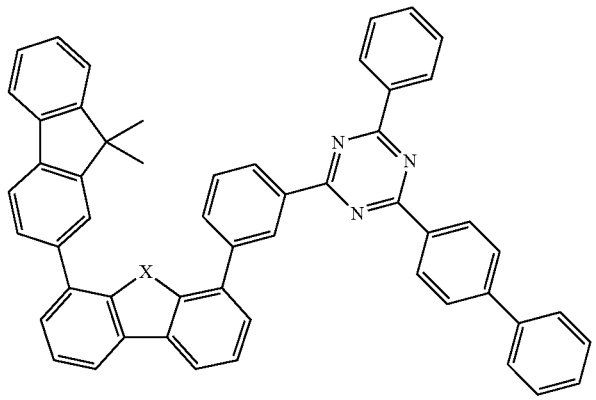
wherein in Compound D31: X = O, in Compound D32, X = S, and in Compound D33, X = Se
Compound D34 through D36, each represented by the formula

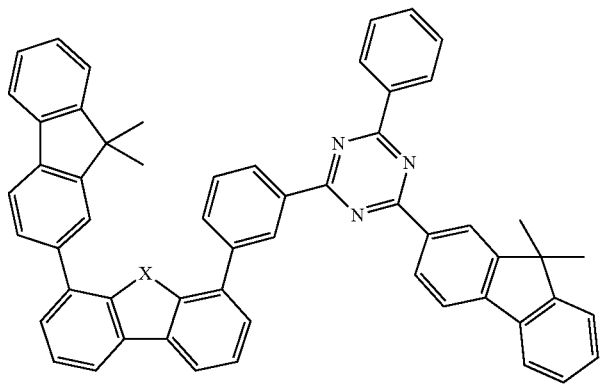
wherein in Compound D34: X = O, in Compound D35, X = S, and in Compound D36, X = Se
Compound D37 through D39, each represented by the formula
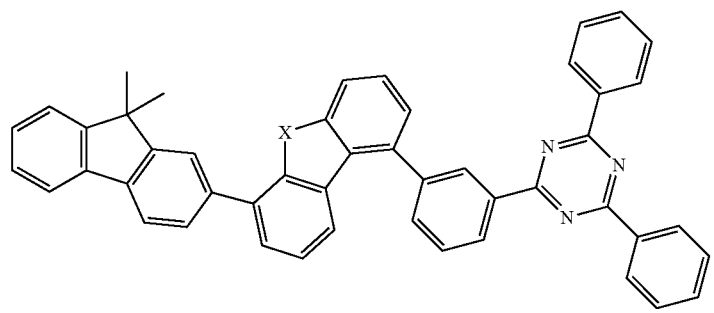
wherein in Compound D37: X = O, in Compound D38, X = S, and in Compound D39, X = Se
Compound D40 through D42, each represented by the formula
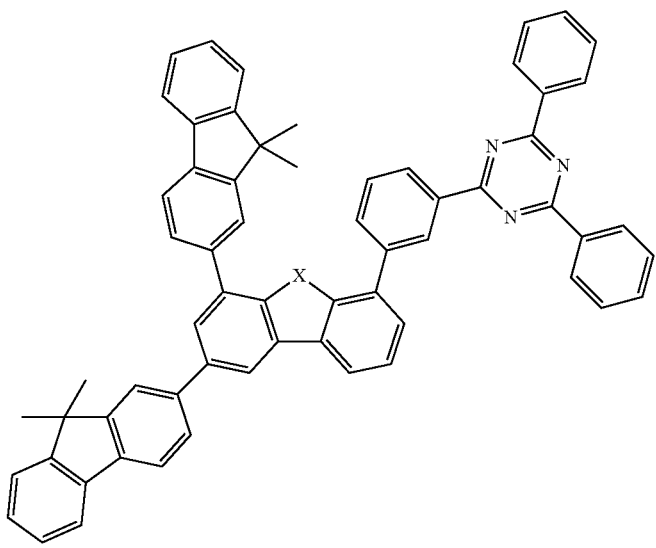
wherein in Compound D40: X = O, in Compound D41, X = S, and in Compound D42, X = Se
Compound D43 through D45, each represented by the formula

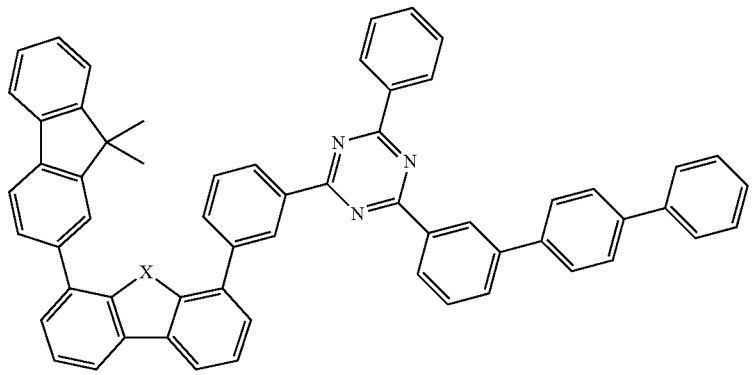
wherein in Compound D43: X = O, in Compound D44, X = S, and in Compound D45, X = Se
Compound D46 through D48, each represented by the formula
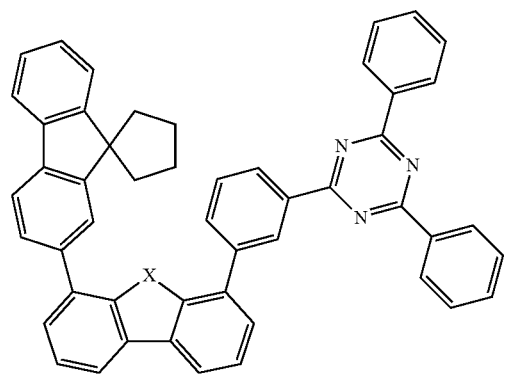
wherein in Compound D46: X = O, in Compound D47, X = S, and in Compound D48, X = Se
Compound D49 through D51, each represented by the formula
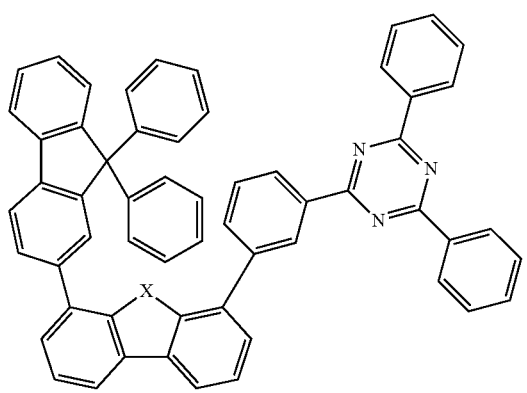
wherein in Compound D49: X = O, in Compound D50, X = S, and in Compound D51, X = Se
Compound D49 through D51, each represented by the formula

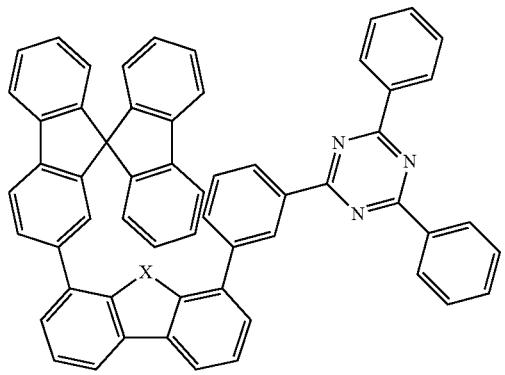
wherein in Compound D52: X = O, in Compound D53, X = S, and in Compound D54, X = Se
Compound D55 through D57, each represented by the formula
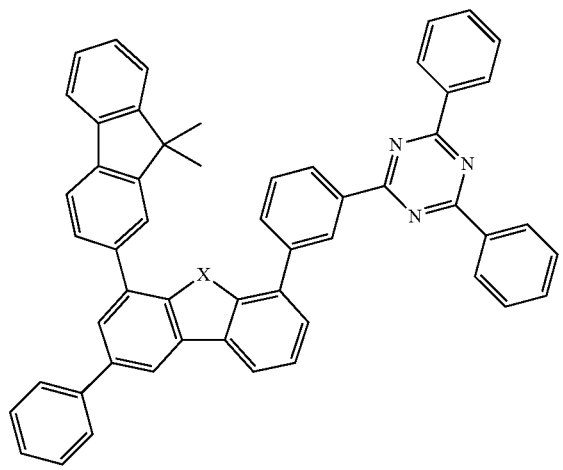
wherein in Compound D55: X = O, in Compound D56, X = S, and in Compound D57, X = Se
Compound D58 through D60, each represented by the formula
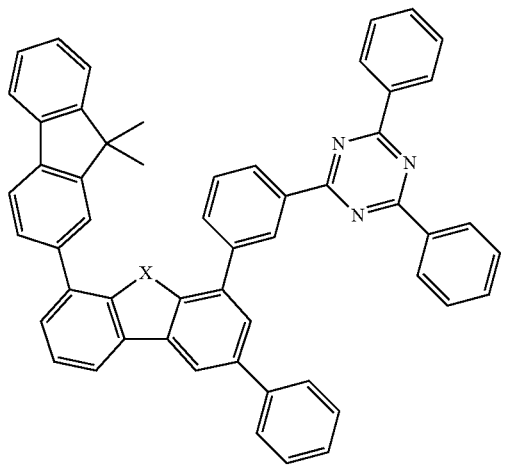
wherein in Compound D58: X = O, in Compound D59, X = S, and in Compound D60, X = Se
Compound D61 through D63, each represented by the formula

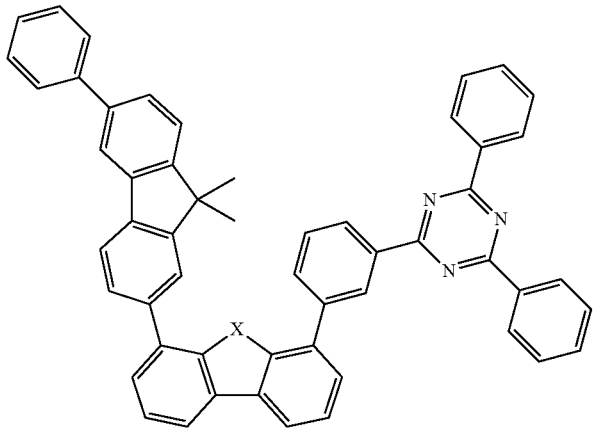
wherein in Compound D61: X = O, in Compound D62, X = S, and in Compound D63, X = Se
Compound D64 through D66, each represented by the formula
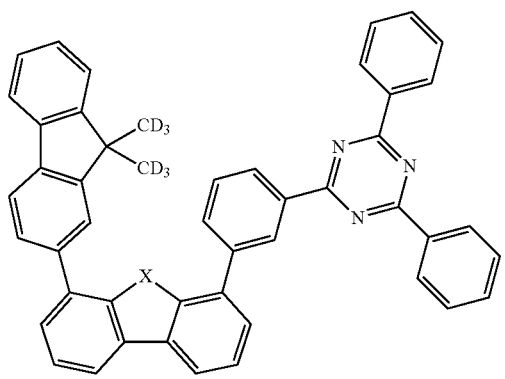
wherein in Compound D64: X = O, in Compound D65, X = S, and in Compound D66, X = Se
Compound D67 through D69, each represented by the formula
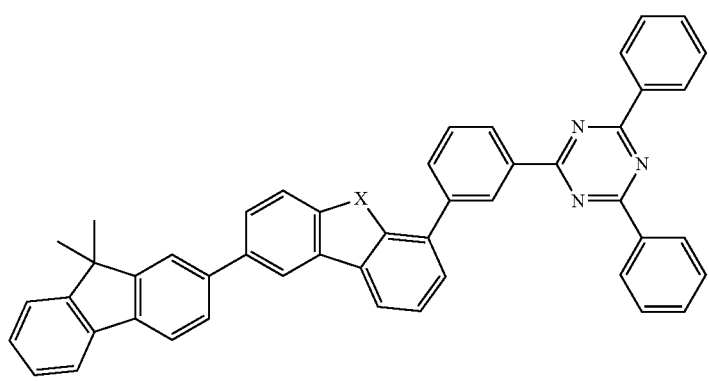
wherein in Compound D67: X = O, in Compound D68, X = S, and in Compound D69, X = Se
Compound D70 through D72, each represented by the formula

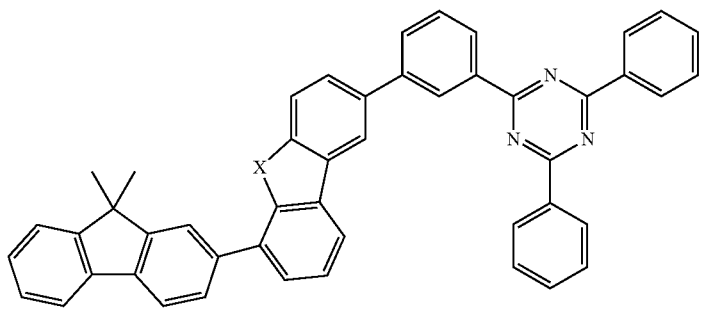

wherein in Compound D70: X = O, in Compound D71, X = S, and in Compound D72, X = Se
Compound D73 through D75, each represented by the formula

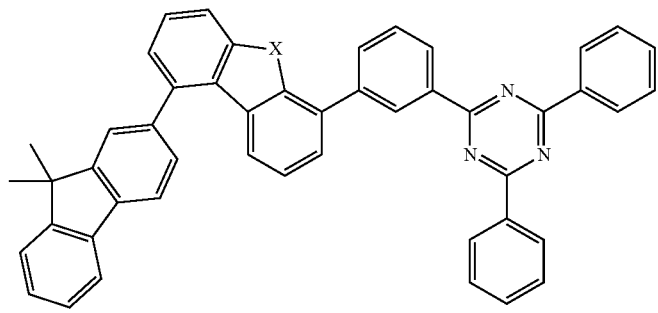

wherein in Compound D73: X = O, in Compound D74, X = S, and in Compound D75, X = Se
Compound D76 through D78, each represented by the formula

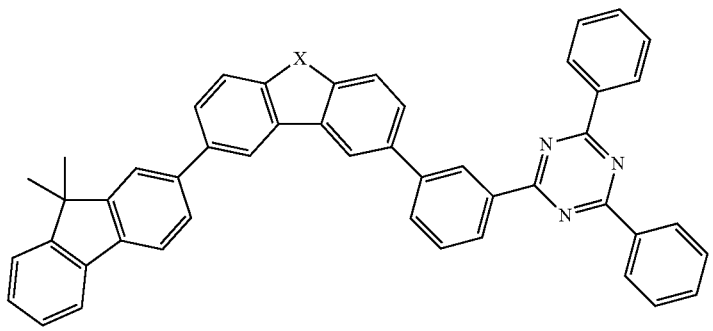

wherein in Compound D76: X = O, in Compound D77, X = S, and in Compound D78, X = Se
Compound D79 through D81, each represented by the formula

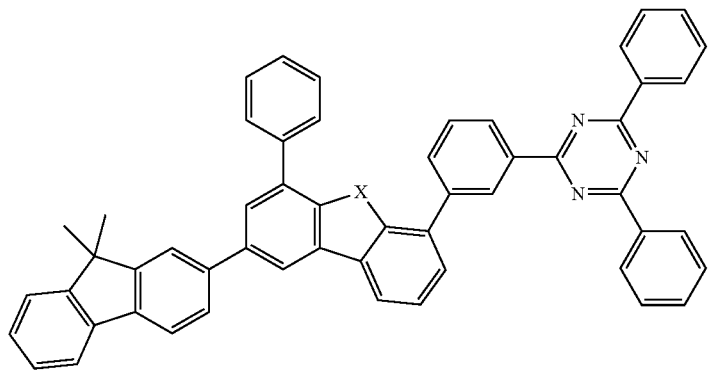

wherein in Compound D79: X = O, in Compound D80, X = S, and in Compound D81, X = Se
Compound D82 through D84, each represented by the formula

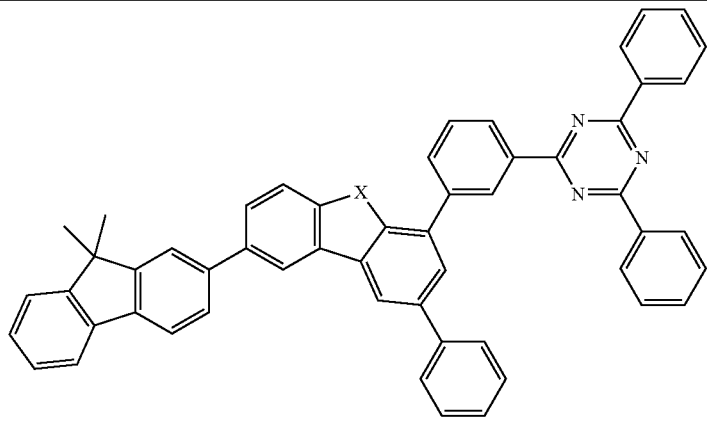
wherein in Compound D82: X = O, in Compound D83, X = S, and in Compound D84, X = Se
Compound D85 through D87, each represented by the formula
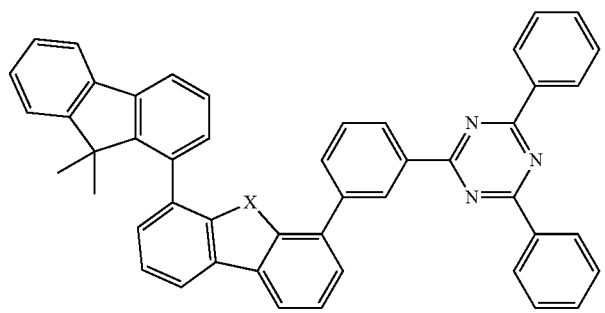
wherein in Compound D85: X = O, in Compound D86, X = S, and in Compound D87, X = Se
Compound D88 through D90, each represented by the formula
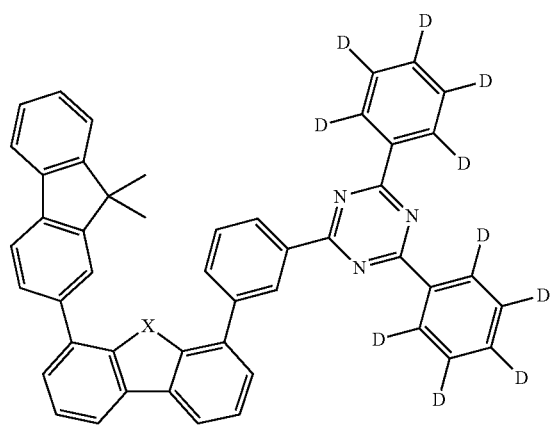
wherein in Compound D88: X = O, in Compound D89, X = S, and in Compound D90, X = Se
Compound D91 through D93, each represented by the formula

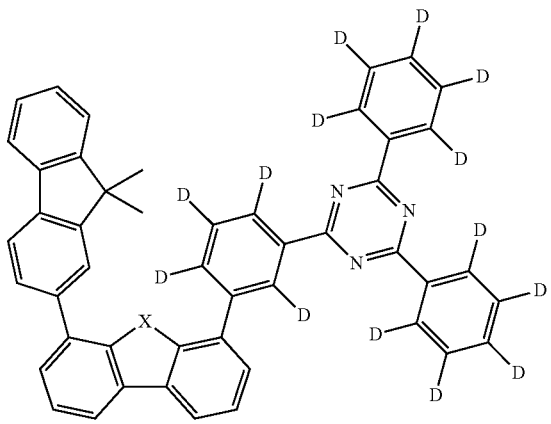
wherein in Compound D91: X = O, in Compound D92, X = S, and in Compound D93, X = Se
Compound D94 through D96, each represented by the formula
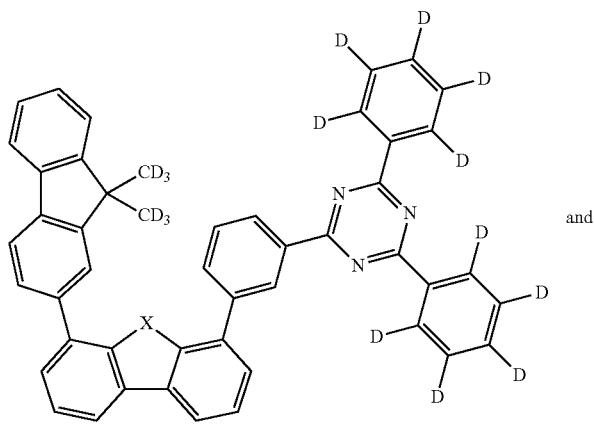 and
wherein in Compound D94: X = O, in Compound D95, X = S, and in Compound D96, X = Se
Compound D97, D98, and D99, each represented by the formula
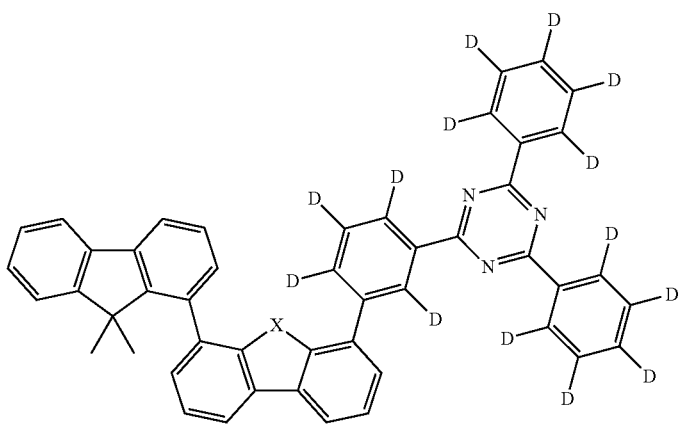
wherein in Compound D97: X = O, in Compound D98, X = S, and in Compound D99, X = Se In some embodiments of the composition, the second compound is selected from the group consisting of:
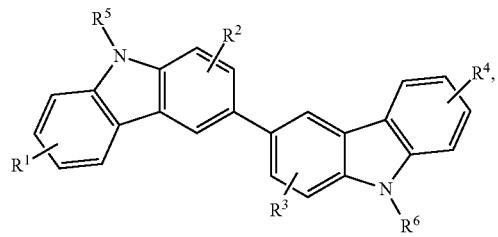
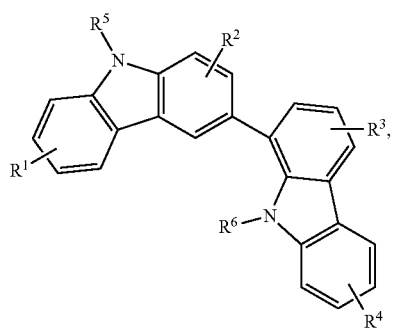
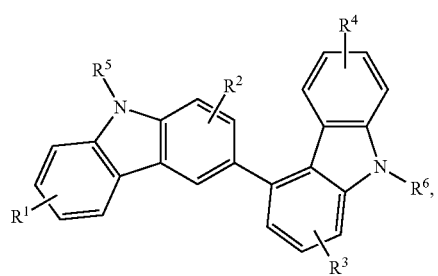
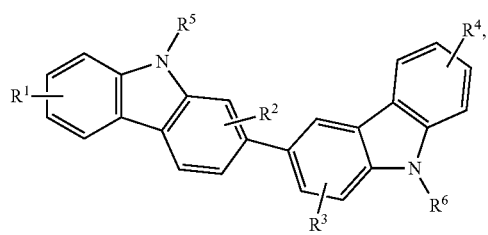
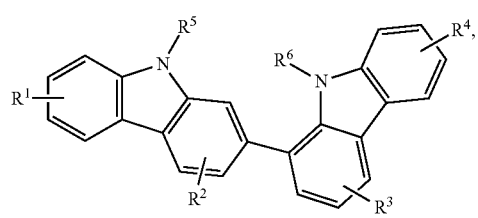
-continued
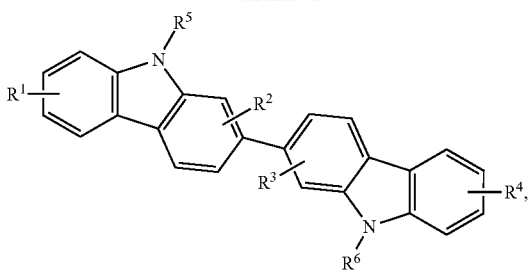
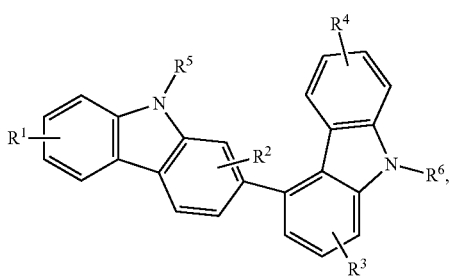
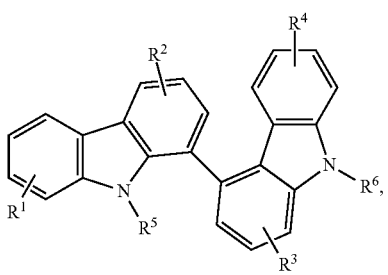
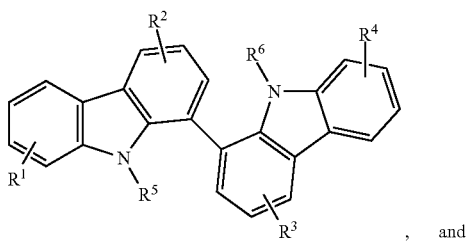
, and
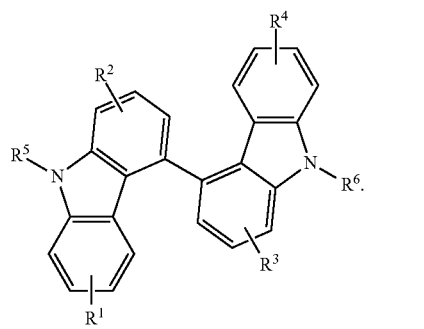

In some embodiments of the composition, the second compound is selected from the group consisting of:
Compound F1
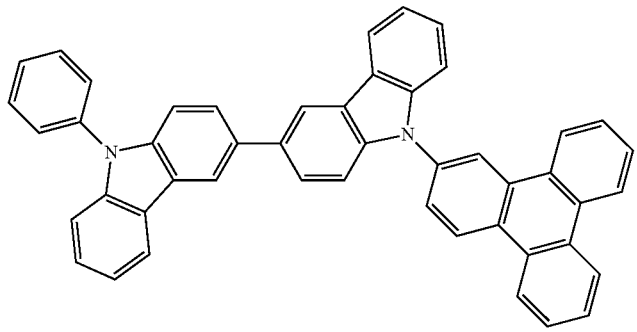 [SMILES: c1ccc(-n2c3ccccc3c3cc(-c4ccc5c(c4)c4ccccc4n5-c4ccc5c6ccccc6c6ccccc6c5c4)ccc32)cc1]
Compound F2
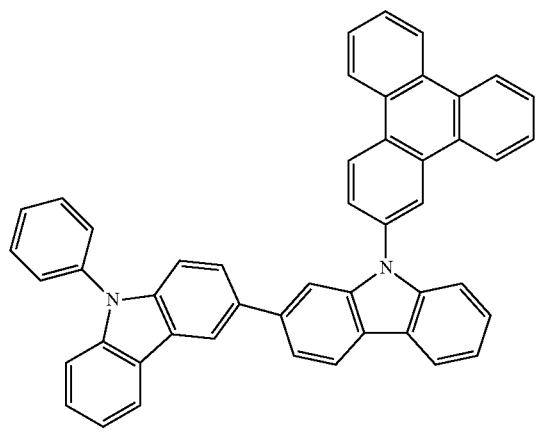 [SMILES: c1ccc(-n2c3ccccc3c3cc(-c4ccc5c6ccccc6n(-c6ccc7c8ccccc8c8ccccc8c7c6)c5c4)ccc32)cc1]
Compound F3
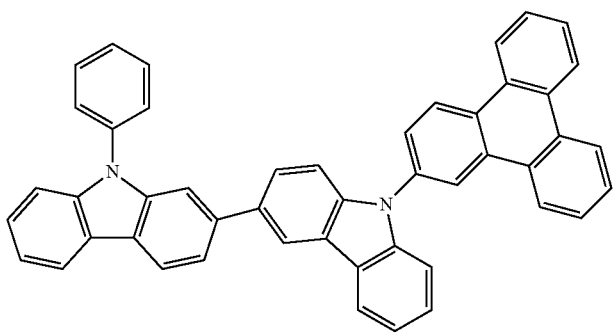 [SMILES: c1ccc(-n2c3ccccc3c3ccc(-c4ccc5c(c4)c4ccccc4n5-c4ccc5c6ccccc6c6ccccc6c5c4)cc32)cc1]
Compound F4
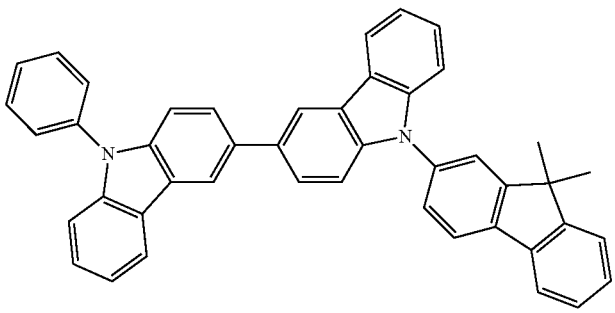 [SMILES: CC1(C)c2ccccc2-c2ccc(-n3c4ccccc4c4cc(-c5ccc6c(c5)c5ccccc5n6-c5ccccc5)ccc43)cc21]

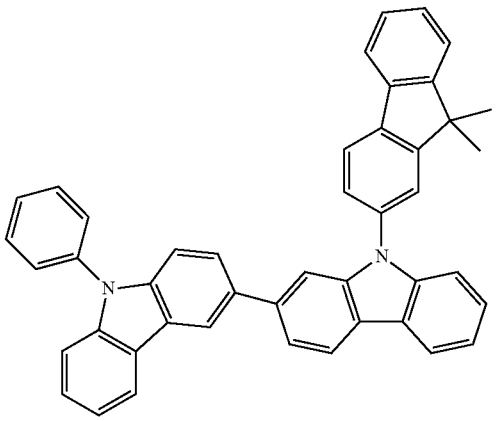 [SMILES: CC1(C)c2ccccc2-c2ccc(-n3c4ccccc4c4ccc(-c5ccc6c(c5)c5ccccc5n6-c5ccccc5)cc43)cc21]
Compound F5
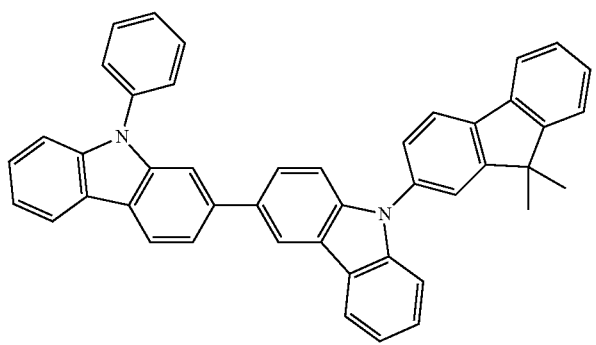 [SMILES: CC1(C)c2ccccc2-c2ccc(-n3c4ccccc4c4cc(-c5ccc6c7ccccc7n(-c7ccccc7)c6c5)ccc43)cc21]
Compound F6
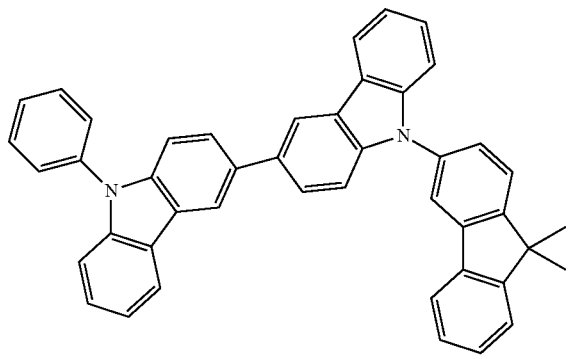 [SMILES: CC1(C)c2ccccc2-c2cc(-n3c4ccccc4c4cc(-c5ccc6c(c5)c5ccccc5n6-c5ccccc5)ccc43)ccc21]
Compound F7
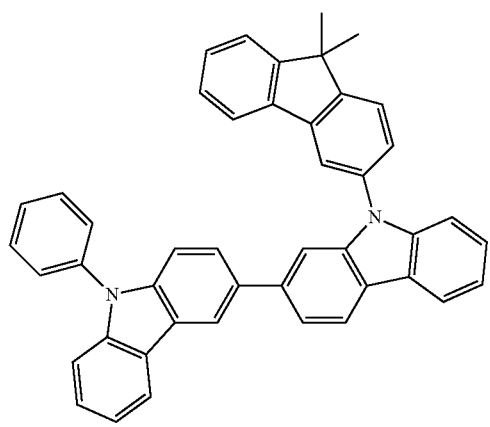 [SMILES: CC1(C)c2ccccc2-c2cc(-n3c4ccccc4c4ccc(-c5ccc6c(c5)c5ccccc5n6-c5ccccc5)cc43)ccc21]
Compound F8

-continued
Compound F9
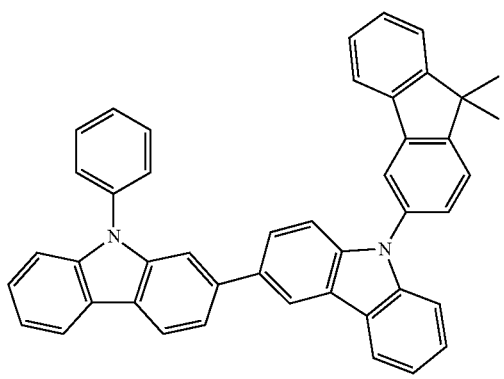 [SMILES: CC1(C)c2ccccc2-c2cc(-n3c4ccccc4c4cc(-c5ccc6c7ccccc7n(-c7ccccc7)c6c5)ccc43)ccc21]
Compound F10
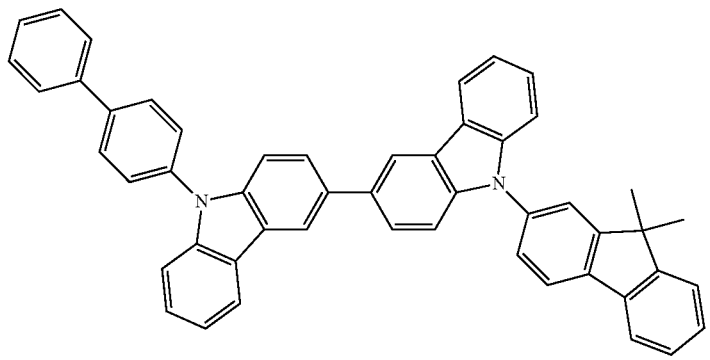 [SMILES: CC1(C)c2ccccc2-c2ccc(-n3c4ccccc4c4cc(-c5ccc6c(c5)c5ccccc5n6-c5ccc(-c6ccccc6)cc5)ccc43)cc21]
Compound F11
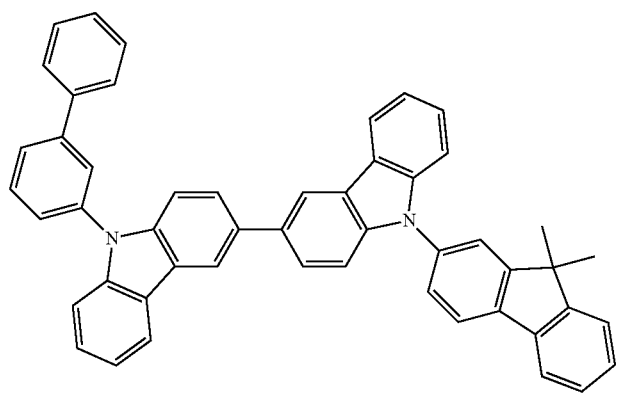 [SMILES: CC1(C)c2ccccc2-c2ccc(-n3c4ccccc4c4cc(-c5ccc6c(c5)c5ccccc5n6-c5cccc(-c6ccccc6)c5)ccc43)cc21]
Compound F12
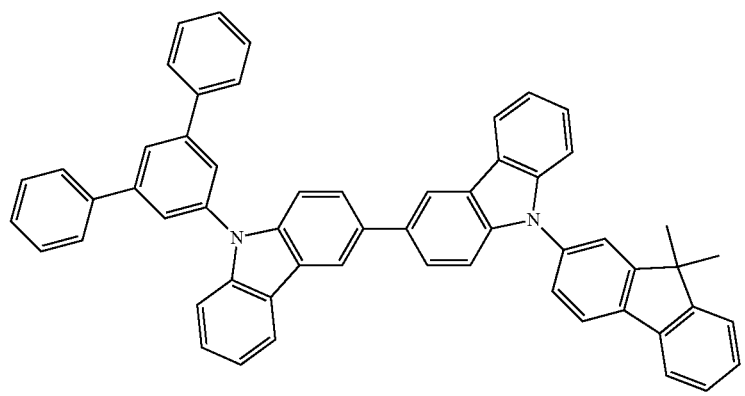 [SMILES: CC1(C)c2ccccc2-c2ccc(-n3c4ccccc4c4cc(-c5ccc6c(c5)c5ccccc5n6-c5cc(-c6ccccc6)cc(-c6ccccc6)c5)ccc43)cc21]

Compound F13
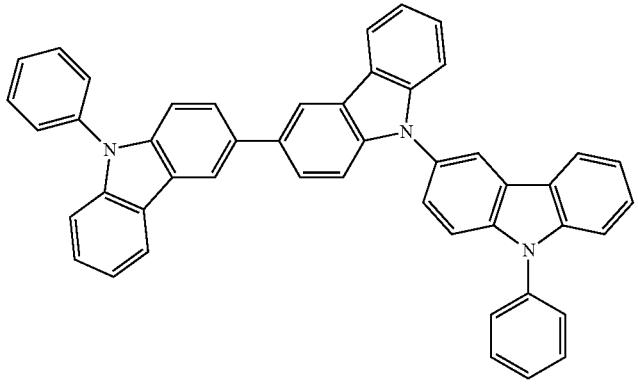 [SMILES: c1ccc(-n2c3ccccc3c3cc(-c4ccc5c(c4)c4ccccc4n5-c4ccc5c(c4)c4ccccc4n5-c4ccccc4)ccc32)cc1]
Compound F14
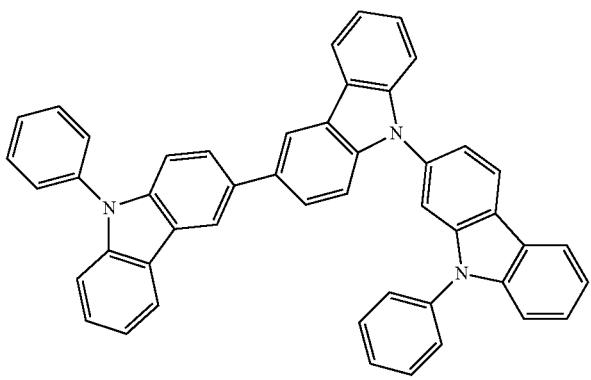 [SMILES: c1ccc(-n2c3ccccc3c3cc(-c4ccc5c(c4)c4ccccc4n5-c4ccc5c6ccccc6n(-c6ccccc6)c5c4)ccc32)cc1]
Compound F15
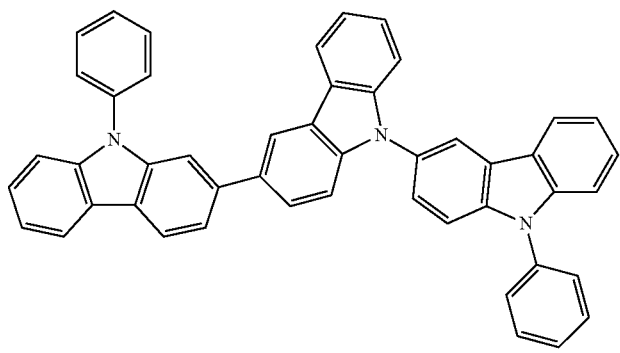 [SMILES: c1ccc(-n2c3ccccc3c3cc(-n4c5ccccc5c5cc(-c6ccc7c8ccccc8n(-c8ccccc8)c7c6)ccc54)ccc32)cc1]
Compounds G1 through G3, each represented by the formula:
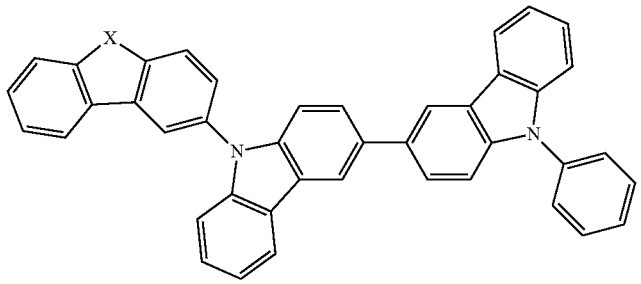
where in Compound G1: X = O, in Compound G2, X = S, and in Compound G3, X = Se
Compounds G4 through G6, each represented by the formula:

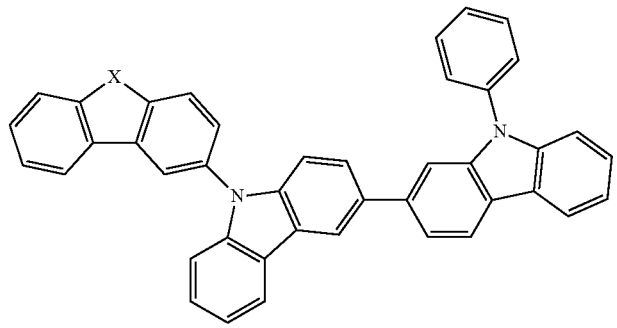

where in Compound G4: X = O, in Compound G5, X = S, and in Compound G6, X = Se

Compounds G7 through G9, each represented by the formula:

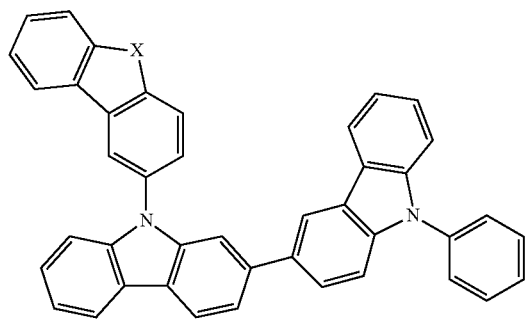

where in Compound G7: X = O, in Compound G8, X = S, and in Compound G9, X = Se

Compounds G10 through G12, each represented by the formula:

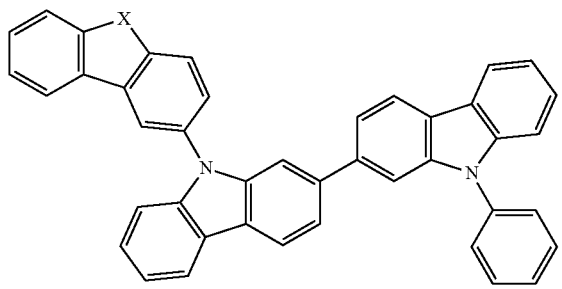

where in Compound G10: X = O, in Compound G11, X = S, and in Compound G12, X = Se Compounds G13 through G15, each represented by the formula:

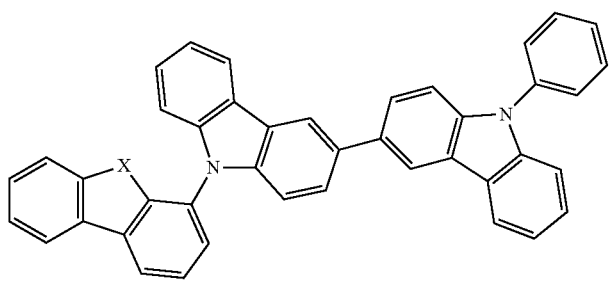

where in Compound G13: X = O, in Compound G14, X = S, and in Compound G15, X = Se Compounds G16 through G18, each represented by the formula:

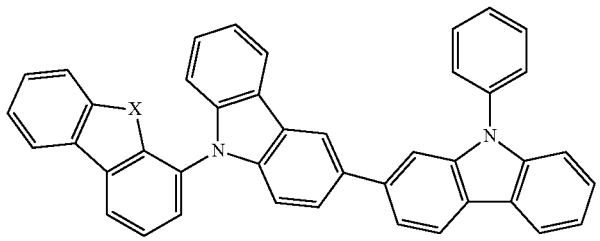

where in Compound G16: X = O, in Compound G17, X = S, and in Compound G18, X = Se
Compounds G19 through G21, each represented by the formula:

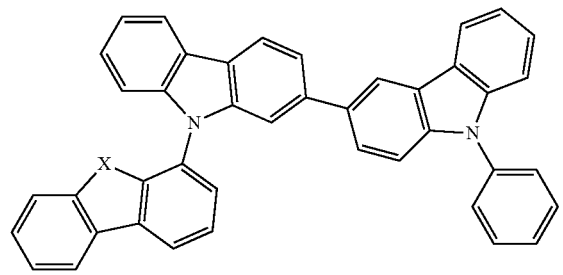

where in Compound G19: X = O, in Compound G20, X = S, and in Compound G21, X = Se
Compounds G22 through G24, each represented by the formula:

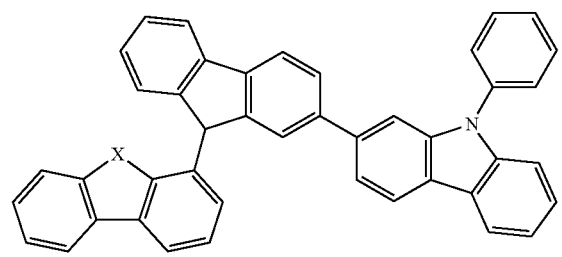

where in Compound G22: X = O, in Compound G23, X = S, and in Compound G24, X = Se
Compounds G25 through G27, each represented by the formula:

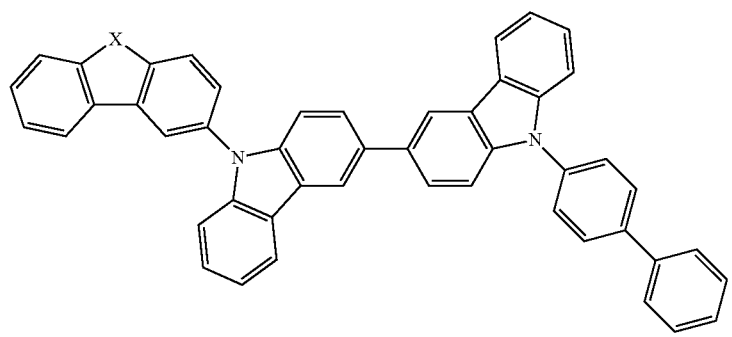

where in Compound G25: X = O, in Compound G26, X = S, and in Compound G27, X = Se
Compounds G28 through G30, each represented by the formula:

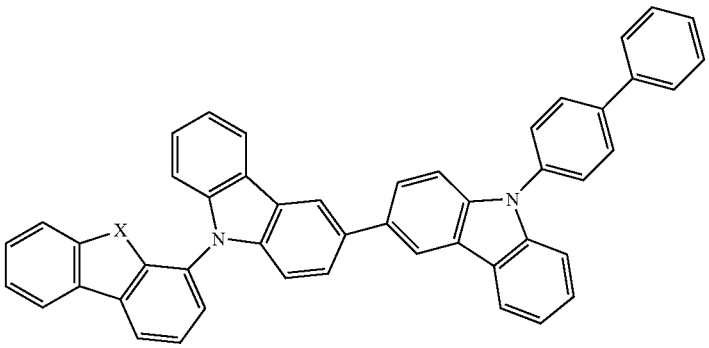

where in Compound G28: X = O, in Compound G29, X = S, and in Compound G30, X = Se Compounds G31 through G33, each represented by the formula:

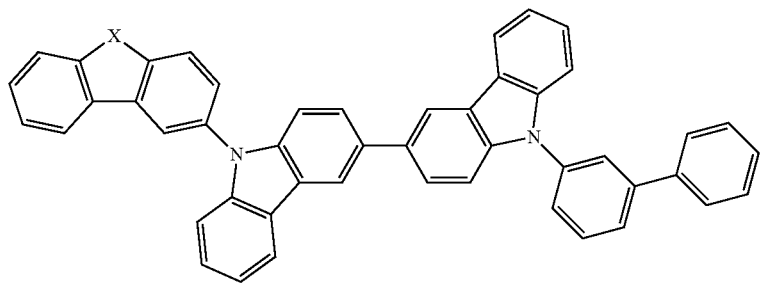

where in Compound G31: X = O, in Compound G32, X = S, and in Compound G33, X = Se Compounds G34 through G36, each represented by the formula:

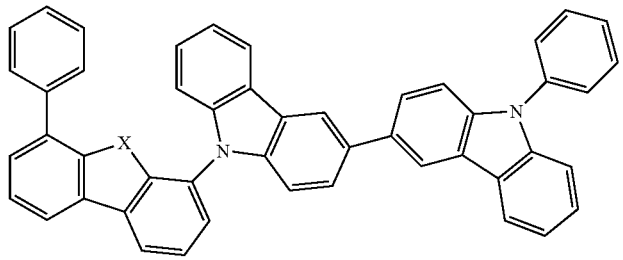

where in Compound G34: X = O, in Compound G35, X = S, and in Compound G36, X = Se Compounds G37 through G39, each represented by the formula:

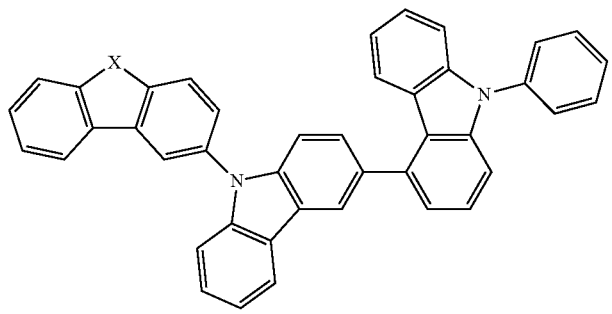

where in Compound G37: X = O, in Compound G38, X = S, and in Compound G39, X = Se Compounds G40 through G42, each represented by the formula:

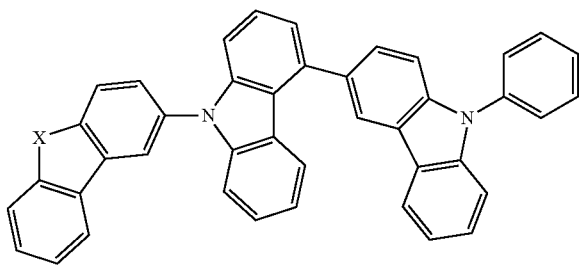

where in Compound G40: X = O, in Compound G41, X = S, and in Compound G42, X = Se
Compounds G43 through G45, each represented by the formula:

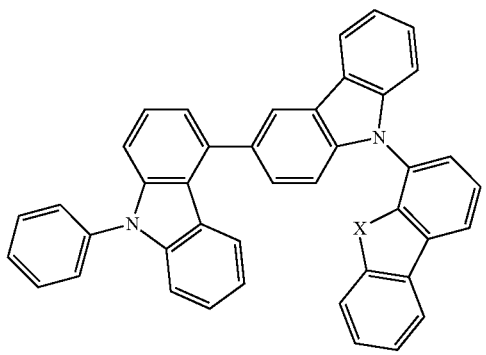

where in Compound G43: X = O, in Compound G44, X = S, and in Compound G45, X = Se
Compounds G46 through G48, each represented by the formula:

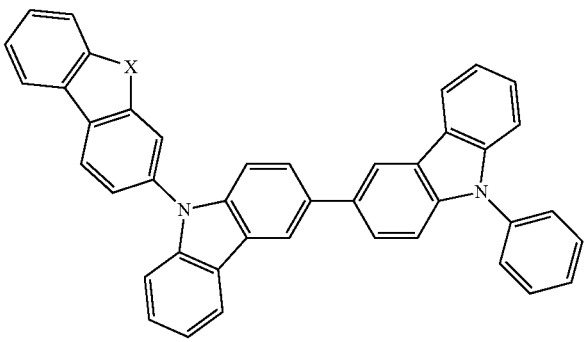

where in Compound G46: X = O, in Compound G47, X = S, and in Compound G48, X = Se
Compounds G49 through G51, each represented by the formula:

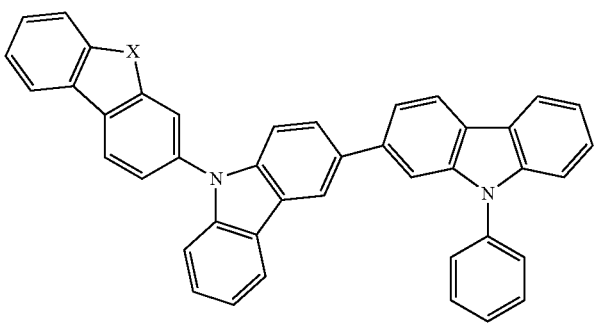

where in Compound G49: X = O, in Compound G50, X = S, and in Compound G51, X = Se
Compounds G52 through G54, each represnted by the formula:

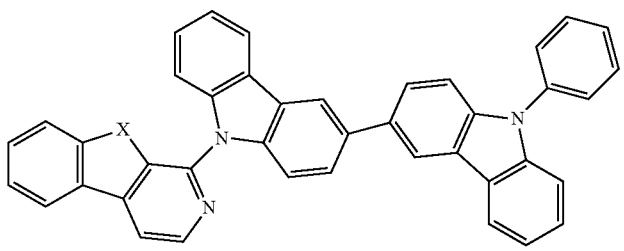
where in Compound G52: X = O, in Compound G53, X = S, and in Compound G54, X = Se
Compounds G55 through G57, each represented by the formula:
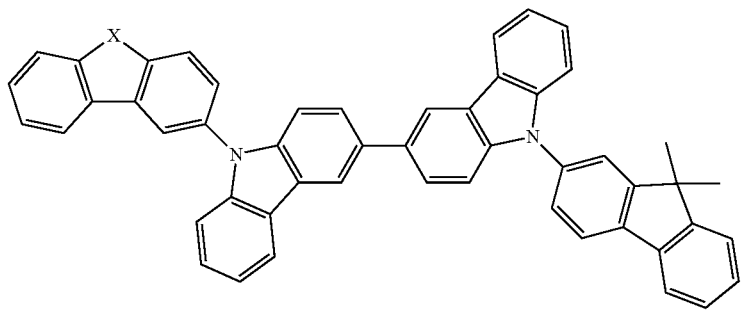
where in Compound G55: X = O, in Compound G56, X = S, and in Compound G57, X = Se
Compounds G58 through G60, each represented by the formula:
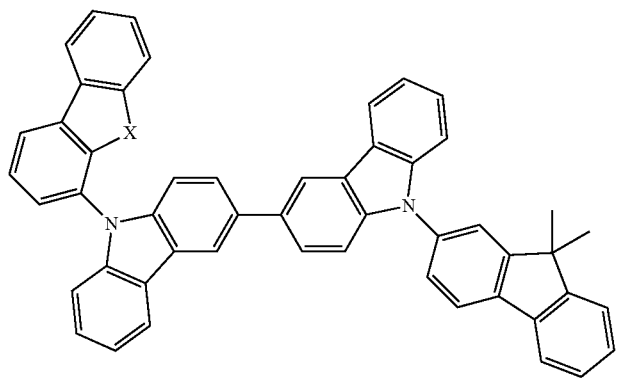
where in Compound G58: X = O, in Compound G59, X = S, and in Compound G60, X = Se
Compound H1
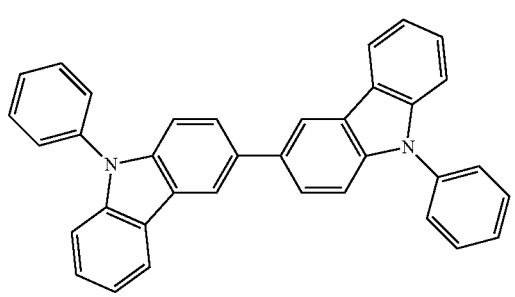 [SMILES: c1ccc(-n2c3ccccc3c3cc(-c4ccc5c(c4)c4ccccc4n5-c4ccccc4)ccc32)cc1]

Compound H2
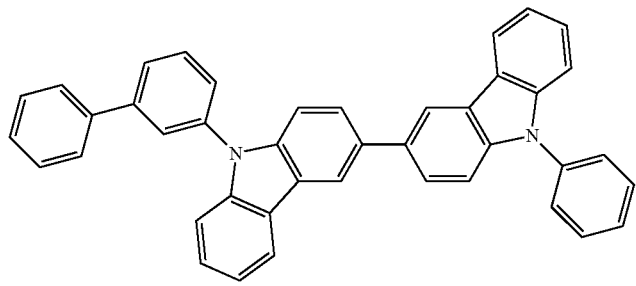 [SMILES: c1ccc(-c2cccc(-n3c4ccccc4c4cc(-c5ccc6c(c5)c5ccccc5n6-c5ccccc5)ccc43)c2)cc1]
Compound H3
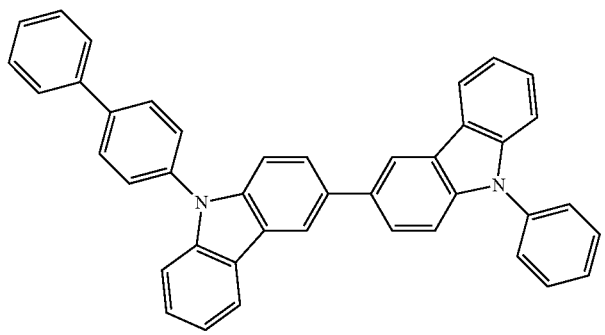 [SMILES: c1ccc(-c2ccc(-n3c4ccccc4c4cc(-c5ccc6c(c5)c5ccccc5n6-c5ccccc5)ccc43)cc2)cc1]
Compound H4
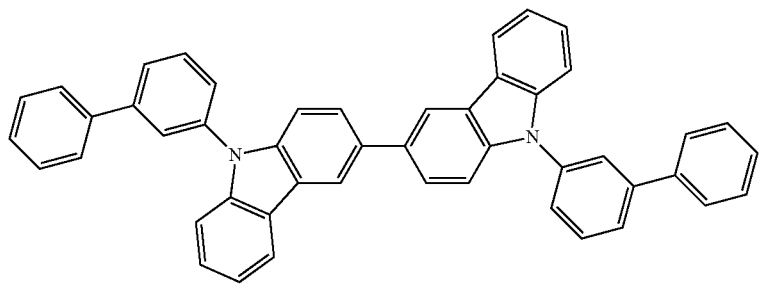 [SMILES: c1ccc(-c2cccc(-n3c4ccccc4c4cc(-c5ccc6c(c5)c5ccccc5n6-c5cccc(-c6ccccc6)c5)ccc43)c2)cc1]
Compound H5
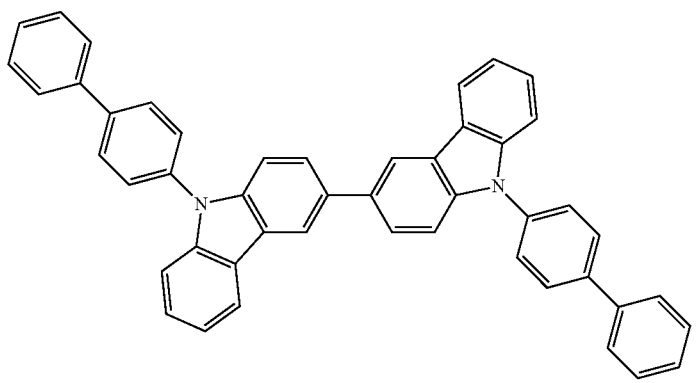 [SMILES: c1ccc(-c2ccc(-n3c4ccccc4c4cc(-c5ccc6c(c5)c5ccccc5n6-c5ccc(-c6ccccc6)cc5)ccc43)cc2)cc1]

-continued
Compound H6
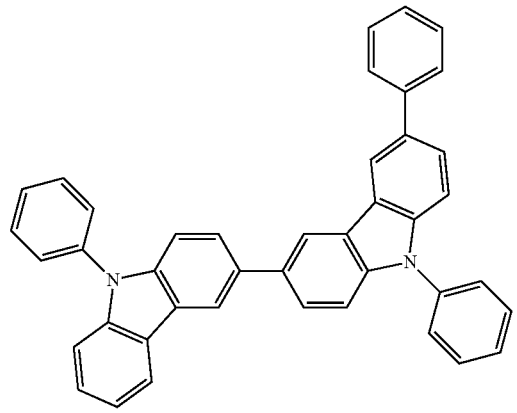 [SMILES: c1ccc(-c2ccc3c(c2)c2cc(-c4ccc5c(c4)c4ccccc4n5-c4ccccc4)ccc2n3-c2ccccc2)cc1]
Compound H7
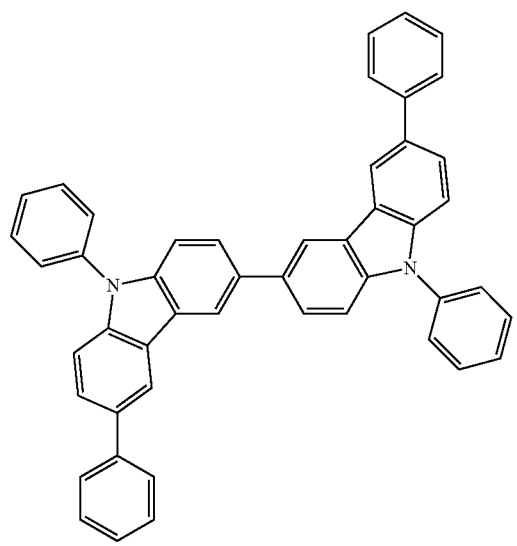 [SMILES: c1ccc(-c2ccc3c(c2)c2cc(-c4ccc5c(c4)c4cc(-c6ccccc6)ccc4n5-c4ccccc4)ccc2n3-c2ccccc2)cc1]
Compound H8
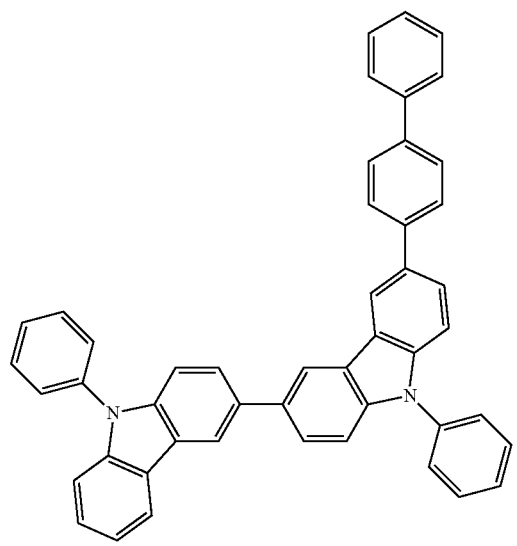 [SMILES: c1ccc(-c2ccc(-c3ccc4c(c3)c3cc(-c5ccc6c(c5)c5ccccc5n6-c5ccccc5)ccc3n4-c3ccccc3)cc2)cc1]

-continued
Compound H9
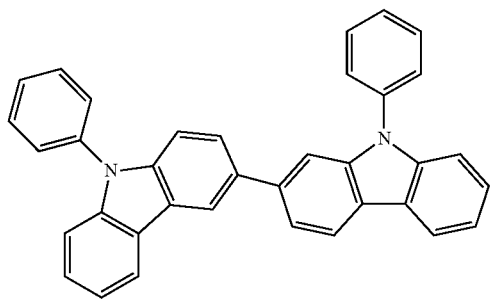 [SMILES: c1ccc(-n2c3ccccc3c3cc(-c4ccc5c6ccccc6n(-c6ccccc6)c5c4)ccc32)cc1]
Compound H10
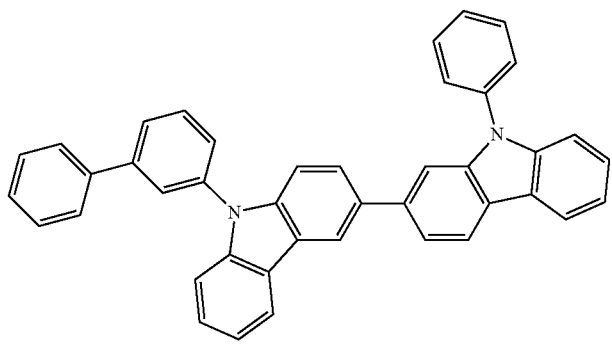 [SMILES: c1ccc(-c2cccc(-n3c4ccccc4c4cc(-c5ccc6c7ccccc7n(-c7ccccc7)c6c5)ccc43)c2)cc1]
Compound H11
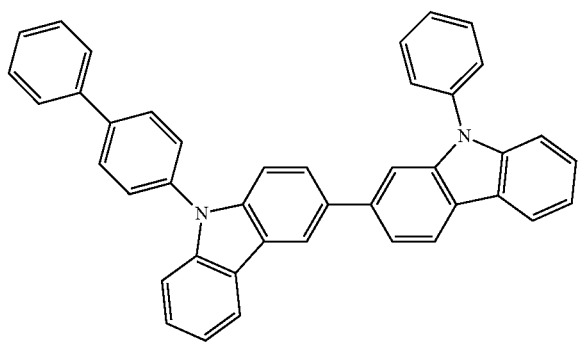 [SMILES: c1ccc(-c2ccc(-n3c4ccccc4c4cc(-c5ccc6c7ccccc7n(-c7ccccc7)c6c5)ccc43)cc2)cc1]
Compound H12
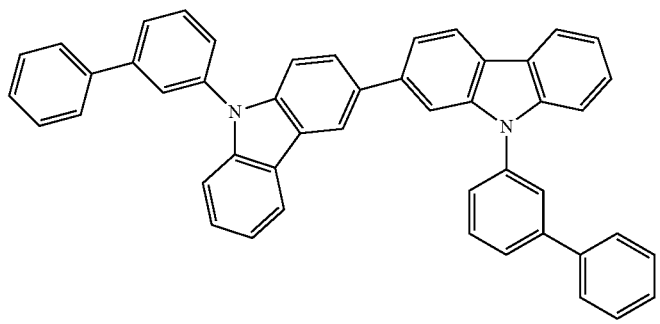 [SMILES: c1ccc(-c2cccc(-n3c4ccccc4c4cc(-c5ccc6c7ccccc7n(-c7cccc(-c8ccccc8)c7)c6c5)ccc43)c2)cc1]

Compound H13
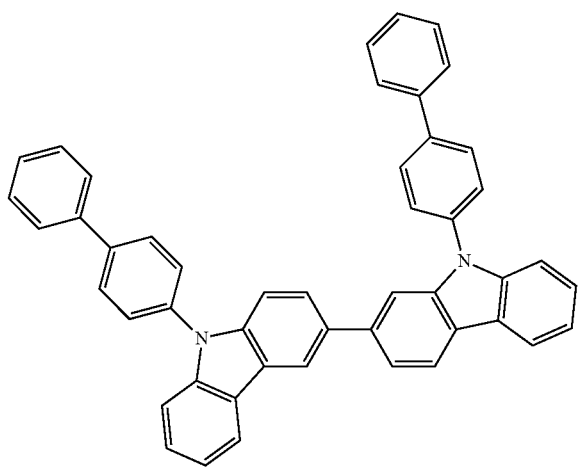 [SMILES: c1ccc(-c2ccc(-n3c4ccccc4c4cc(-c5ccc6c7ccccc7n(-c7ccc(-c8ccccc8)cc7)c6c5)ccc43)cc2)cc1]
Compound H14
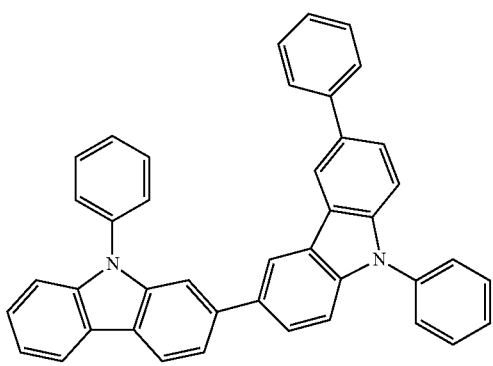 [SMILES: c1ccc(-c2ccc3c(c2)c2cc(-c4ccc5c6ccccc6n(-c6ccccc6)c5c4)ccc2n3-c2ccccc2)cc1]
Compound H15
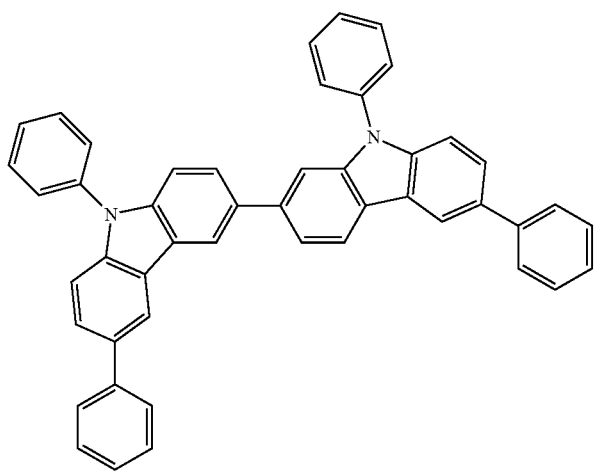 [SMILES: c1ccc(-c2ccc3c(c2)c2cc(-c4ccc5c6cc(-c7ccccc7)ccc6n(-c6ccccc6)c5c4)ccc2n3-c2ccccc2)cc1]

Compound H16
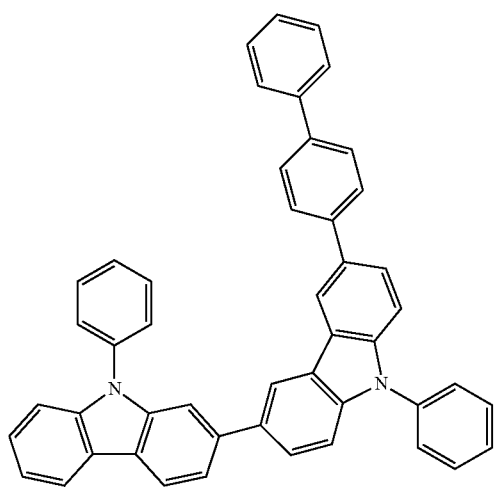 [SMILES: c1ccc(-c2ccc(-c3ccc4c(c3)c3cc(-c5ccc6c7ccccc7n(-c7ccccc7)c6c5)ccc3n4-c3ccccc3)cc2)cc1]
Compound H17
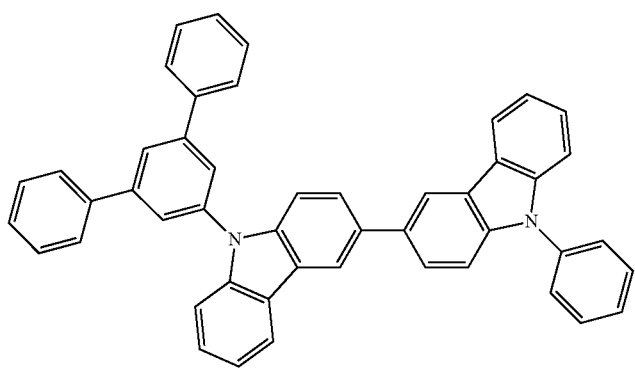 [SMILES: c1ccc(-c2cc(-c3ccccc3)cc(-n3c4ccccc4c4cc(-c5ccc6c(c5)c5ccccc5n6-c5ccccc5)ccc43)c2)cc1]
Compound H18
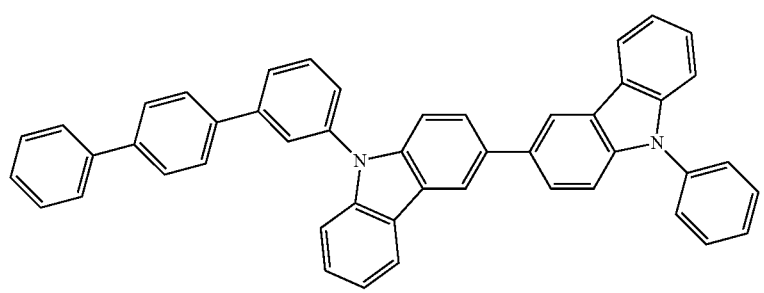 [SMILES: c1ccc(-c2ccc(-c3cccc(-n4c5ccccc5c5cc(-c6ccc7c(c6)c6ccccc6n7-c6ccccc6)ccc54)c3)cc2)cc1]
Compound H19
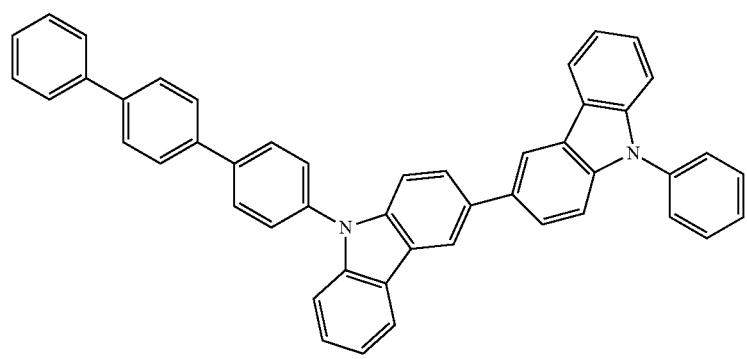 [SMILES: c1ccc(-c2ccc(-c3ccc(-n4c5ccccc5c5cc(-c6ccc7c(c6)c6ccccc6n7-c6ccccc6)ccc54)cc3)cc2)cc1]
and

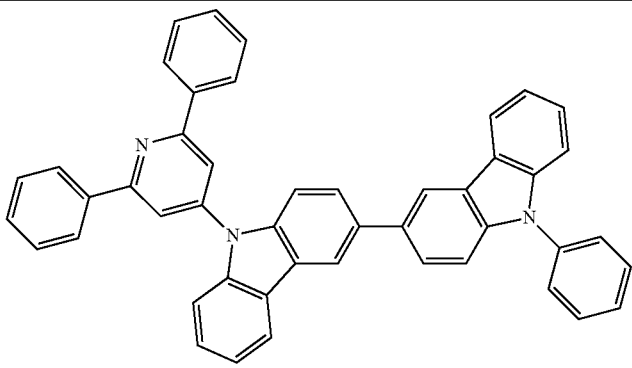

Compound H20

In some embodiments of the composition, the mixture of the first compound and the second compound is selected from the group consisting of the following pairs of first compound and second compound: (Compound A5 and Compound H7), (Compound A11 and Compound F4), (Compound A11 and Compound H3), (Compound A14 and Compound F1), (Compound A14 and Compound G26), (Compound A14 and Compound G59), (Compound A14 and Compound H5), (Compound A17 and Compound G2), (Compound A17 and Compound H5), (Compound A17 and Compound H7), (Compound C74 and Compound G14), (Compound C74 and Compound G44), (Compound C83 and Compound G2), (Compound C83 and Compound H7), (Compound C248 and Compound G14), (Compound D2 and Compound G14), and (Compound D5 and Compound H5).

In some embodiments of the composition, the first compound has an evaporation temperature T1 of 150 to 350° C.; wherein the second compound has an evaporation temperature T2 of 150 to 350° C.;

wherein absolute value of T1-T2 is less than 20° C.;

wherein the first compound has a concentration C1 in said mixture and a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface position at a predefined distance away from the mixture being evaporated; and wherein absolute value of (C1-C2)/C1 is less than 5%.

In some embodiment of the composition, the first compound has a vapor pressure of P1 at T1 at 1 atm, the second compound has a vapor pressure of P2 at T2 at 1 atm; and wherein the ratio of P1/P2 is within the range of 0.90 to 1.10.

In some embodiment of the composition, the first compound has a first mass loss rate and the second compound has a second mass loss rate, wherein the ratio between the first mass loss rate and the second mass loss rate is within the range of 0.90 to 1.10.

In some embodiment of the composition, the first compound and the second compound each has a purity in excess of 99% as determined by high pressure liquid chromatography.

In some embodiments of the composition, the composition further comprises a third compound, wherein the third compound has a different chemical structure than the first and second compounds, wherein the third compound has an evaporation temperature T3 of 150 to 350° C., and wherein absolute value of T1-T3 is less than 20° C.

In some embodiments of the composition, the composition further comprises a third compound, wherein the third compound has a different chemical structure than the first and second compounds, wherein the third compound has a third mass loss rate and the ratio between the first mass loss rate and third mass loss rate is within the range of 0.90 to 1.10.

In some embodiments of the composition, the composition is in a liquid form at a temperature less than T1 and T2.

The composition of materials comprising a mixture of organic materials consisting of carbazole and triazine derivatives can be thermally evaporated from one crucible to fabricate thin films for electroluminescent devices such as organic light emitting devices (OLEDs).

According to another aspect of the present disclosure, a first OLED comprising: an anode; a cathode; and an organic layer, disposed between the anode and the cathode, is disclosed. The organic layer of the device comprises a composition of materials comprising a mixture of first compound and a second compound, wherein the first compound is an e-host and has a formula:

Formula I

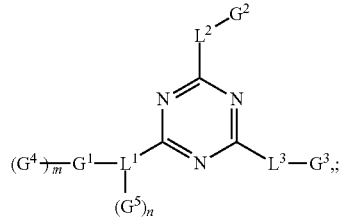

wherein $G^1$ is selected from the group consisting of dibenzofuran, dibenzothiophene, dibenzoselenophene, and fluorene;

wherein $L^1$, $L^2$ and $L^3$ are each independently selected from the group consisting of direct bond, phenyl, biphenyl, terphenyl, pyridine, pyrimidine, and combinations thereof;

wherein $G^4$ is selected from the group consisting of phenyl, biphenyl, terphenyl, naphthalene, phenanthrene, pyridine, pyrimidine, pyrazine, quinoline, isoquinoline, phenanthroline, fluorene, and combinations thereof;

wherein $G^2$, $G^3$, and $G^5$ are each independently selected from the group consisting of phenyl, biphenyl, terphenyl, fluorene, naphthalene, phenanthrene, pyridine, pyrimidine, pyrazine, quinoline, isoquinoline, phenanthroline, aza-fluorene, and combinations thereof;

wherein $G^2$, $G^3$, $G^4$, and $G^5$ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof;

wherein m is an integer from 0 to 7,
wherein n is an integer from 0 to 4;
wherein, when m or n is larger than 1, each $G^4$ or $G^5$ can be same or different;
wherein when n is 0, m is equal to or greater than 1, and each $G^4$ is selected from the group consisting of phenyl, and biphenyl;
wherein when n is equal to or greater than 1, $L^1$ is not a direct bond;
wherein when m and n are both 0, $L^1$ is biphenyl;
wherein when $G^4$ is present and is fluorene, $L^1$ is not a direct bond;
wherein the second compound is a h-host and has a formula:

Formula II

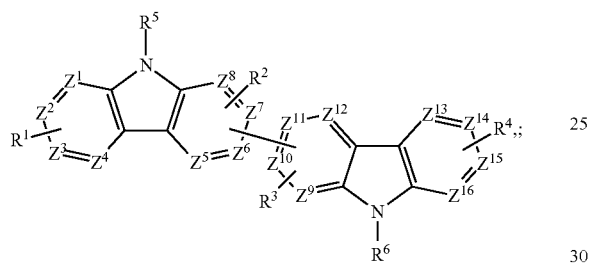

wherein each $Z^1$ to $Z^{16}$ is C or N;
wherein one of $Z^5$ to $Z^8$ bonds to one of $Z^9$ to $Z^{12}$ through a C—C bond;
wherein $R^1$, $R^4$ each independently represents mono, di, tri, or tetra substitution, or no substitution;
wherein $R^2$, $R^3$ each independently represents mono, di, or tri substitution, or no substitution; and
wherein $R^1$ to $R^6$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and any two adjacent substituents are optionally joined or fused into a ring.

In some embodiments of the first OLED, the organic layer is an emissive layer and the composition is a host.

In some embodiments of the first OLED, the organic layer further comprises a phosphorescent emissive dopant; wherein the phosphorescent emissive dopant is a transition metal complex having at least one ligand or part of the ligand if the ligand is more than bidentate selected from the group consisting of:

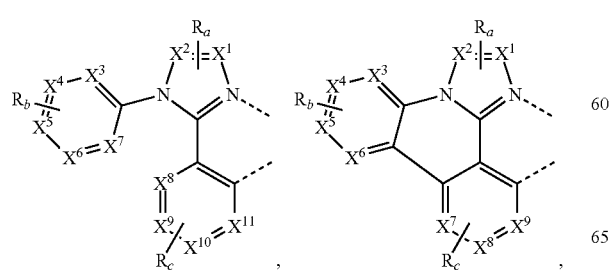

-continued

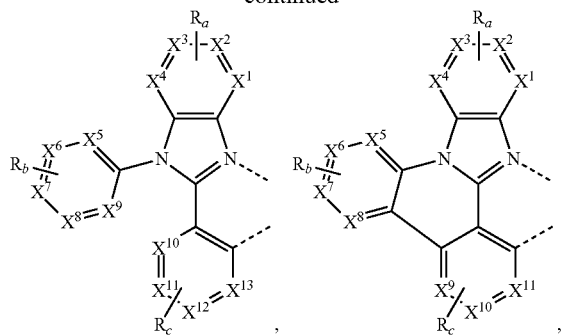

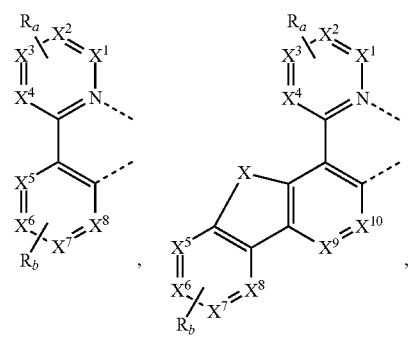

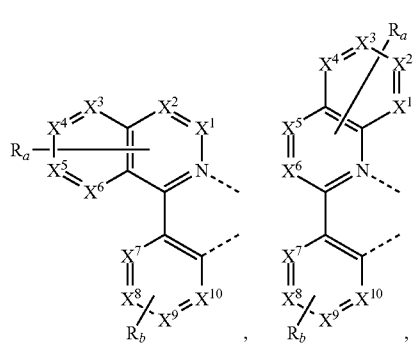

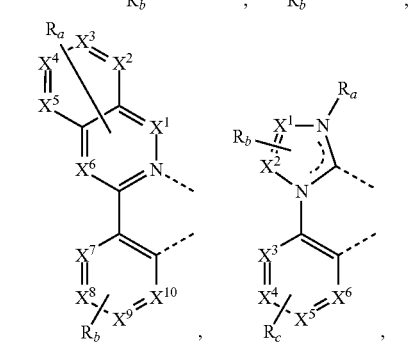

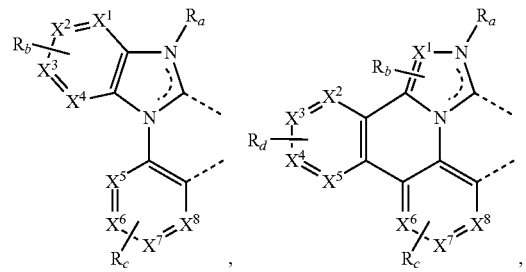

155
-continued

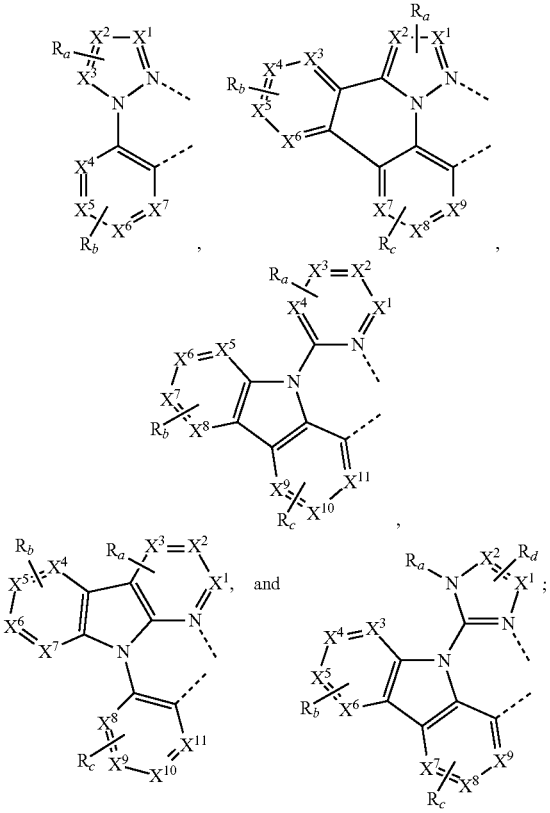

wherein each $X^1$ to $X^{13}$ are independently selected from the group consisting of carbon and nitrogen;

wherein X is selected from the group consisting of BR', NR', PR', O, S, Se, C=O, S=O, SO$_2$, CR'R'', SiR'R'', and GeR'R'';

wherein R' and R'' are optionally fused or joined to form a ring;

wherein each $R_a$, $R_b$, $R_c$, and $R_d$ may represent from mono substitution to the possible maximum number of substitution, or no substitution;

wherein R', R'', $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substitutents of $R_a$, $R_b$, $R_c$, and $R_d$ are optionally fused or joined to form a ring or form a multidentate ligand.

In some embodiments of the first OLED, the organic layer is a charge carrier blocking layer and the composition is a charge carrier blocking material in the organic layer.

In some embodiments of the first OLED, the organic layer is a charge carrier transporting layer and the composition is a charge carrier transporting material in the organic layer.

According to another aspect of the present disclosure, a method for fabricating an OLED comprising a first electrode, a second electrode, and a first organic layer disposed between the first electrode and the second electrode is disclosed, wherein the first organic layer comprises a first composition of material comprising a mixture of a first compound and a second compound, the method comprising:

156 providing a substrate having the first electrode disposed thereon;

depositing the first organic layer over the first electrode; and depositing the second electrode over the first organic layer, wherein the first compound has a formula:

Formula I

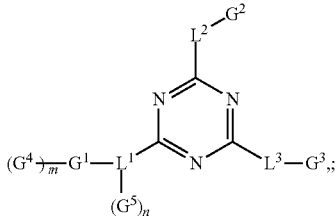

wherein $G^1$ is selected from the group consisting of dibenzofuran, dibenzothiophene, dibenzoselenophene, and fluorene;

wherein $L^1$, $L^2$ and $L^3$ are each independently selected from the group consisting of direct bond, phenyl, biphenyl, terphenyl, pyridine, pyrimidine, and combinations thereof;

wherein $G^4$ is selected from the group consisting of phenyl, biphenyl, terphenyl, naphthalene, phenanthrene, pyridine, pyrimidine, pyrazine, quinoline, isoquinoline, phenanthroline, fluorene, and combinations thereof;

wherein $G^2$, $G^3$, and $G^5$ are each independently selected from the group consisting of phenyl, biphenyl, terphenyl, fluorene, naphthalene, phenanthrene, pyridine, pyrimidine, pyrazine, quinoline, isoquinoline, phenanthroline, aza-fluorene, and combinations thereof;

wherein $G^2$, $G^3$, $G^4$, and $G^5$ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof;

wherein m is an integer from 0 to 7, wherein n is an integer from 0 to 4;

wherein, when m or n is larger than 1, each $G^4$ or $G^5$ can be same or different;

wherein when n is 0, m is equal to or greater than 1, and each $G^4$ is selected from the group consisting of phenyl, and biphenyl;

wherein when n is equal to or greater than 1, $L^1$ is not a direct bond;

wherein when m and n are both 0, $L^1$ is biphenyl;

wherein when $G^4$ is present and is fluorene, Cis not a direct bond;

wherein the second compound has a formula:

Formula II

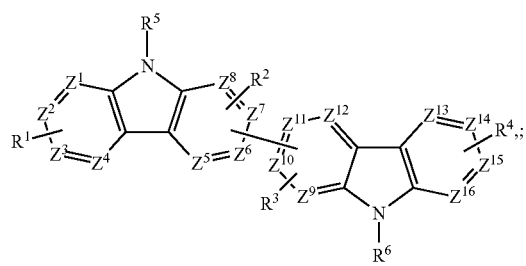

wherein each $Z^1$ to $Z^{16}$ is C or N;

wherein one of $Z^5$ to $Z^8$ bonds to one of $Z^9$ to $Z^{12}$ through a C—C bond;

wherein $R^1$, $R^4$ each independently represents mono, di, tri, or tetra substitution, or no substitution;

wherein $R^2$, $R^3$ each independently represents mono, di, or tri substitution, or no substitution; and wherein $R^1$ to $R^6$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and any two adjacent substituents are optionally joined or fused into a ring.

The mixture of the e-host type compound and the h-host type compound disclosed herein is useful as a host material in the organic emissive layer in an OLED that includes one or more emitter dopants. The emitter dopants can be phosphorescent dopants and/or fluorescent dopants.

The OLED can be incorporated into one or more of a consumer product, an electronic component module, and a lighting panel.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804 and US2012146012.

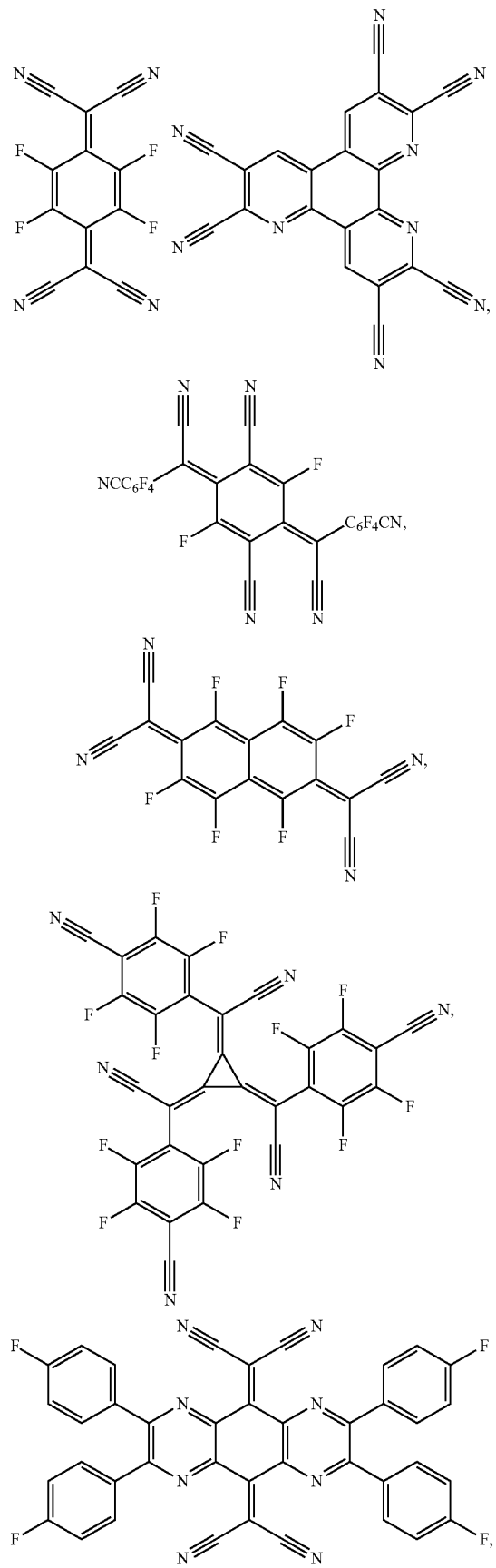

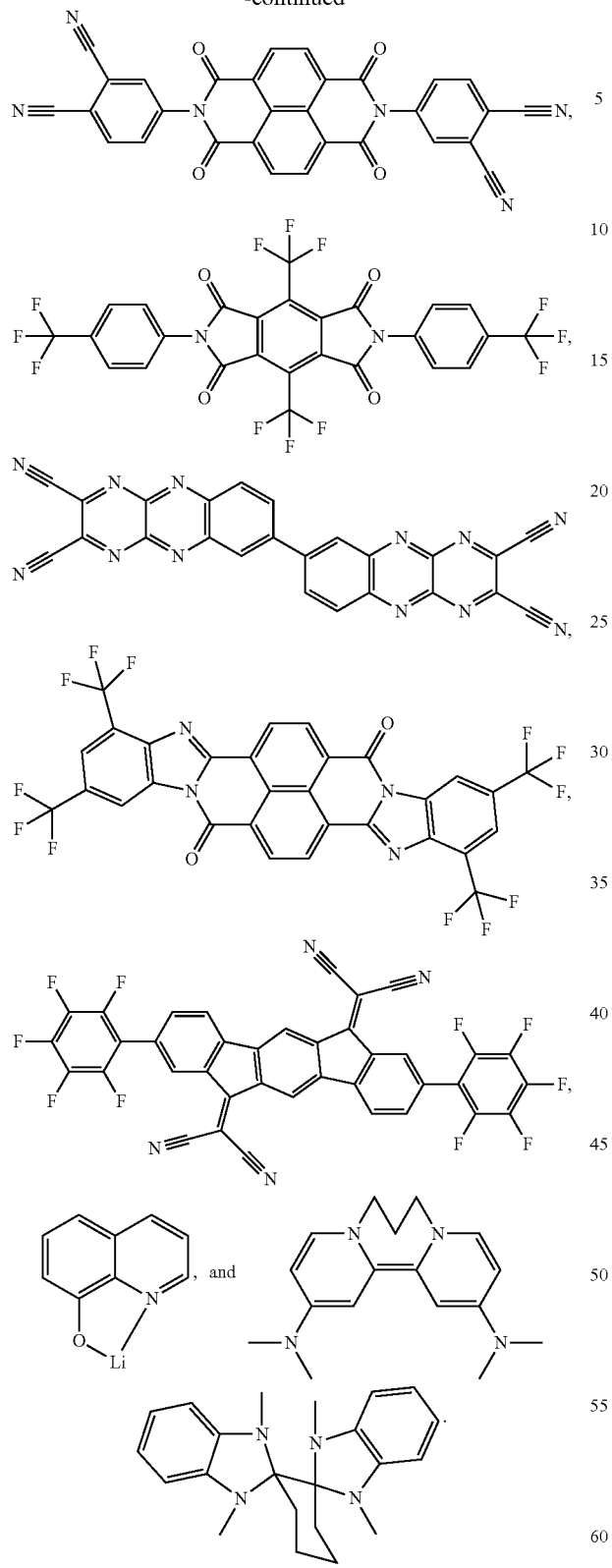

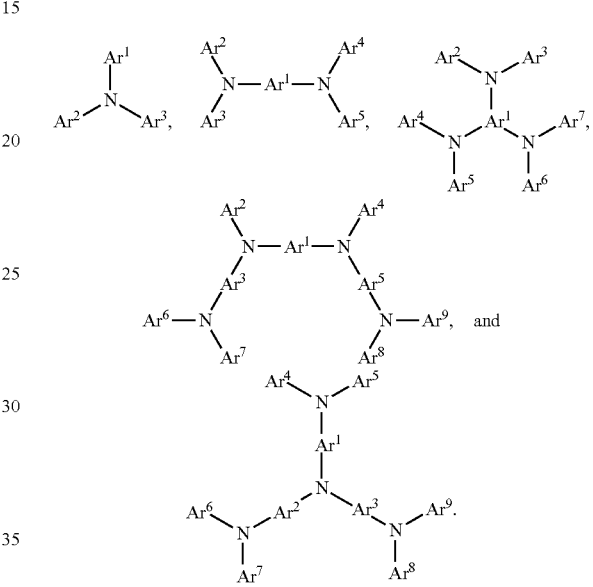

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but are not limited to the following general structures:

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

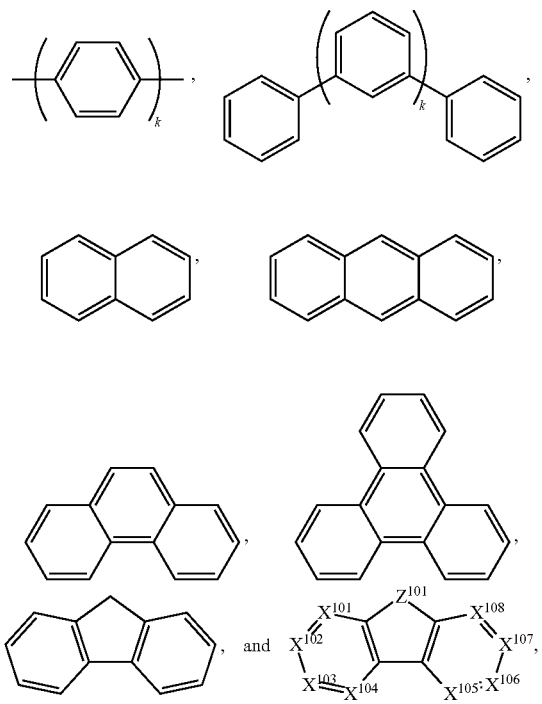

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

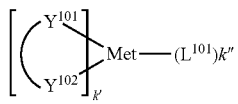

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018,

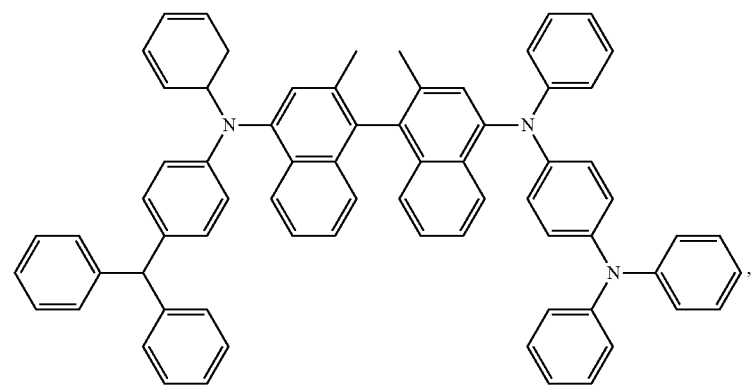

-continued
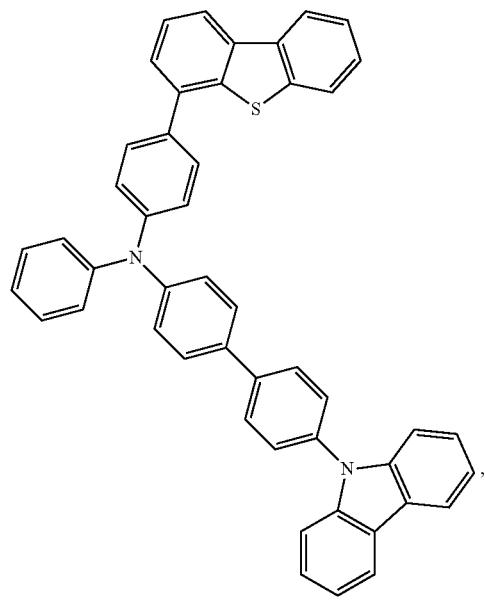
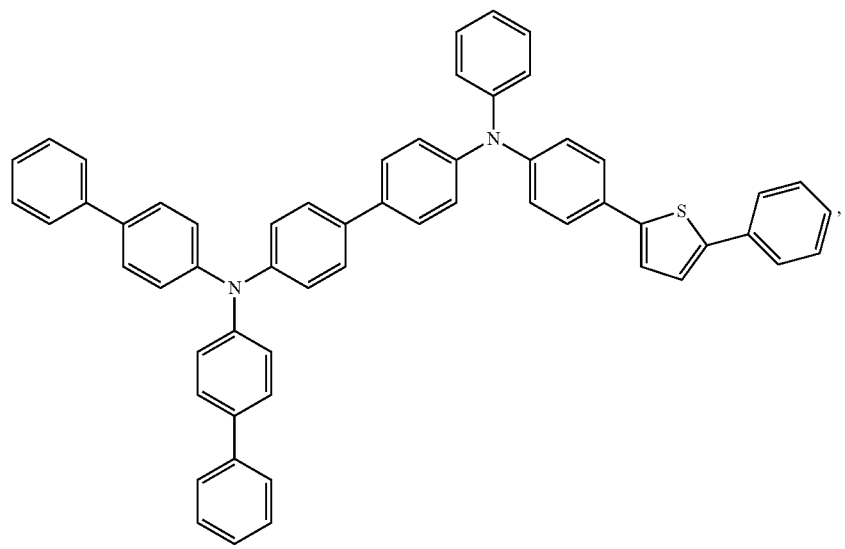
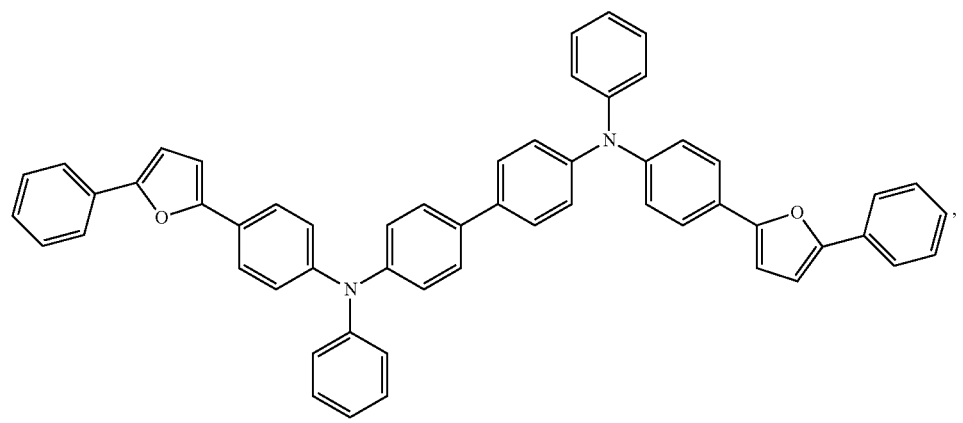

165
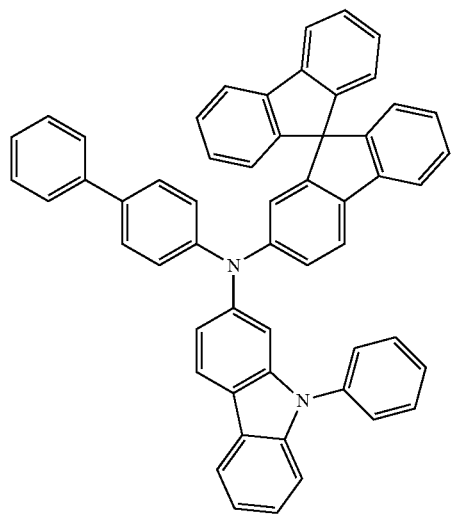
-continued
166
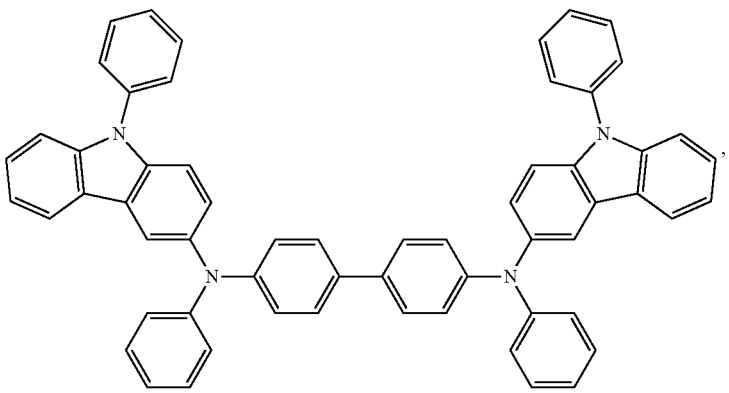
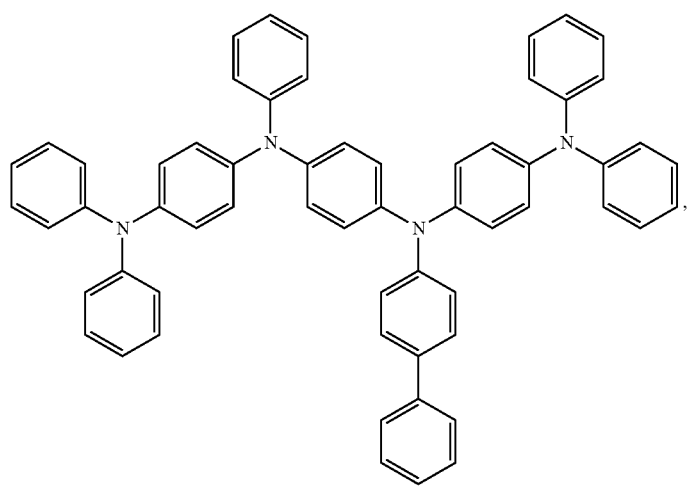
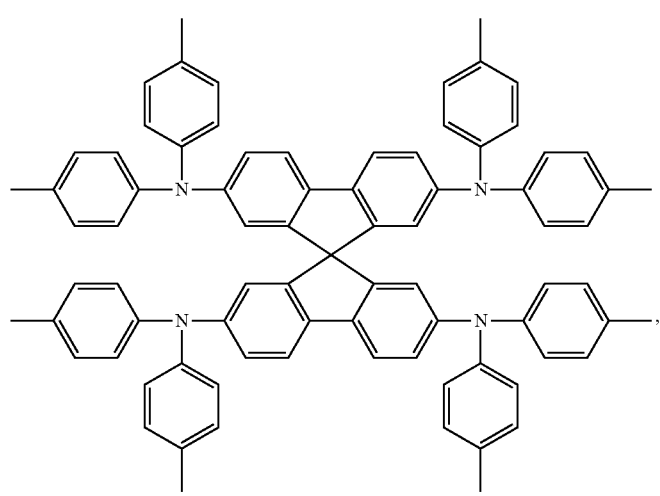

-continued
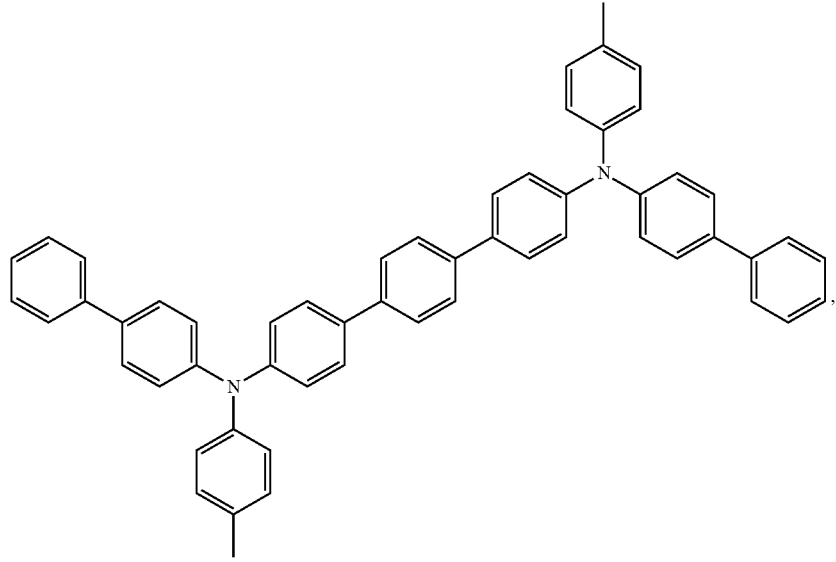
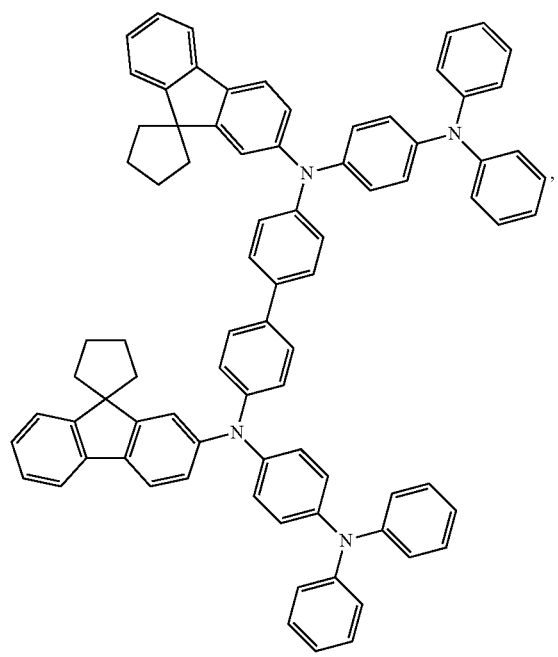
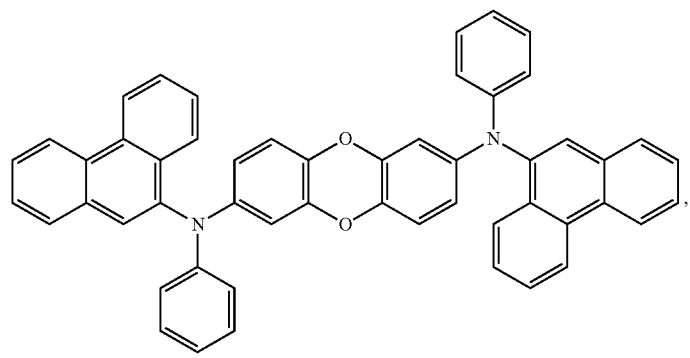

-continued
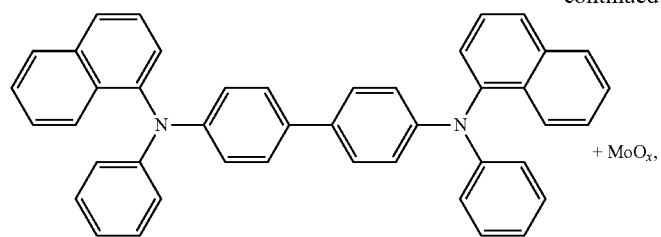
+ MoO$_x$,
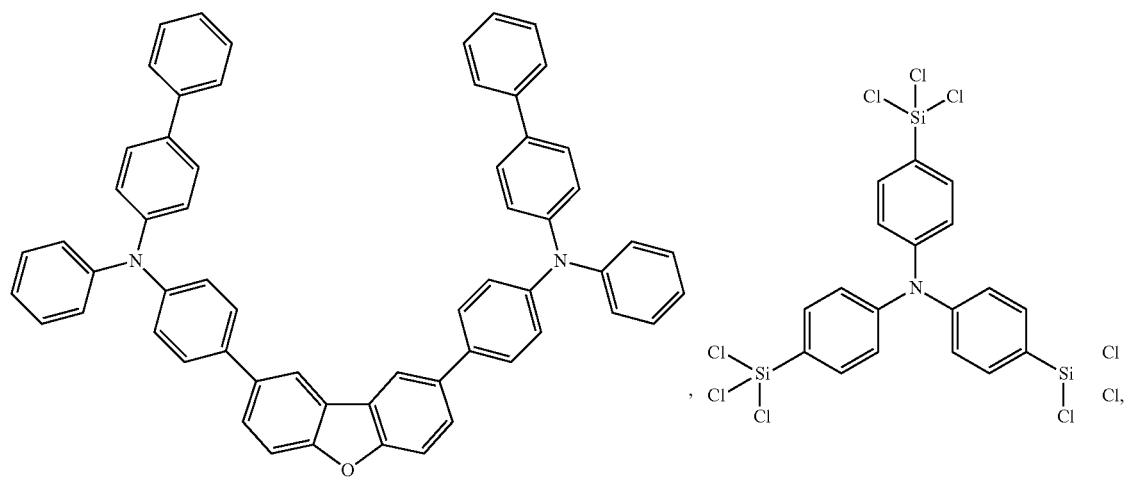
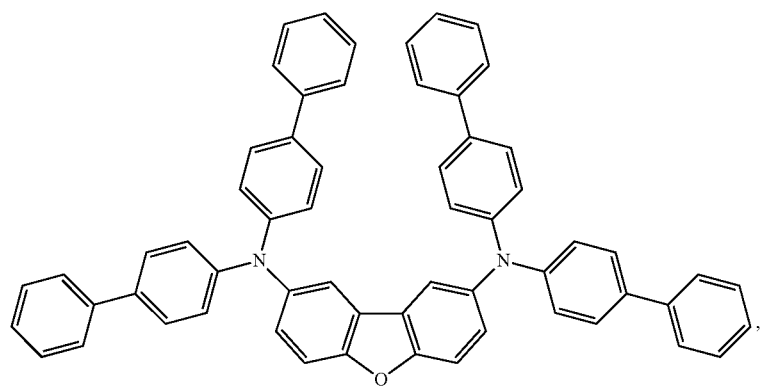
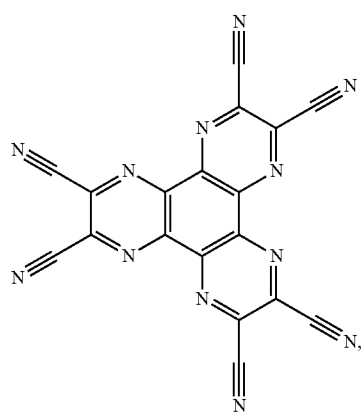

-continued
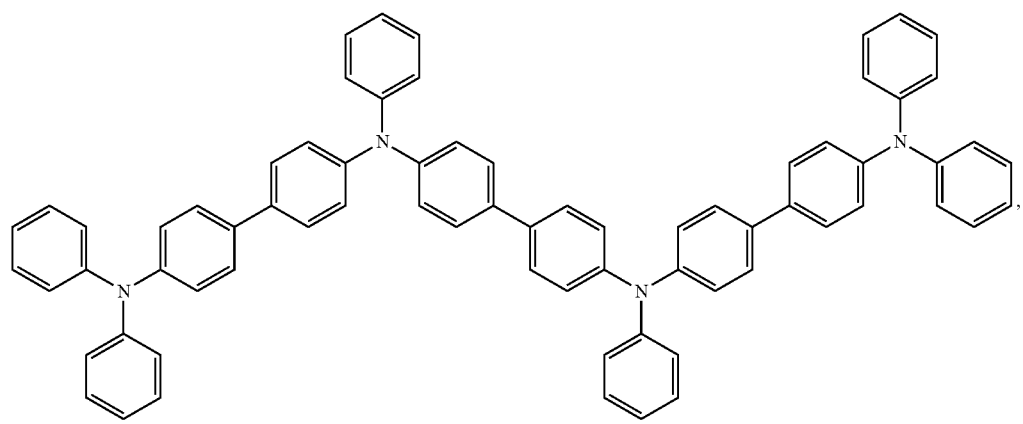
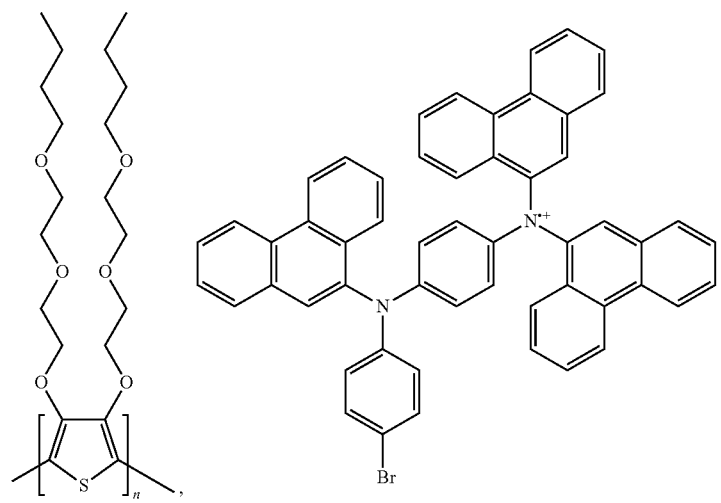
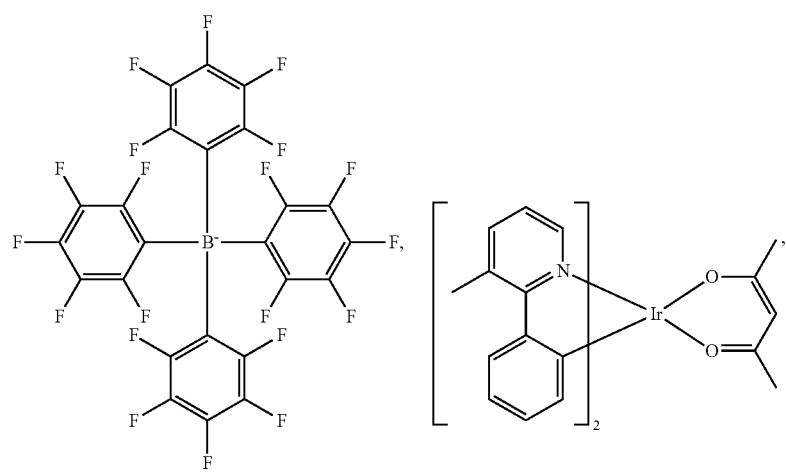

-continued
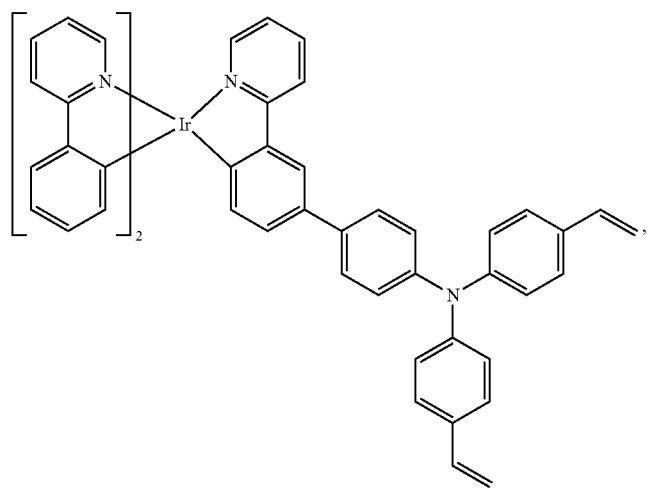
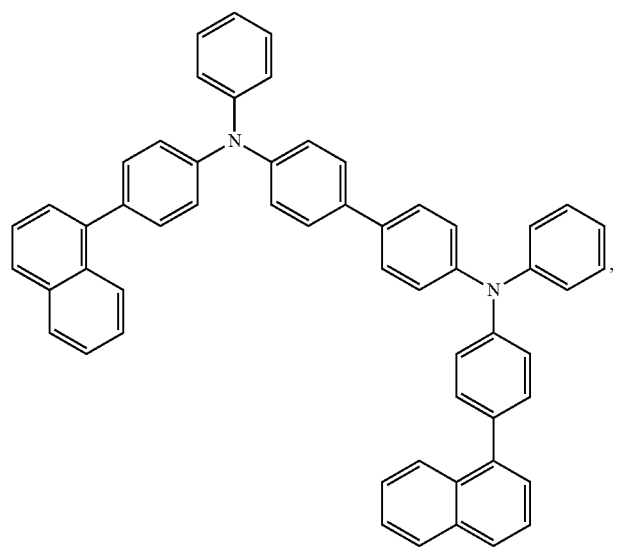
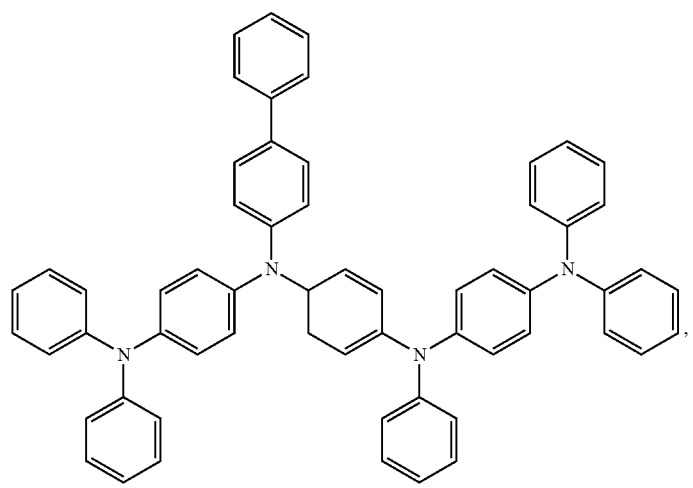

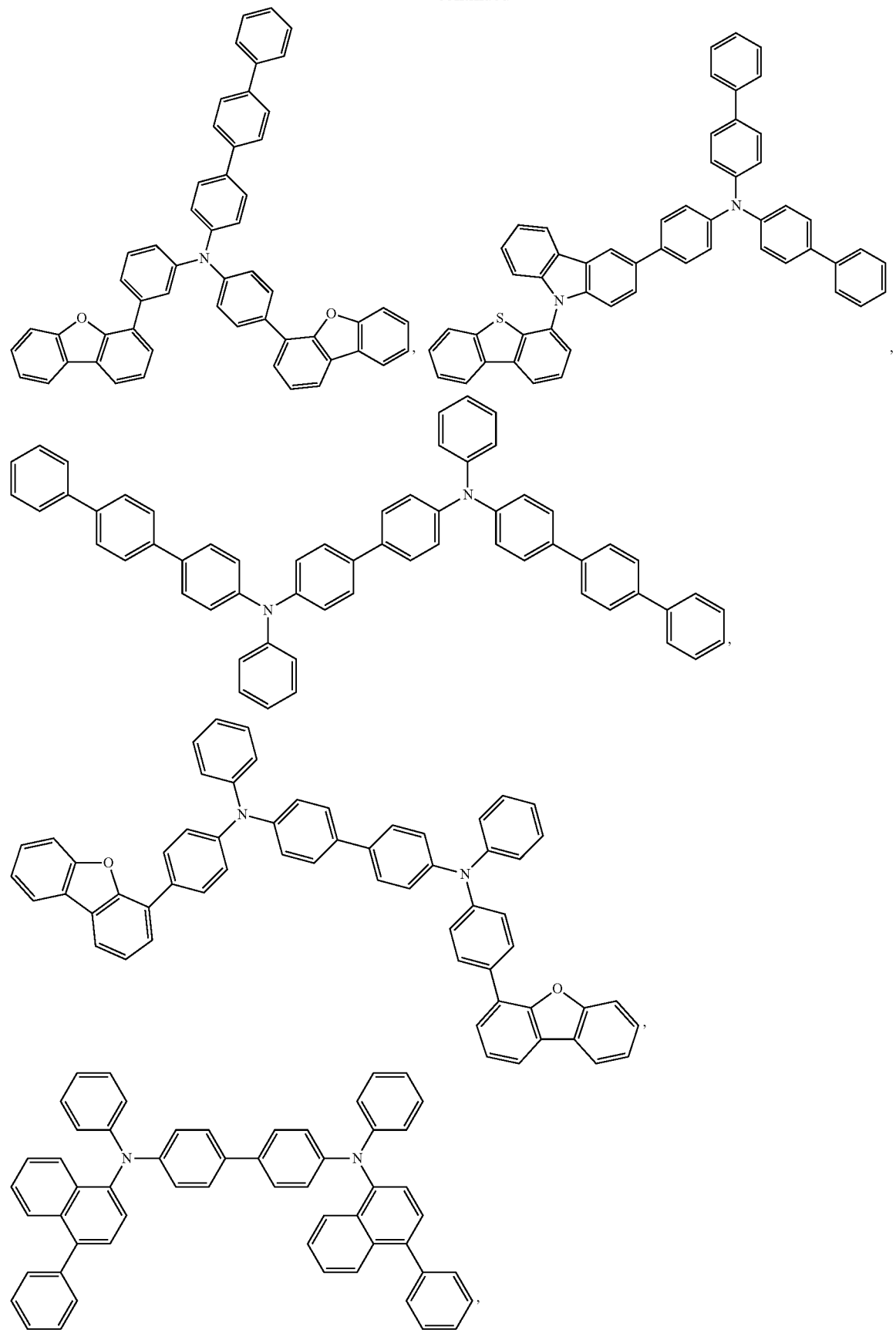

177 178
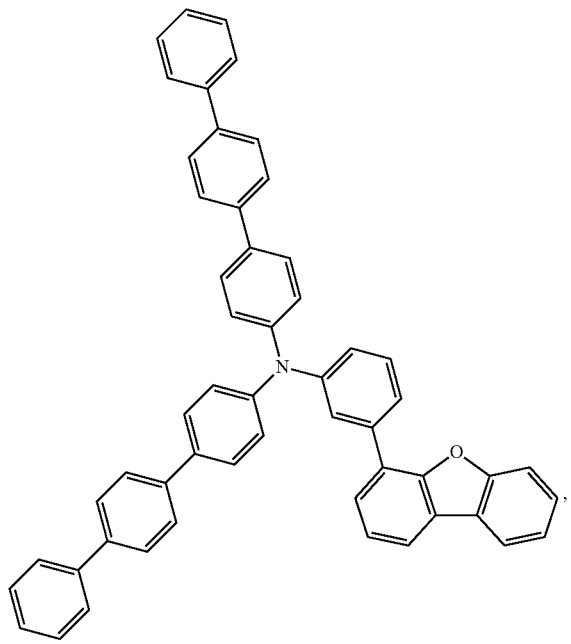 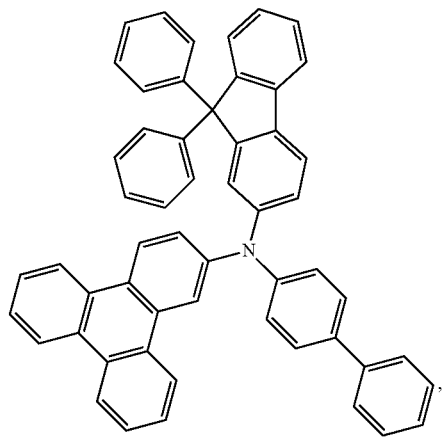
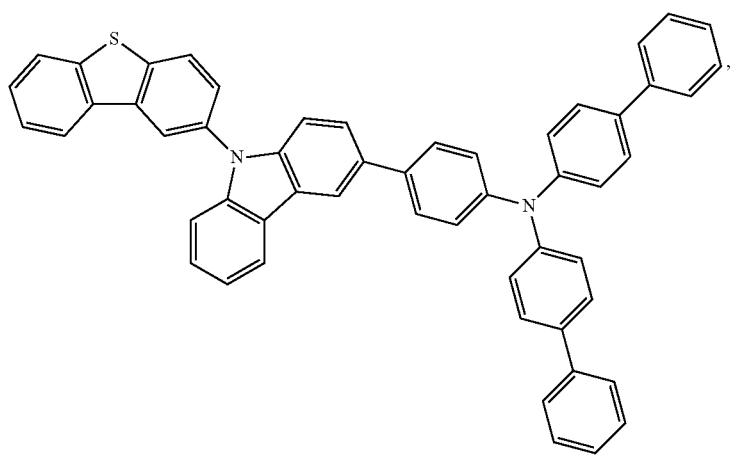
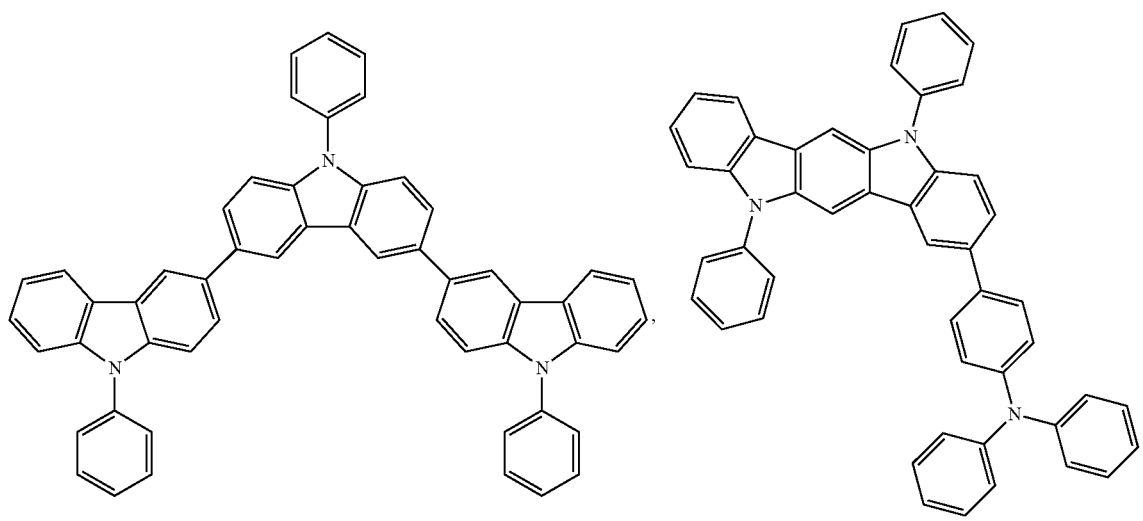

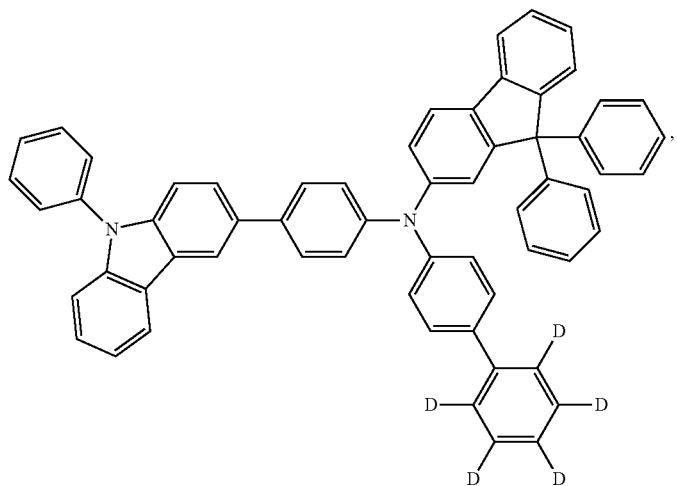
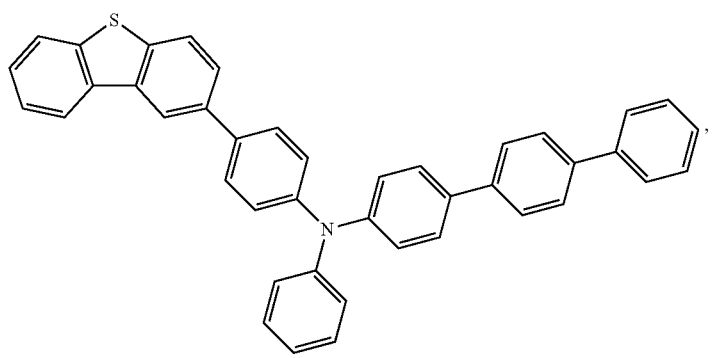
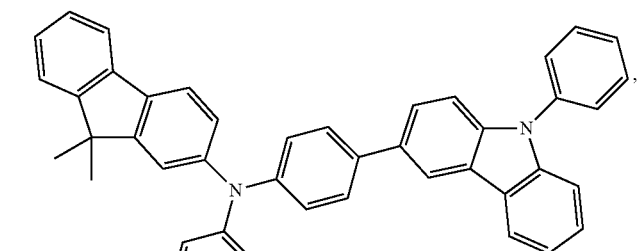
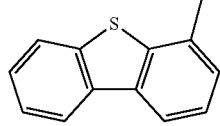
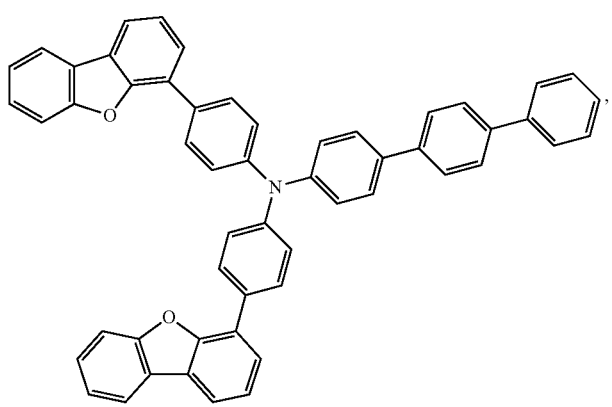
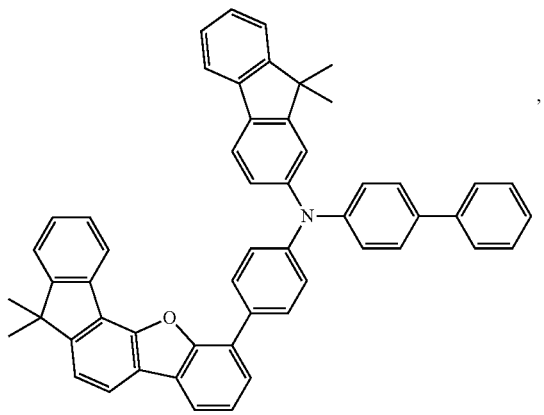

-continued
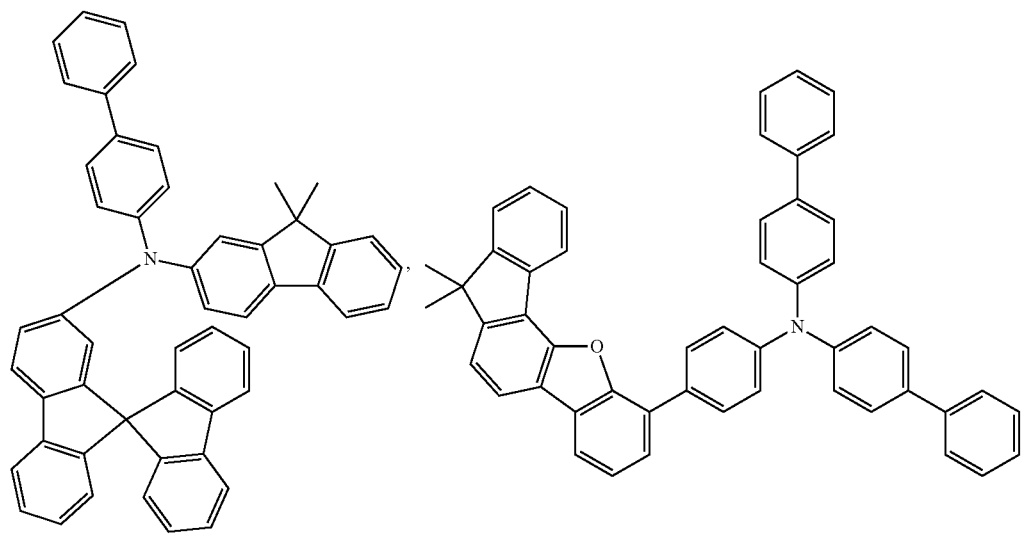
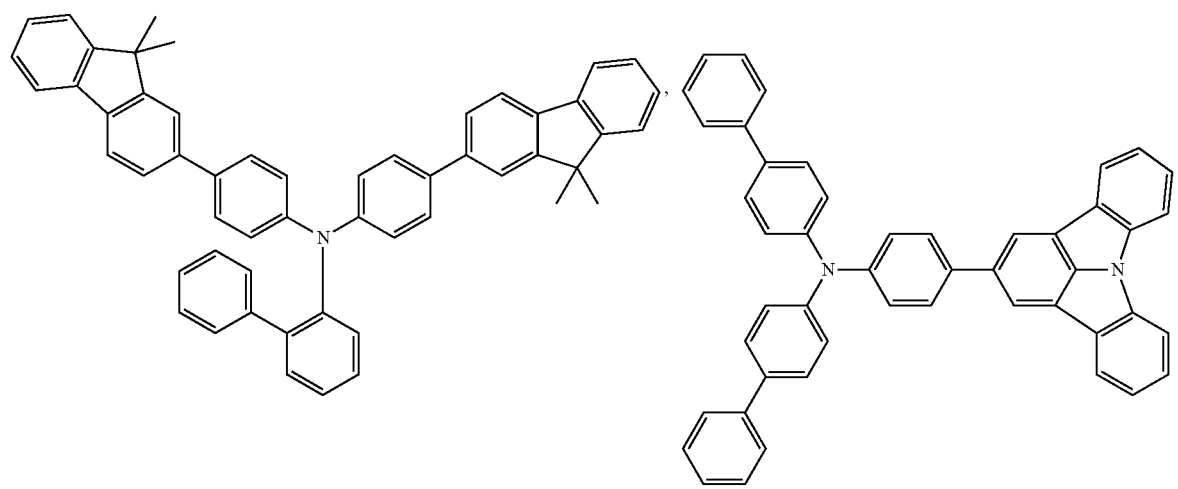
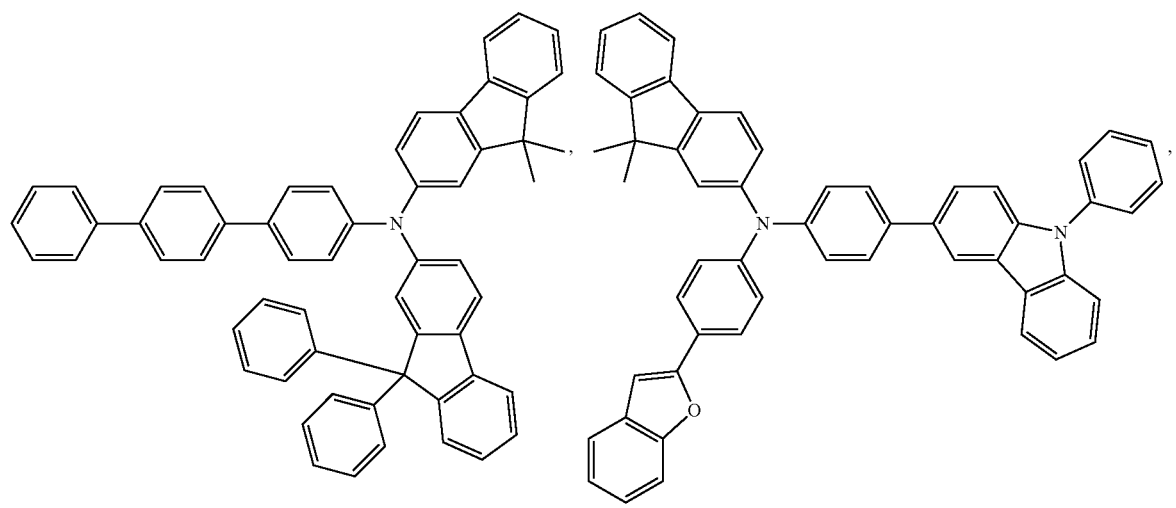

183 184
-continued
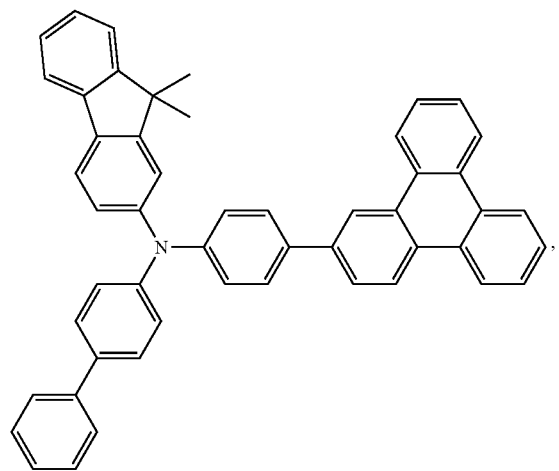
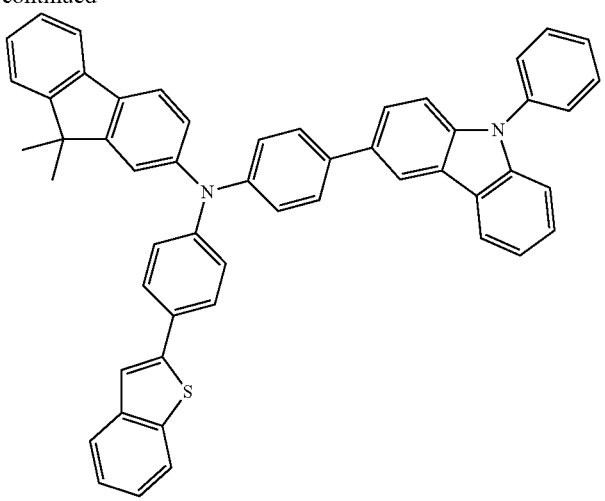
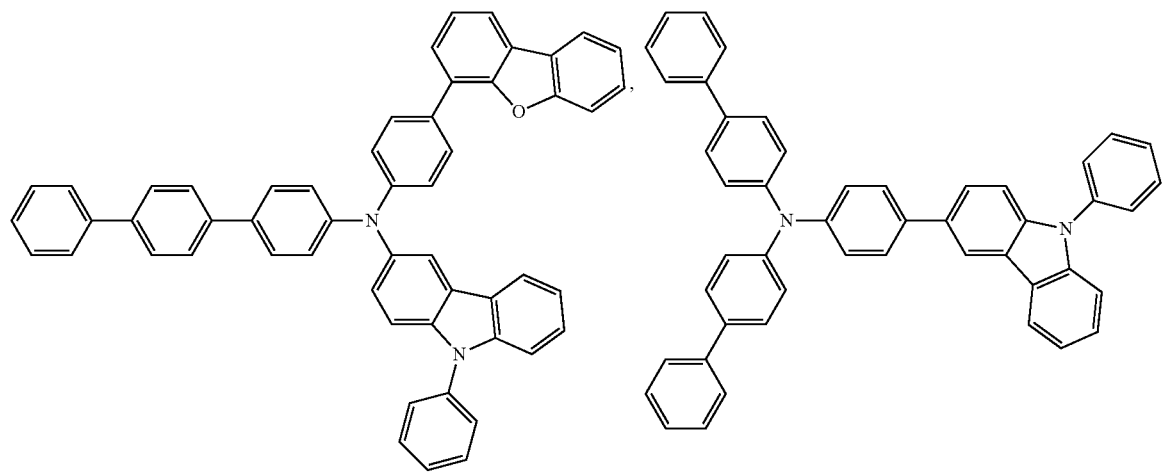
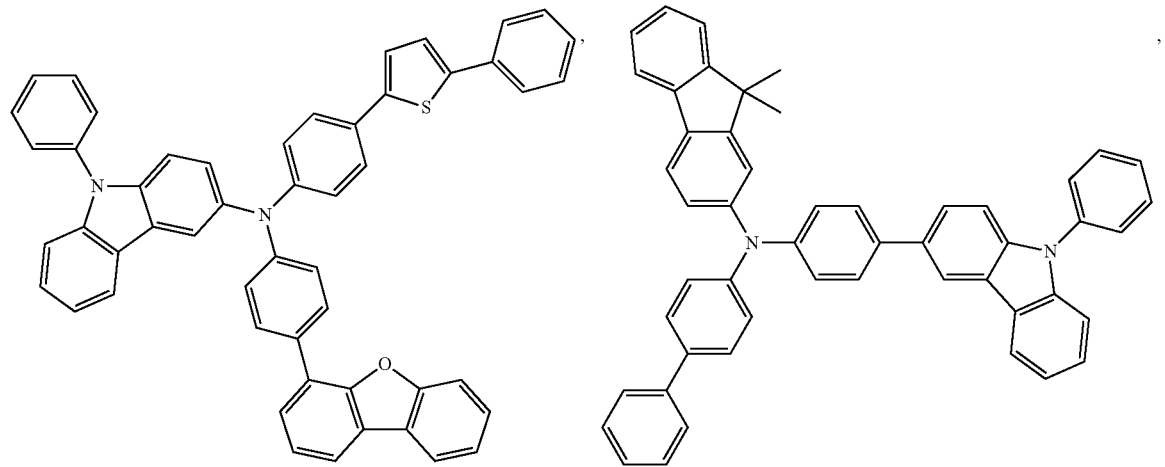

-continued
185
186
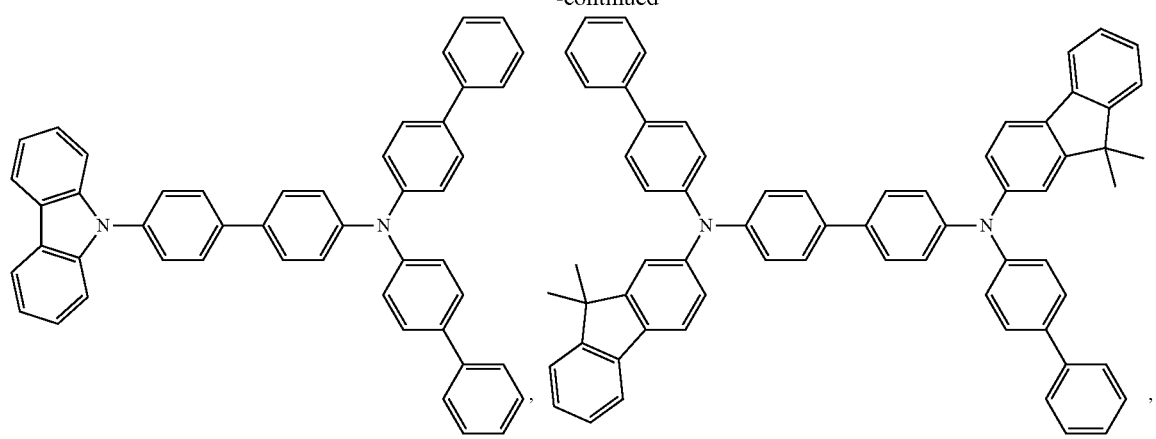
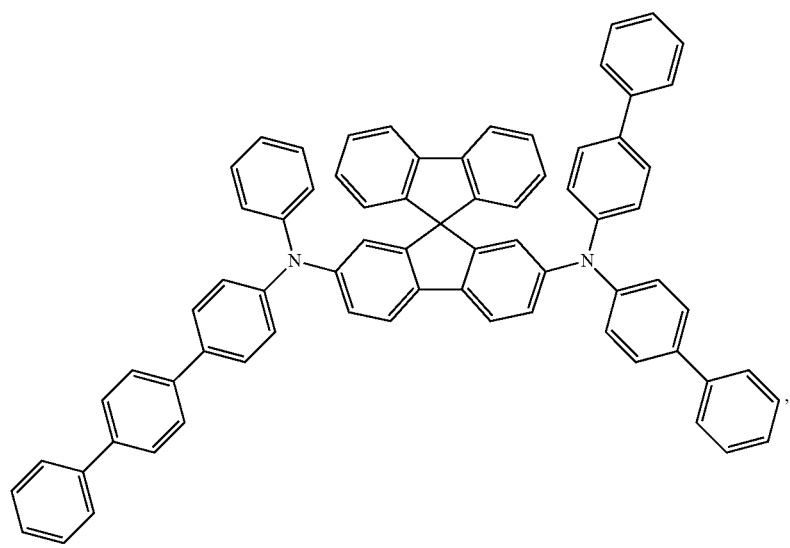
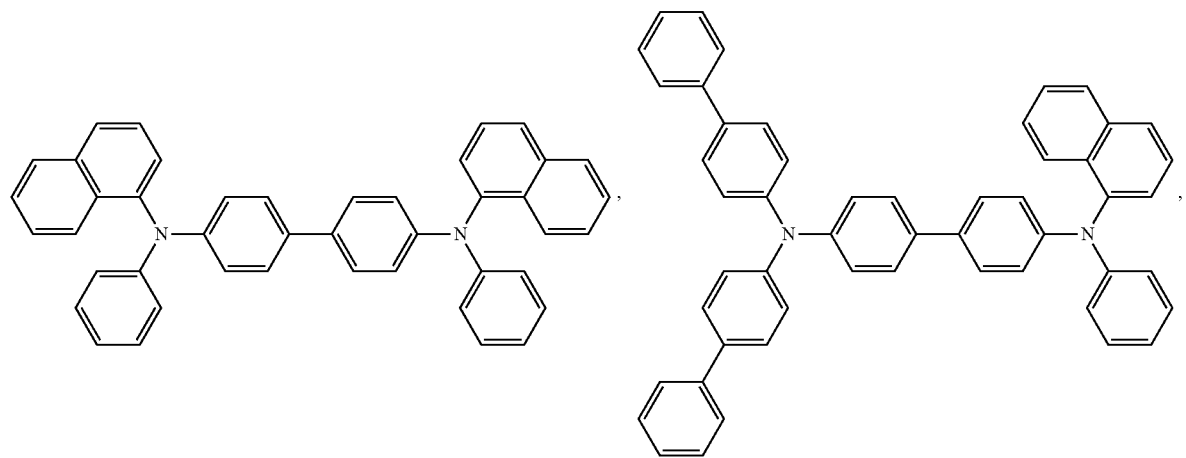

-continued
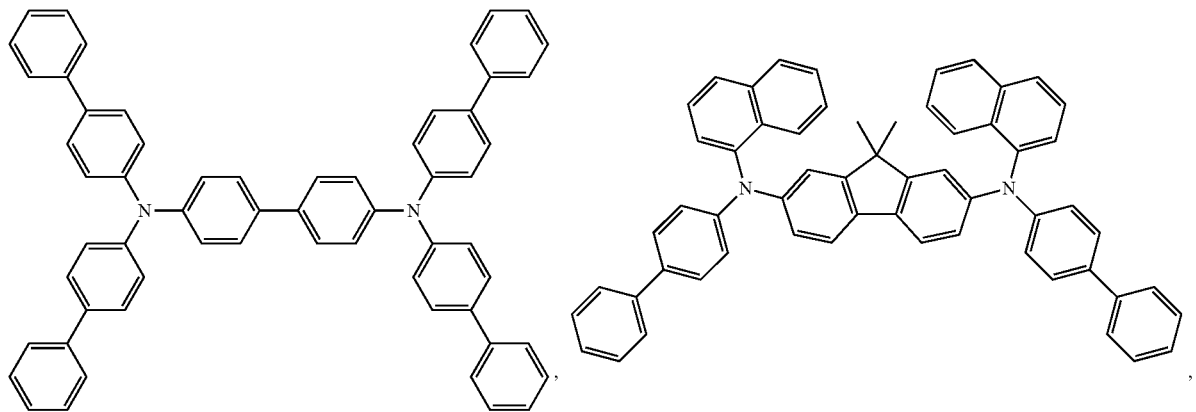
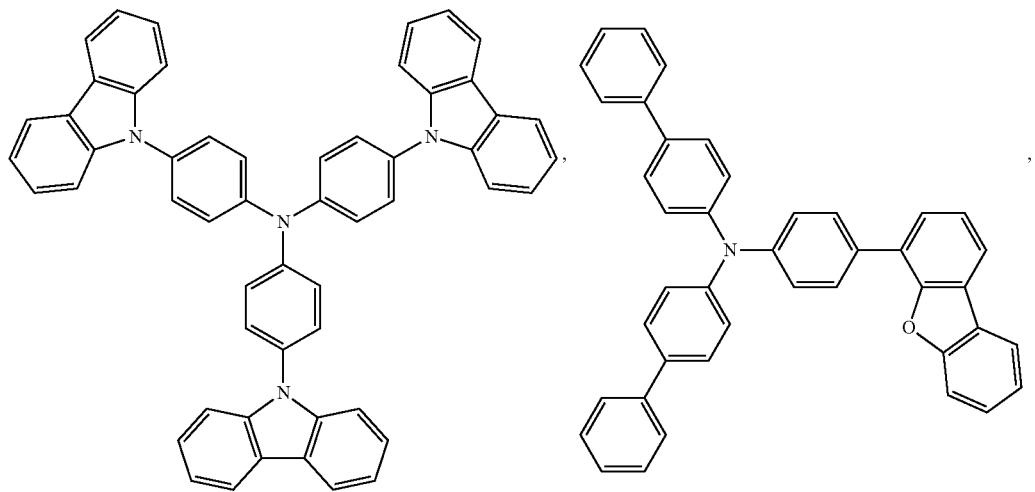
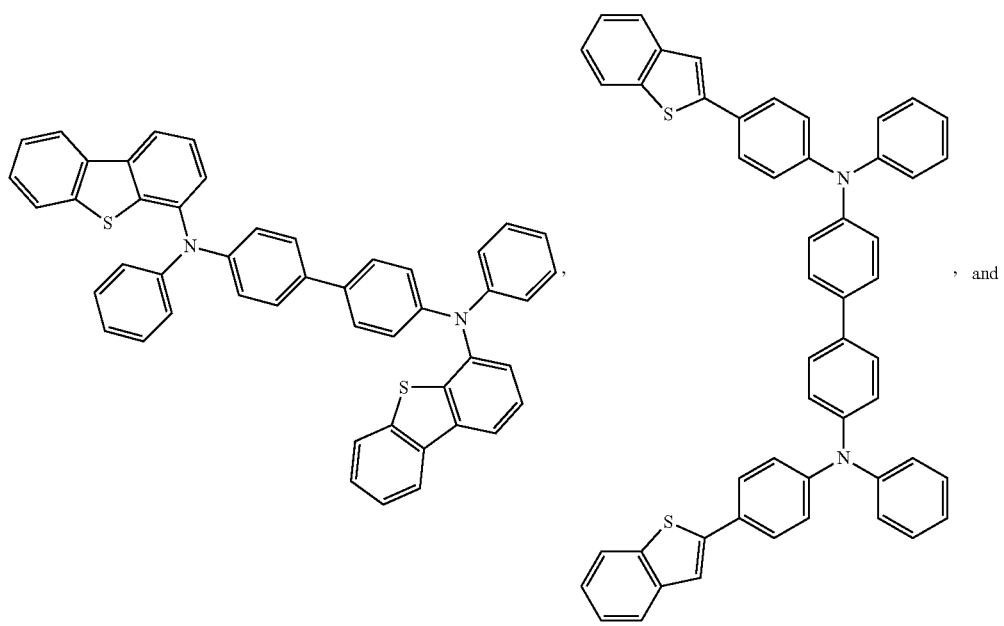

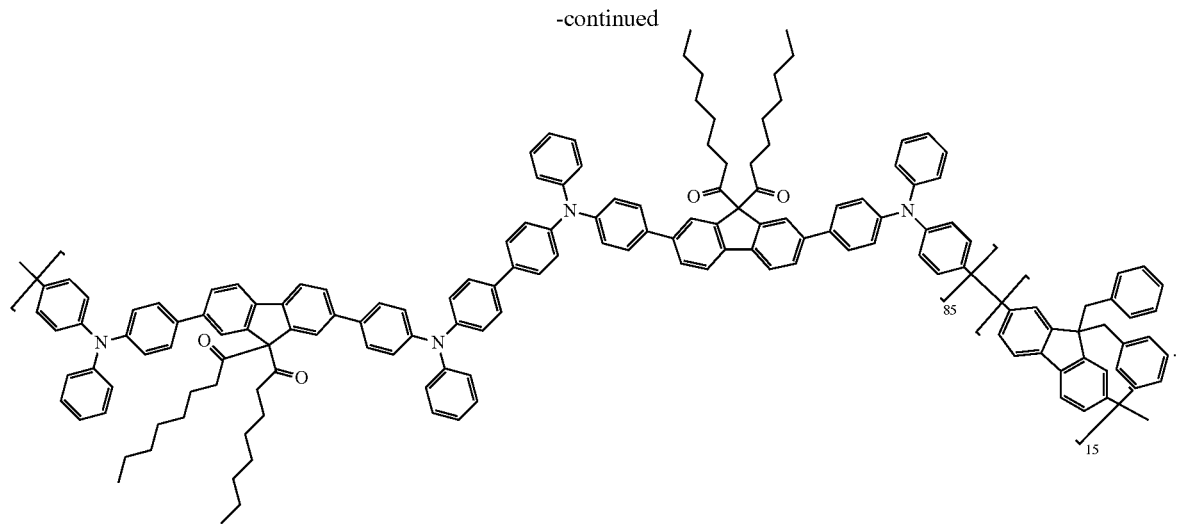

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Additional Hosts:

The light emitting layer of the organic EL device of the present invention preferably contains at least a metal complex as light emitting dopant material, and may contain one or more additional host materials using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

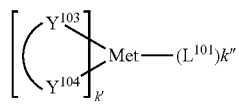

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

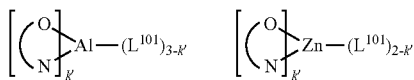

wherein (O—N) is a bidentate ligand, having metal coordinated to atoms O and N.

In another aspect, Met is selected from Ir and Pt. In a further aspect, $(Y^{103}\text{-}Y^{104})$ is a carbene ligand.

Examples of other organic compounds used as additional host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

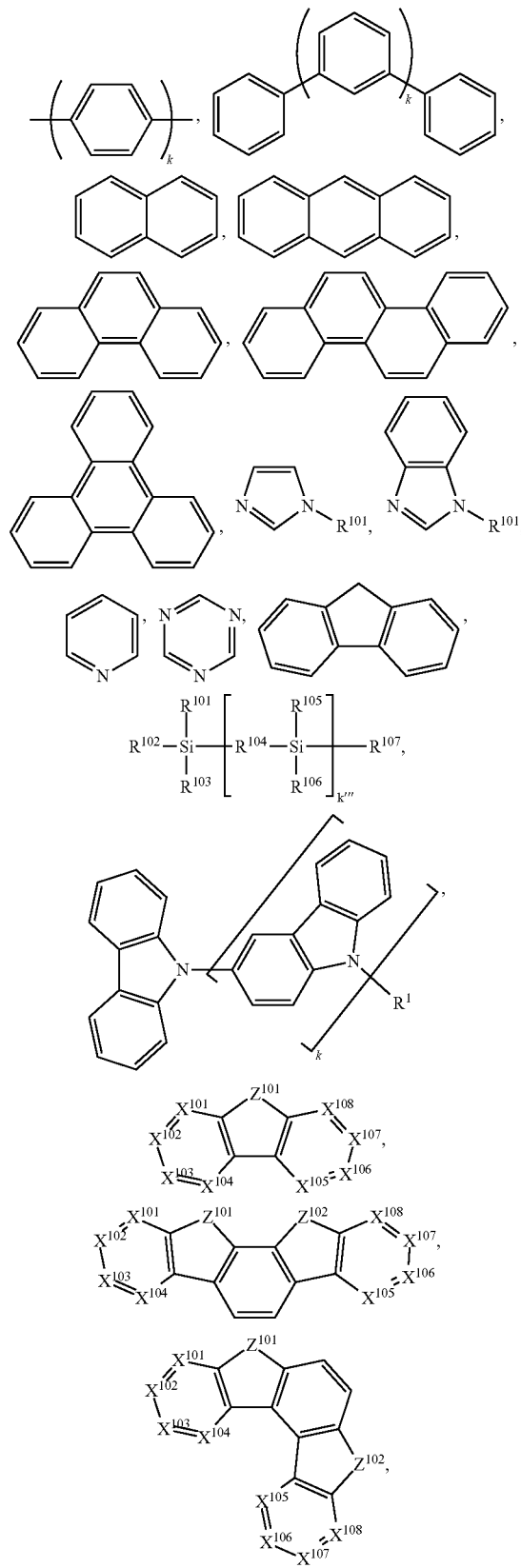
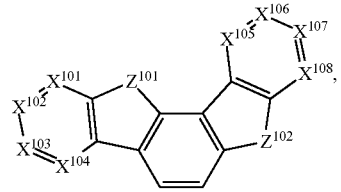
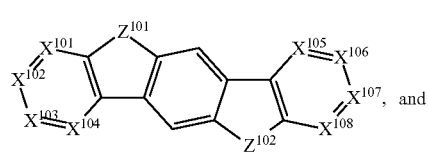
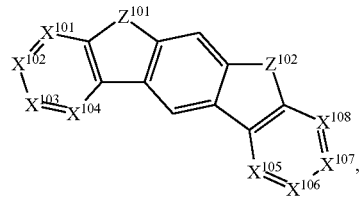

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N.

$Z^{101}$ and $Z^{102}$ is selected from $NR^{101}$, O, or S.

Non-limiting examples of the additional host materials that may be used in an OLED in combination with the host compound disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, US7154114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, 193 194
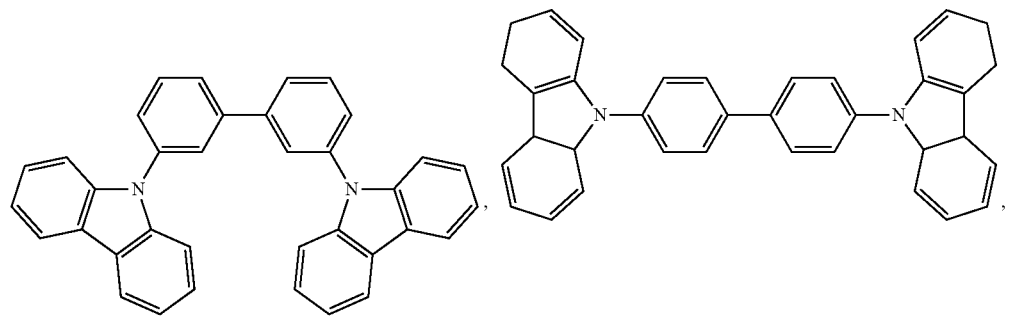
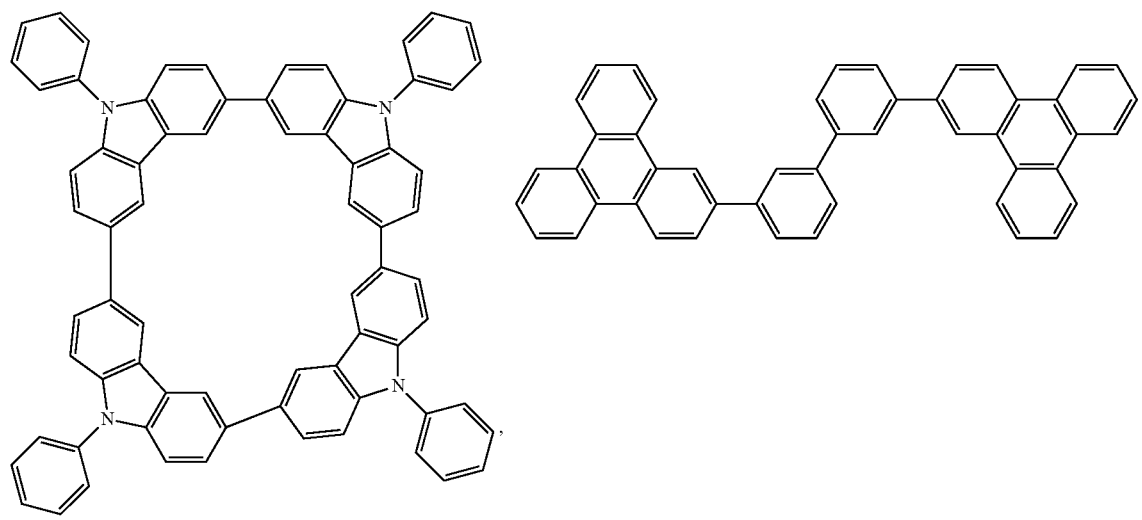
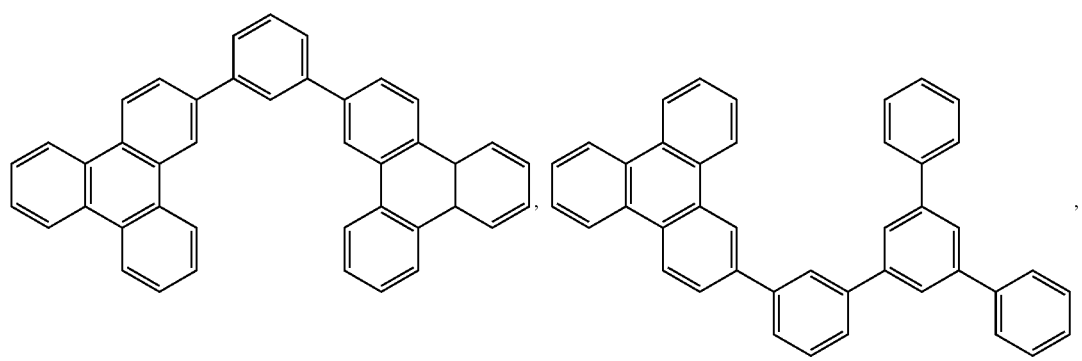
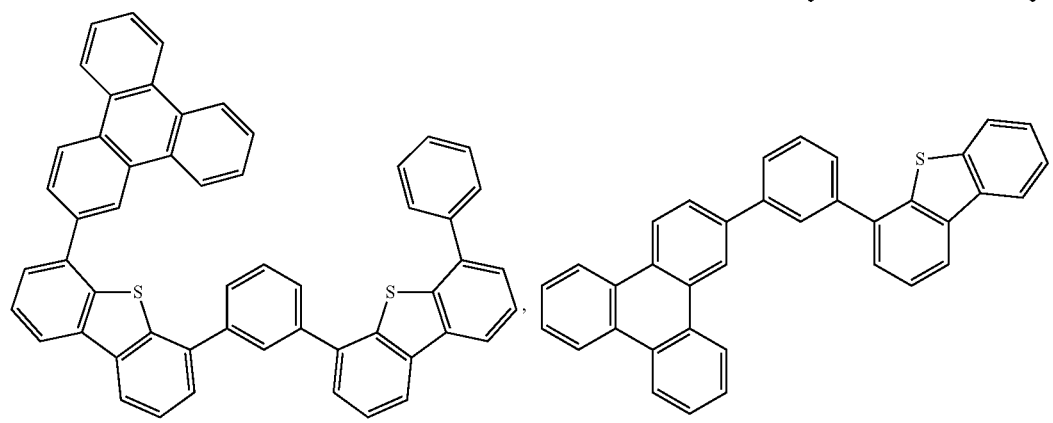

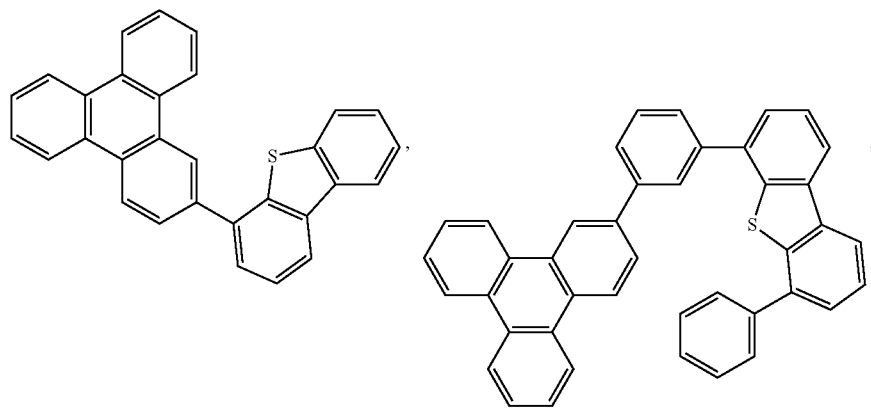
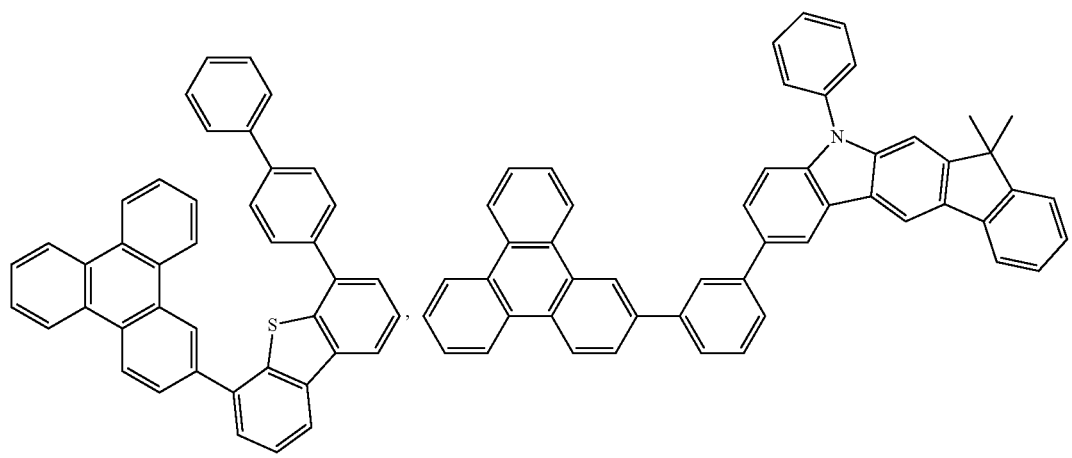
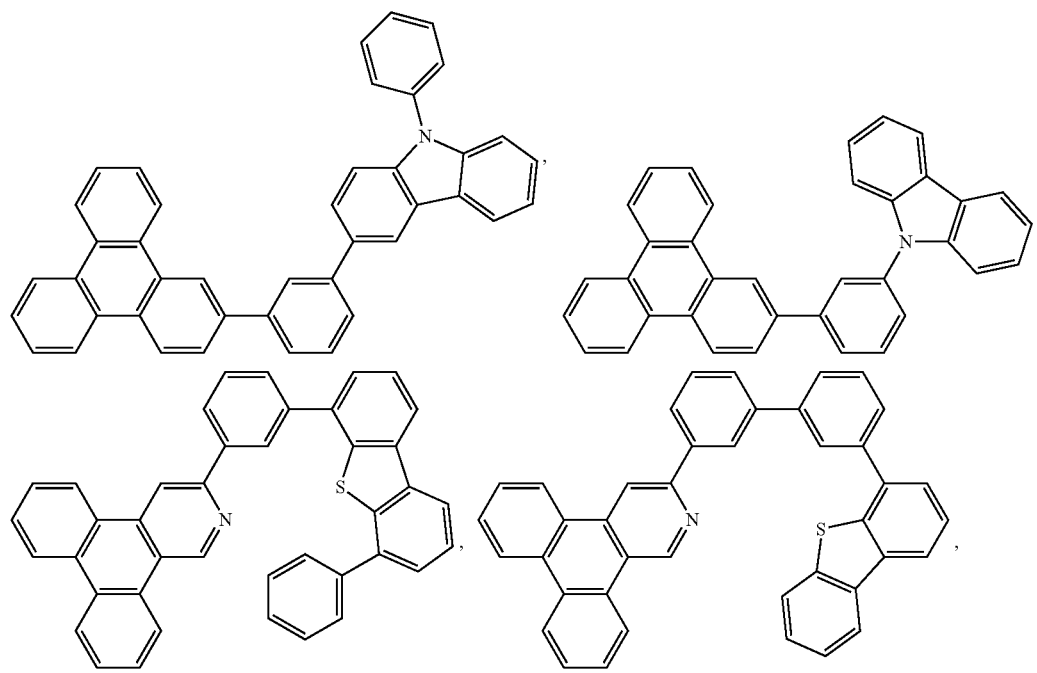

-continued
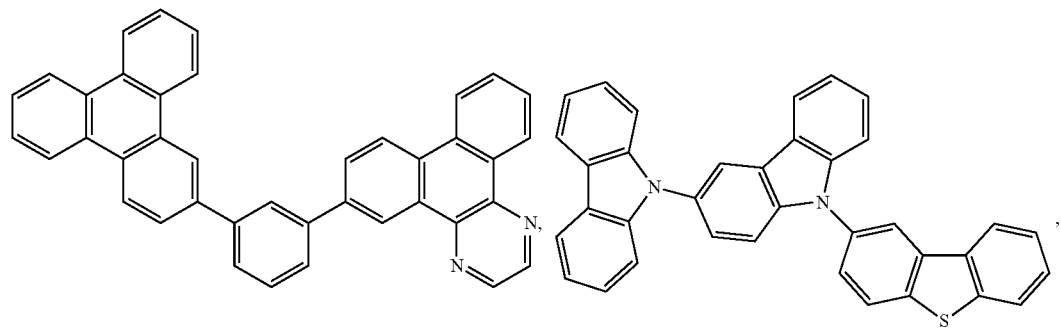
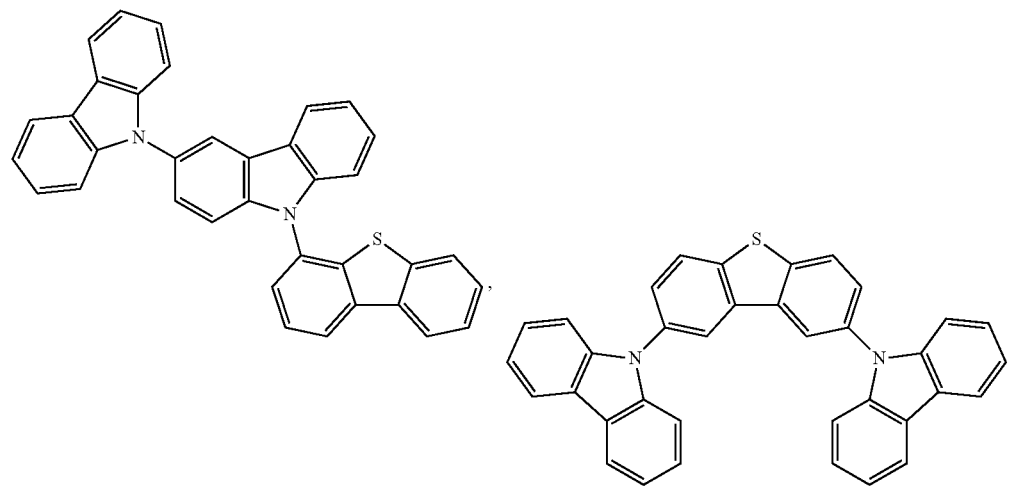
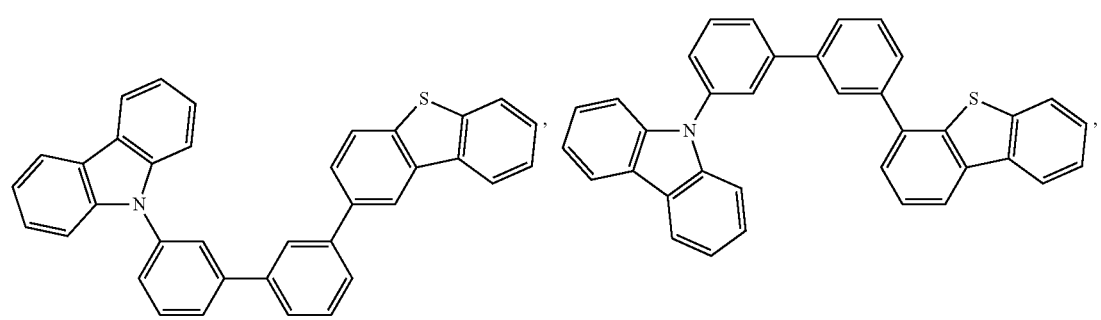
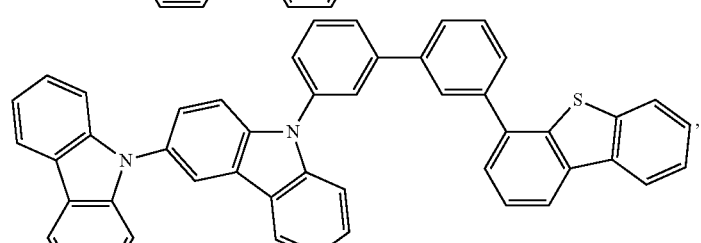
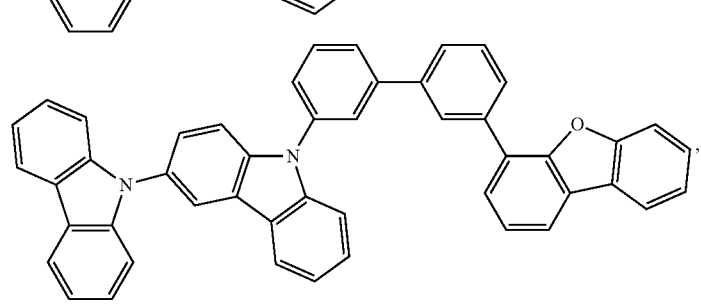

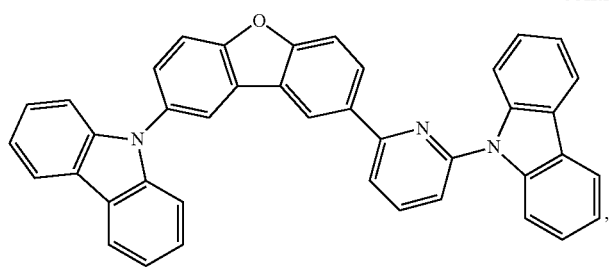
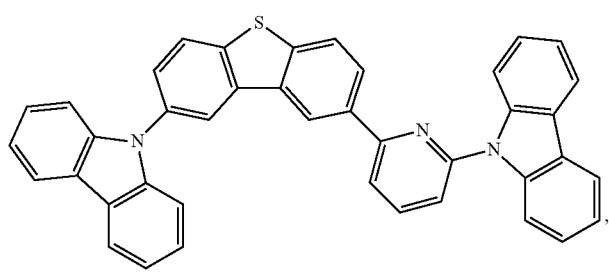
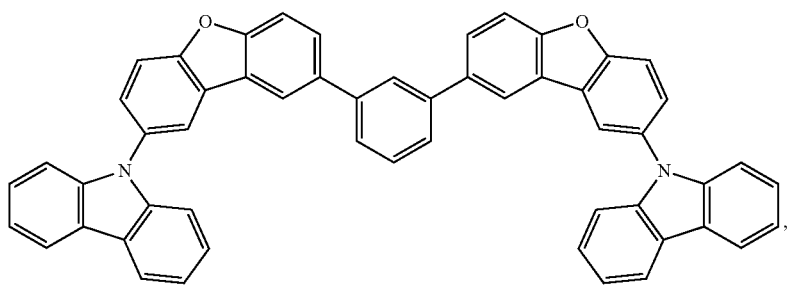
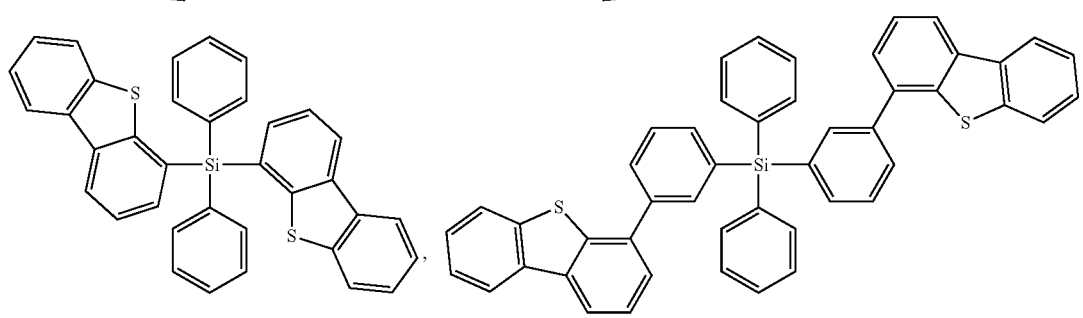
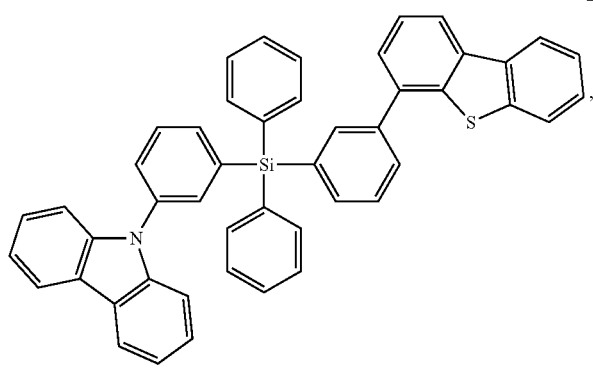

-continued
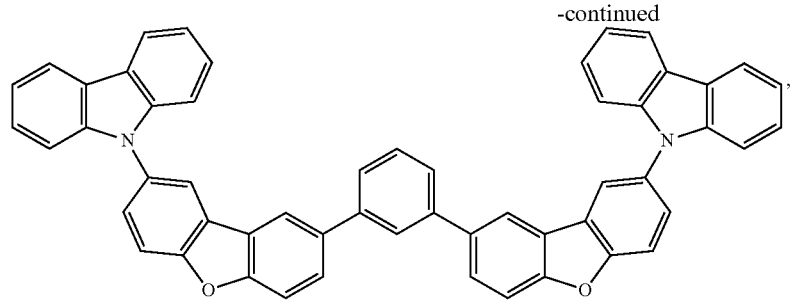
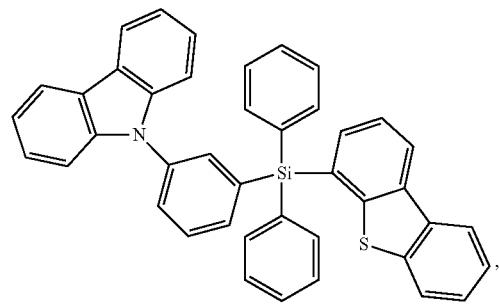
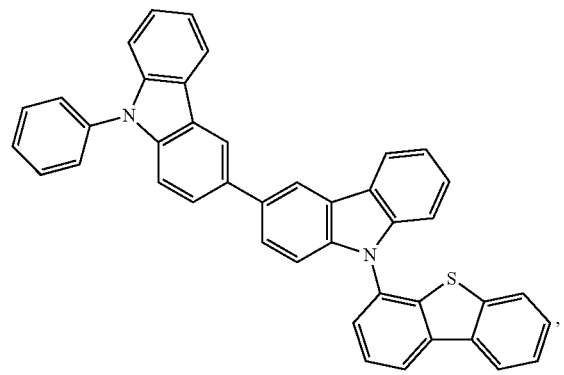
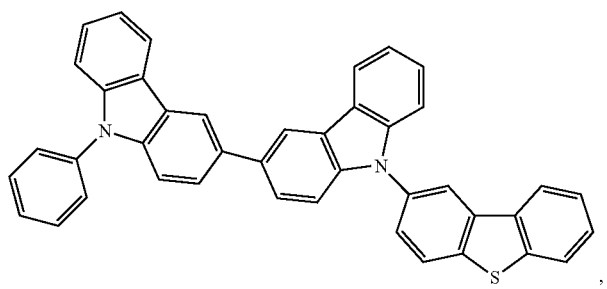
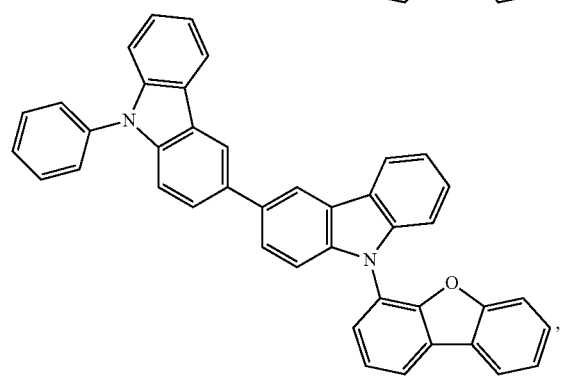
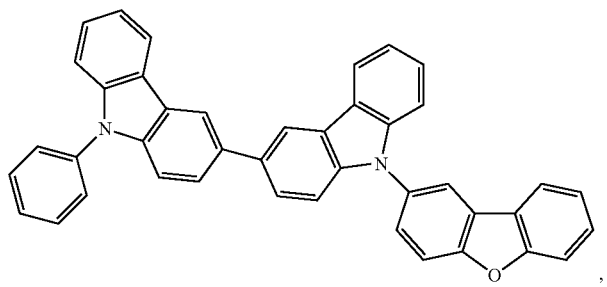
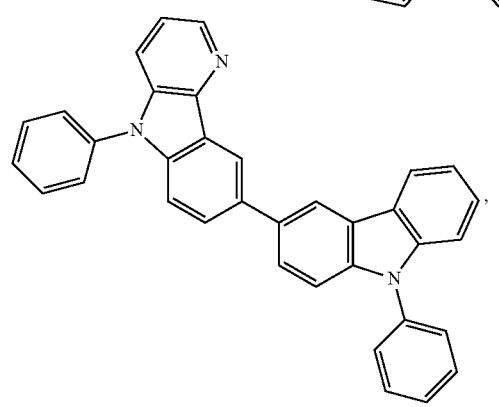
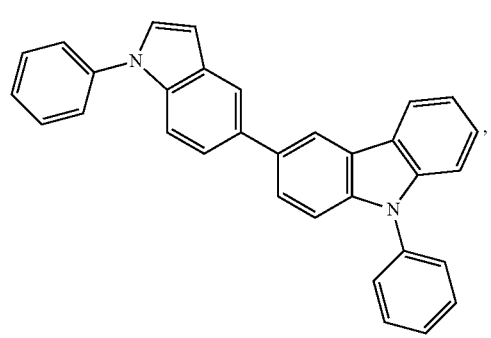

-continued
203 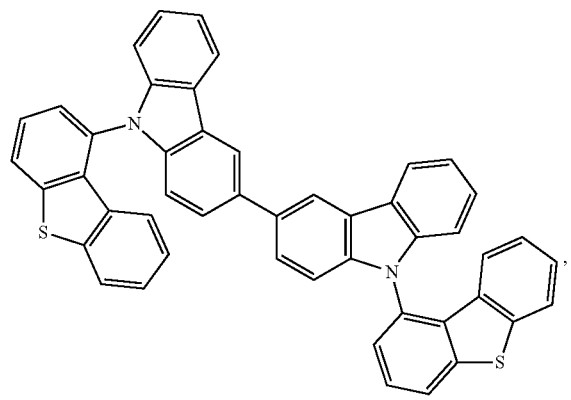
204 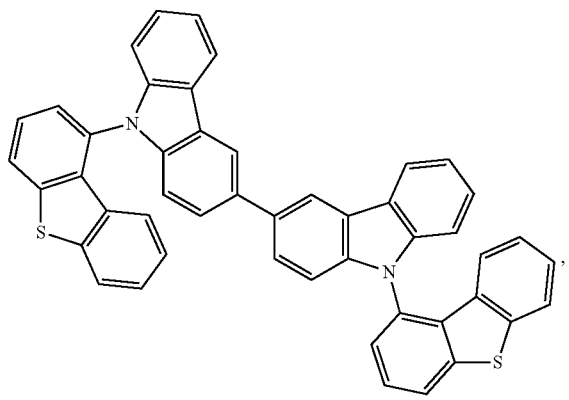
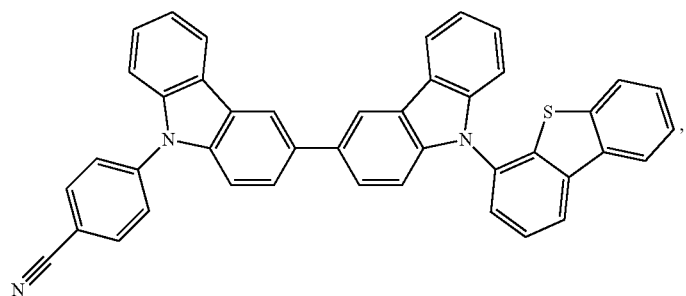
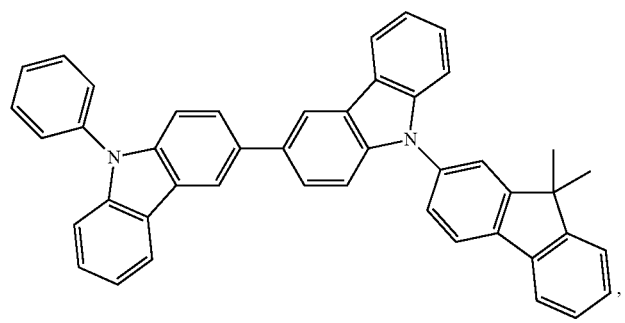
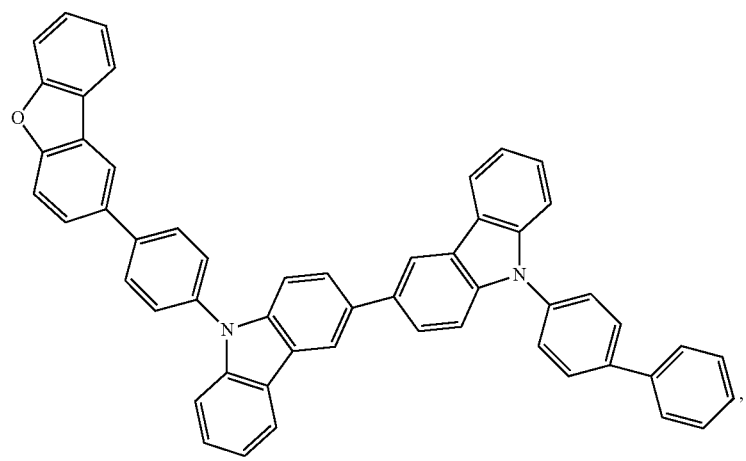

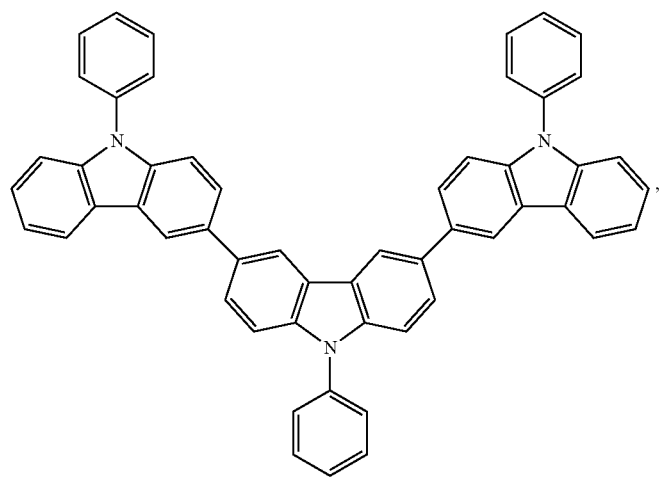
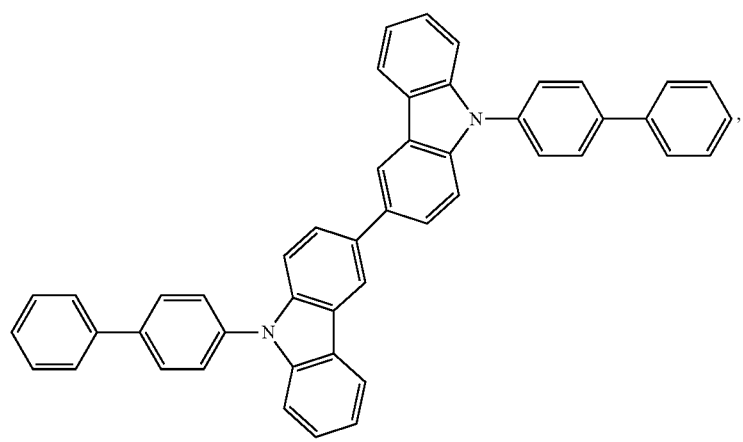
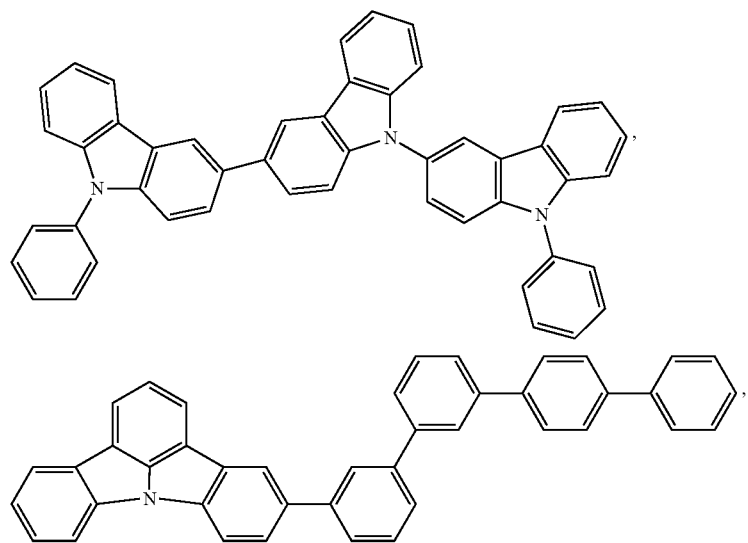

-continued
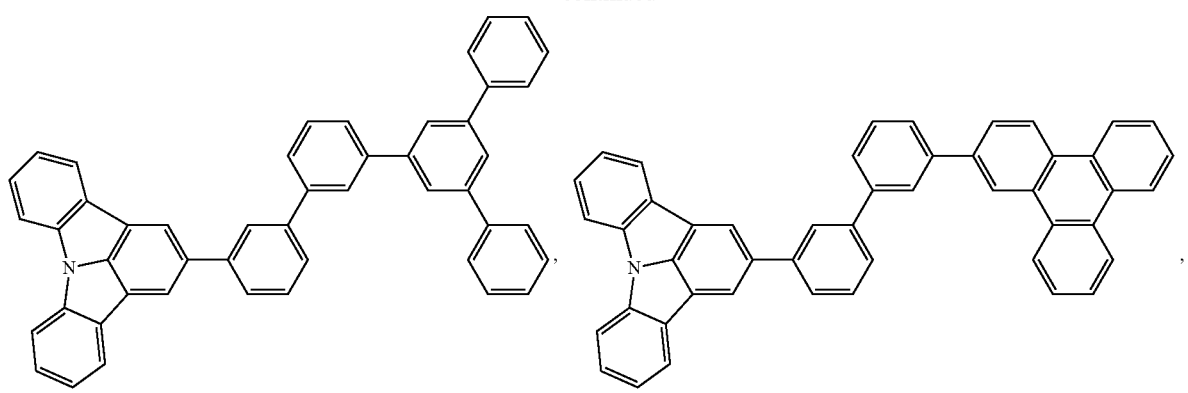
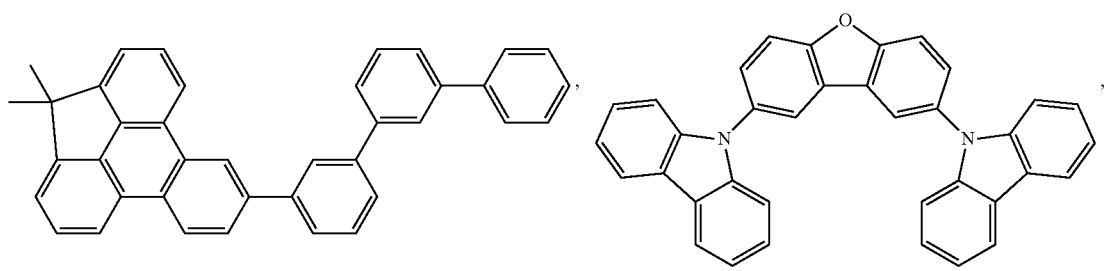
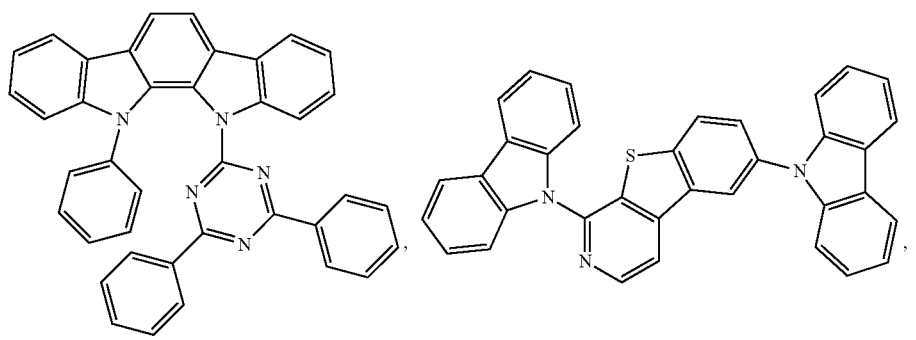
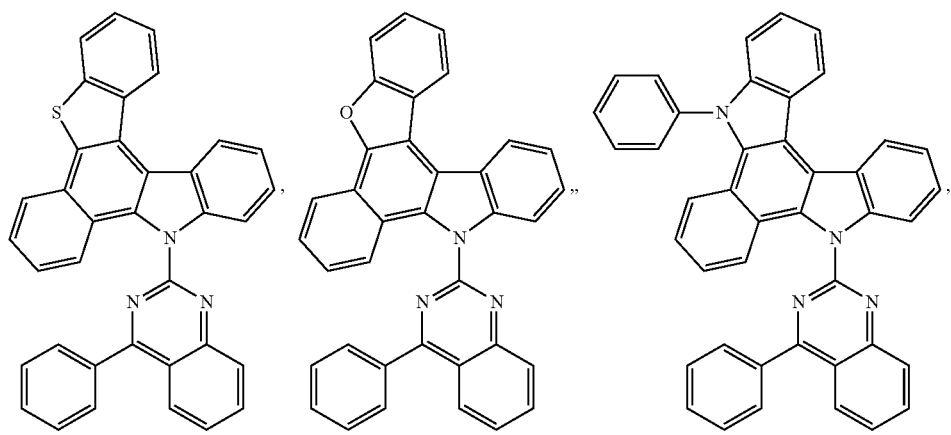

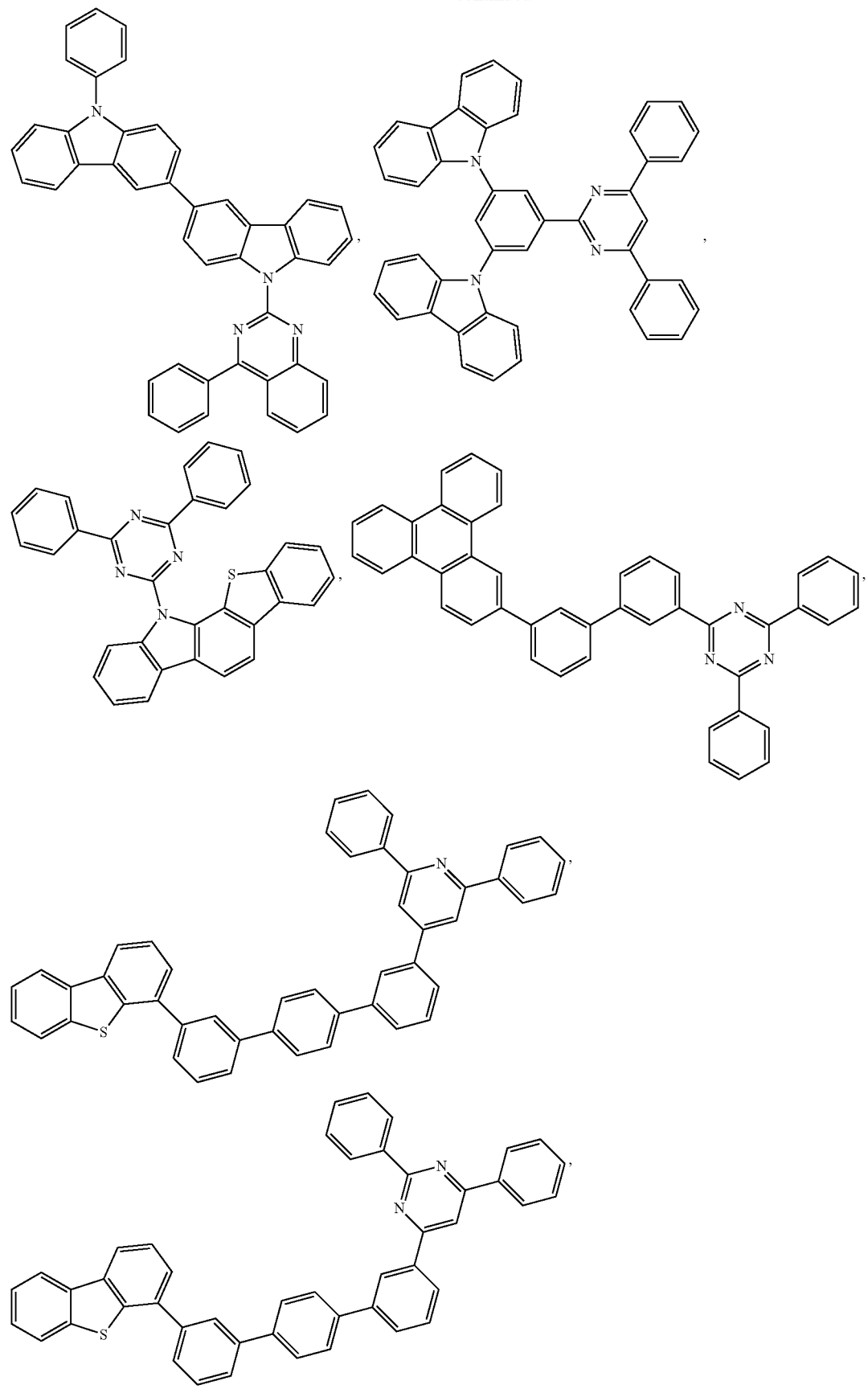

-continued
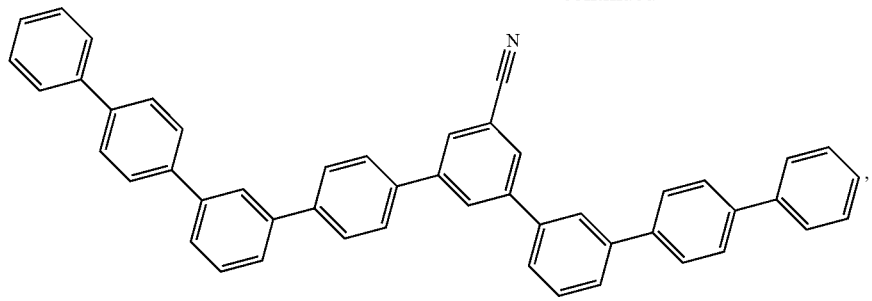
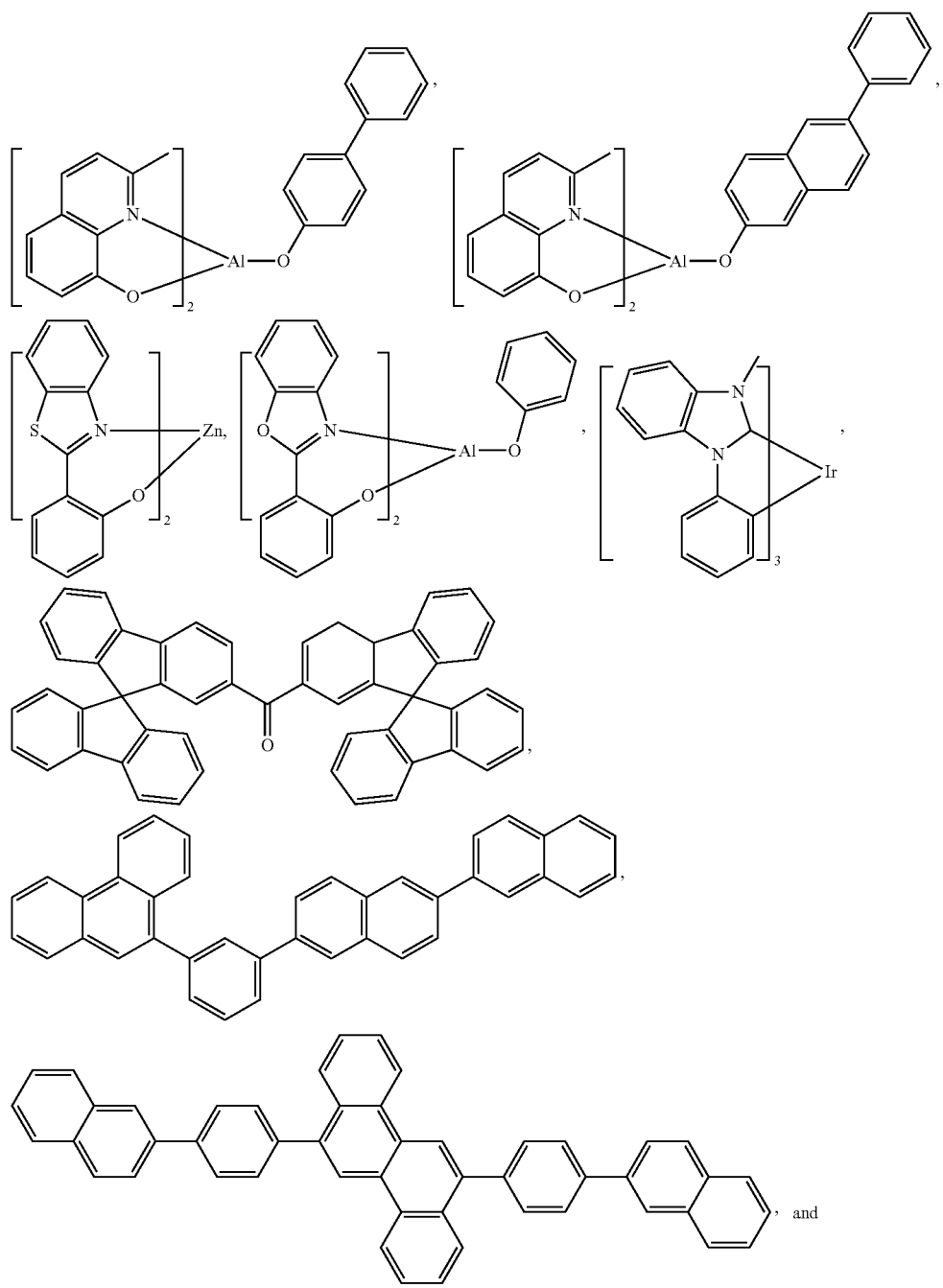

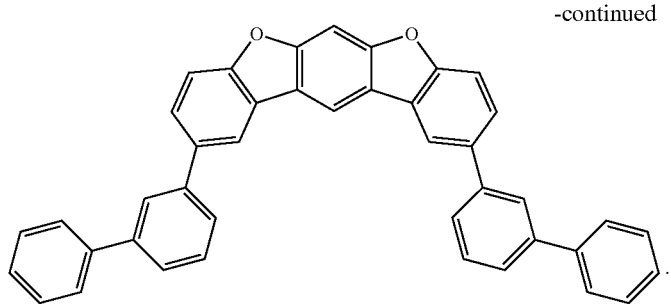

Emitter:

An emitter example is not particularly limited, and any compound may be used as long as the compound is typically used as an emitter material. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450,

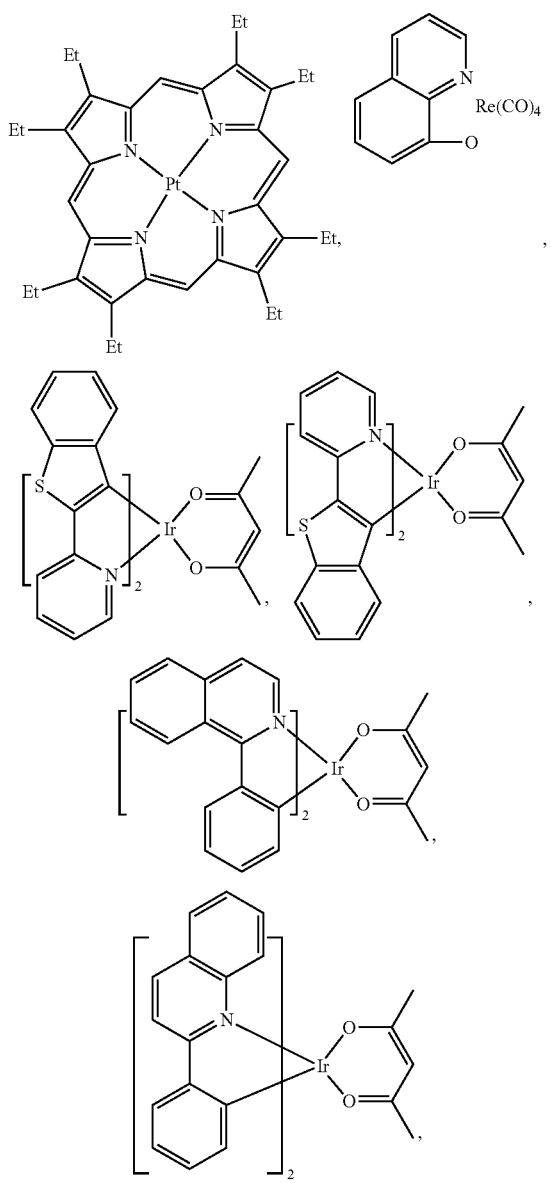

-continued
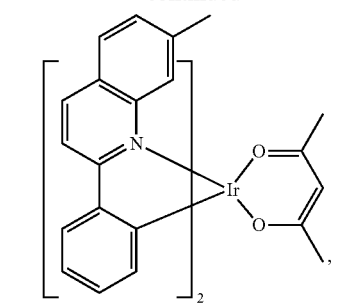
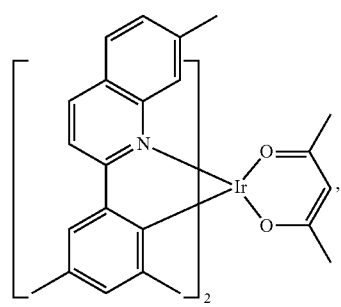
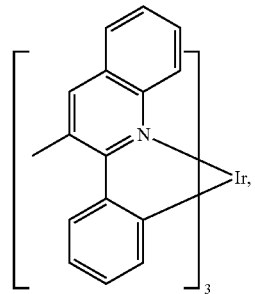
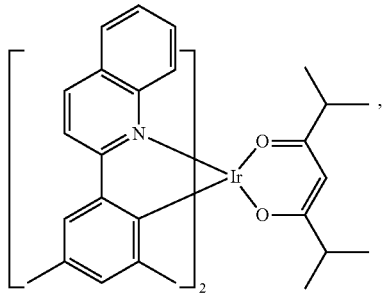
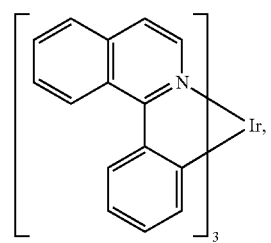
-continued
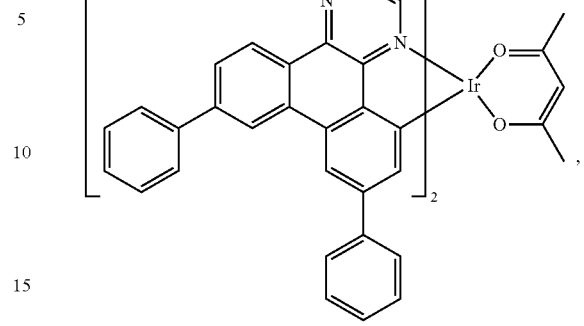
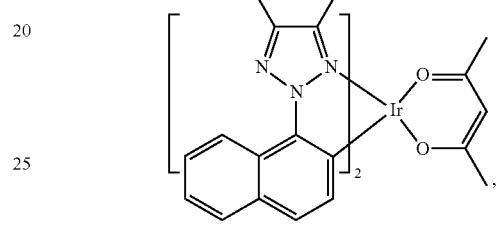
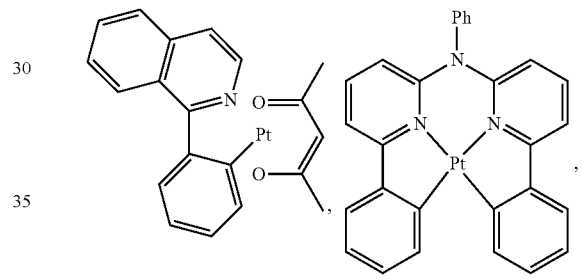
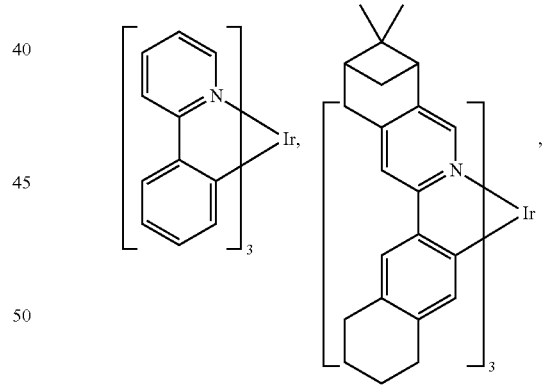
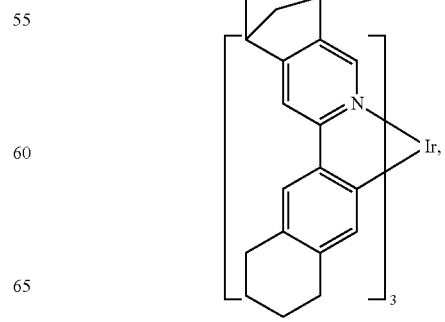

217
-continued
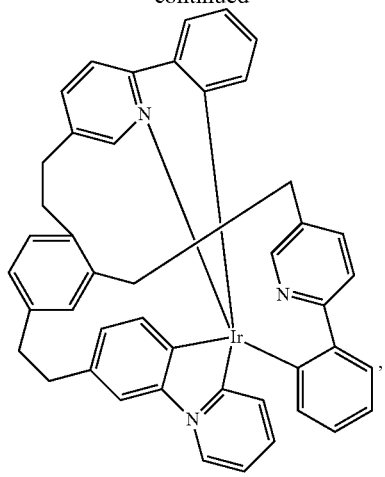
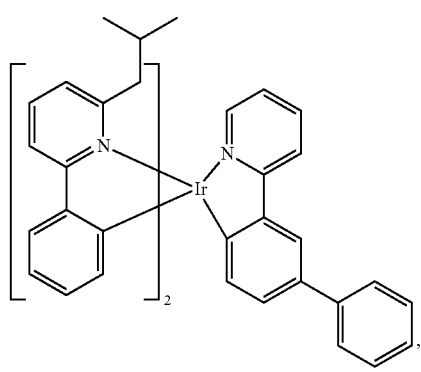
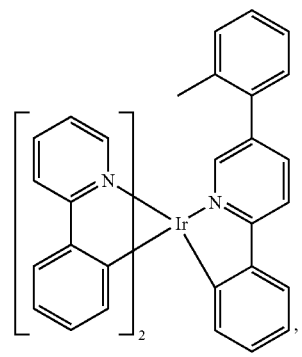
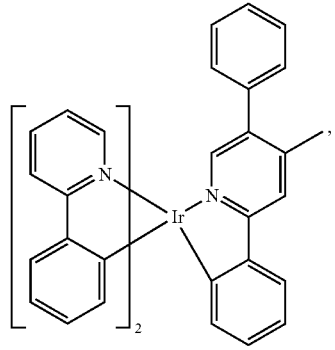
218
-continued
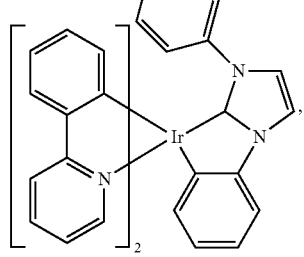
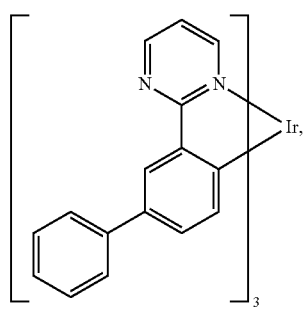
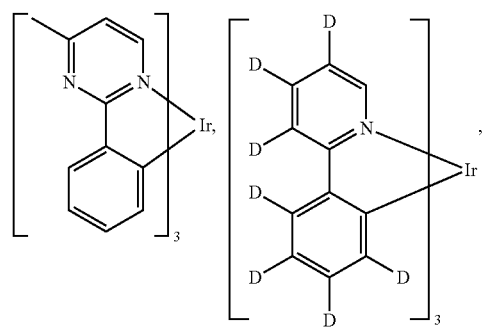
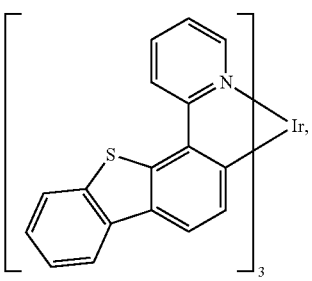
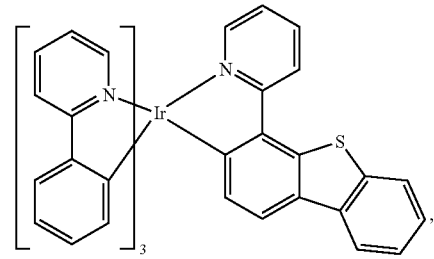

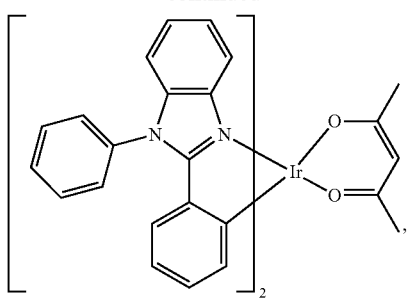
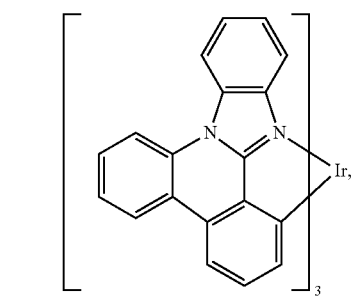
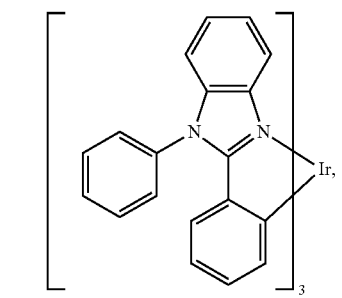
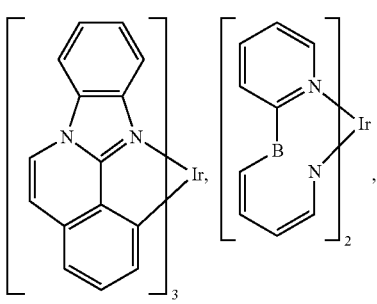
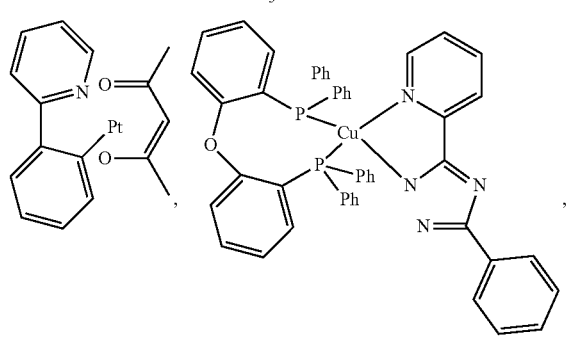
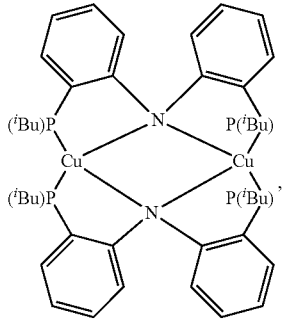
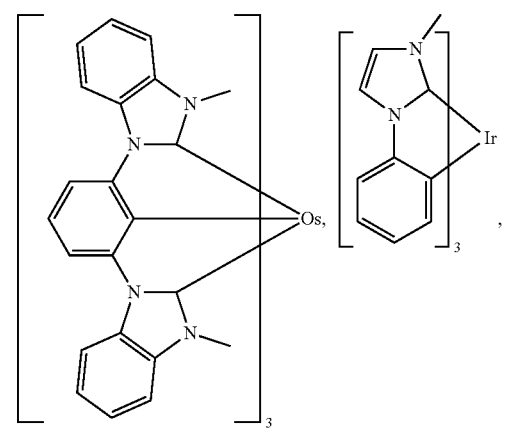
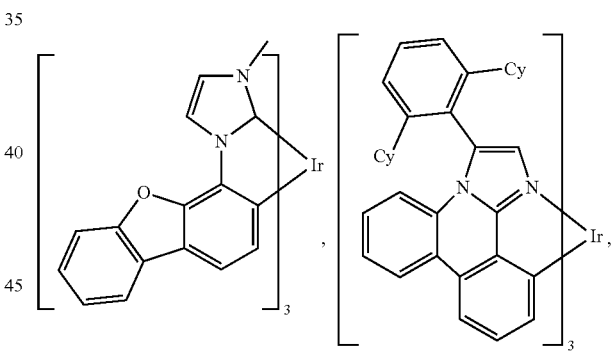
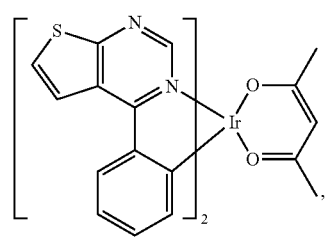
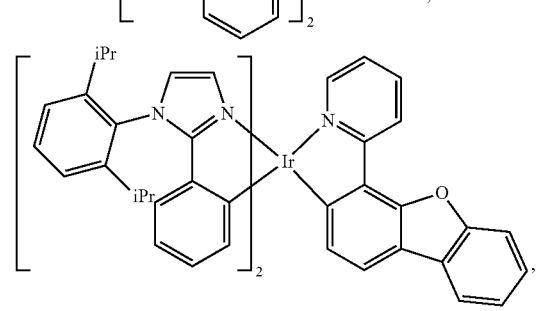

221
-continued
222
-continued
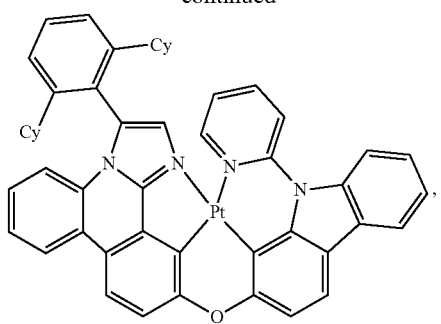
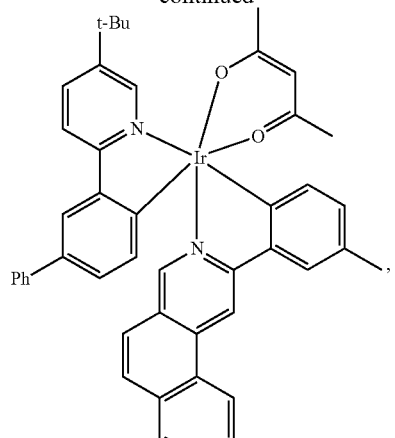
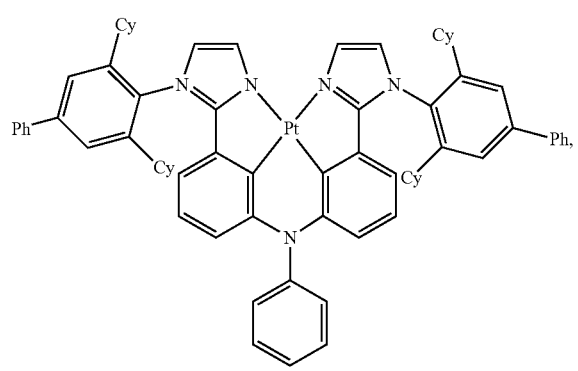
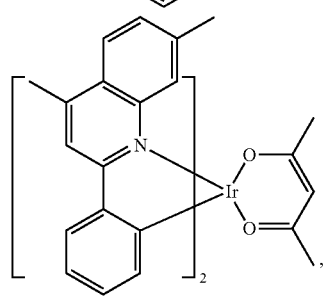
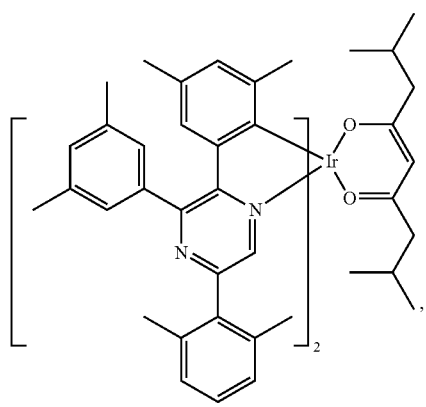
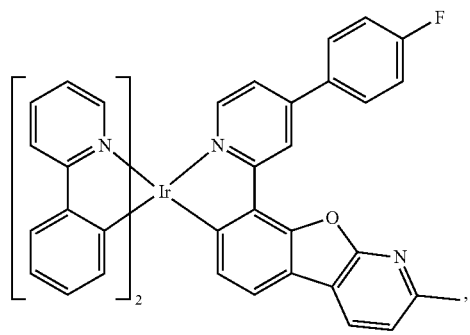
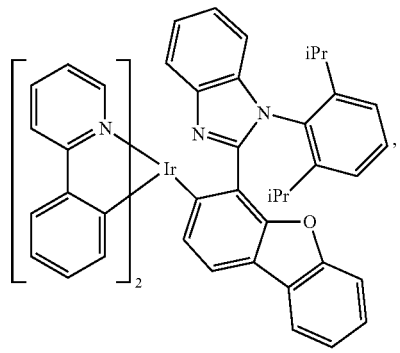
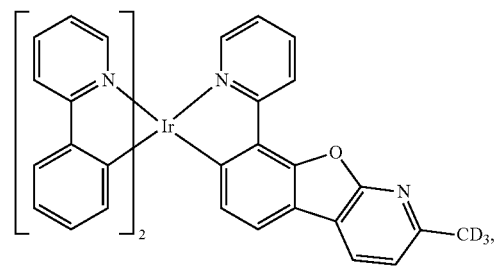
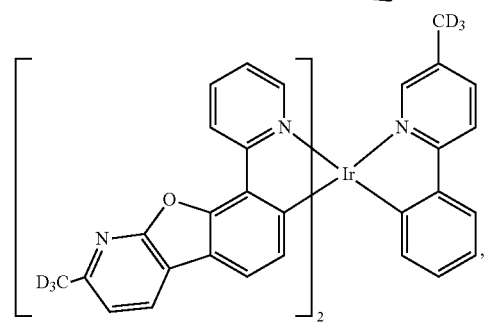

223
-continued
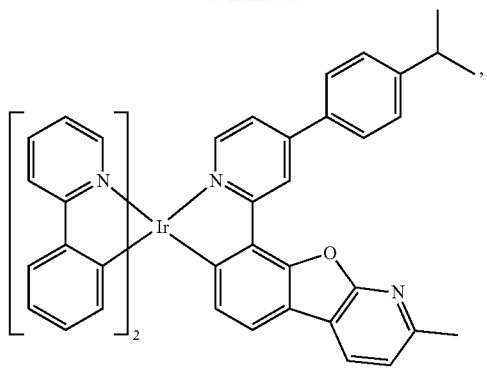
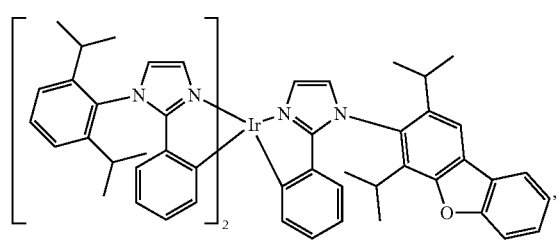
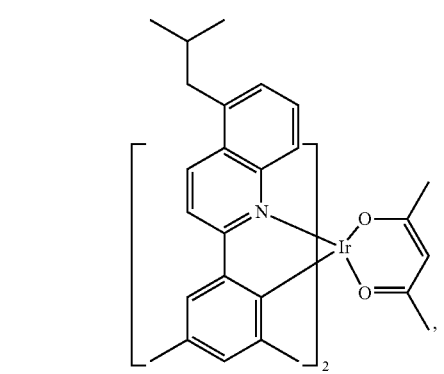
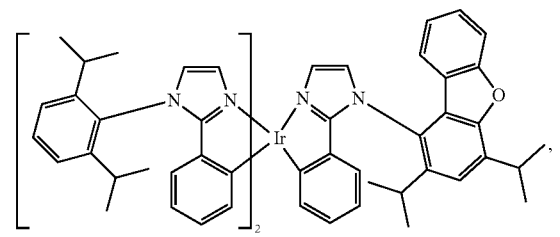
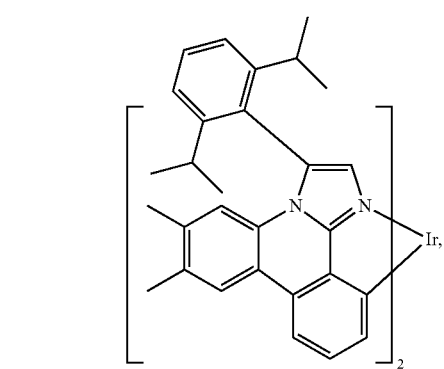
224
-continued
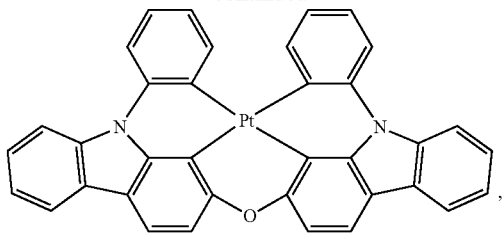
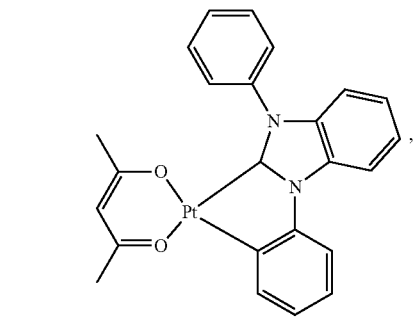
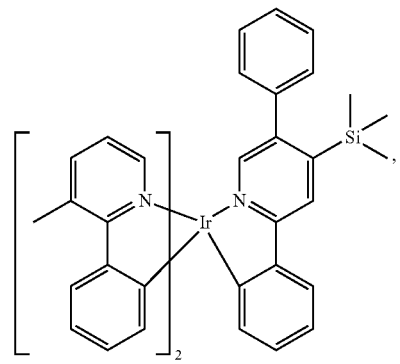
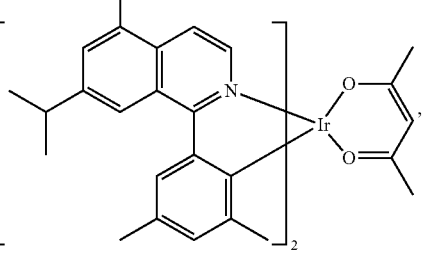
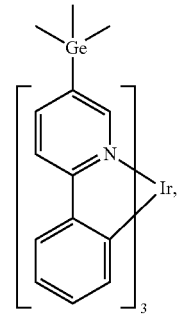

225
-continued
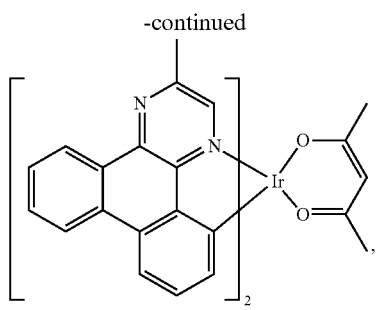
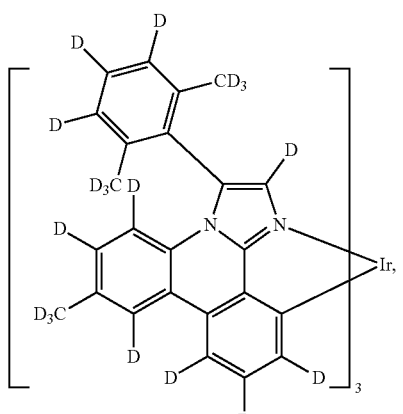
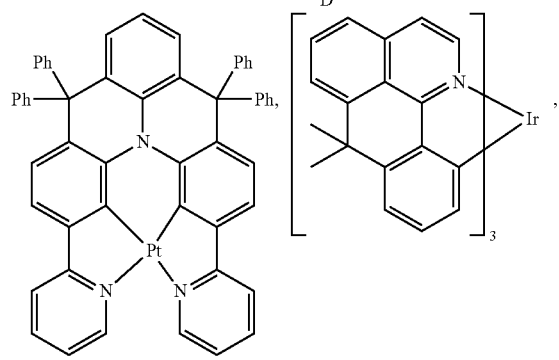
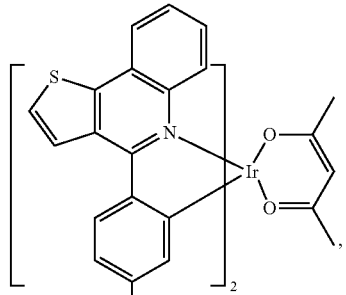
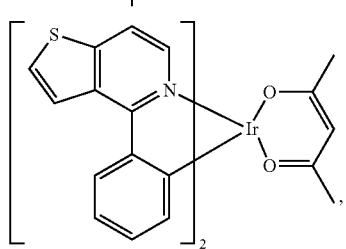
226
-continued
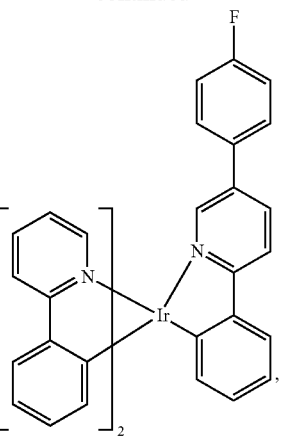
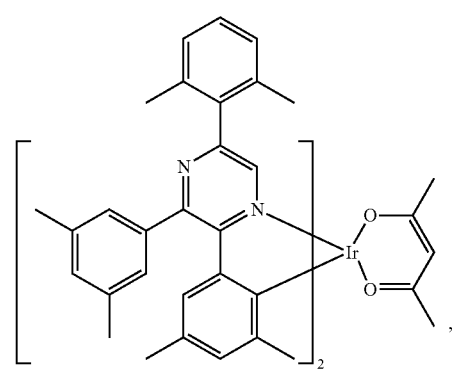
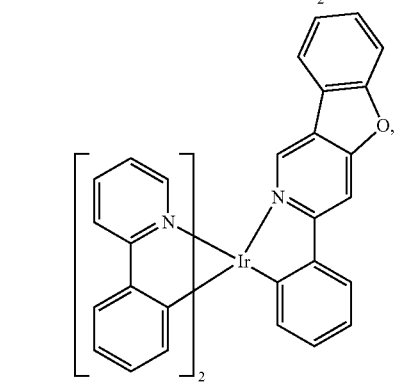
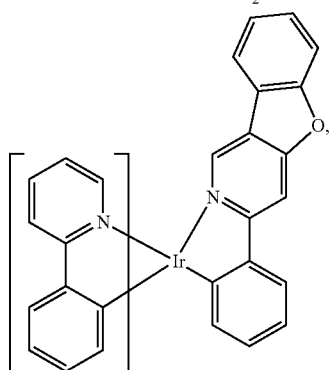
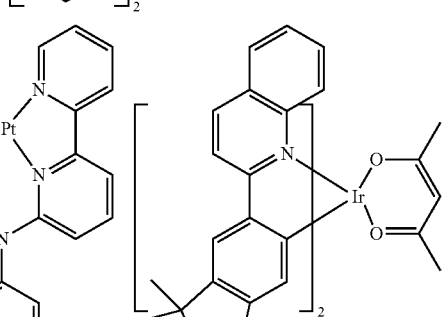
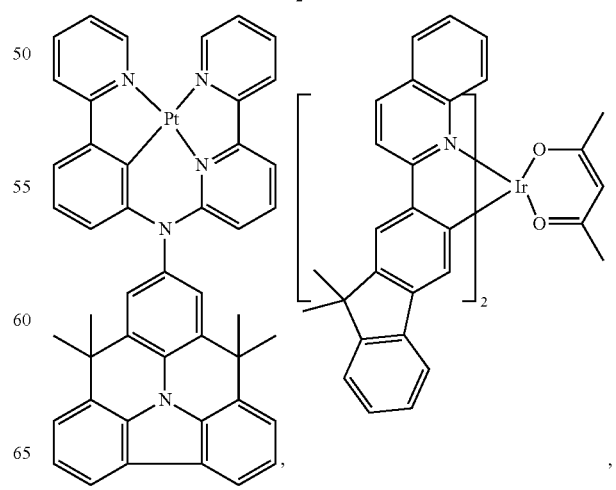

227
-continued
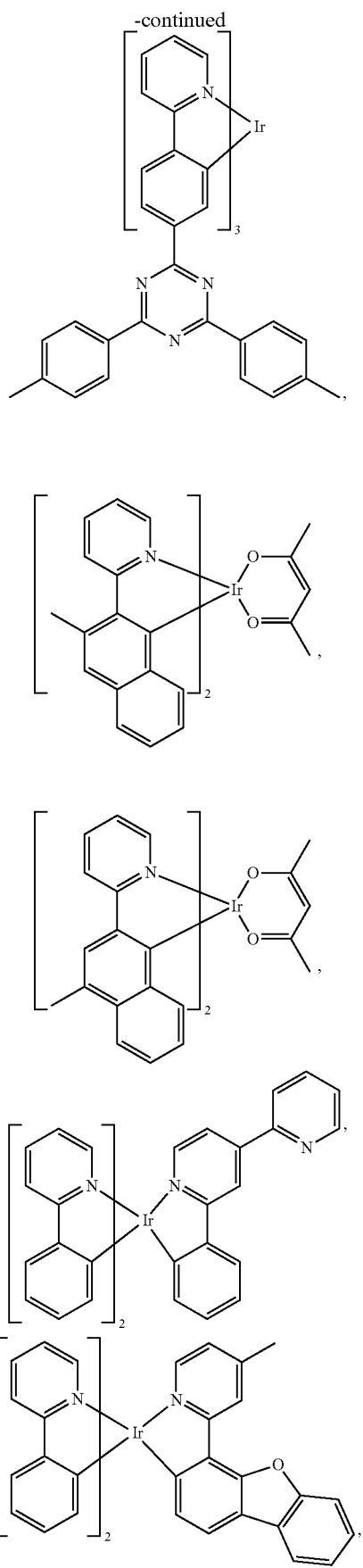
228
-continued
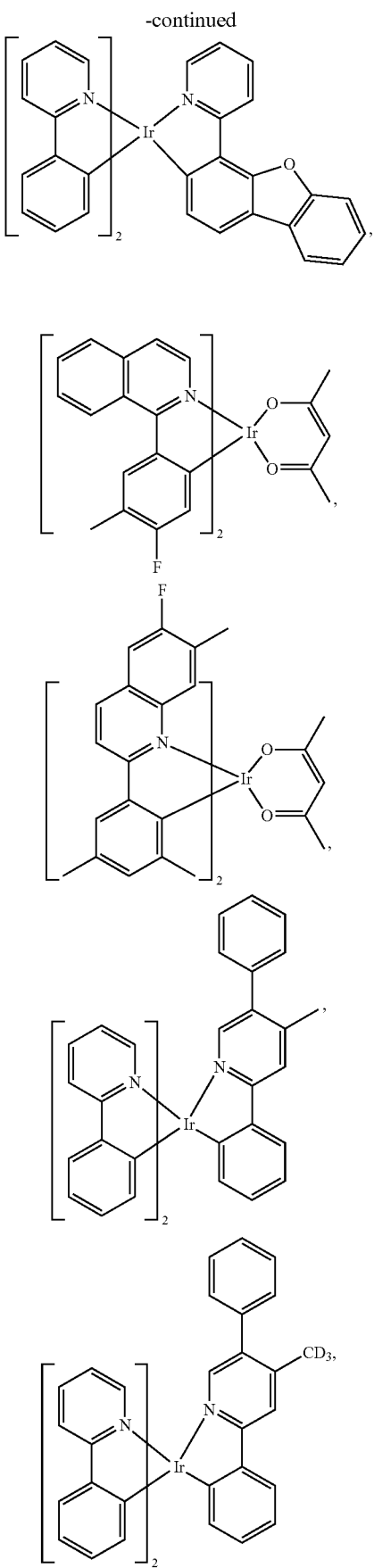

229
-continued
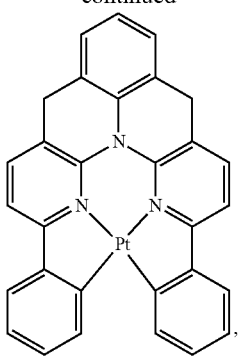
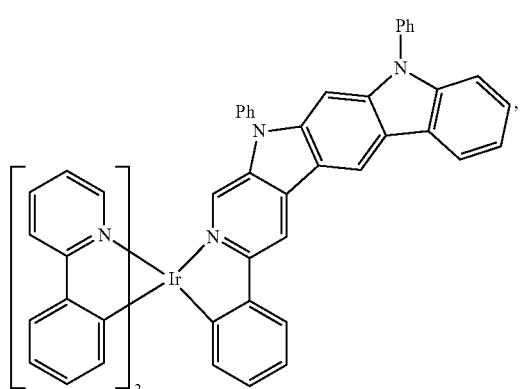
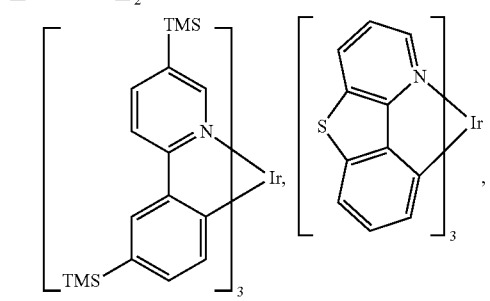
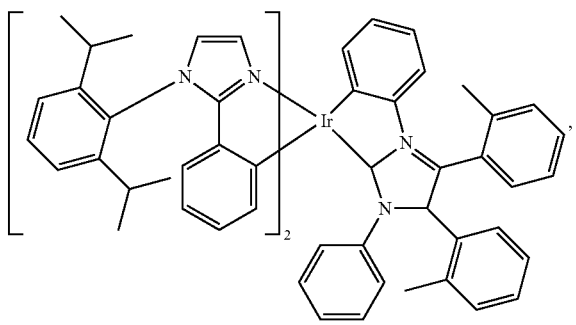
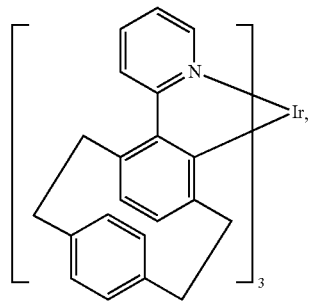
230
-continued
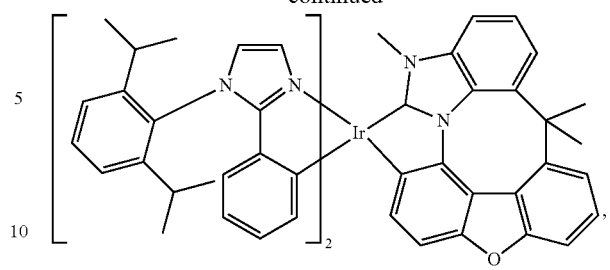
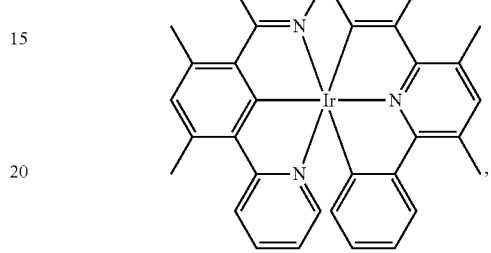
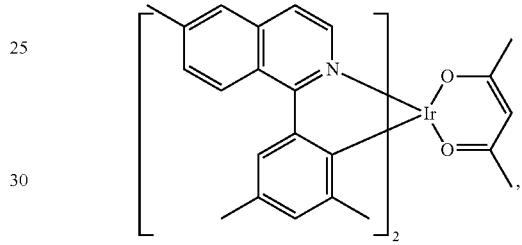
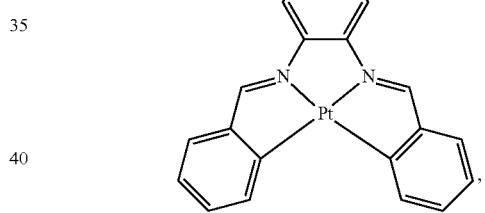
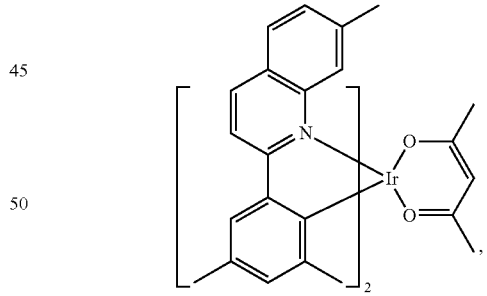
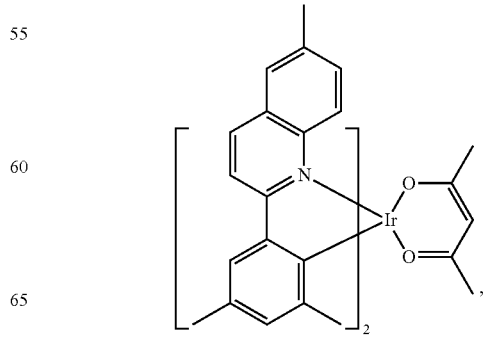

231
-continued
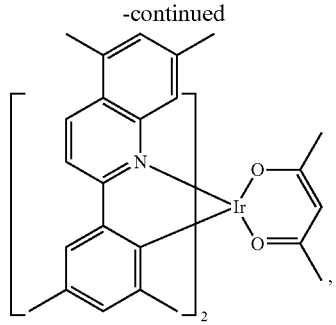
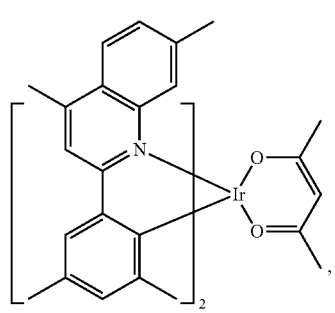
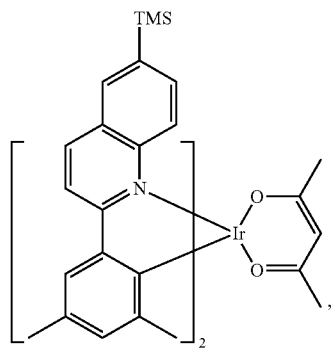
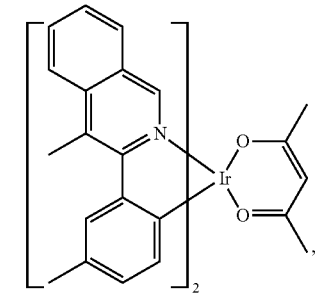
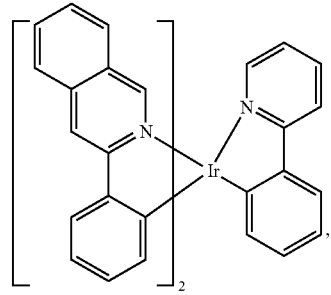
232
-continued
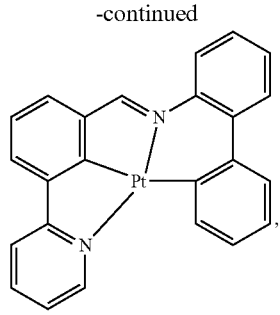
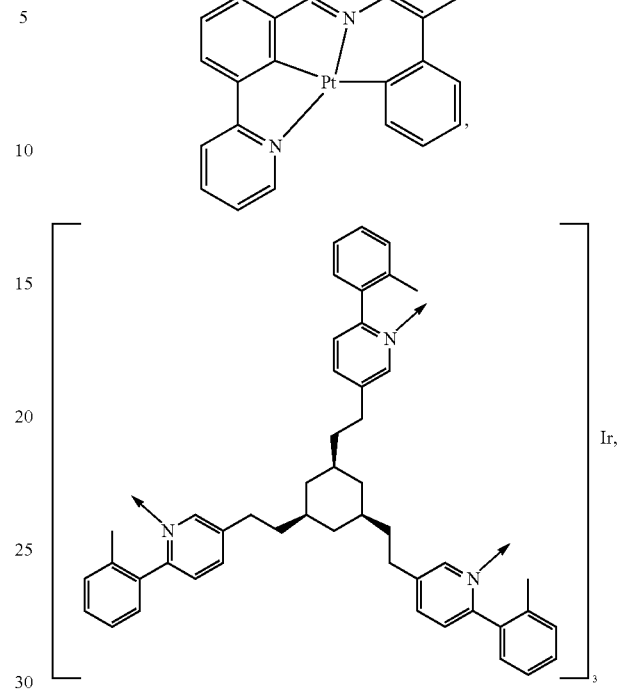
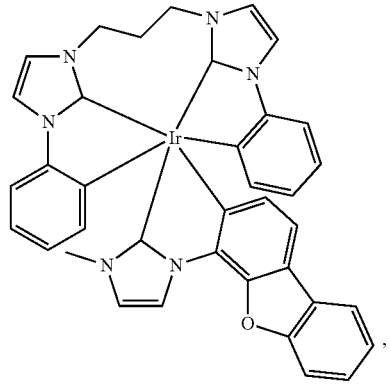
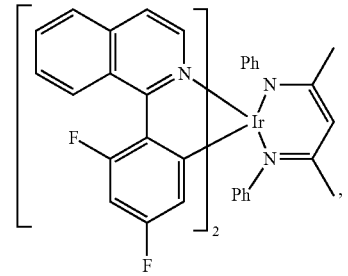
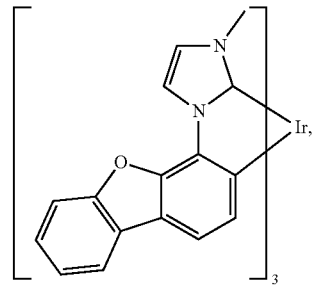

-continued
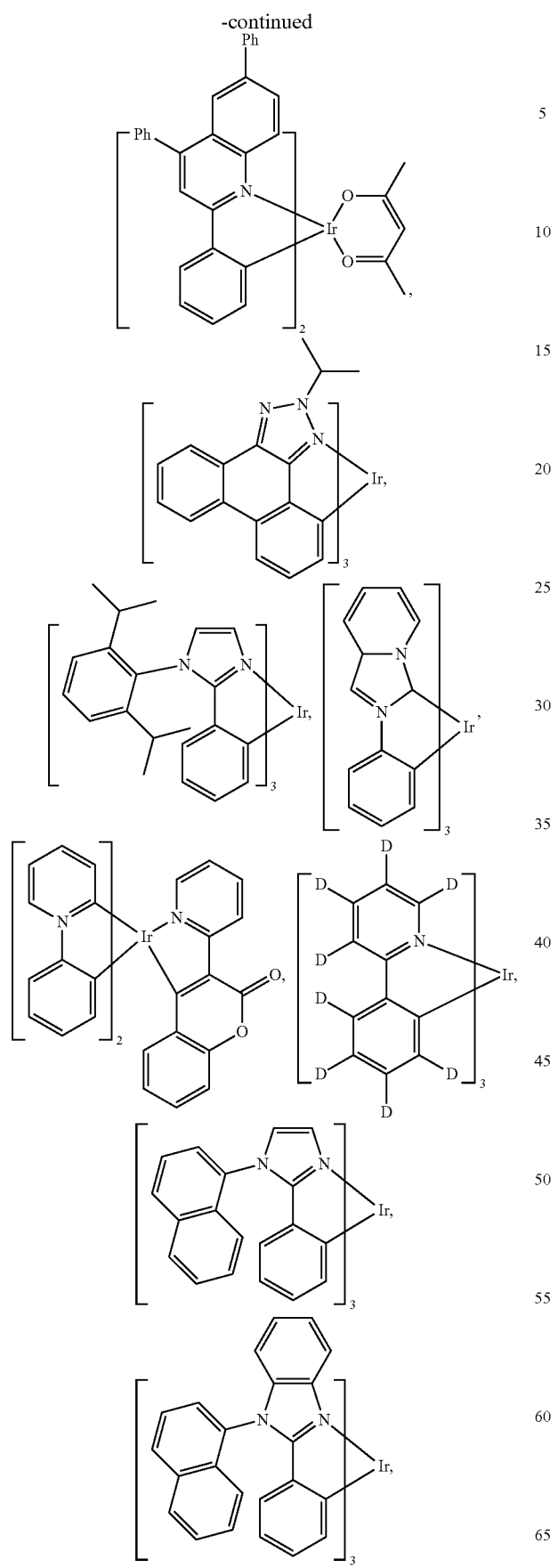
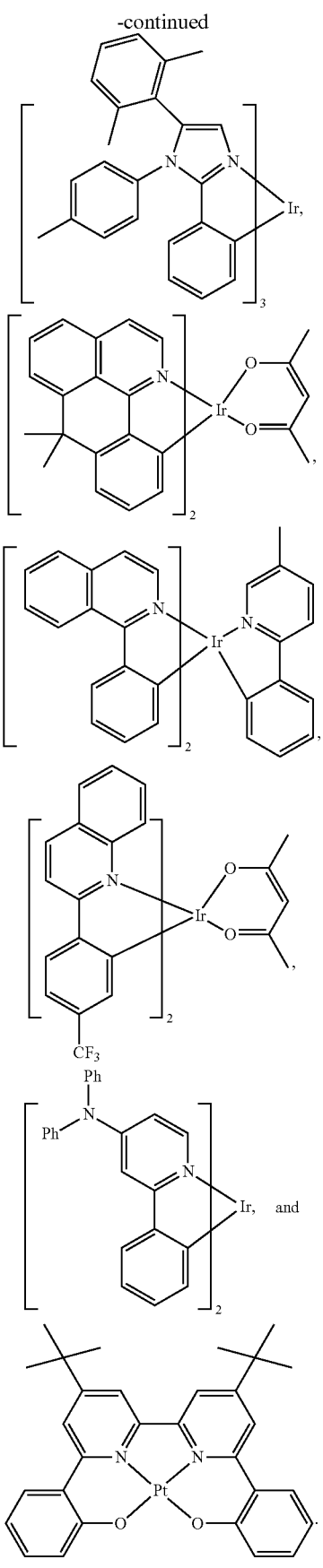

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

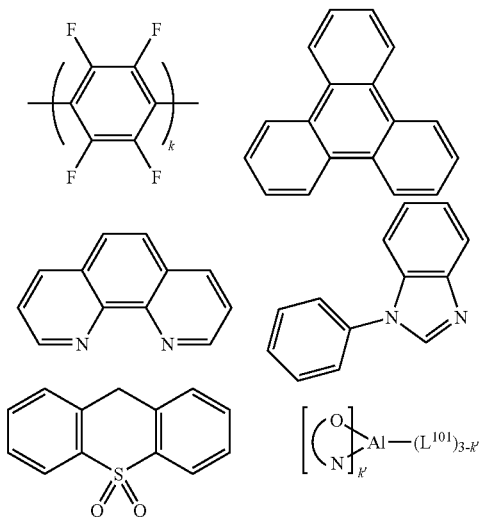

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

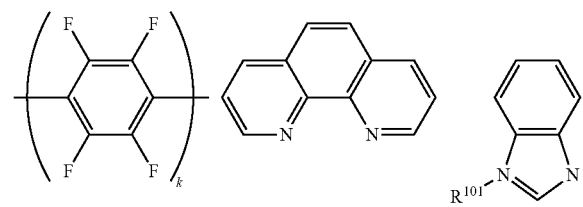

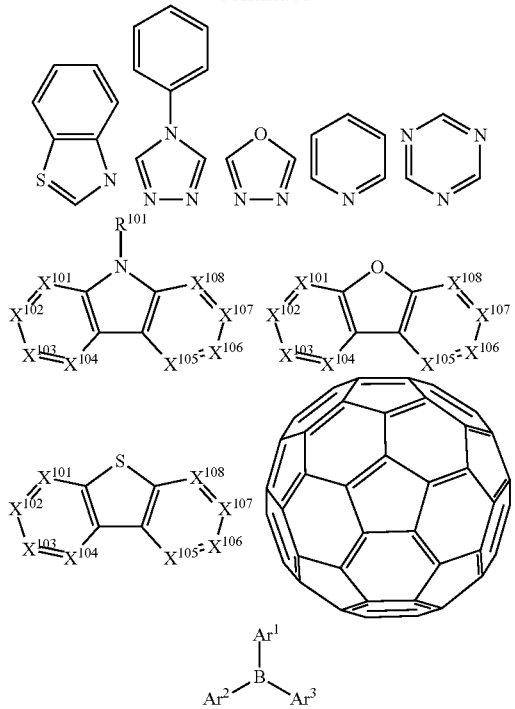

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

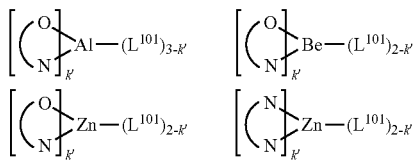

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,
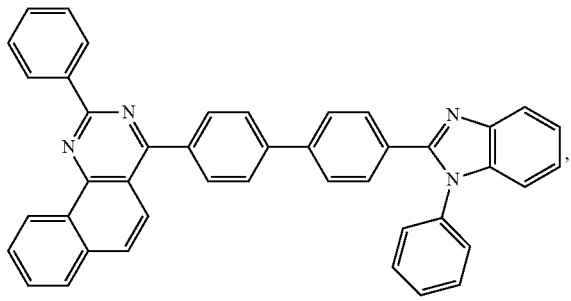
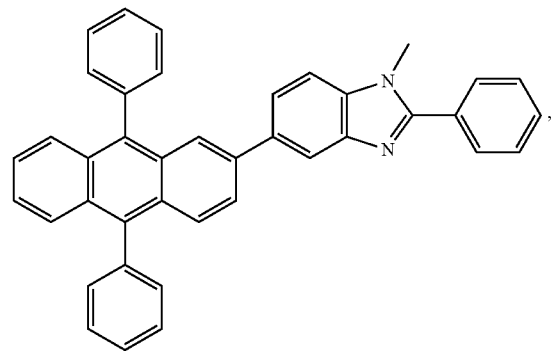
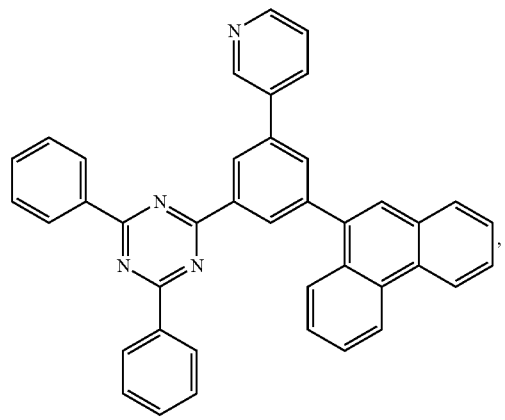
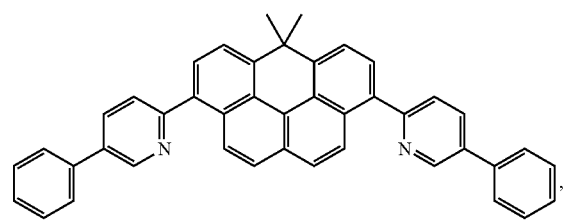
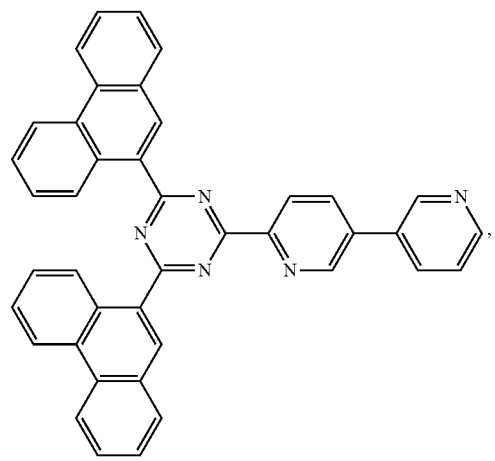
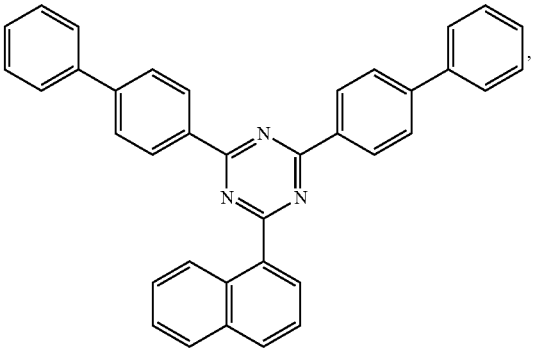
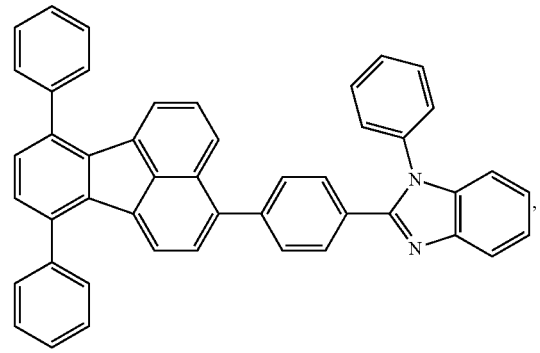
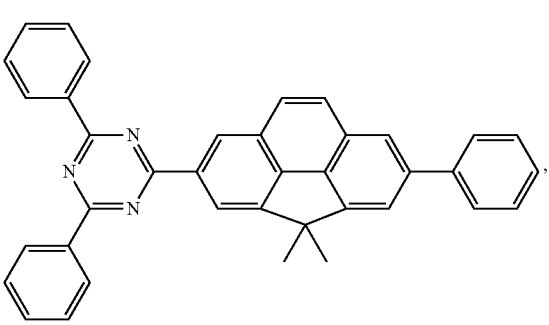

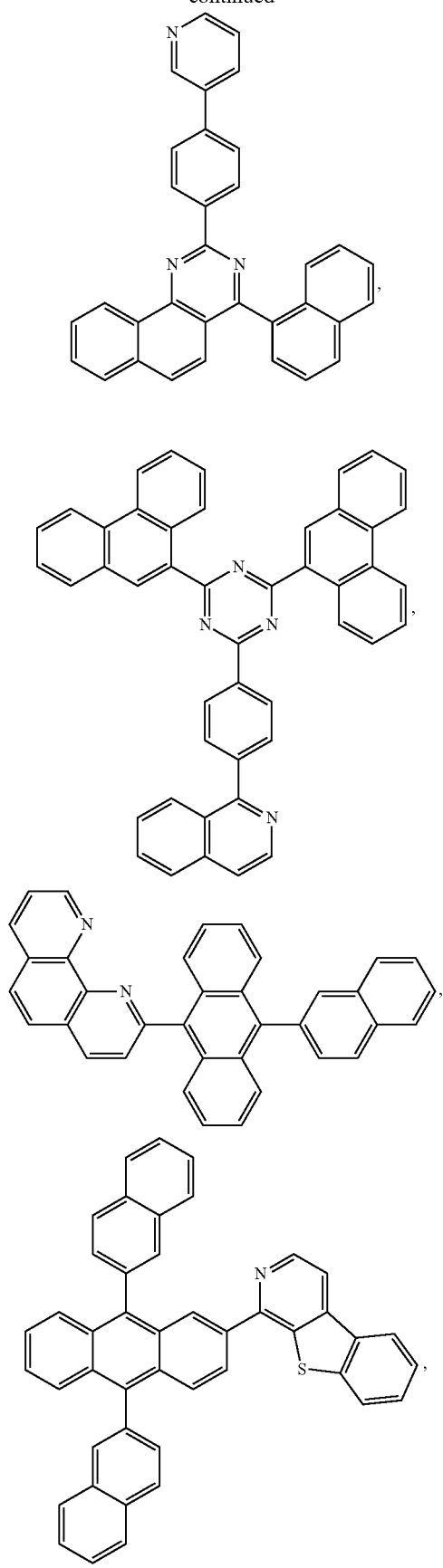
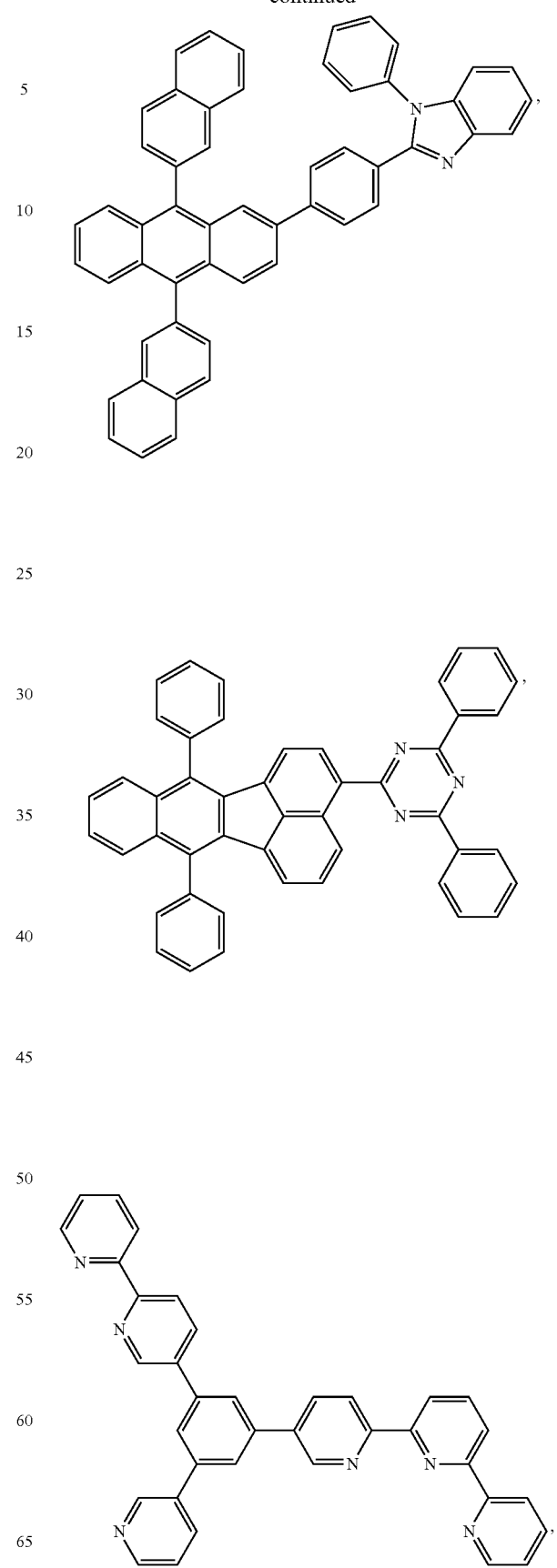

241
-continued
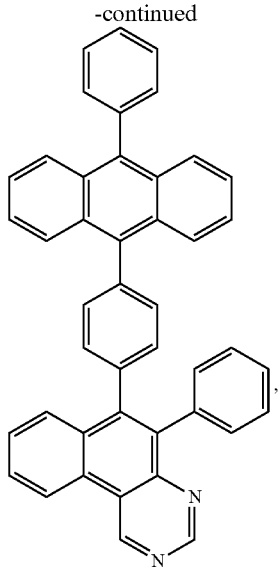
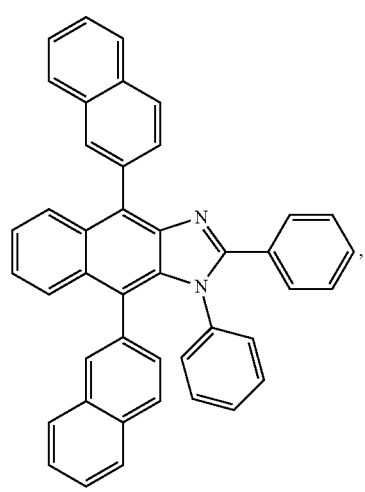
242
-continued
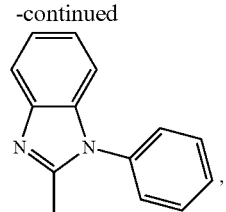
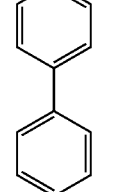
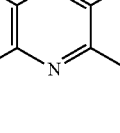
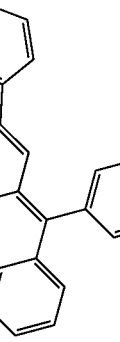
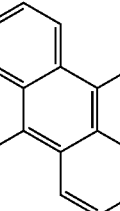
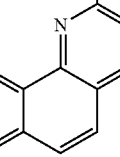
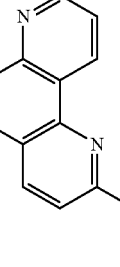

243
-continued
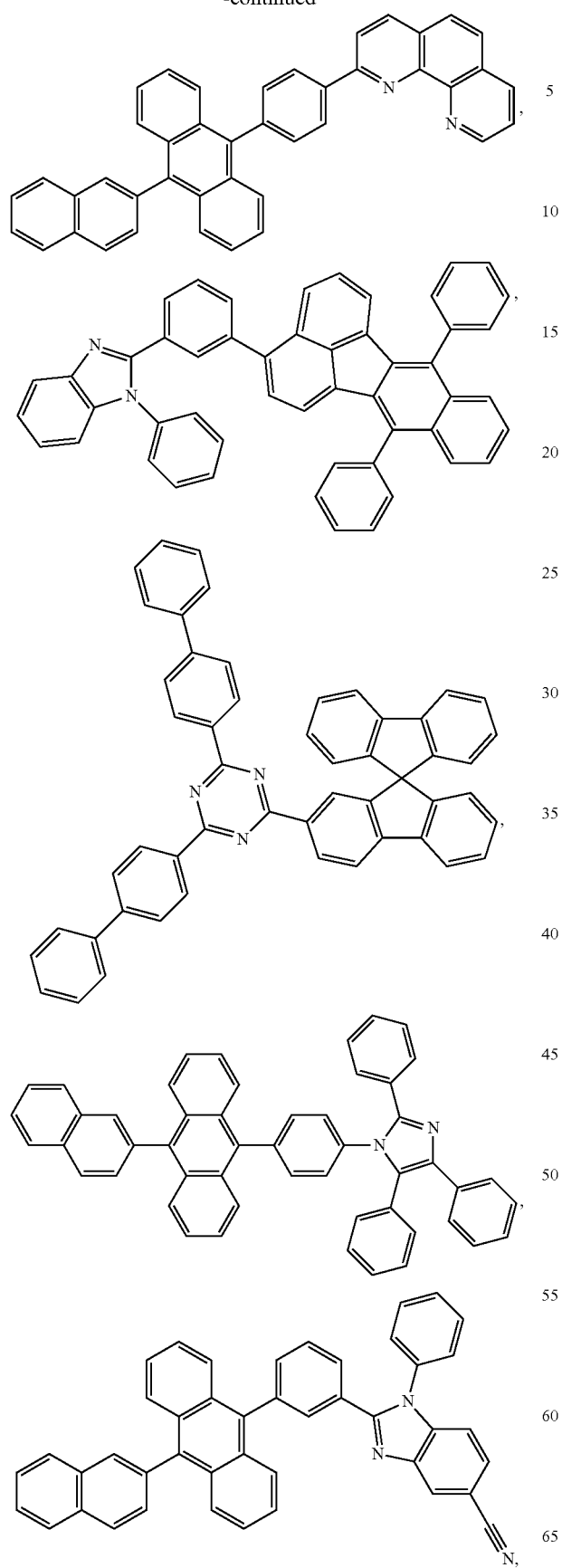
244
-continued
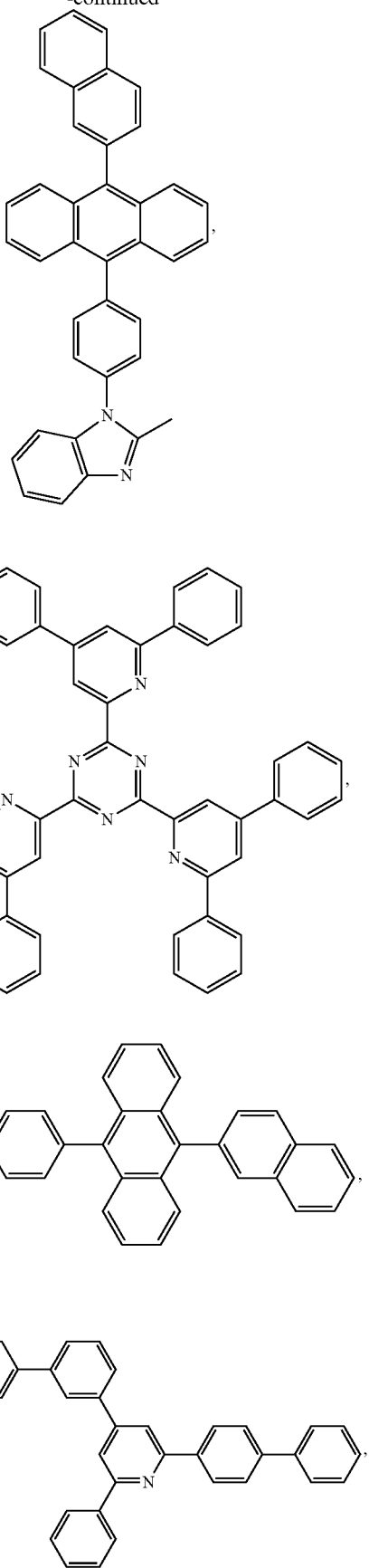

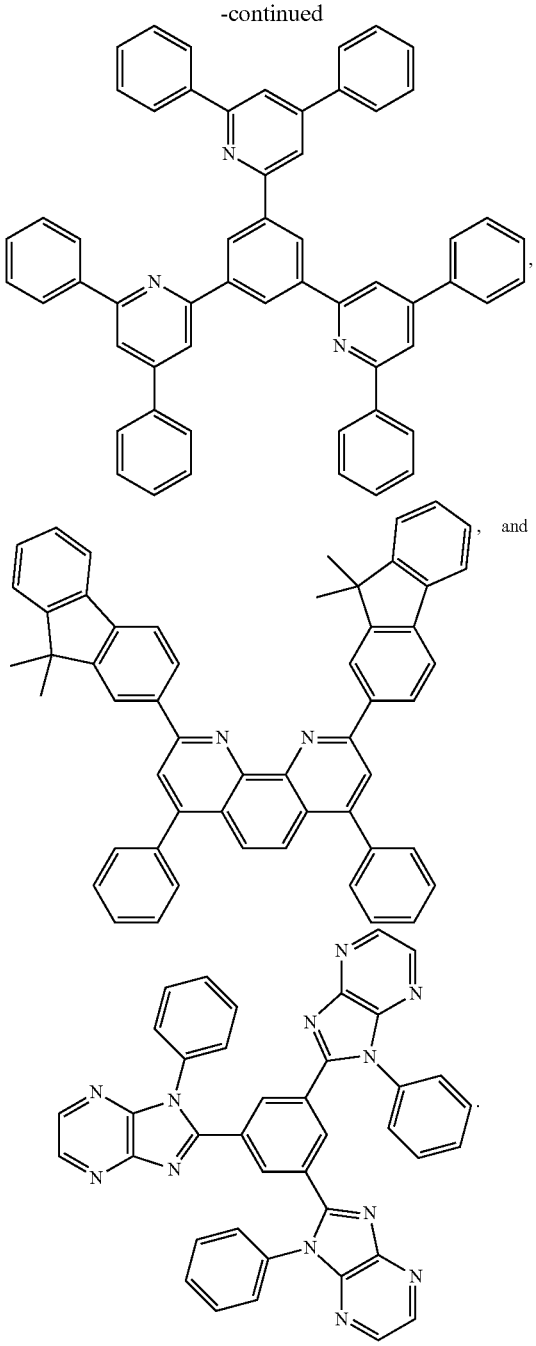

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

EXPERIMENTAL

The compatibility of selected h- and e-hosts was evaluated by compositional analysis of films fabricated by single-source co-evapoaration of the premixture of these two components. A first set of potential premixtures of selected h- and e-hosts are presented in Table 1.

TABLE 1

Potential premixtures comprising selected h- and e-hosts

| Premixtures | e-hosts | h-host |
|---|---|---|
| PM-1 | Compound A5 | Compound H7 |
| PM-2 | Compound A11 | Compound F4 |
| PM-3 | Compound A11 | Compound H3 |
| PM-4 | Compound A14 | Compound F1 |
| PM-5 | Compound A14 | Compound G26 |
| PM-6 | Compound A14 | Compound G59 |
| PM-7 | Compound A14 | Compound H5 |
| PM-8 | Compound A17 | Compound G2 |
| PM-9 | Compound A17 | Compound H5 |
| PM-10 | Compound A17 | Compound H7 |
| PM-11 | Compound C74 | Compound G14 |
| PM-12 | Compound C74 | Compound G44 |
| PM-13 | Compound C83 | Compound G2 |
| PM-14 | Compound C83 | Compound H7 |
| PM-15 | Compound C248 | Compound G14 |
| PM-16 | Compound D2 | Compound G14 |
| PM-17 | Compound D5 | Compound H5 |

Premixture PM-1: Compound A5 and Compound H7 were provided at a weight ratio of 1:2, physically mixed, grinded and loaded into an evaporation source. The premixed compositions were thermally co-evaporated at a rate of 2 Å/s in a vacuum chamber under a pressure less than $10^{-7}$ Torr, and deposited onto glass substrates. The substrates were replaced continuously after deposition of 500 Å of film without stopping the deposition and cooling the source. The composition of the films were analyzed by high-performance liquid chromatography (HPLC) and the results are shown in Table 2.

TABLE 2

HPLC composition (%) of sequentially deposited films from premixture (PM-1) comprising Compound A5 and Compound H7 with weight ratio 1:2. HPLC conditions were C18 reverse phase column, 100% acetonitrile as mobile phase, and detection wavelength of 254 nm. Because of different absorption coefficients, the HPLC composition may or may not agree with the weight ratio.

|  | Compound A5 | Compound H7 |
|---|---|---|
| Plate1 | 37.7 | 62.3 |
| Plate2 | 36.9 | 63.1 |
| Plate3 | 38.0 | 62.0 |
| Plate4 | 37.4 | 62.6 |
| Plate5 | 34.8 | 65.2 |
| Plate6 | 32.8 | 67.2 |

Premixture PM-9: Premixture PM-9 comprising Compound A17 and Compound H5 was evaluated in the same way as premixture PM-1, except that a weight ratio of 1:1 for Compound A17 and Compound H5 was used, and the results are presented in Table 3.

TABLE 3

HPLC composition (%) of sequentially deposited films from premixture (PM-9) comprising Compound A17 and Compound H5 with weight ratio 1:1. HPLC Conditions were C18 reverse phase column, 100% acetonitrile as mobile phase, and detection wavelength of 254 nm. Because of different absorption coefficients, the HPLC composition may or may not agree with the weight ratio.

|  | Compound A17 | Compound H5 |
|---|---|---|
| Plate1 | 57.6 | 42.4 |
| Plate2 | 58.9 | 41.1 |
| Plate3 | 59.2 | 40.8 |
| Plate4 | 59.0 | 41.0 |
| Plate5 | 58.6 | 41.4 |
| Plate6 | 59.2 | 40.8 |
| Plate7 | 60.0 | 40.0 |

Premixture PM-11: Premixture PM-11 comprising Compound C74 and Compound G14 was evaluated in the same way as premixture PM-9, and the results are presented in Table 4.

TABLE 4

HPLC composition (%) of sequentially deposited films from premixture (PM-11) comprising Compound C74 and Compound G14 with weight ratio 1:1. HPLC conditions were C18 reverse phase column, 100% acetonitrile as mobile phase, and detection wavelength of 254 nm. Because of different absorption coefficients, the HPLC composition may or may not agree with the weight ratio.

|  | Compound C74 | Compound G14 |
|---|---|---|
| Plate1 | 57.0 | 43.0 |
| Plate2 | 58.4 | 41.6 |
| Plate3 | 57.8 | 42.2 |
| Plate4 | 56.9 | 43.1 |
| Plate5 | 56.0 | 44.0 |
| Plate6 | 54.9 | 45.1 |
| Plate7 | 53.9 | 46.1 |
| Plate8 | 52.6 | 47.4 |

Premixture PM-14: Premixture PM-14 comprising Compound C83 and Compound H7 was evaluated in the same way as premixture PM-1, except that a weight ratio of 2:1 for Compound C83 and Compound H7 was used, and the results are presented in Table 5.

TABLE 5

HPLC composition (%) of sequentially deposited films from premixture (PM-14) comprising Compound C83 and Compound H7 with weight ratio 2:1. HPLC conditions were C18 reverse phase column, 100% acetonitrile as mobile phase, and detection wavelength of 254 nm. Because of different absorption coefficients, the HPLC composition may or may not agree with the weight ratio.

|  | Compound C83 | Compound H7 |
|---|---|---|
| Plate1 | 61.2 | 38.8 |
| Plate2 | 64.1 | 35.9 |
| Plate3 | 64.6 | 35.4 |
| Plate4 | 63.8 | 36.2 |
| Plate5 | 63.5 | 36.5 |
| Plate6 | 62.4 | 37.6 |
| Plate7 | 62.4 | 37.6 |

The data in Tables 2, 3, 4, and 5 show that the ratio of the two components in premixtures PM-1, PM-9, PM-11 and PM-14 does not change significantly over a continuous single-source coevaporation. The minor fluctuations in the concentrations do not reveal any trend and can be explained by the accuracy of HPLC analysis. Normally, the change of the concentration before and after depositions within 5% throughout the process is considered to be good and useful for commercial OLED application. These experiments conclude that PM-1, PM-9, PM-11 and PM-14 are stable premixtures for coevaporation. The coevaporation stability of these premixtures is believed to be tracable to the unique chemical structures associated with these two classes of materials.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A premixed co-evaporation source comprising a mixture of a first compound and a second compound,
wherein the premixed co-evaporation source is a co-evaporation source for a vacuum deposition process;
wherein the first compound has a formula:

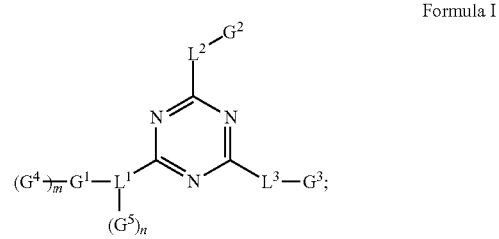

Formula I wherein $G^1$ is dibenzoselenophene;
wherein $L^1$, $L^2$ and $L^3$ are each independently selected from the group consisting of direct bond, phenyl, biphenyl, terphenyl, pyridine, pyrimidine, and combinations thereof;
wherein $G^4$ is selected from the group consisting of phenyl, biphenyl, terphenyl, naphthalene, phenanthrene, pyridine, pyrimidine, pyrazine, quinoline, isoquinoline, phenanthroline, fluorene, and combinations thereof;
wherein $G^2$, $G^3$, and $G^5$ are each independently selected from the group consisting of phenyl, biphenyl, terphenyl, naphthalene, phenanthrene, pyridine, pyrimidine, pyrazine, quinoline, isoquinoline, phenanthroline, azafluorene, and combinations thereof;
wherein $G^2$, $G^3$, $G^4$, and $G^5$ are each optionally further substituted with one or more unfused substituents selected from the group consisting of deuterium, alkyl, alkoxyl, cycloalkyl, cycloalkoxyl, halogen, nitro, nitrile, phenyl, biphenyl, terphenyl, pyridine, and combinations thereof;
wherein m is an integer from 0 to 7,
wherein n is an integer from 0 to 4;
wherein, when m or n is larger than 1, each or $G^4$ or $G^5$ can be same or different;

wherein the second compound has a formula:

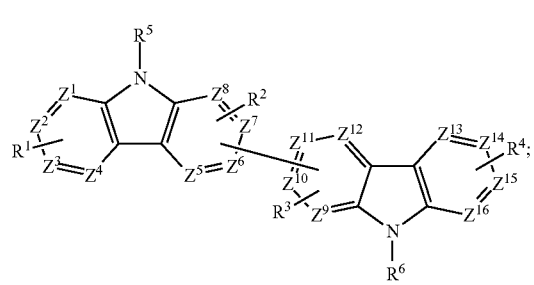

Formula II wherein each $Z^1$ to $Z^{16}$ is C or N;

wherein one of $Z^5$ to $Z^8$ bonds to one of $Z^9$ to $Z^{12}$ through a C—C bond;

wherein $R^1$, and $R^4$ each independently represent mono, di, tri, or tetra substitution, or no substitution;

wherein $R^2$, and $R^3$ each independently represent mono, di, or tri substitution, or no substitution;

wherein $R^1$ to $R^6$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; and wherein any two adjacent substituents are optionally joined or fused into a ring.

2. The premixed co-evaporation source of claim 1, wherein n is 0.

3. The premixed co-evaporation source of claim 1, wherein n is equal to or greater than 1.

4. The premixed co-evaporation source of claim 1, wherein m is an integer from 1 to 7, and fragment $G^4$ has the structure selected from the group consisting of:

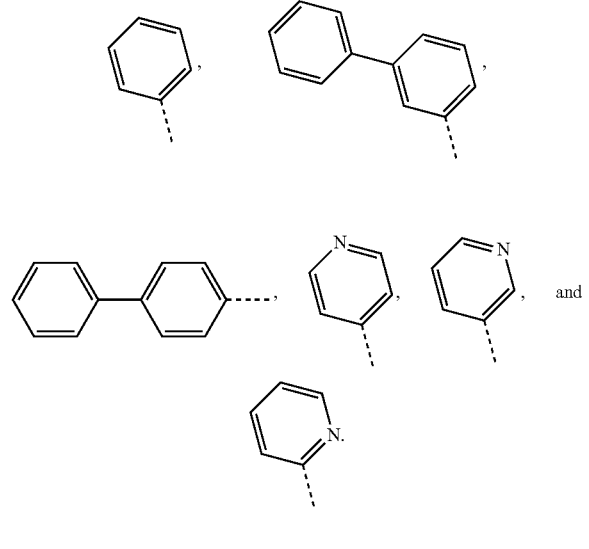

5. The premixed co-evaporation source of claim 1, wherein $L^1$ is

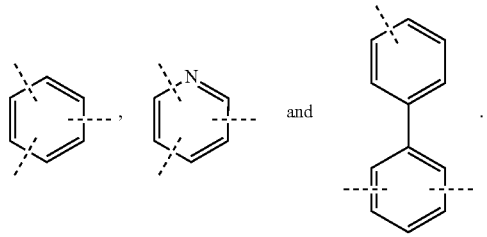

6. The premixed co-evaporation source of claim 1, wherein $G^2$, $G^5$ and $G^6$ are independently selected from the group consisting of:

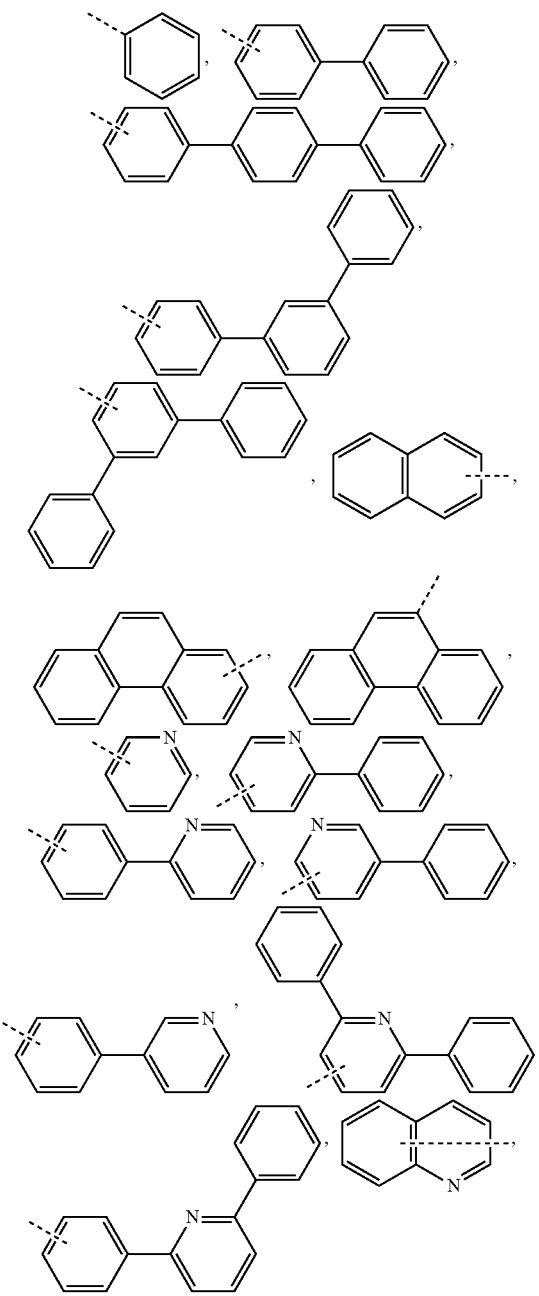

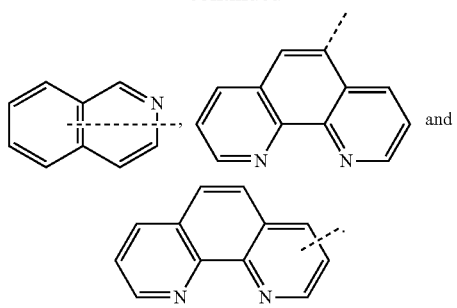
7. The premixed co-evaporation source of claim 1, wherein the first compound has the formula:
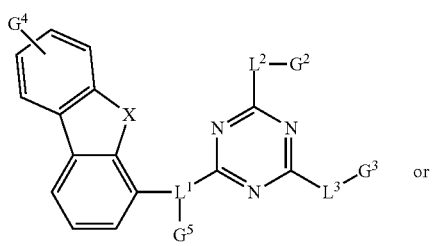
or
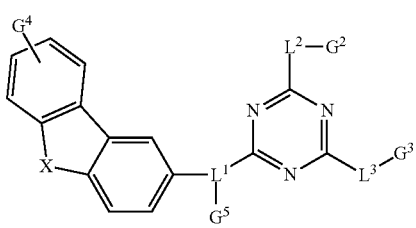
wherein X is Se.
8. The premixed co-evaporation source of claim 1, wherein the second compound is selected from the group consisting of:
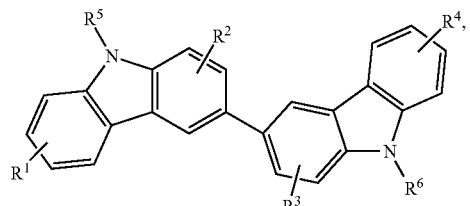
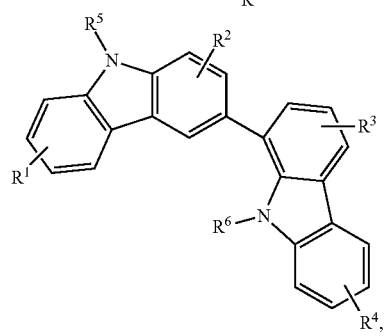
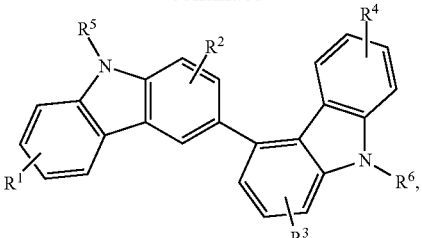
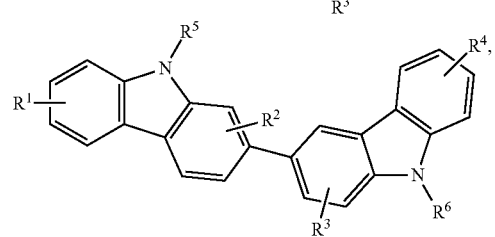
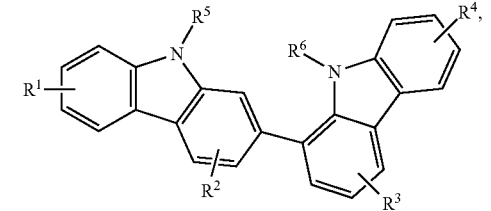
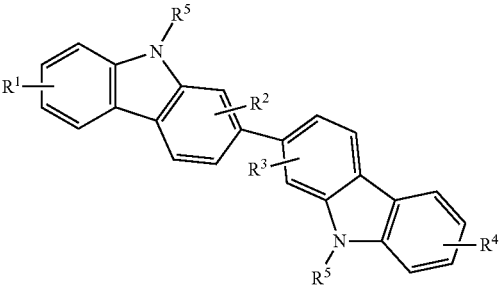
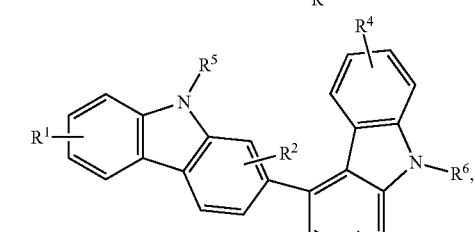
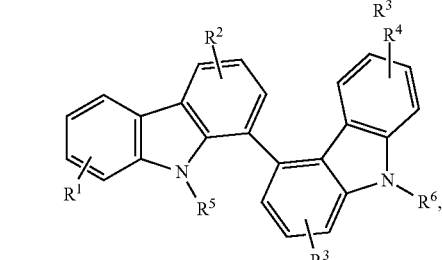
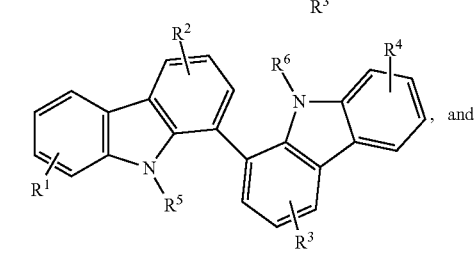

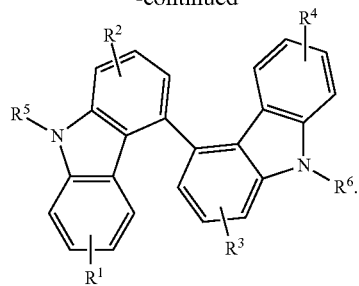
9. The premixed co-evaporation source of claim 1, wherein the second compound is selected from the group consisting of:
Compound F1
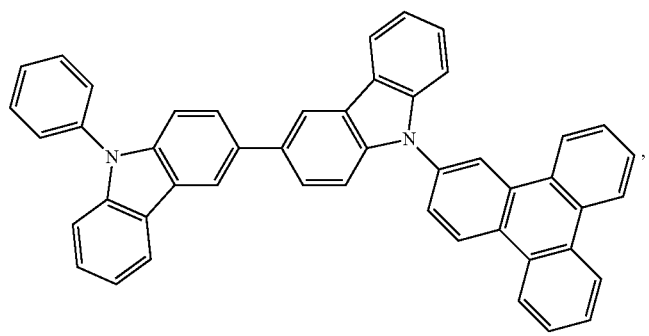 [SMILES: c1ccc(-n2c3ccccc3c3cc(-c4ccc5c(c4)c4ccccc4n5-c4ccc5c6ccccc6c6ccccc6c5c4)ccc32)cc1]
Compound F2
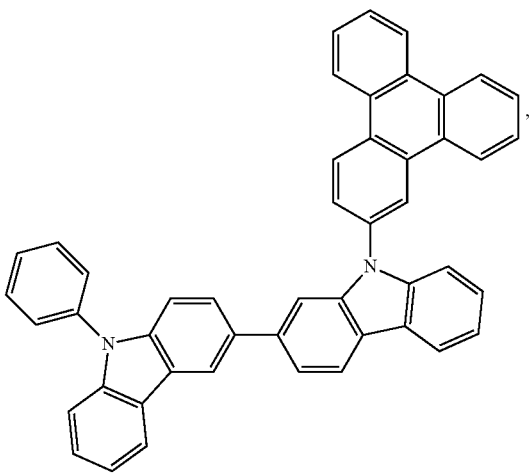 [SMILES: c1ccc(-n2c3ccccc3c3cc(-c4ccc5c6ccccc6n(-c6ccc7c8ccccc8c8ccccc8c7c6)c5c4)ccc32)cc1]
Compound F3
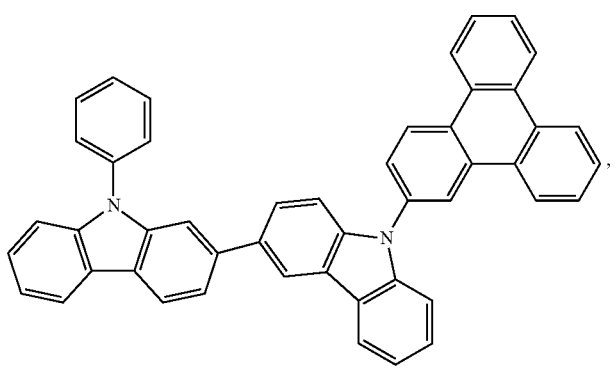 [SMILES: c1ccc(-n2c3ccccc3c3ccc(-c4ccc5c(c4)c4ccccc4n5-c4ccc5c6ccccc6c6ccccc6c5c4)cc32)cc1]

-continued
Compound F4
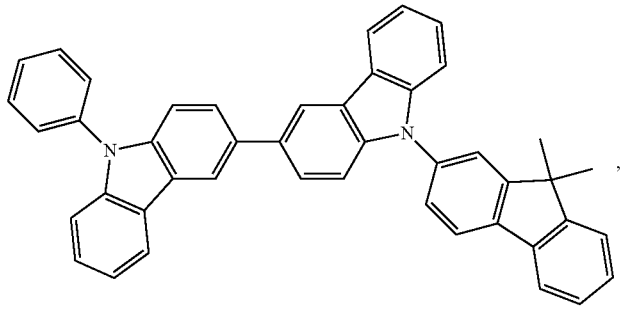 [SMILES: CC1(C)c2ccccc2-c2ccc(-n3c4ccccc4c4cc(-c5ccc6c(c5)c5ccccc5n6-c5ccccc5)ccc43)cc21]
Compound F5
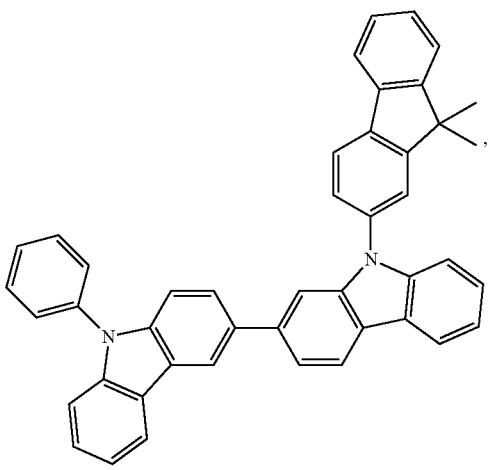 [SMILES: CC1(C)c2ccccc2-c2ccc(-n3c4ccccc4c4ccc(-c5ccc6c(c5)c5ccccc5n6-c5ccccc5)cc43)cc21]
Compound F6
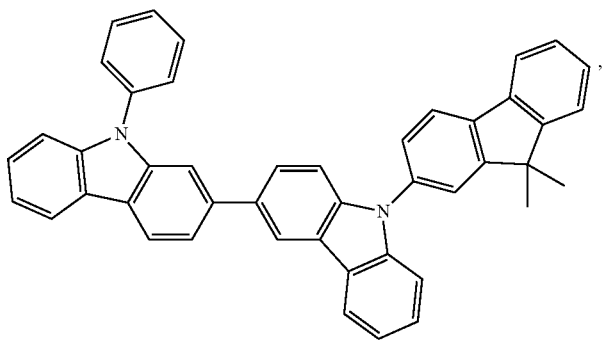 [SMILES: CC1(C)c2ccccc2-c2ccc(-n3c4ccccc4c4cc(-c5ccc6c7ccccc7n(-c7ccccc7)c6c5)ccc43)cc21]
Compound F7
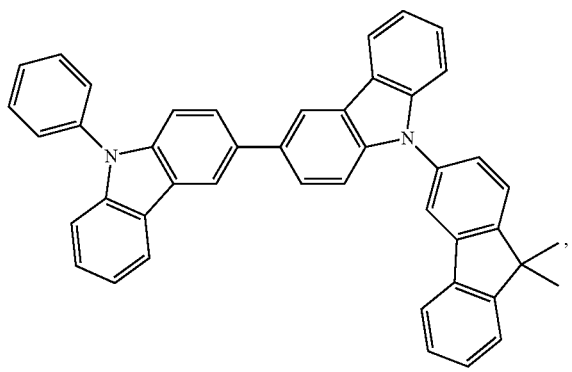 [SMILES: CC1(C)c2ccccc2-c2cc(-n3c4ccccc4c4cc(-c5ccc6c(c5)c5ccccc5n6-c5ccccc5)ccc43)ccc21]

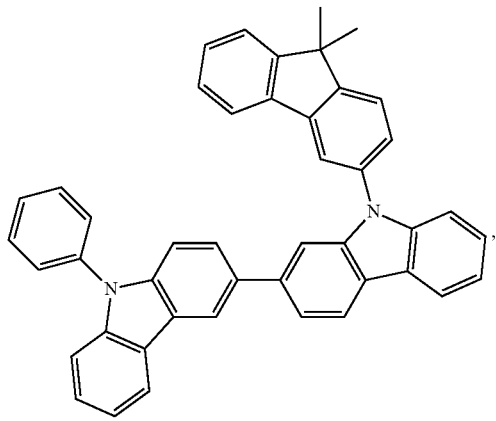 [SMILES: CC1(C)c2ccccc2-c2cc(-n3c4ccccc4c4ccc(-c5ccc6c(c5)c5ccccc5n6-c5ccccc5)cc43)ccc21]
Compound F8
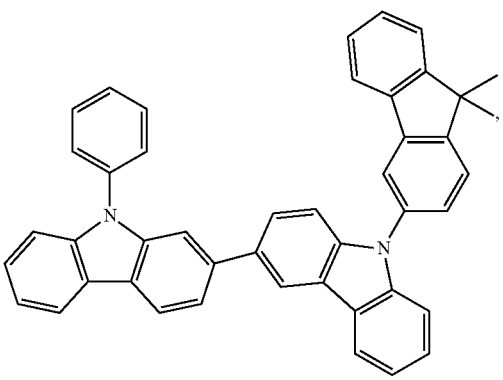
Compound F9
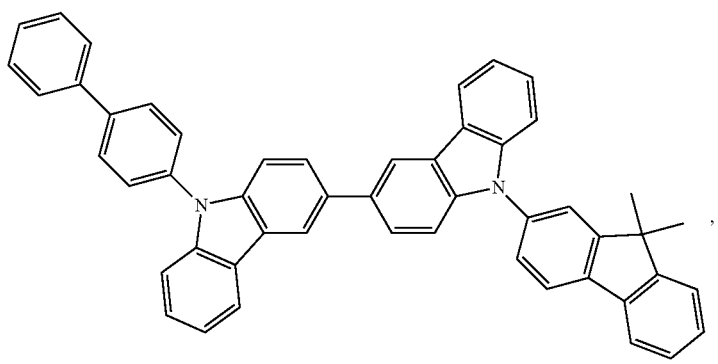 [SMILES: CC1(C)c2ccccc2-c2ccc(-n3c4ccccc4c4cc(-c5ccc6c(c5)c5ccccc5n6-c5ccc(-c6ccccc6)cc5)ccc43)cc21]
Compound F10
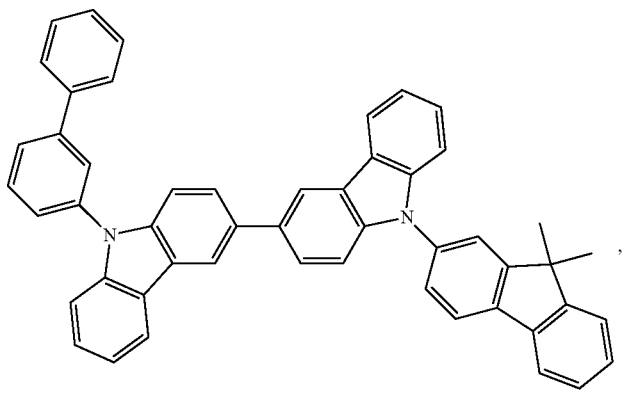 [SMILES: CC1(C)c2ccccc2-c2ccc(-n3c4ccccc4c4cc(-c5ccc6c(c5)c5ccccc5n6-c5cccc(-c6ccccc6)c5)ccc43)cc21]
Compound F11

Compound F12
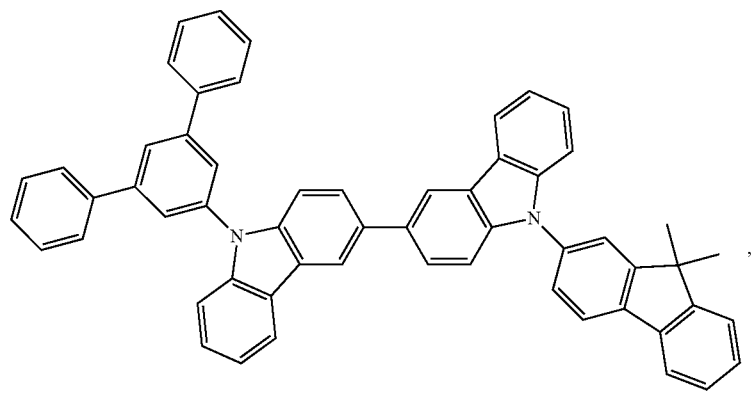 [SMILES: CC1(C)c2ccccc2-c2ccc(-n3c4ccccc4c4cc(-c5ccc6c(c5)c5ccccc5n6-c5cc(-c6ccccc6)cc(-c6ccccc6)c5)ccc43)cc21]
Compound F13
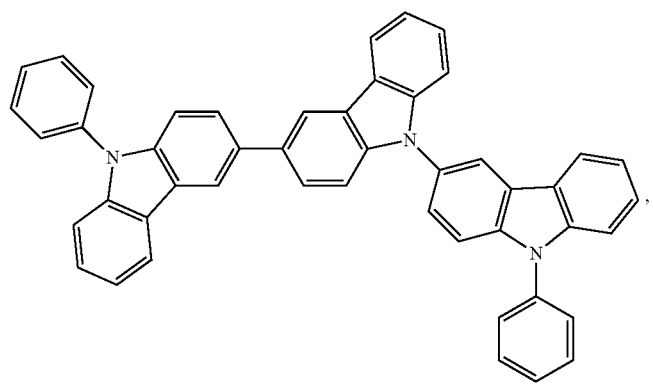 [SMILES: c1ccc(-n2c3ccccc3c3cc(-c4ccc5c(c4)c4ccccc4n5-c4ccc5c(c4)c4ccccc4n5-c4ccccc4)ccc32)cc1]
Compound F14
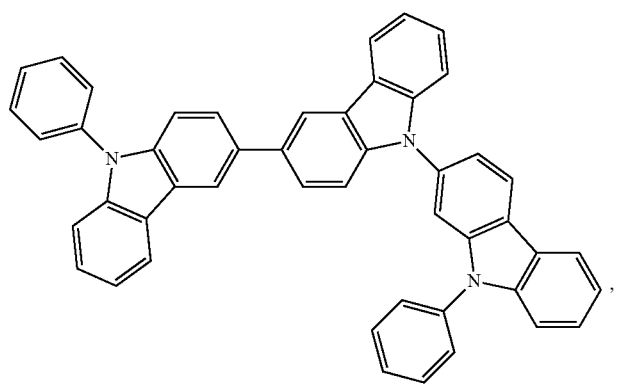 [SMILES: c1ccc(-n2c3ccccc3c3cc(-c4ccc5c(c4)c4ccccc4n5-c4ccc5c6ccccc6n(-c6ccccc6)c5c4)ccc32)cc1]

Compound F15

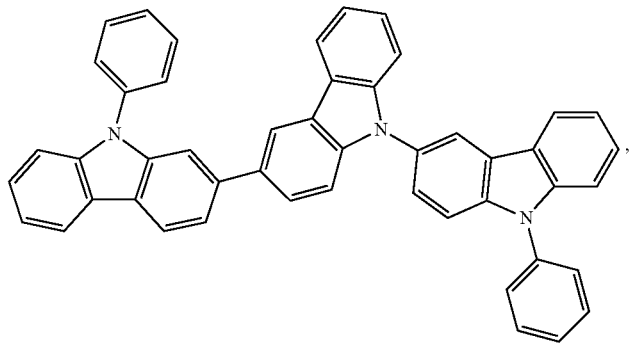 [SMILES: c1ccc(-n2c3ccccc3c3cc(-n4c5ccccc5c5cc(-c6ccc7c8ccccc8n(-c8ccccc8)c7c6)ccc54)ccc32)cc1]

Compounds G1 through G3, each represented by the formula:

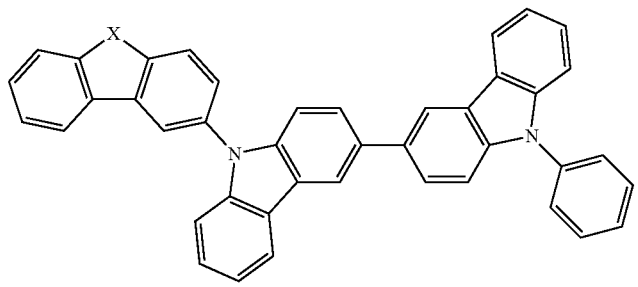

where in Compound G1: X = O, in Compound G2, X = S, and in Compound G3, X = Se,
Compounds G4 through G6, each represented by the formula:

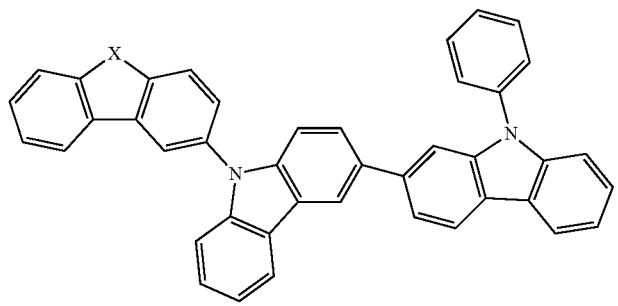

where in Compound G4: X = O, in Compound G5, X = S, and in Compound G6, X = Se,
Compounds G7 through G9, each represented by the formula:

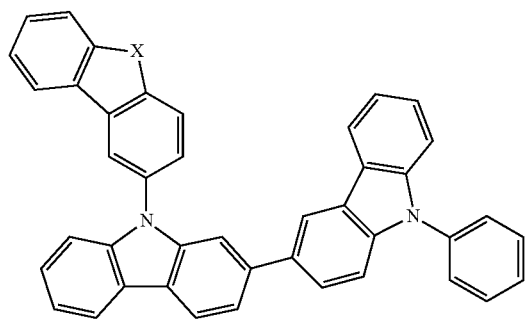

where in Compound G7: X = O, in Compound G8, X = S, and in Compound G9, X = Se,
Compounds G10 through G12, each represented by the formula:

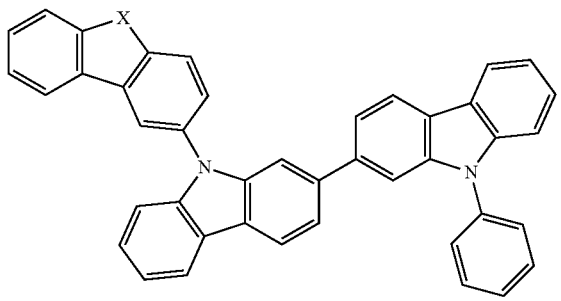

where in Compound G10: X = O, in Compound G11, X = S, and in Compound G12, X = Se,
Compounds G13 through G15, each represented by the formula:

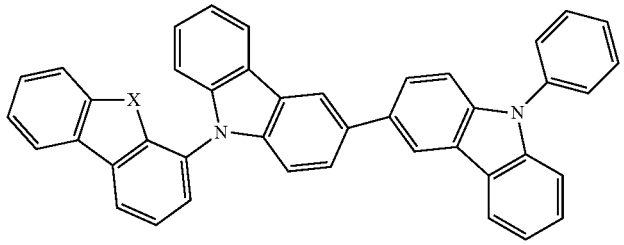

where in Compound G13: X = O, in Compound G14, X = S, and in Compound G15, X = Se,
Compounds G16 through G18, each represented by the formula:

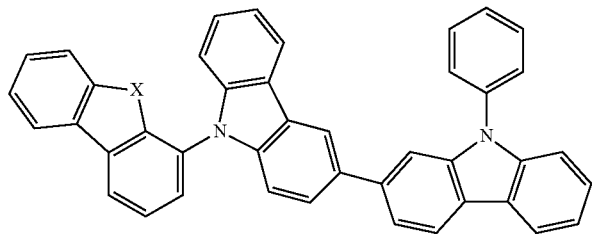

where in Compound G16: X = O, in Compound G17, X = S, and in Compound G18, X = Se,
Compounds G19 through G21, each represented by the formula:

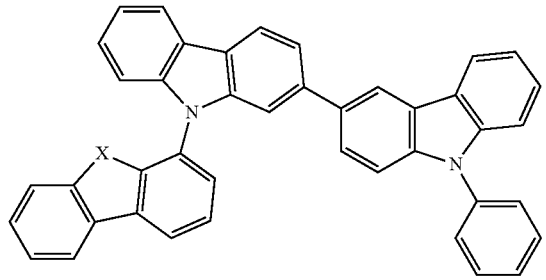

where in Compound G19: X = O, in Compound G20, X = S, and in Compound G21, X = Se,
Compounds G22 through G24, each represented by the formula:

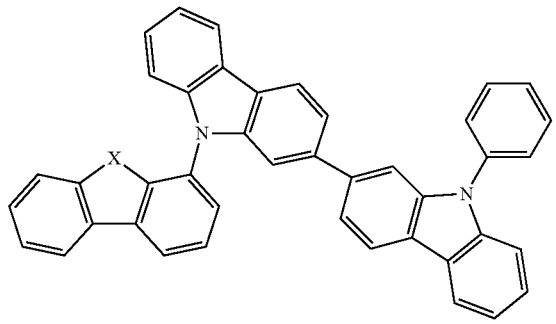

where in Compound G22: X = O, in Compound G23, X = S, and in Compound G24, X = Se,
Compounds G25 through G27, each represented by the formula:

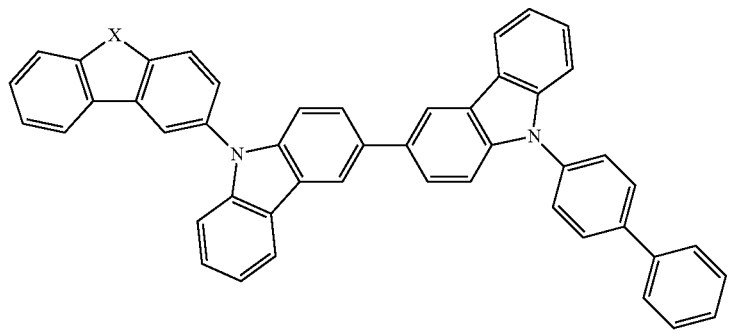

where in Compound G25: X = O, in Compound G26, X = S, and in Compound G27, X = Se,
Compounds G28 through G30, each represented by the formula:

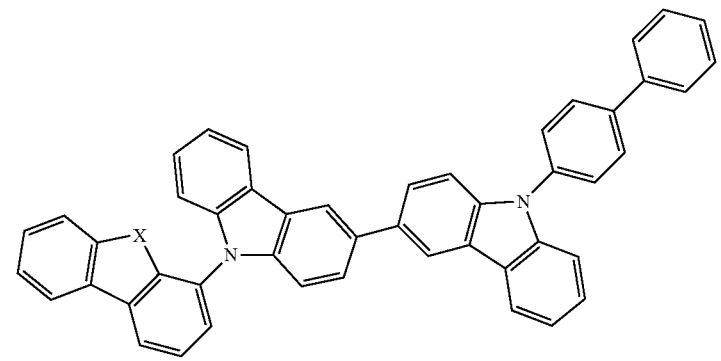

where in Compound G28: X = O, in Compound G29, X = S, and in Compound G30, X = Se,
Compounds G31 through G33, each represented by the formula:

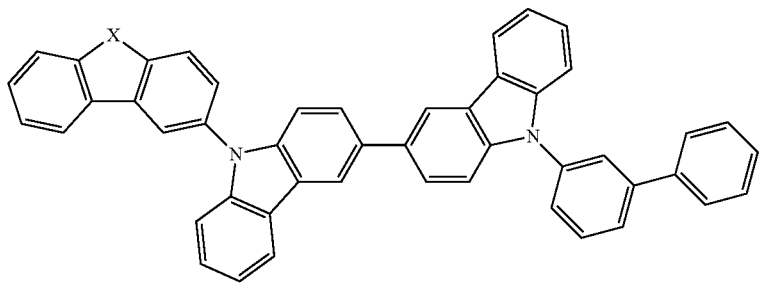

where in Compound G31: X = O, in Compound G32, X = S, and in Compound G33, X = Se,
Compounds G34 through G36, each represented by the formula:

-continued

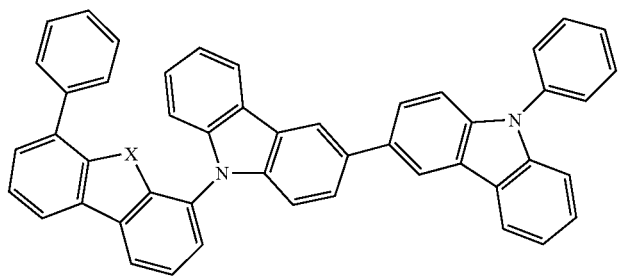

where in Compound G34: X = O, in Compound G35, X = S, and in Compound G36, X = Se,
Compounds G37 through G39, each represented by the formula:

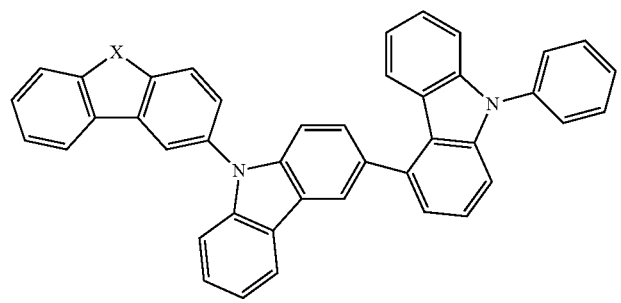

where in Compound G37: X = O, in Compound G38, X = S, and in Compound G39, X = Se,
Compounds G40 through G42, each represented by the formula:

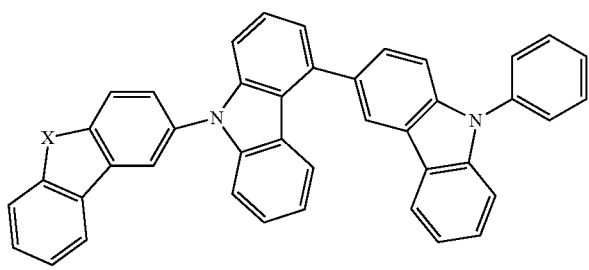

where in Compound G40: X = O, in Compound G41, X = S, and in Compound G42, X = Se,
Compounds G43 through G45, each represented by the formula:

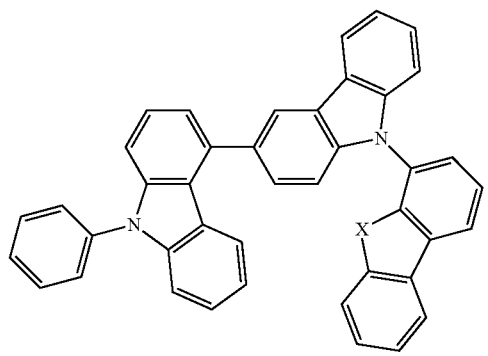

where in Compound G43: X = O, in Compound G44, X = S, and in Compound G45, X = Se,
Compounds G46 through G48, each represented by the formula:

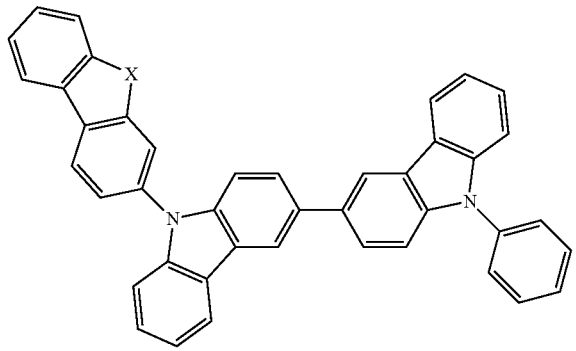

where in Compound G46: X = O, in Compound G47, X = S, and in Compound G48, X = Se,
Compounds G49 through G51, each represented by the formula:

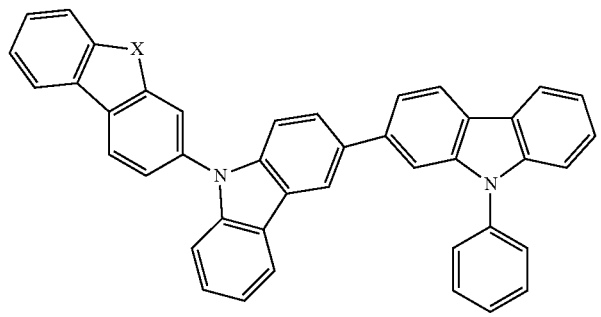

where in Compound G49: X = O, in Compound G50, X = S, and in Compound G51, X = Se,
Compounds G52 through G54, each represented by the formula:

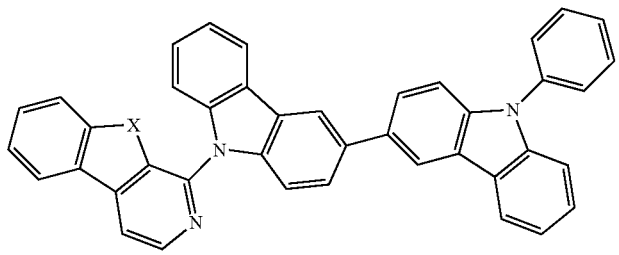

where in Compound G52: X = O, in Compound G53, X = S, and in Compound G54, X = Se,
Compounds G55 through G56, each represented by the formula:

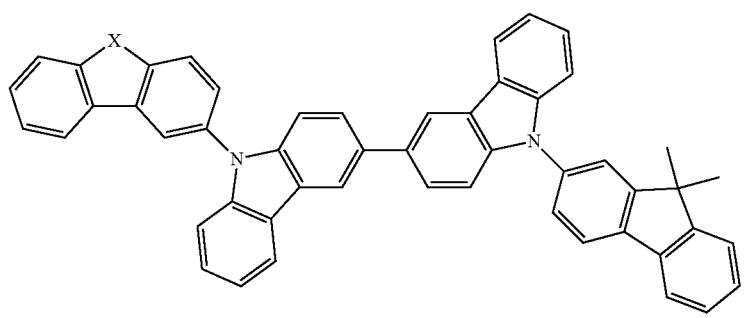

where in Compound G55: X = O, in Compound G56, X = S, and in Compound G57, X = Se,
Compounds G58 through G60, each represented by the formula:

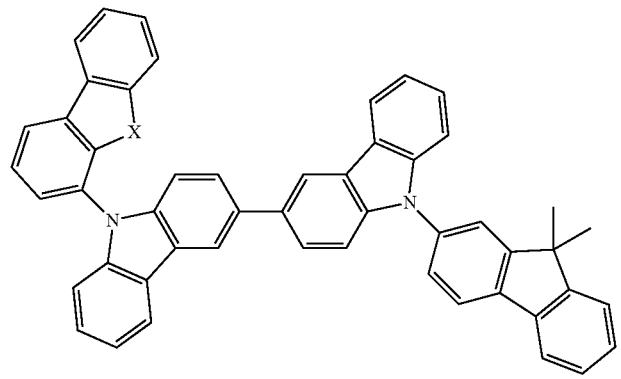
where in Compound G58: X = O, in Compound G59, X = S, and in Compound G60, X = Se,
Compound H1
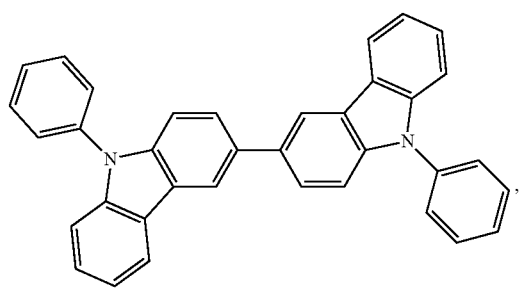 [SMILES: c1ccc(-n2c3ccccc3c3cc(-c4ccc5c(c4)c4ccccc4n5-c4ccccc4)ccc32)cc1]
Compound H2
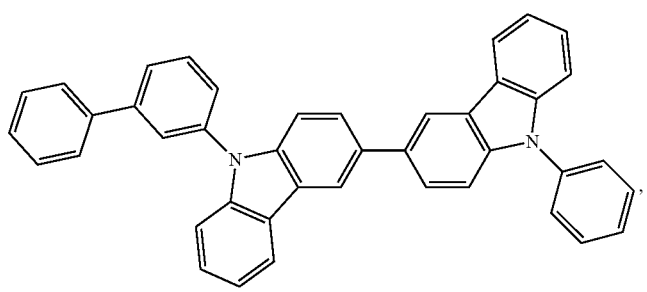 [SMILES: c1ccc(-c2cccc(-n3c4ccccc4c4cc(-c5ccc6c(c5)c5ccccc5n6-c5ccccc5)ccc43)c2)cc1]
Compound H3
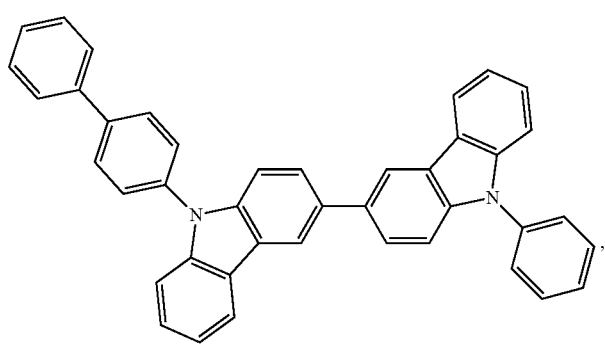 [SMILES: c1ccc(-c2ccc(-n3c4ccccc4c4cc(-c5ccc6c(c5)c5ccccc5n6-c5ccccc5)ccc43)cc2)cc1]
Compound H4
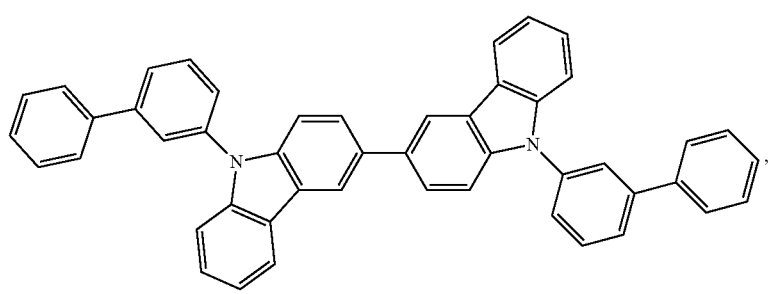 [SMILES: c1ccc(-c2cccc(-n3c4ccccc4c4cc(-c5ccc6c(c5)c5ccccc5n6-c5cccc(-c6ccccc6)c5)ccc43)c2)cc1]

Compound H5
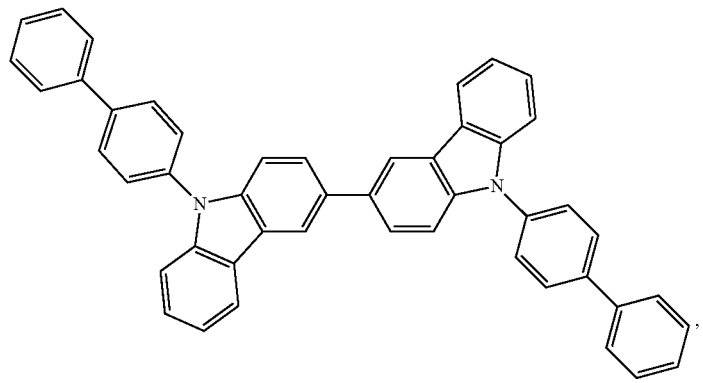 [SMILES: c1ccc(-c2ccc(-n3c4ccccc4c4cc(-c5ccc6c(c5)c5ccccc5n6-c5ccc(-c6ccccc6)cc5)ccc43)cc2)cc1]
Compound H6
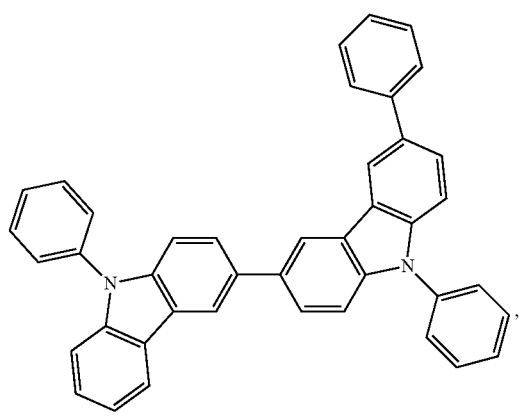 [SMILES: c1ccc(-c2ccc3c(c2)c2cc(-c4ccc5c(c4)c4ccccc4n5-c4ccccc4)ccc2n3-c2ccccc2)cc1]
Compound H7
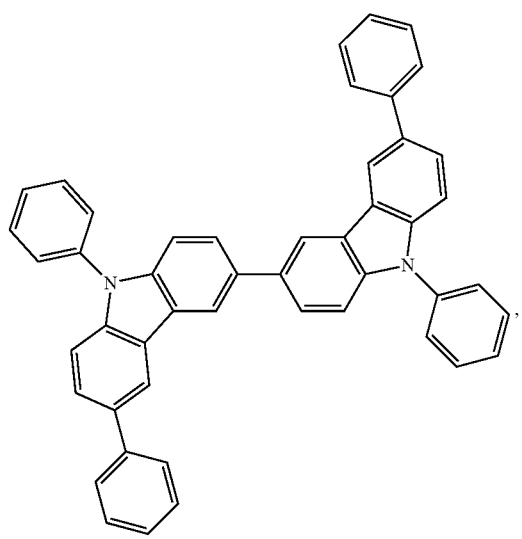 [SMILES: c1ccc(-c2ccc3c(c2)c2cc(-c4ccc5c(c4)c4cc(-c6ccccc6)ccc4n5-c4ccccc4)ccc2n3-c2ccccc2)cc1]

Compound H8
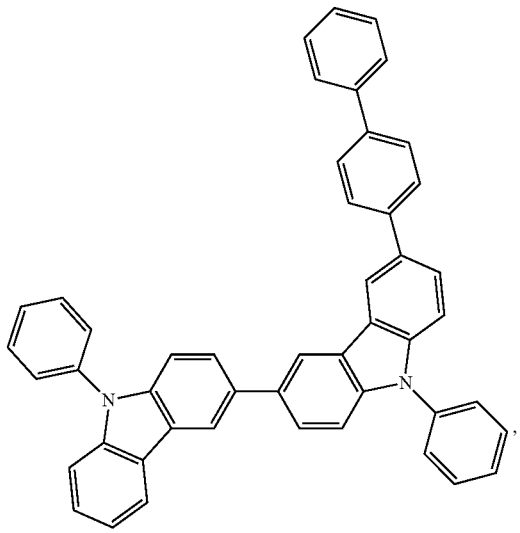 [SMILES: c1ccc(-c2ccc(-c3ccc4c(c3)c3cc(-c5ccc6c(c5)c5ccccc5n6-c5ccccc5)ccc3n4-c3ccccc3)cc2)cc1]
Compound H9
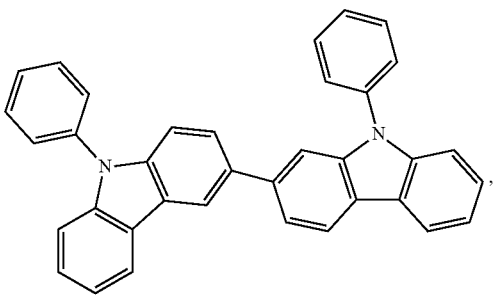 [SMILES: c1ccc(-n2c3ccccc3c3cc(-c4ccc5c6ccccc6n(-c6ccccc6)c5c4)ccc32)cc1]
Compound H10
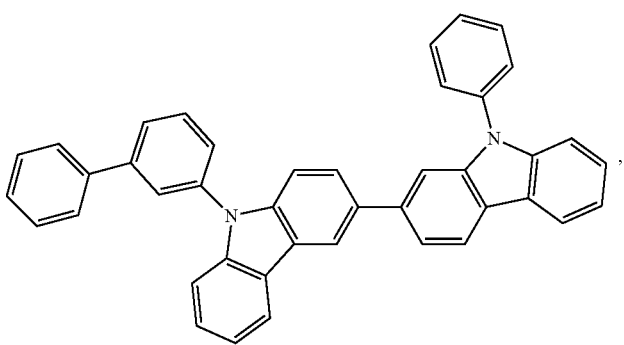 [SMILES: c1ccc(-c2cccc(-n3c4ccccc4c4cc(-c5ccc6c7ccccc7n(-c7ccccc7)c6c5)ccc43)c2)cc1]
Compound H11
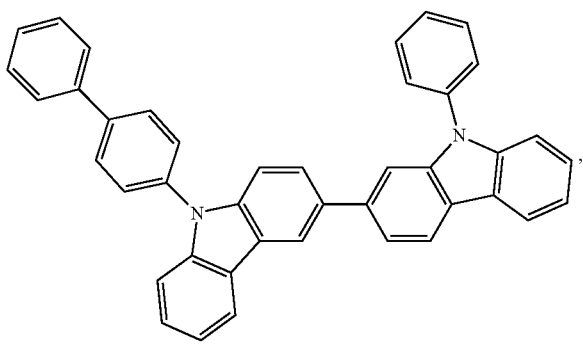 [SMILES: c1ccc(-c2ccc(-n3c4ccccc4c4cc(-c5ccc6c7ccccc7n(-c7ccccc7)c6c5)ccc43)cc2)cc1]

-continued
Compound H12
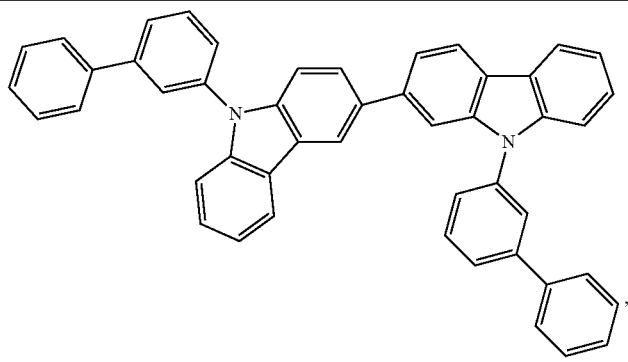
Compound H13
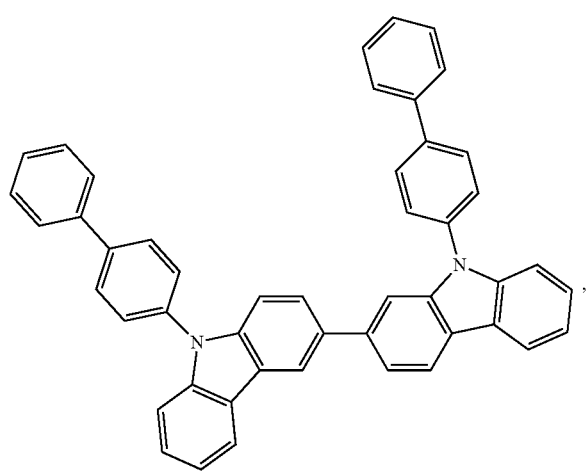 [SMILES: c1ccc(-c2ccc(-n3c4ccccc4c4cc(-c5ccc6c7ccccc7n(-c7ccc(-c8ccccc8)cc7)c6c5)ccc43)cc2)cc1]
Compound H14
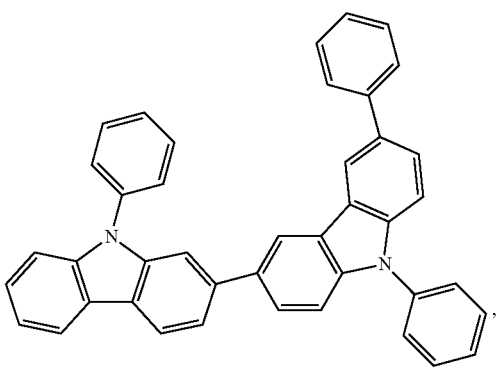 [SMILES: c1ccc(-c2ccc3c(c2)c2cc(-c4ccc5c6ccccc6n(-c6ccccc6)c5c4)ccc2n3-c2ccccc2)cc1]
Compound H15
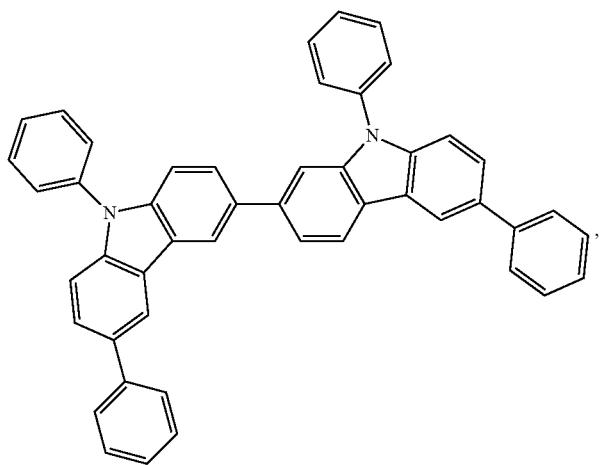 [SMILES: c1ccc(-c2ccc3c(c2)c2cc(-c4ccc5c6cc(-c7ccccc7)ccc6n(-c6ccccc6)c5c4)ccc2n3-c2ccccc2)cc1]

Compound H16
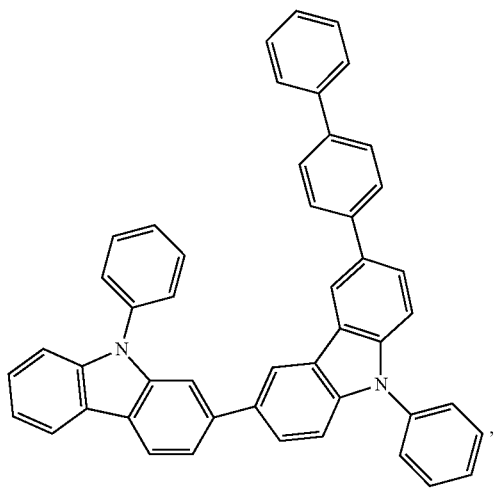 [SMILES: c1ccc(-c2ccc(-c3ccc4c(c3)c3cc(-c5ccc6c7ccccc7n(-c7ccccc7)c6c5)ccc3n4-c3ccccc3)cc2)cc1]
Compound H17
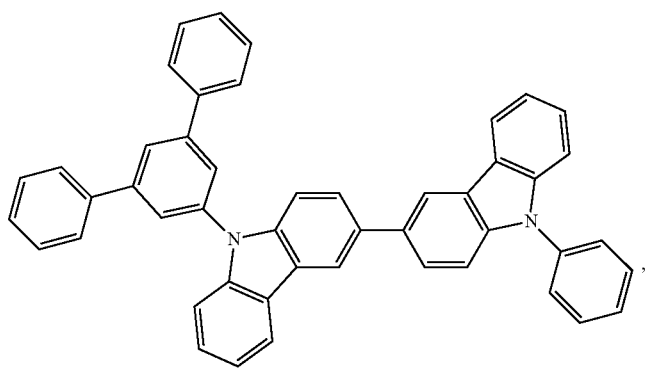 [SMILES: c1ccc(-c2cc(-c3ccccc3)cc(-n3c4ccccc4c4cc(-c5ccc6c(c5)c5ccccc5n6-c5ccccc5)ccc43)c2)cc1]
Compound H18
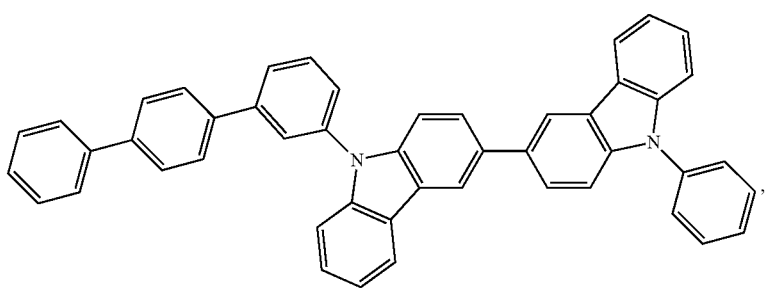 [SMILES: c1ccc(-c2ccc(-c3cccc(-n4c5ccccc5c5cc(-c6ccc7c(c6)c6ccccc6n7-c6ccccc6)ccc54)c3)cc2)cc1]
Compound H19
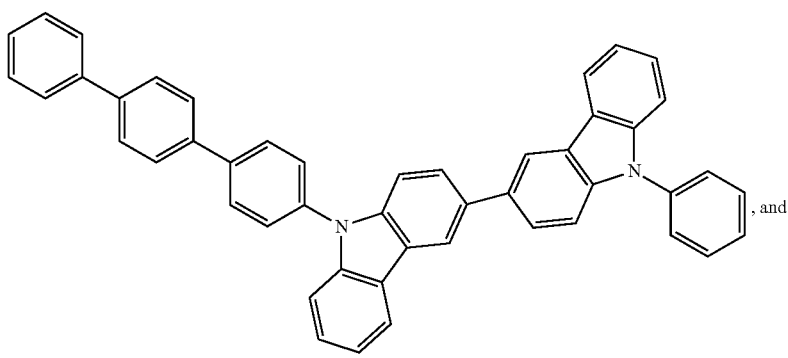 [SMILES: c1ccc(-c2ccc(-c3ccc(-n4c5ccccc5c5cc(-c6ccc7c(c6)c6ccccc6n7-c6ccccc6)ccc54)cc3)cc2)cc1]
, and Compound H20

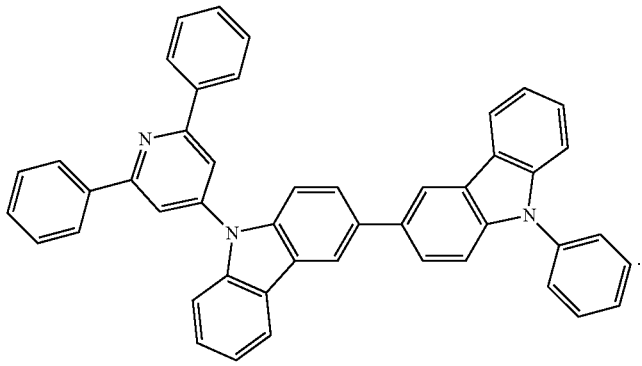 [SMILES: c1ccc(-c2cc(-n3c4ccccc4c4cc(-c5ccc6c(c5)c5ccccc5n6-c5ccccc5)ccc43)cc(-c3ccccc3)n2)cc1]

10. A premixed co-evaporation source comprising a mixture of a first compound and a second compound, wherein the mixture of the first compound and the second compound is selected from the group consisting of (Compound A5, Compound H7), (Compound A11, Compound F4), (Compound A11, Compound H3), (Compound A14, Compound F1), (Compound A14, Compound G26), (Compound A14, Compound G59), (Compound A14, Compound H5), (Compound A17, Compound G2), (Compound A17, Compound H5), (Compound A17, Compound H7), (Compound C74, Compound G14), (Compound C74, Compound G44), (Compound C83, Compound G2), (Compound C83, Compound H7), (Compound C248, Compound G14), (Compound D2, Compound G14), and (Compound D5, Compound 115), wherein the compounds are defined as follows:

Compound A5

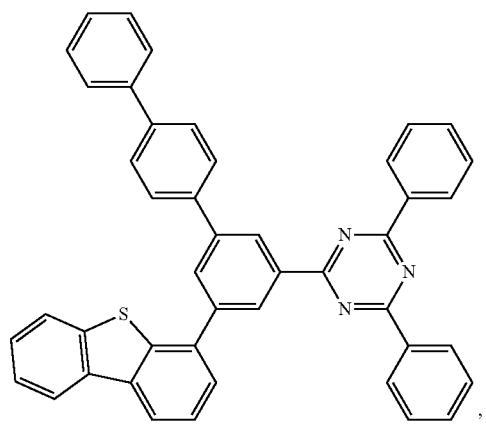

Compound A11

Compound A14

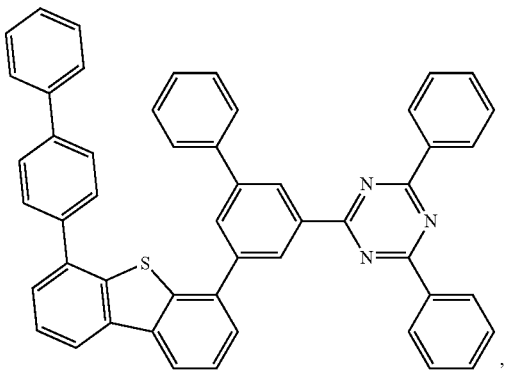

Compound A17

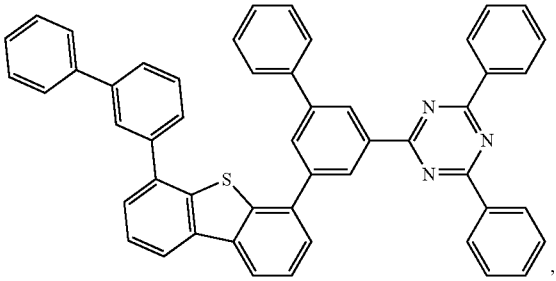

Compound C74

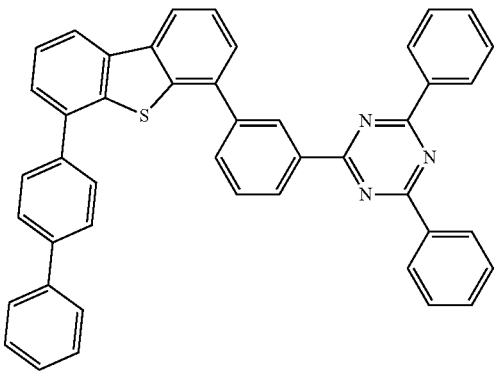

Compound C83
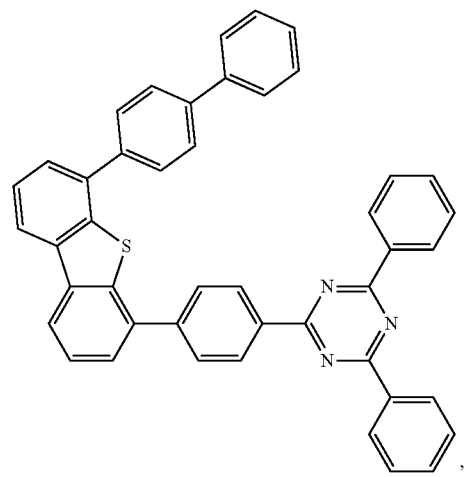
Compound C248
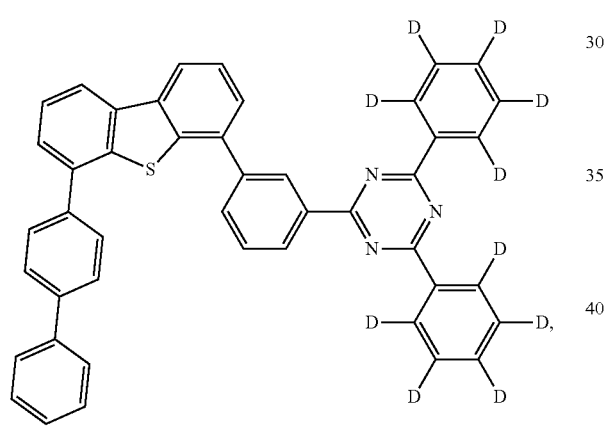
Compound D2
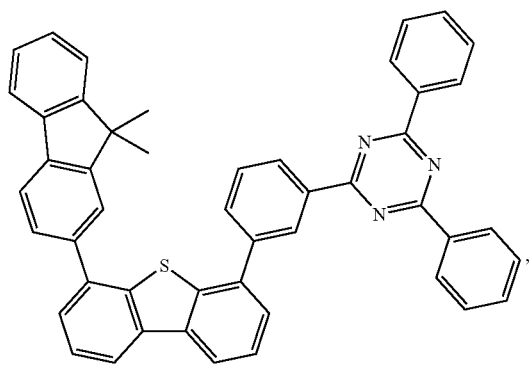
Compound D5
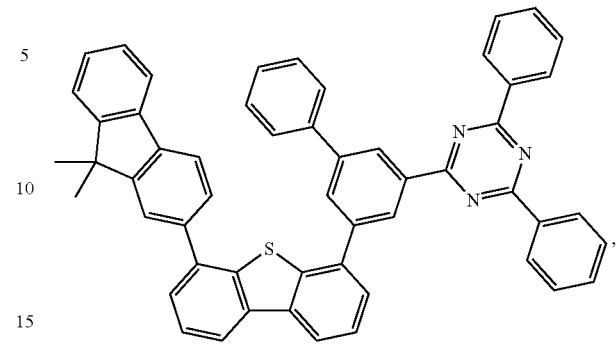
Compound F1
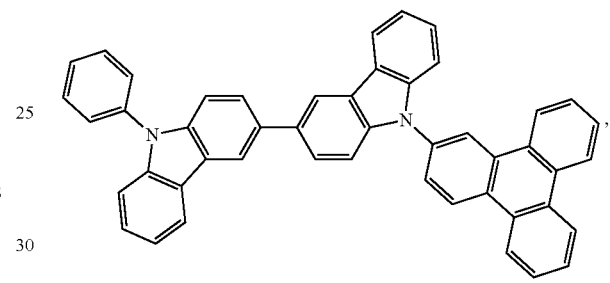
Compound F4
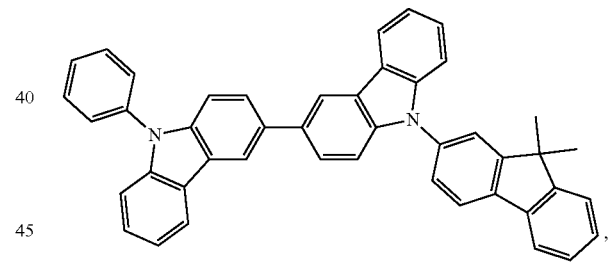
Compound G2
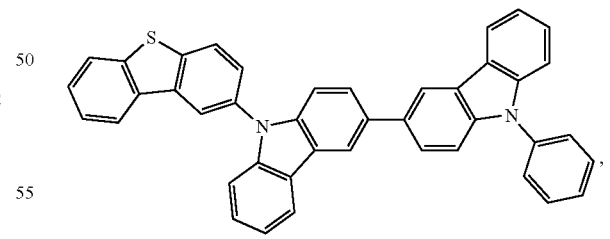
Compound G14
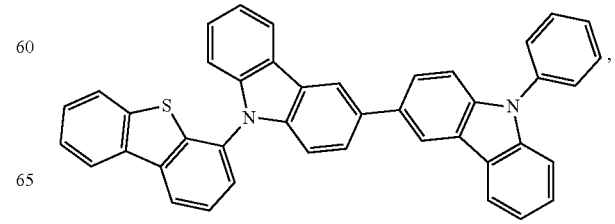

Compound G26

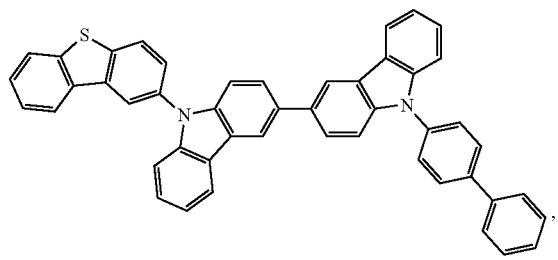

Compound G44

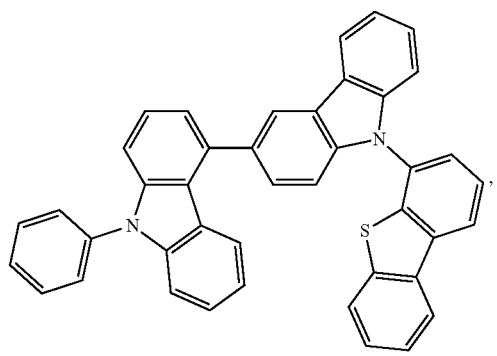

Compound G59

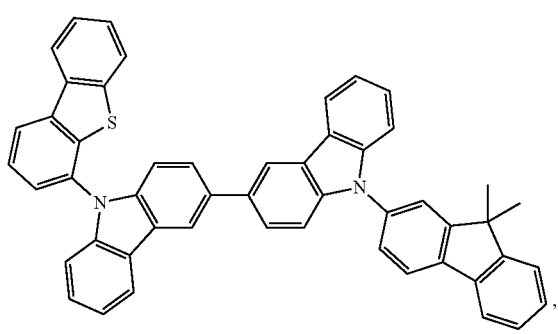

Compound H3

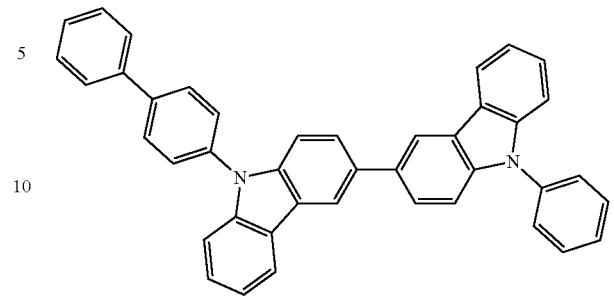

Compound H5

, and

Compound H7

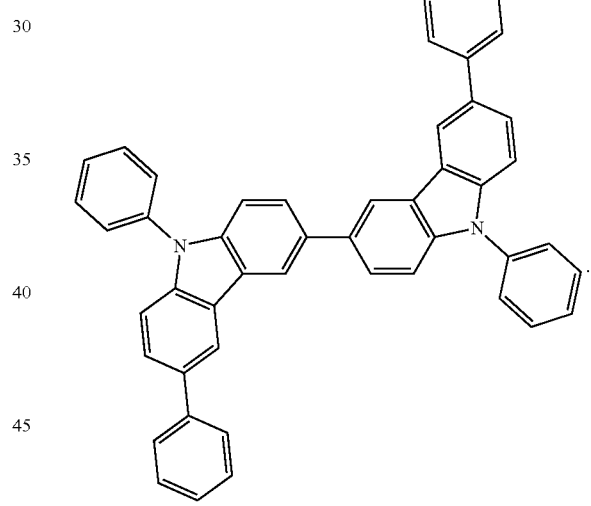

11. The premixed co-evaporation source or claim 1, wherein the first compound has a vapor pressure of P1 at T1 at 1 atm, the second compound has a vapor pressure of P2 at T2 at 1 atm; and wherein the ratio of P1/P2 is within the range of 0.90 to 1.10.

12. The premixed co-evaporation source of claim 1, wherein the first compound has a first mass loss rate and the second compound has a second mass loss rate, wherein the ratio between the first mass loss rate and the second mass loss rate is within the range of 0.90 to 1.10.

13. The premixed co-evaporation source of claim 1, wherein the premixed co-evaporation source further comprises a third compound, wherein the third compound has a different chemical structure than the first and second compounds.

14. A method for fabricating an organic light emitting device comprising a first electrode, a second electrode, and a first organic layer disposed between the first electrode and the second electrode, the method comprising:
providing a substrate having the first electrode disposed thereon;
depositing the first organic layer over the first electrode by evaporating a premixed co-evaporation source that is a mixture of a first compound and a second compound in a vacuum deposition tool; and
depositing the second electrode over the first organic layer,
wherein the first compound has a formula:

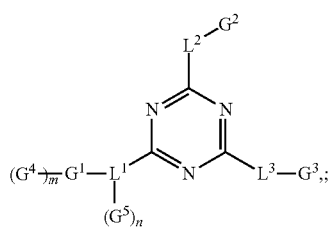

Formula I wherein $G^1$ is dibenzoselenophene;
wherein $L^1$, $L^2$ and $L^3$ are each independently selected from the group consisting of direct bond, phenyl, biphenyl, terphenyl, pyridine, pyrimidine, and combinations thereof;
wherein $G^4$ is selected from the group consisting of phenyl, biphenyl, terphenyl, naphthalene, phenanthrene, pyridine, pyrimidine, pyrazine, quinoline, isoquinoline, phenanthroline, fluorene, and combinations thereof;
wherein $G^2$, $G^3$, and $G^5$ are each independently selected from the group consisting of phenyl, biphenyl, terphenyl, naphthalene, phenanthrene, pyridine, pyrimidine, pyrazine, quinoline, isoquinoline, phenanthroline, azafluorene, and combinations thereof;
wherein $G^2$, $G^3$, $G^4$, and $G^5$ are each optionally further substituted with one or more unfused substituents selected from the group consisting of deuterium, alkyl, alkoxyl, cycloalkyl, cycloalkoxyl, halogen, nitro, nitrile, phenyl, biphenyl, terphenyl, pyridine, and combinations thereof;

wherein m is an integer from 0 to 7,
wherein n is an integer from 0 to 4;
wherein, when m or n is larger than 1, each or $G^4$ or $G^5$ can be same or different;
wherein the second compound has a formula:

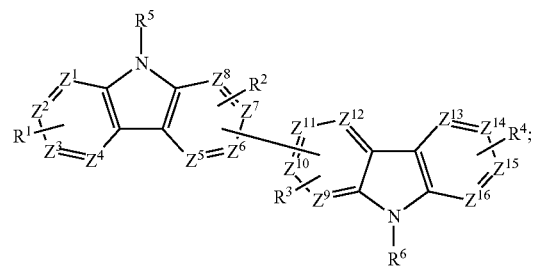

Formula II wherein each $Z^1$ to $Z^{16}$ is C or N;
wherein one of $Z^5$ to $Z^8$ bonds to one of $Z^9$ to $Z^{12}$ through a C—C bond;
wherein $R^1$, $R^4$ each independently represents mono, di, tri, or tetra substitution, or no substitution;
wherein $R^2$, $R^3$ each independently represent mono, di, or tri substitution, or no substitution; and
wherein $R^1$ to $R^6$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, and any two adjacent substituents are optionally joined or fused into a ring.

15. The method of claim 14, wherein the vacuum deposition tool comprises a chamber with a pressure between $1 \times 10^{-6}$ Torr to $1 \times 10^{-9}$ Torr, and the depositing step comprises a 2 Å/sec deposition rate on a surface position at a predefined distance away from the premixed co-evaporation source.

16. The premixed co-evaporation source of claim 1, wherein the first compound is selected from the group consisting of:

Compound A3, represented by the formula

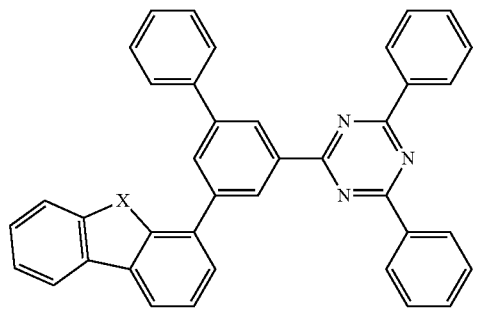

wherein in Comopund A3: X = Se,

Compound A6, represented by the formula

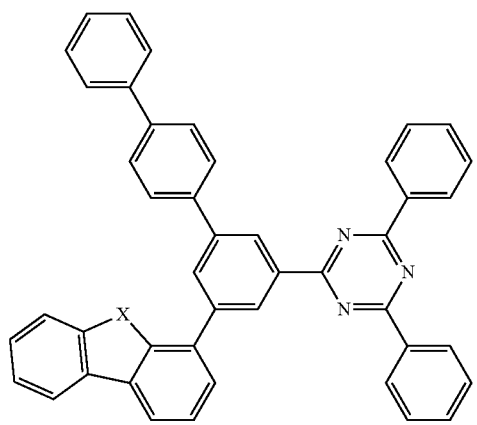
wherein in Comopund A6: X = Se,
Compound A9, represented by the formula
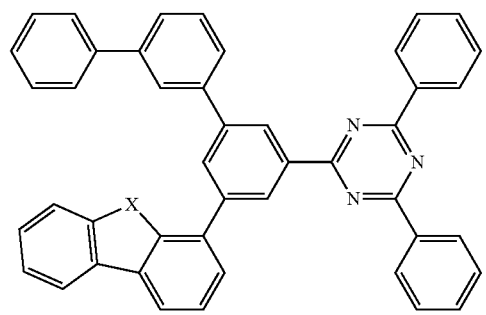
wherein in Comopund A9: X = Se,
Compound A12, represented by the formula
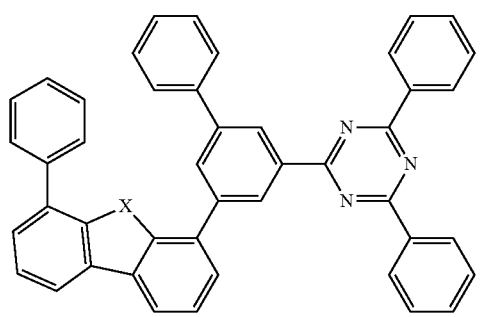
wherein in Comopund A12: X = Se,
Compound A15, represented by the formula

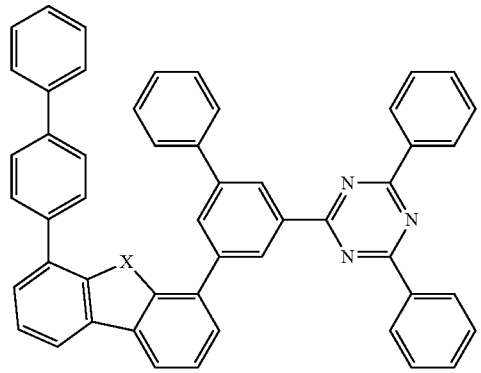
wherein in Comopund A15: X = Se,
Compound A18, represented by the formula
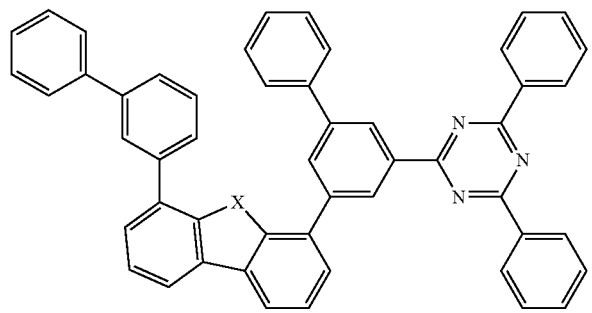
wherein in Comopund A18: X = Se,
Compound A21, represented by the formula
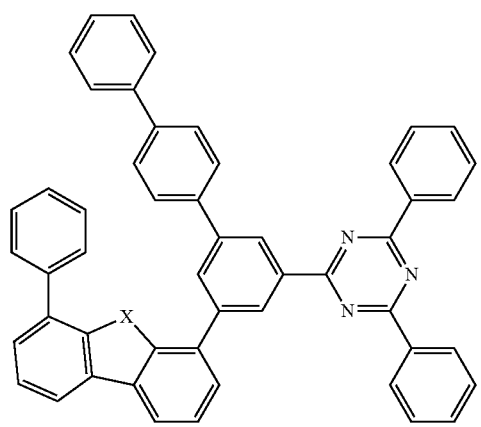
wherein in Comopund A24: X = Se,
Compound A24, represented by the formula

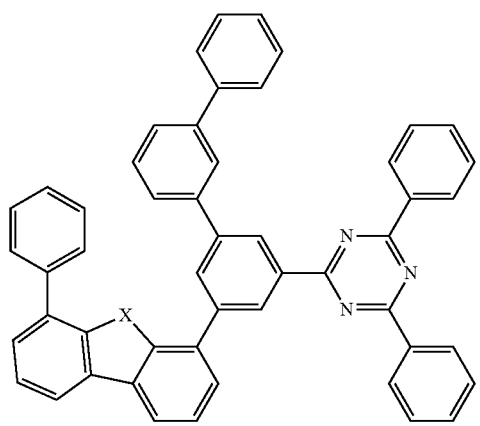
wherein in Comopund A24: X = Se,
Compound A27, represented by the formula
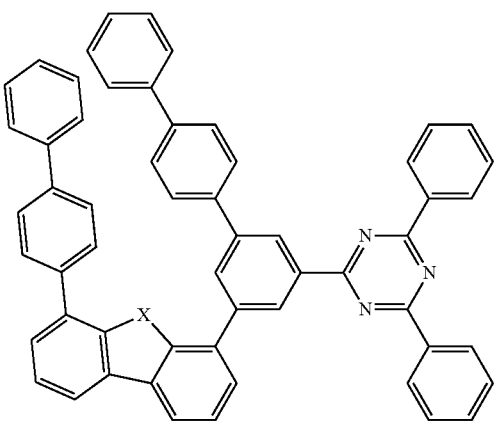
wherein in Comopund A27: X = Se,
Compound A30, represented by the formula
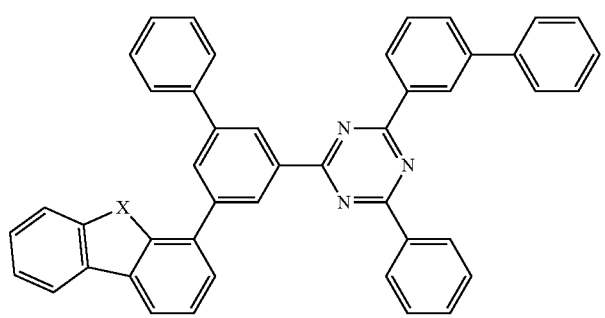
wherein in Comopund A30: X = Se,
Compound A33, represented by the formula

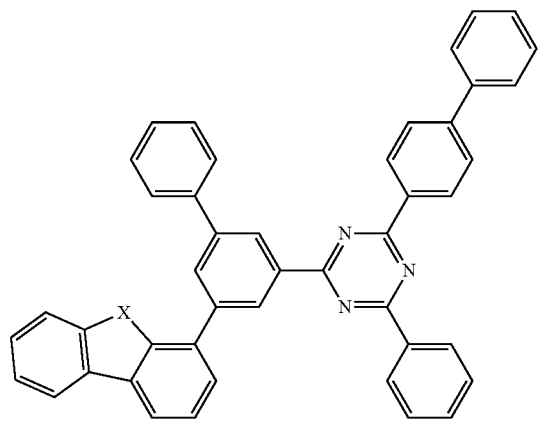
wherein in Comopund A33: X = Se,
Compound A36, represented by the formula
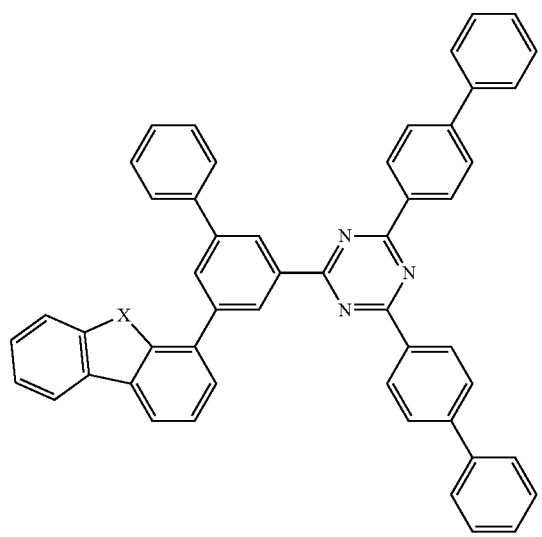
wherein in Comopund A36: X = Se,
Compound A42, represented by the formula
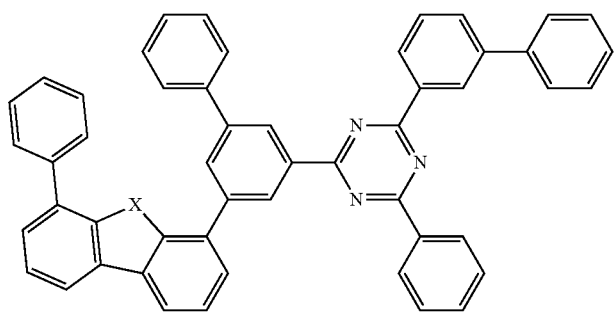
wherein in Comopund A42: X = Se,
Compound A45, represented by the formula -continued
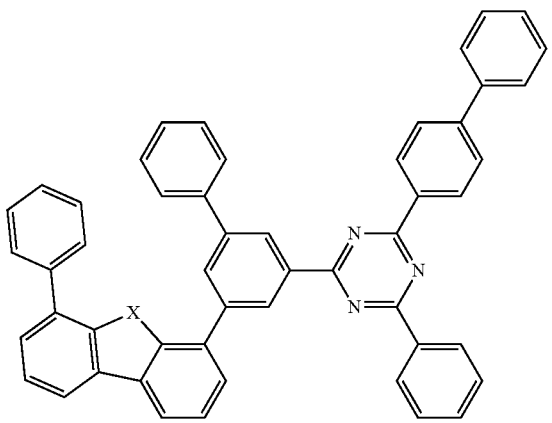
wherein in Comopund A45: X = Se,
Compound A51, represented by the formula
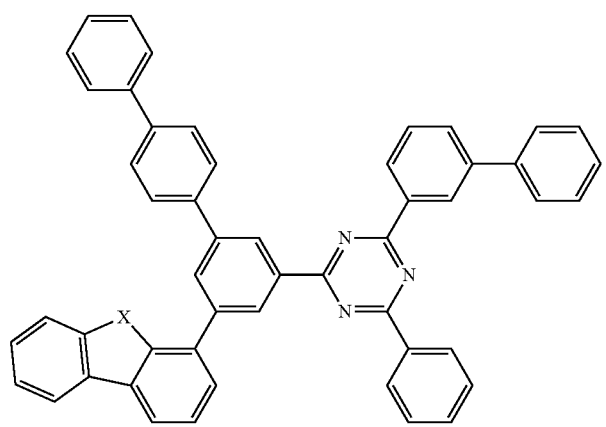
wherein in Comopund A51: X = Se,
Compound A54, represented by the formula
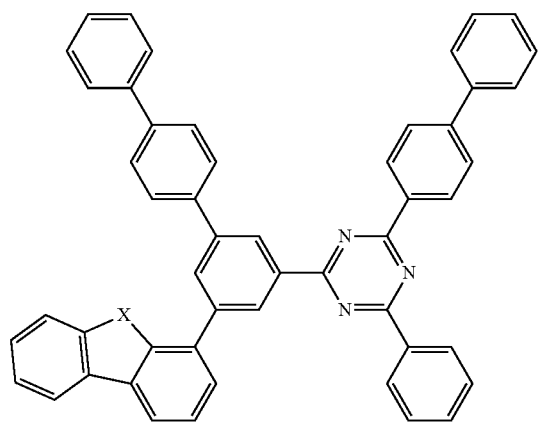
wherein in Comopund A54: X = Se,
Compound A60, represented by the formula

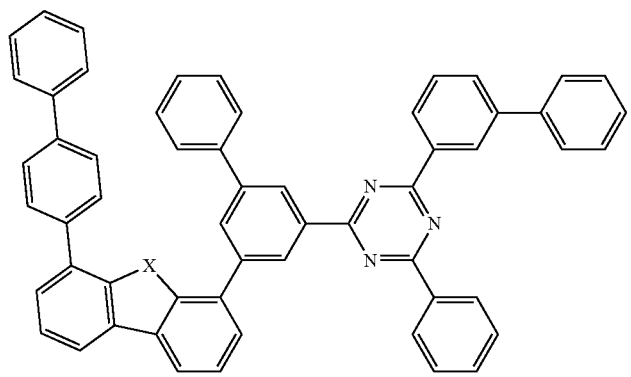
wherein in Comopund A60: X = Se,
Compound A63, represented by the formula
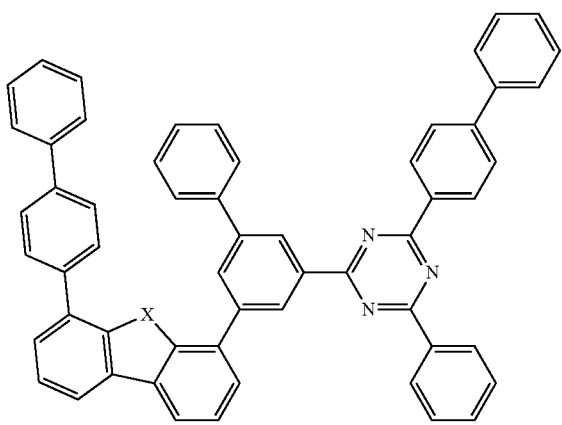
wherein in Comopund A63: X = Se,
Compound A69, represented by the formula
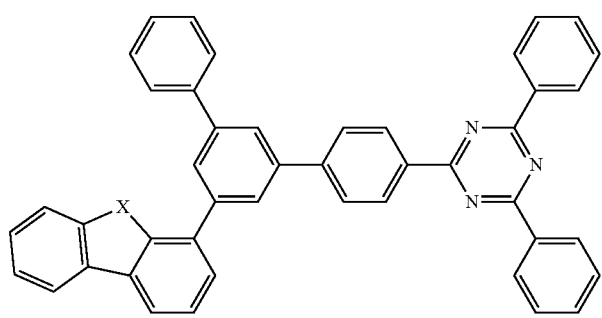
wherein in Comopund A69: X = Se,
Compound A72, represented by the formula

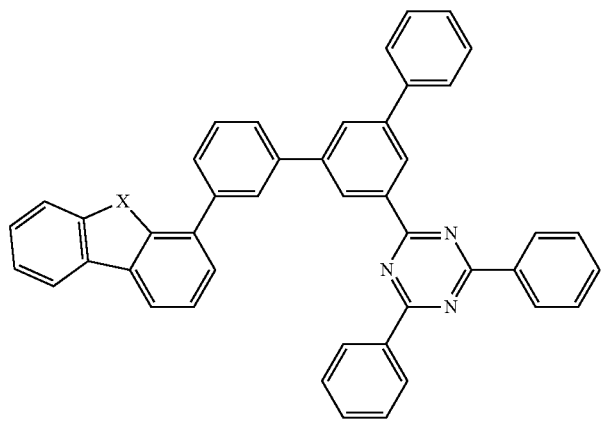
wherein in Comopund A72: X = Se,
Compound A75, represented by the formula
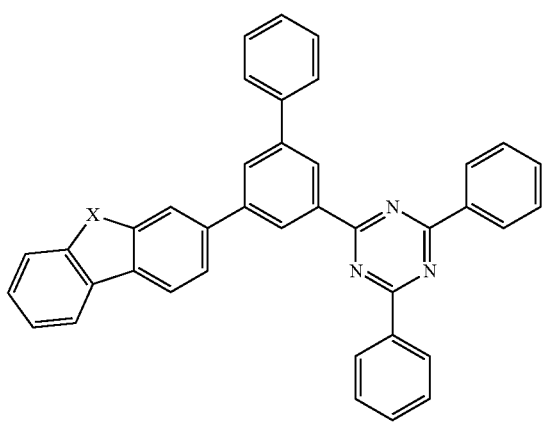
wherein in Comopund A75: X = Se,
Compound A78, represented by the formula
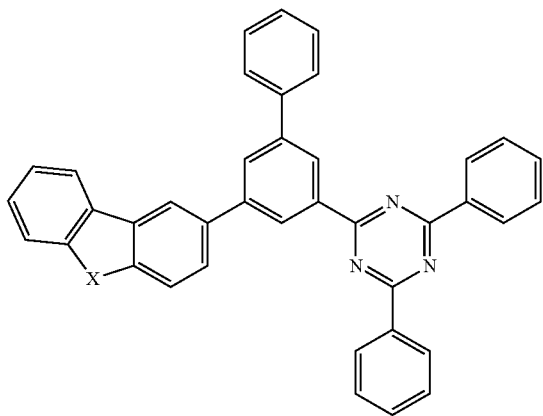
wherein in Comopund A78: X = Se,
Compound A81, represented by the formula

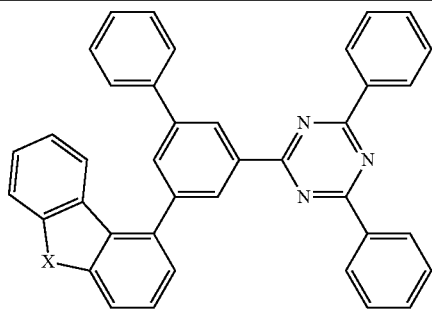
wherein in Comopund A81: X = Se,
Compound A84, represented by the formula
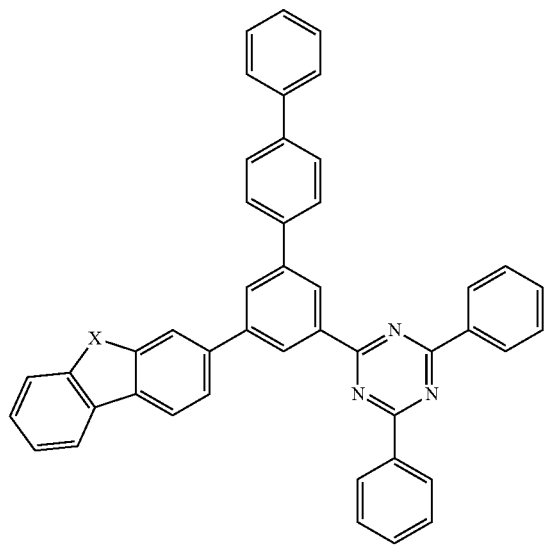
wherein in Comopund A84: X = Se,
Compound A87, represented by the formula
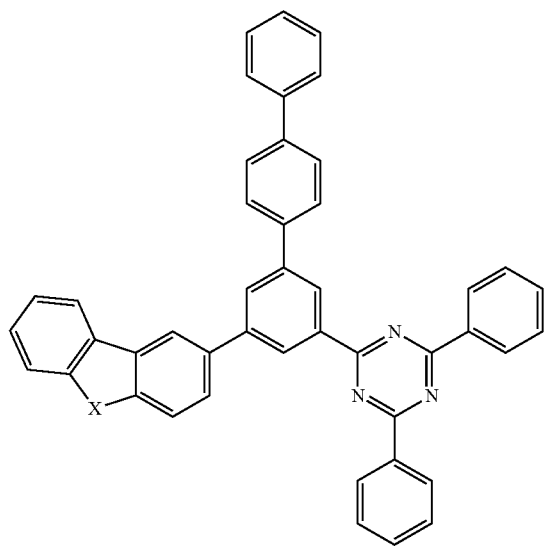
wherein in Comopund A87: X = Se,
Compound A90, represented by the formula

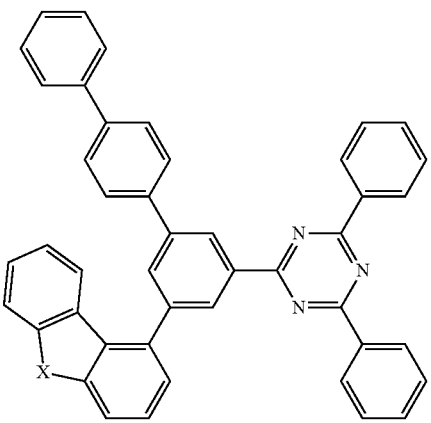
wherein in Comopund A90: X = Se,
Compound A93, represented by the formula
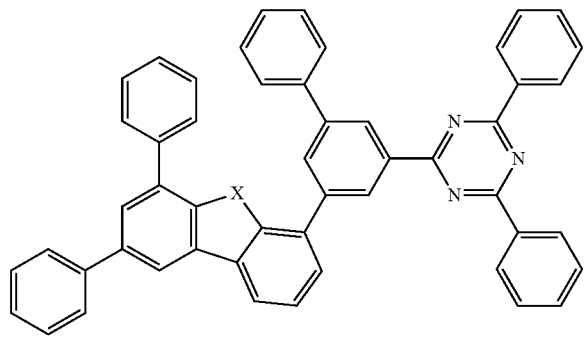
wherein in Comopund A93: X = Se,
Compound A96, repreented by the formula
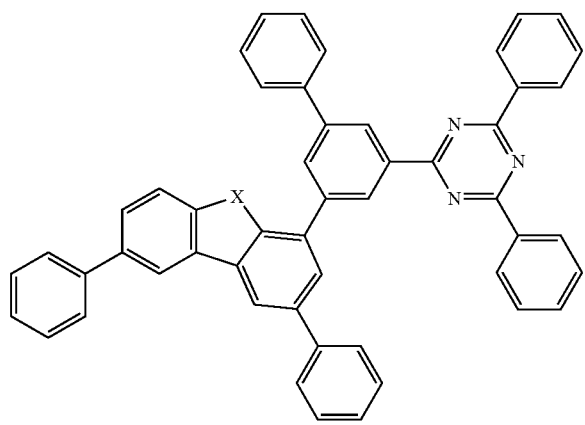
wherein in Comopund A96: X = Se,
Compound A99, represented by the formula

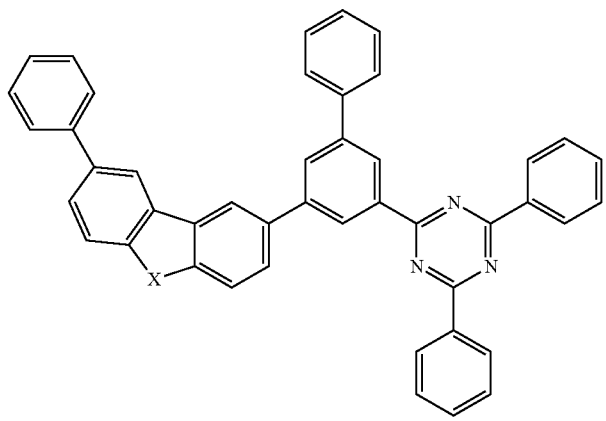
wherein in Comopund A99: X = Se,
Compound A102, represented by the formula
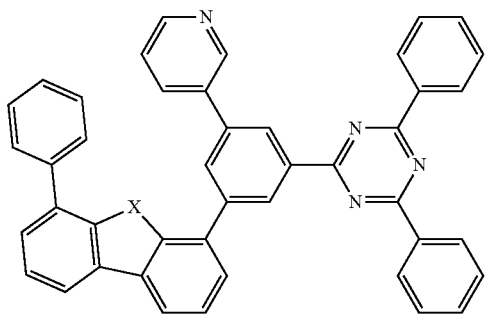
wherein in Comopund A102: X = Se,
Compound A105, represented by the formula
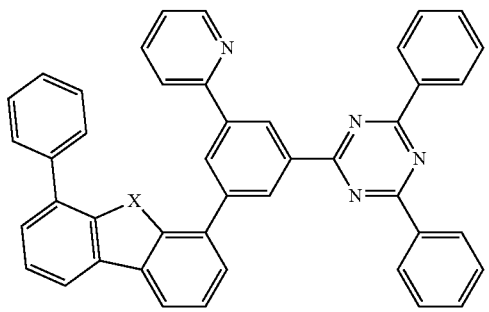
wherein in Comopund A105: X = Se,
Compound A108, represented by the formula
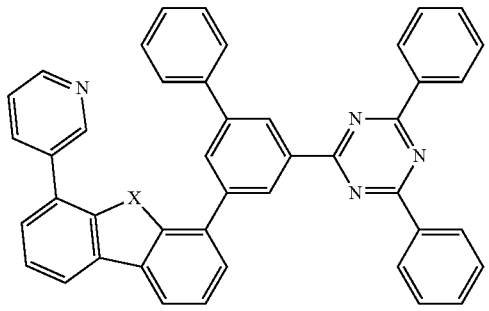
wherein in Comopund A111: X = Se,
Compound A111, represented by the formula

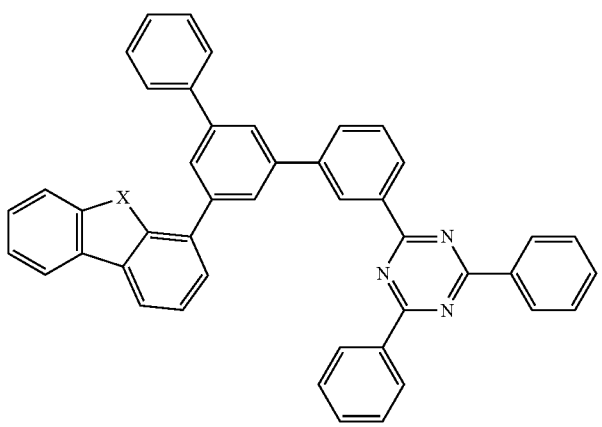
wherein in Comopund A111: X = Se,
Compound A114, represented by the formula
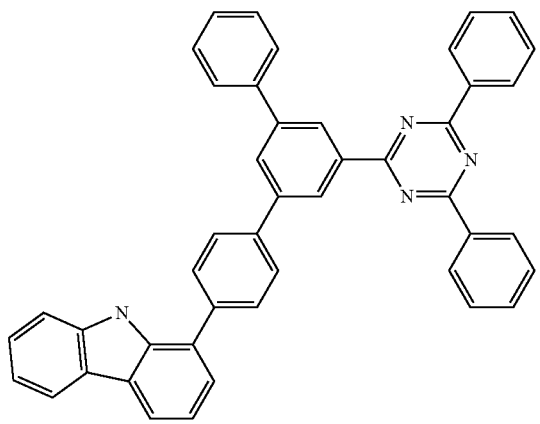 [SMILES: c1ccc(-c2cc(-c3ccc(-c4cccc5c4[nH]c4ccccc45)cc3)cc(-c3nc(-c4ccccc4)nc(-c4ccccc4)n3)c2)cc1]
wherein in Comopund A114: X = Se,
Compound C69, represented by the formula
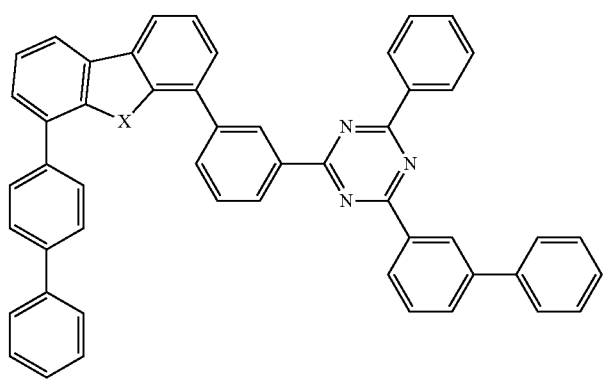
wherein in Comopund C69: X = Se,
Compound C72, represented by the formula

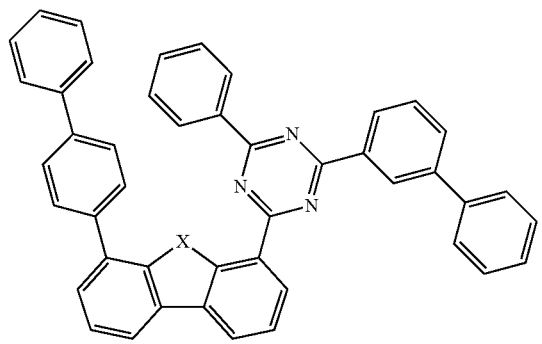
wherein in Comopund C72: X = Se,
Compound C75, represented by the formula
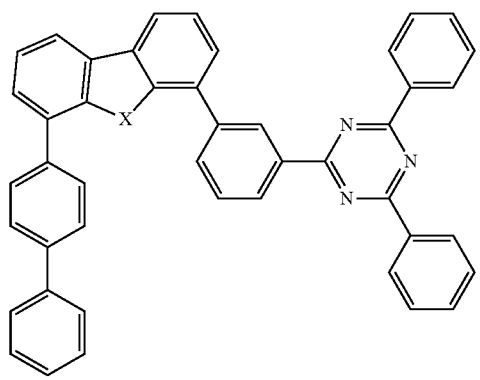
wherein in Comopund C75: X = Se,
Compound C78, represented by the formula
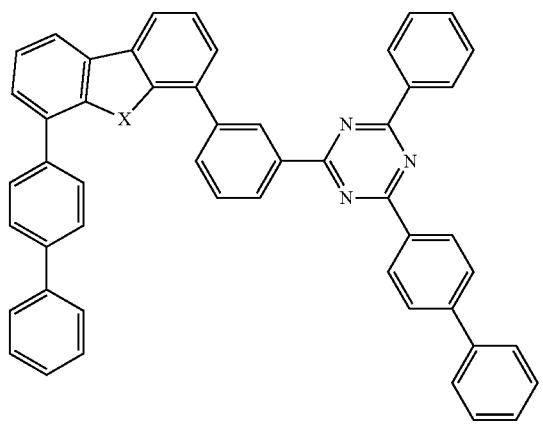
wherein in Comopund C78: X = Se,
Compound C81, represented by the formula

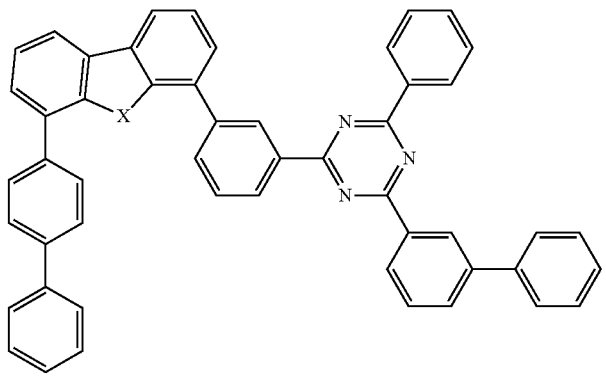
wherein in Comopund C81: X = Se,
Compound C84, represented by the formula
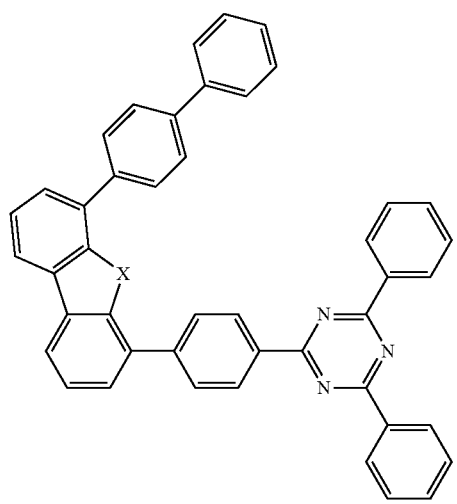
wherein in Comopund C84: X = Se,
Compound C87, represented by the formula
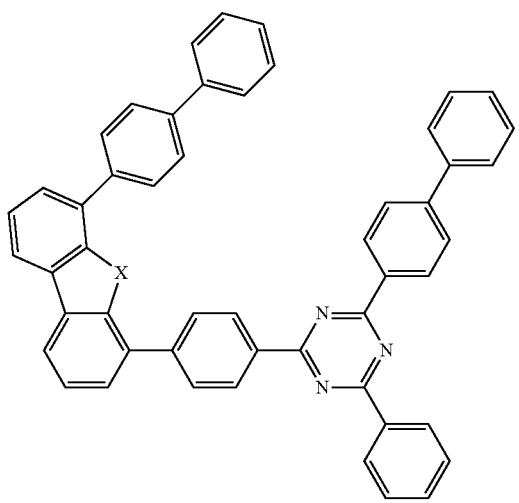
wherein in Comopund C87: X = Se,
Compound C90, represented by the formula

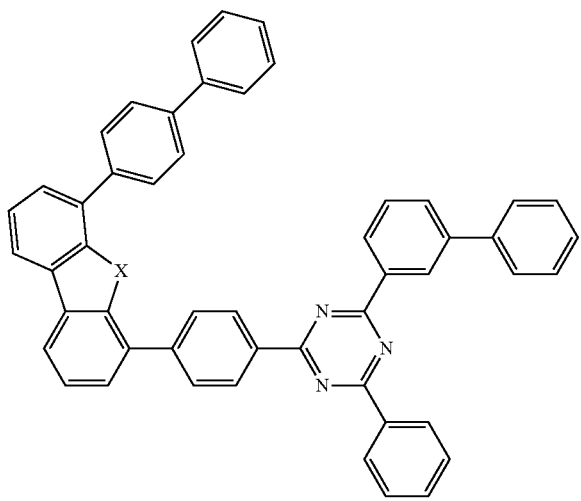
wherein in Comopund C90: X = Se,
Compound C93, represented by the formula
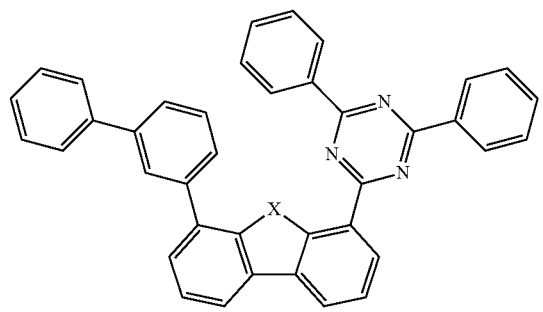
wherein in Comopund C93: X = Se,
Compound C96, represented by the formula
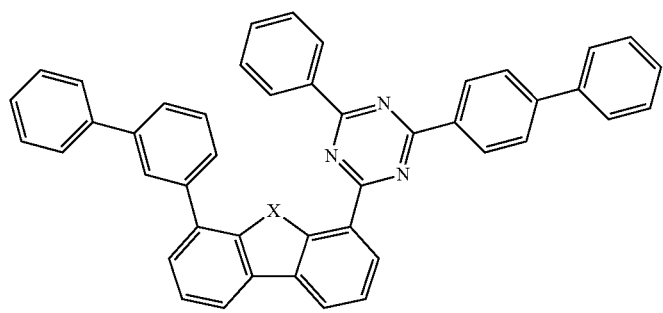
wherein in Comopund C96: X = Se,
Compound C99, represented by the formula

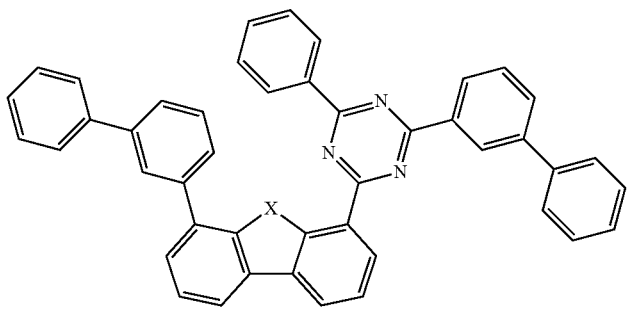
wherein in Comopund C99: X = Se,
Compound C102, represented by the formula
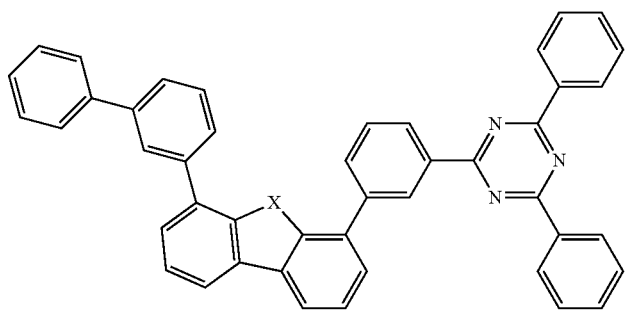
wherein in Comopund C102: X = Se,
Compound C105, represented by the formula
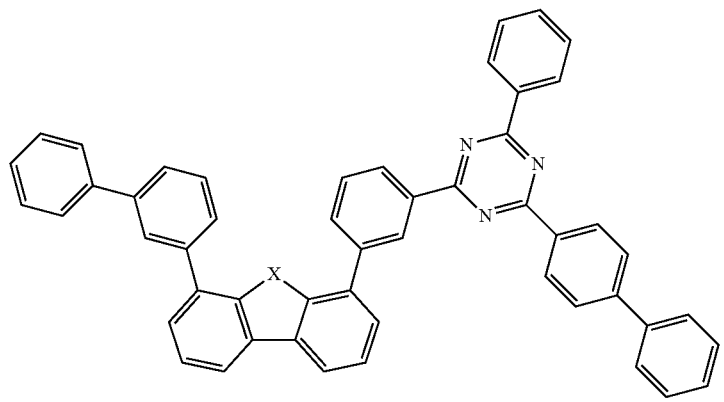
wherein in Comopund C105: X = Se,
Compound C108, represented by the formula
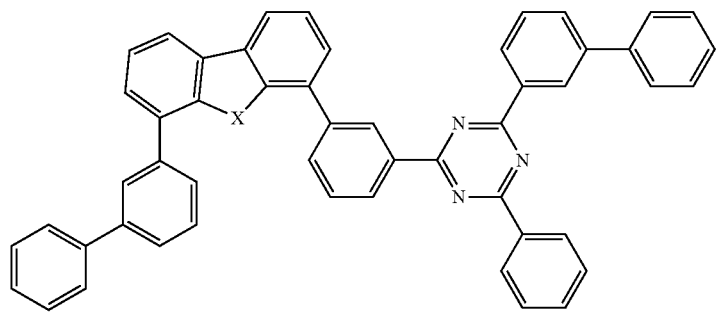
wherein in Comopund C108: X = Se,
Compound C111, represented by the formula

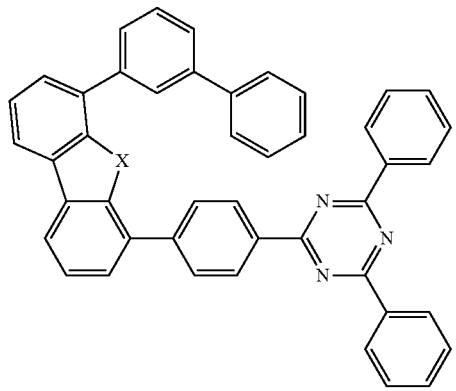
wherein in Comopund C111: X = Se,
Compound C114, represented by the formula
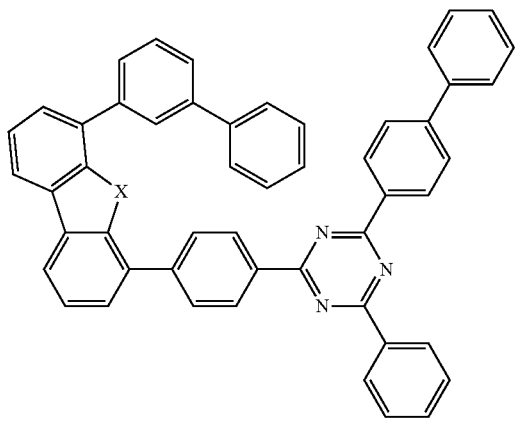
wherein in Comopund C114: X = Se,
Compound C117, represented by the formula
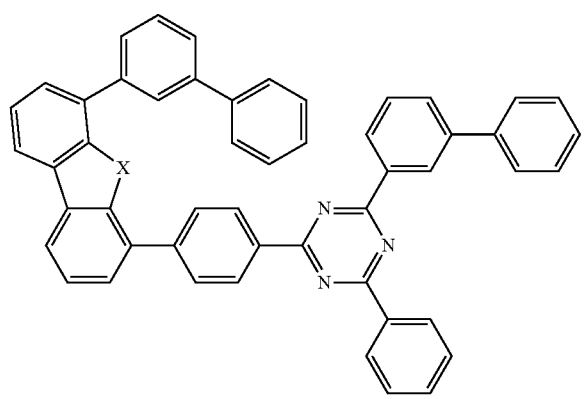
wherein in Comopund C117: X = Se,
Compound C171, represented by the formula

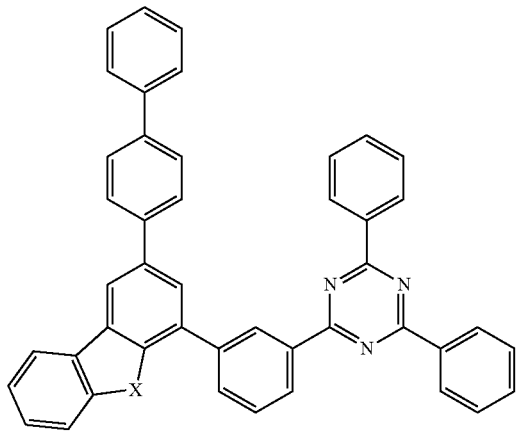
wherein in Comopund C171: X = Se,
Compound C180, represented by the formula
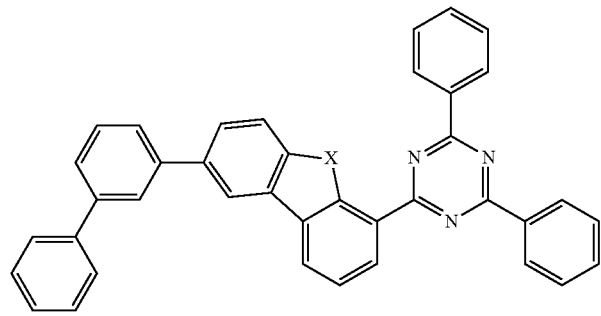
wherein in Comopund C180: X = Se,
Compound C183, represented by the formula
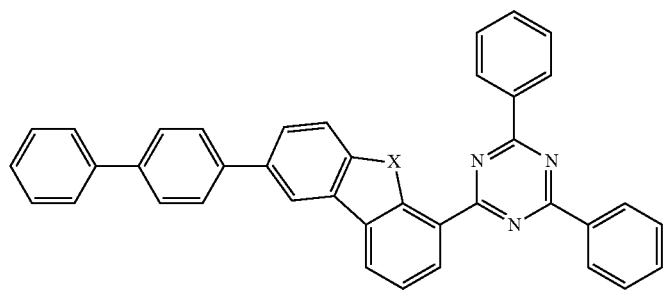
wherein in Comopund C183: X = Se,
Compound C189, represented by the formula
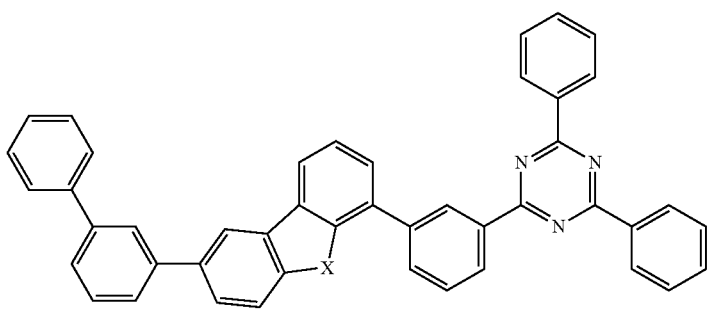
wherein in Comopund C189: X = Se,
Compound C201, represented by the formula

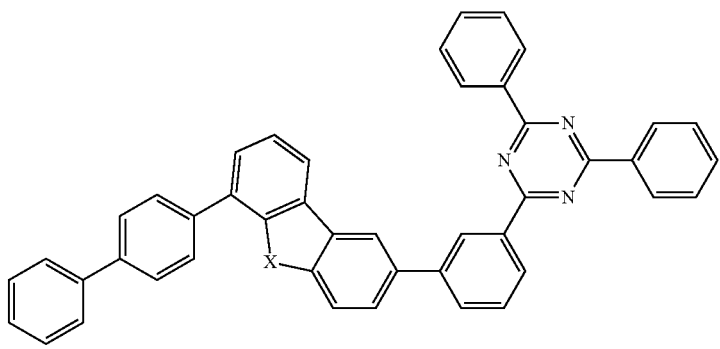
wherein in Comopund C201: X = Se,
Compound C204, represented by the formula
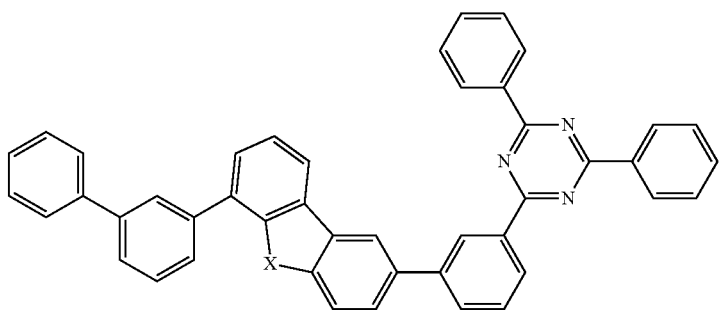
wherein in Comopund C204: X = Se,
Compound C219, represented by the formula
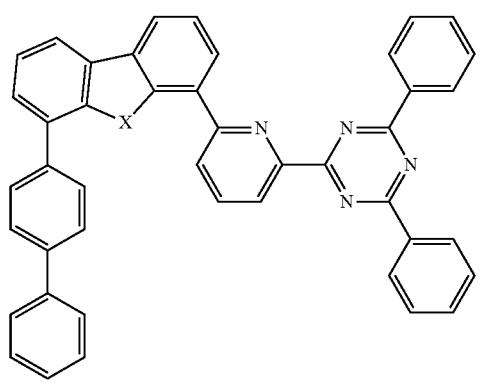
wherein in Comopund C219: X = Se,
Compound C240, represented by the formula

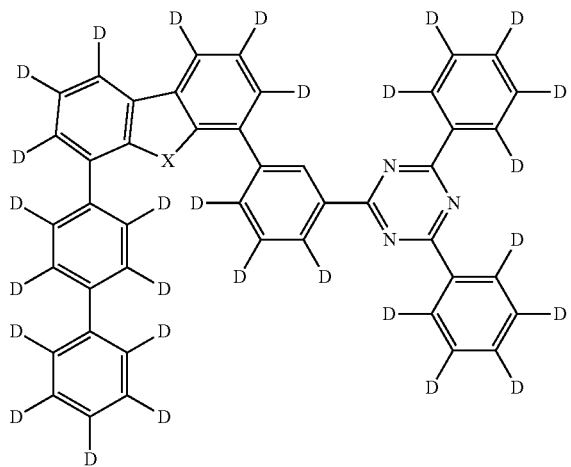
wherein in Comopund C240: X = Se,
Compound C246, represented by the formula
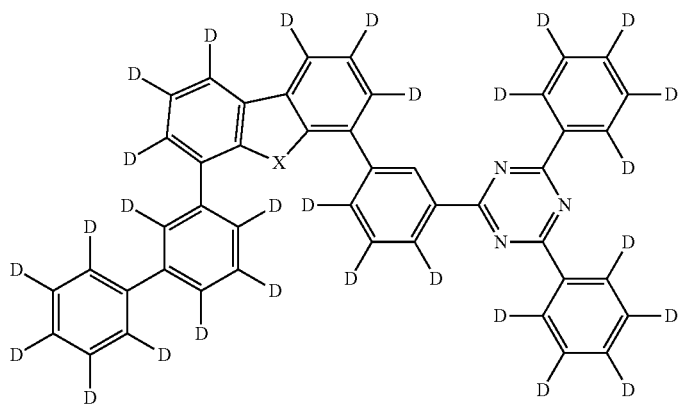
wherein in Comopund C246: X = Se,
Compound C249, represented by the formula
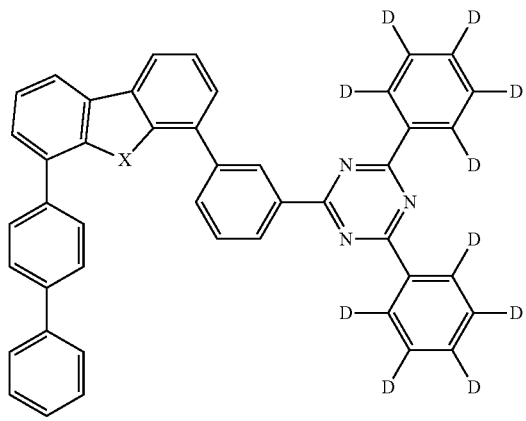
wherein in Comopund C249: X = Se,
Compound C252, represented by the formula

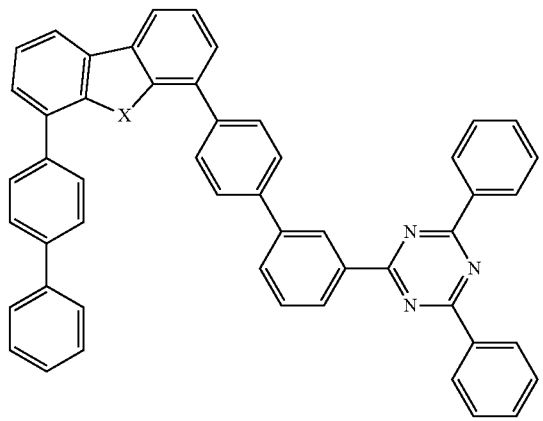
wherein in Comopund C252: X = Se,
Compound C255, represented by the formula
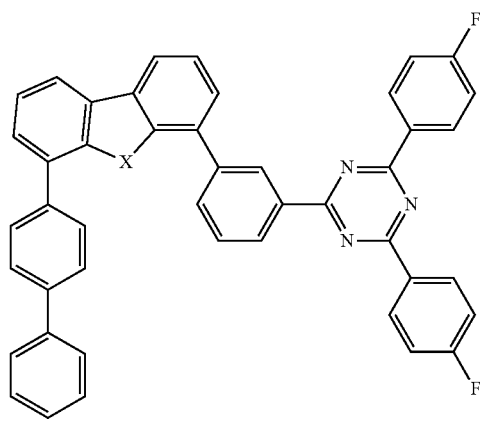
wherein in Comopund C255: X = Se,
Compound D6, represented by the formula:
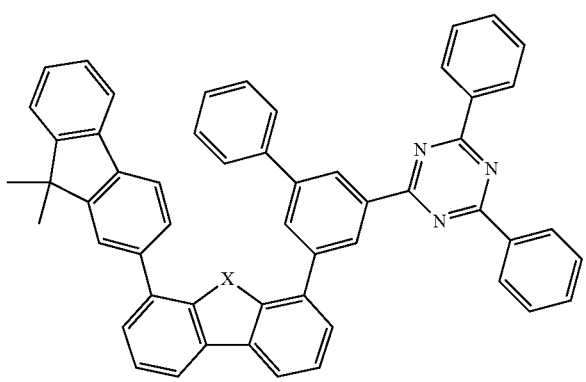
wherein in Comopund D6, X = Se,
Compound C3, represented by the formula

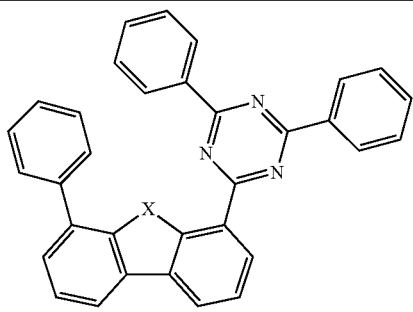
wherein in Compound C3: X = Se,
wherein in Comopund C3: X = Se,
Compound C6, represented by the formula
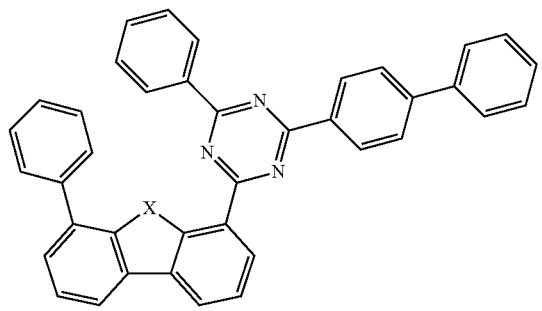
wherein in Comopund C6: X = Se,
Compound C9, represented by the formula
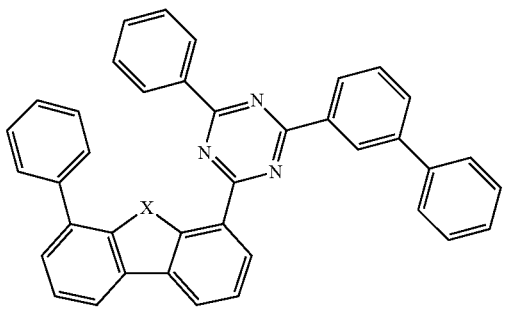
wherein in Comopund C9: X = Se,
Compound C12, represented by the formula
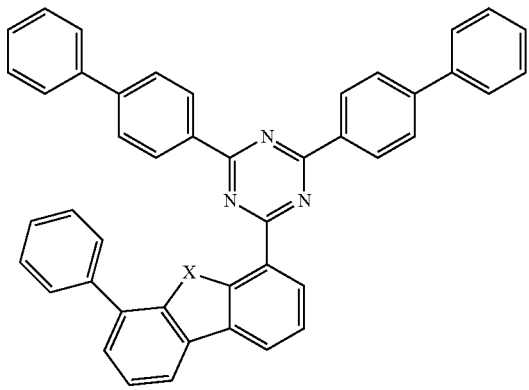
wherein in Comopund C12: X = Se,
Compound C15, represented by the formula

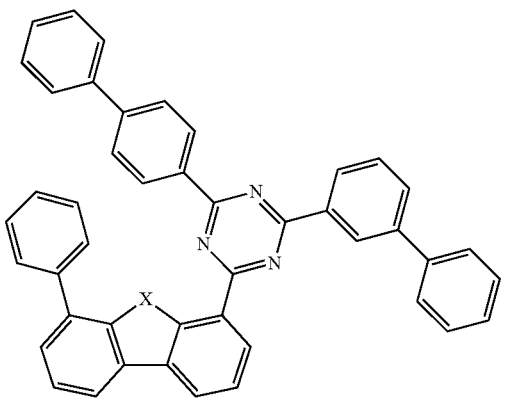
wherein in Comopund C15: X = Se,
Compound C18, represented by the formula
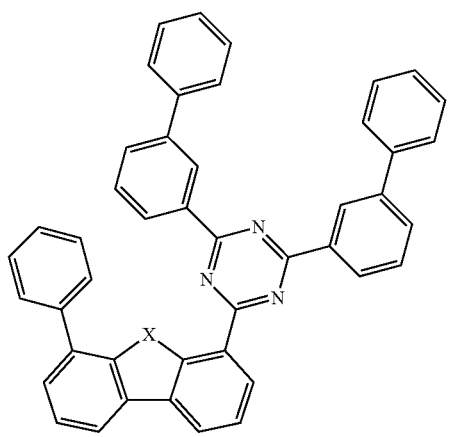
wherein in Comopund C18: X = Se,
Compound C21, represented by the formula
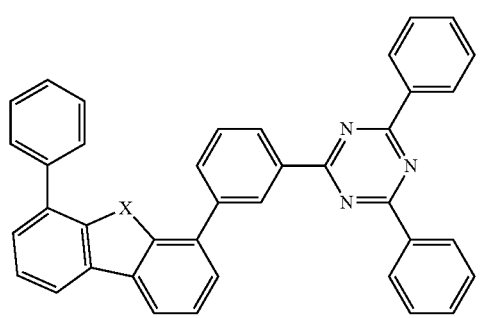
wherein in Comopund C21: X = Se,
Compound C24, represented by the formula

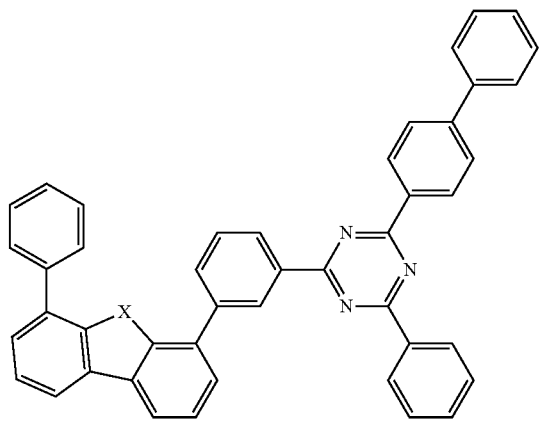
wherein in Compound C24: X = Se,
Compound C27, represented by the formula
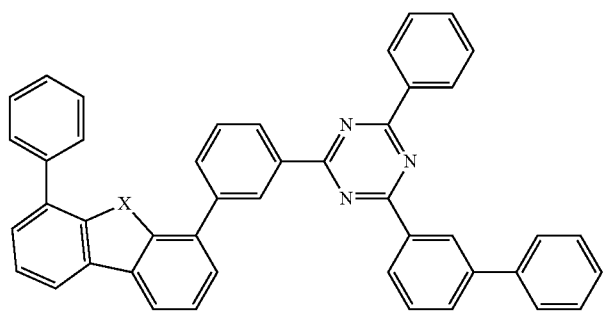
wherein in Compound C27: X = Se,
Compound C30, represented by the formula
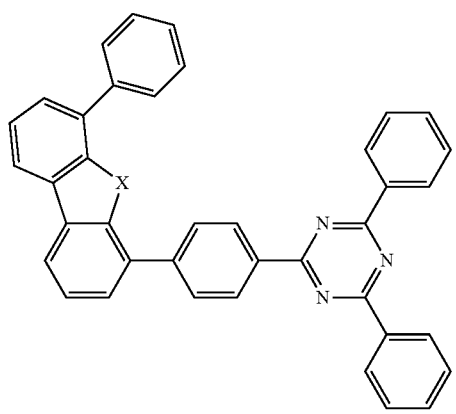
wherein in Compound C30: X = Se,
Compound C33, represented by the formula

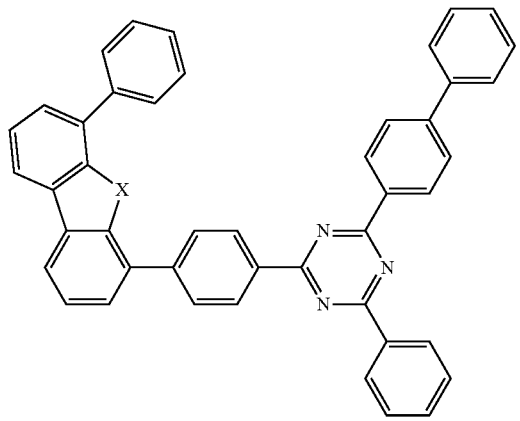
wherein in Comopund C33: X = Se,
Compound C36, represented by the formula
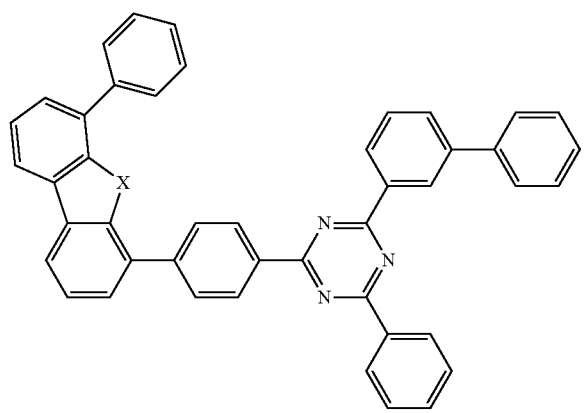
wherein in Comopund C36: X = Se,
Compound C39, represented by the formula
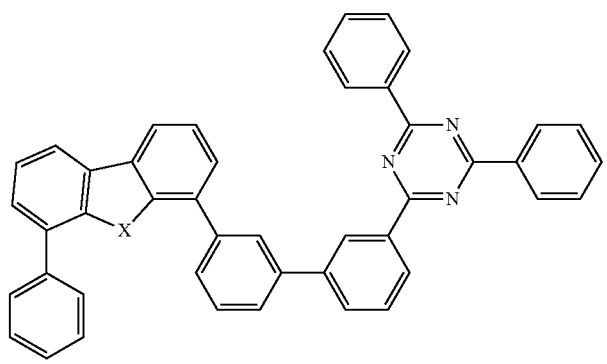
wherein in Comopund C39: X = Se,
Compound C42, represented by the formula

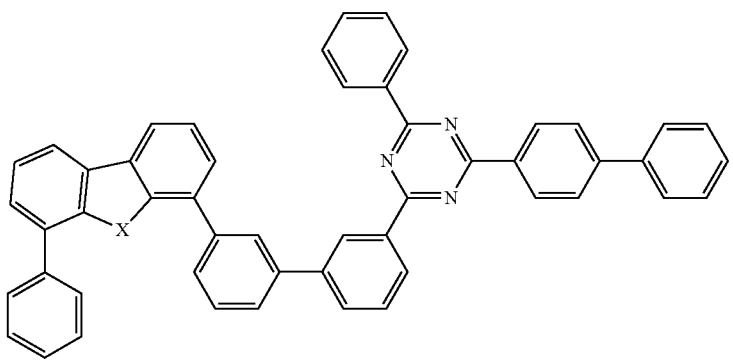
wherein in Comopund C42: X = Se,
Compound C45, represented by the formula
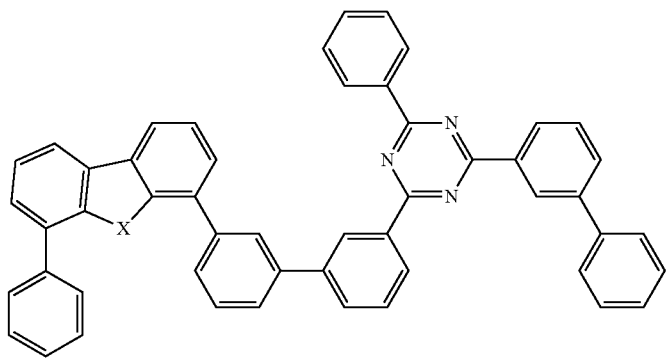
wherein in Comopund C45: X = Se,
Compound C48, represented by the formula
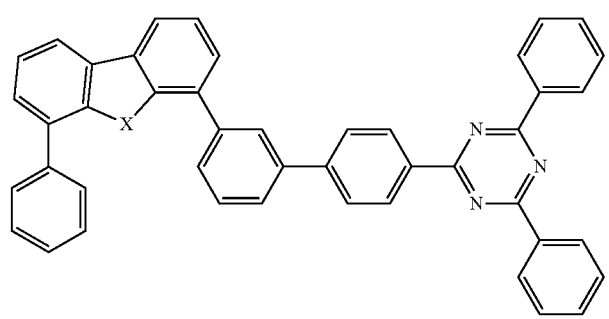
wherein in Comopund C48: X = Se,
Compound C51, represented by the formula -continued
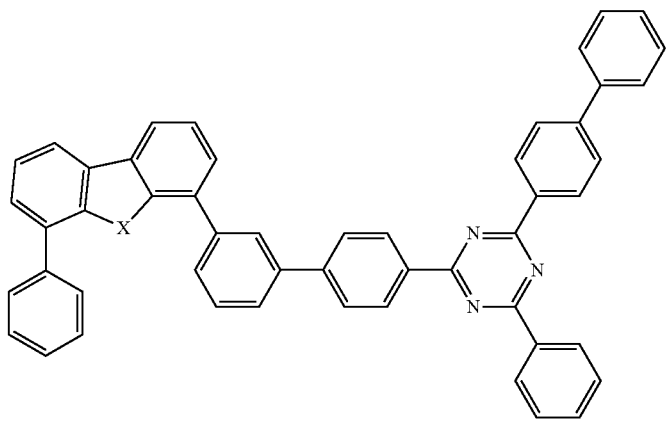
wherein in Comopund C51: X = Se,
Compound C54, represented by the formula
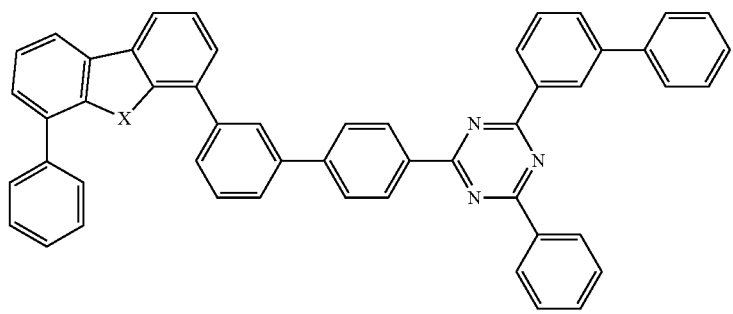
wherein in Comopund C54: X = Se,
Compound C57, represented by the formula
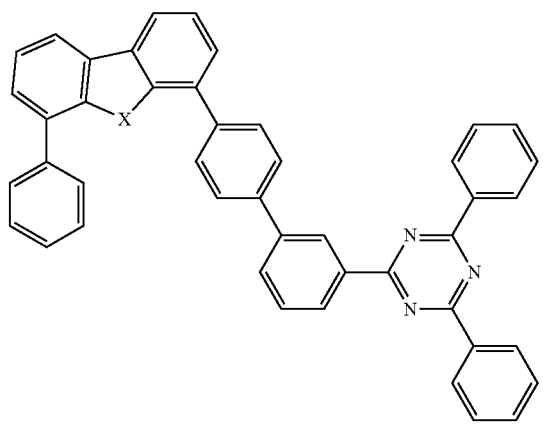
wherein in Comopund C57: X = Se,
Compound C60, represented by the formula

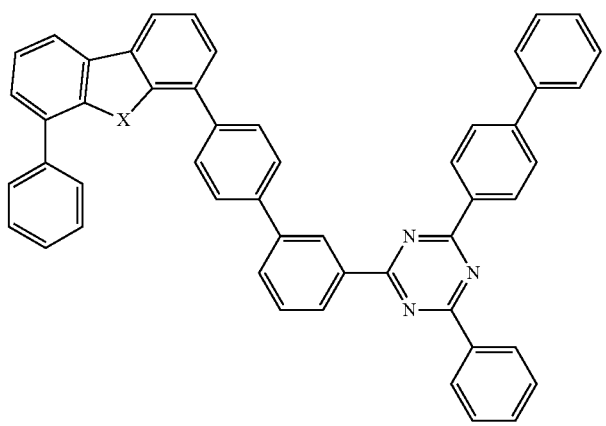
wherein in Comopund C60: X = Se,
Compound C63, represented by the formula
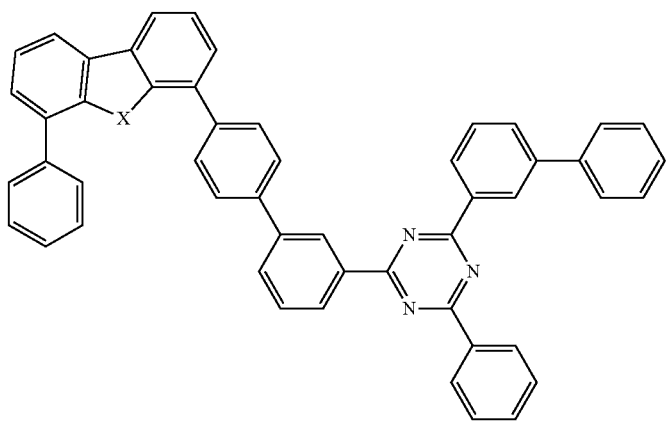
wherein in Comopund C63: X = Se,
Compound C66, represented by the formula
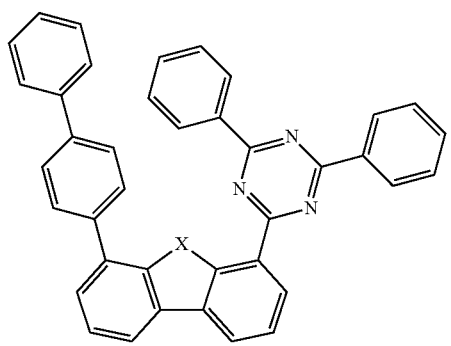
wherein in Comopund C66: X = Se,
Compound C165, represented by the formula

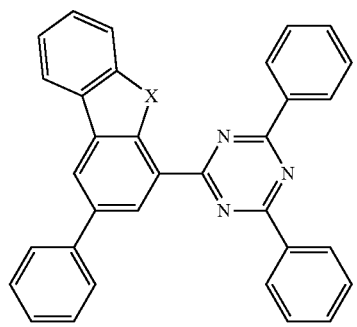
wherein in Comopund C165: X = Se,
Compound C168, represented by the formula
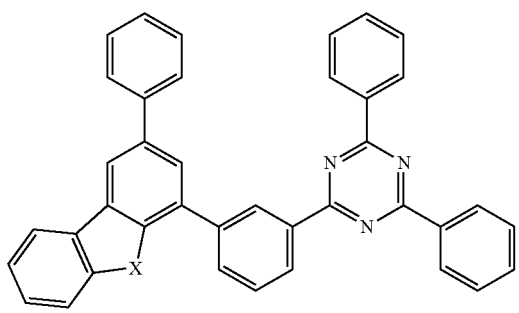
wherein in Comopund C168: X = Se,
Compound C174, represented by the formula
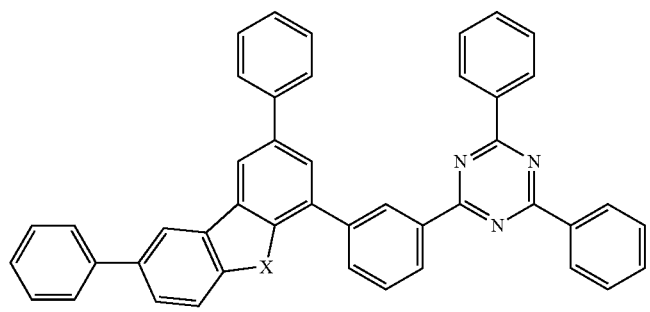
wherein in Comopund C174: X = Se,
Compound C177, represented by the formula
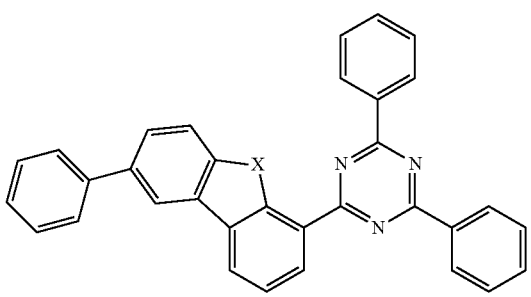
wherein in Comopund C177: X = Se,
Compound C183, represented by the formula

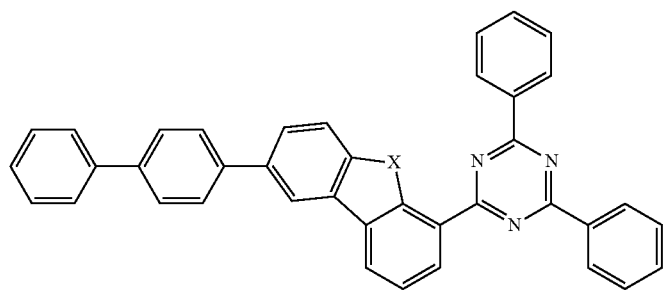
wherein in Comopund C183: X = Se,
Compound C192, represented by the formula
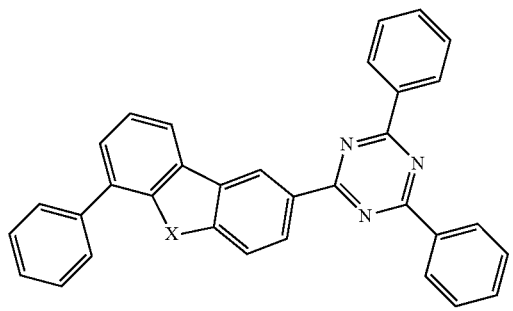
wherein in Comopund C192: X = Se,
Compound C195, represented by the formula
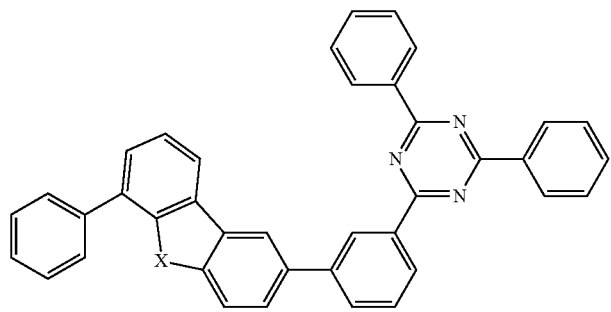
wherein in Comopund C195: X = Se,
Compound C198, represented by the formula
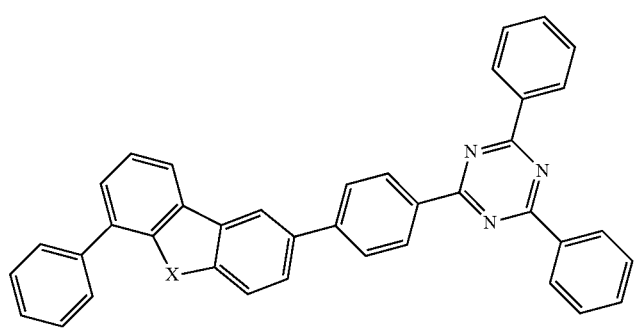
wherein in Comopund C198: X = Se,
Compound C207, represented by the formula

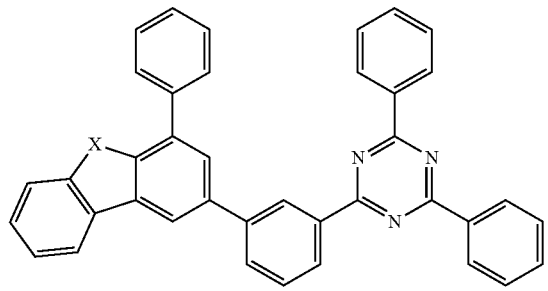
wherein in Compound C207: X = Se,
Compound C210, represented by the formula
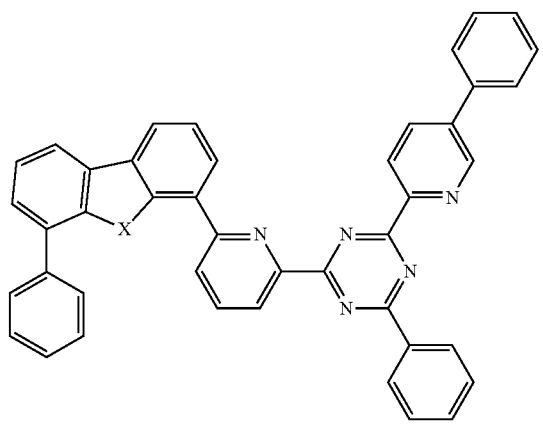
wherein in Compound C210: X = Se,
Compound C216, represented by the formula
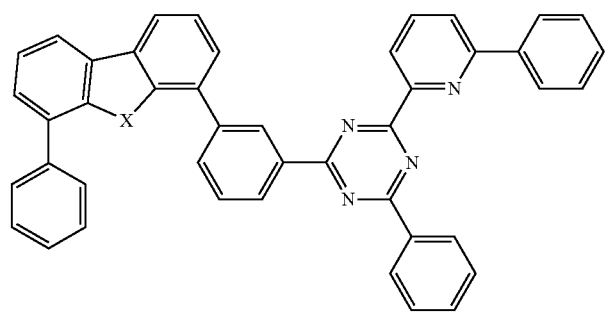
wherein in Compound C216: X = Se,
Compound C222, represented by the formula
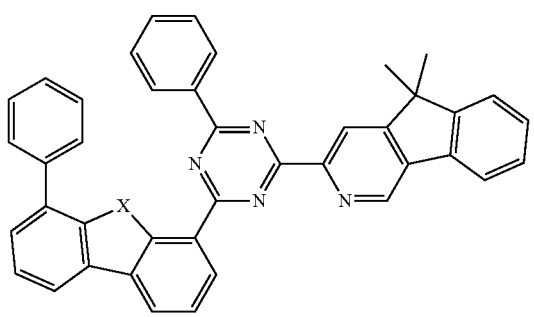
wherein in Compound C222: X = Se,
Compound C225, represented by the formula

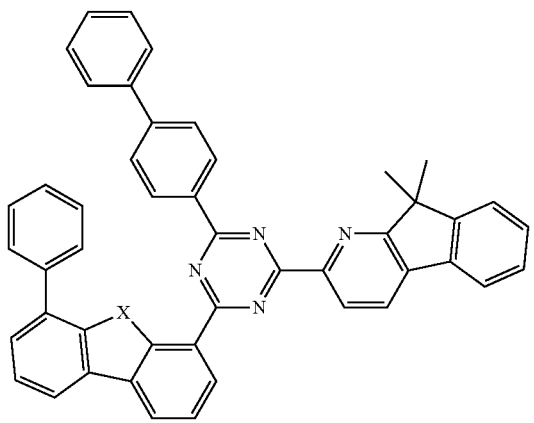
wherein in Comopund C225: X = Se,
Compound C228, represented by the formula
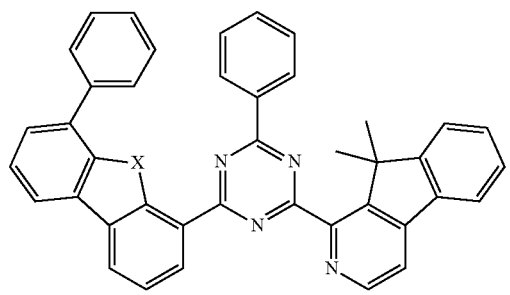
wherein in Comopund C228: X = Se,
Compound C237, represented by the formula
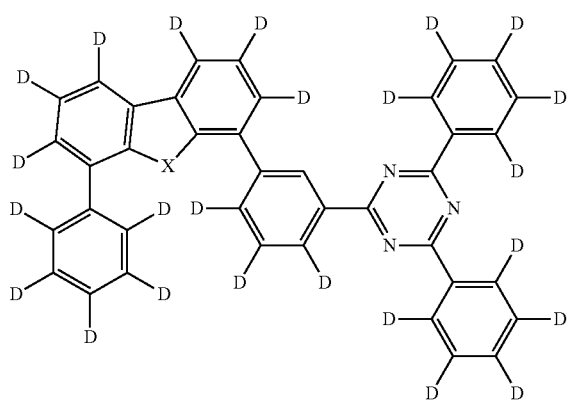
wherein in Comopund C237: X = Se,
Compound D3, represented by the formula:

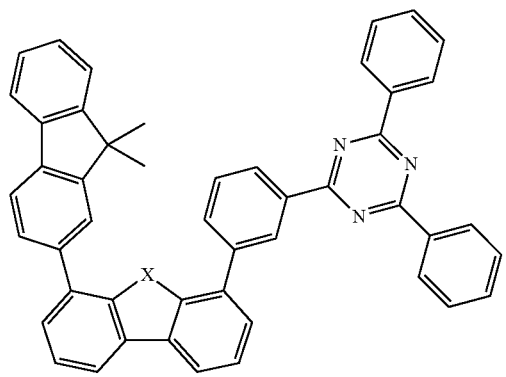
wherein in Comopund D3, X = Se,
Compound D9, represented by the formula:
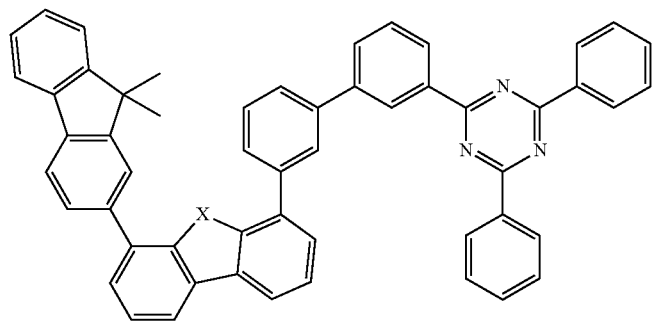
wherein in Comopund D9, X = Se,
Compound D12, represented by the formula:
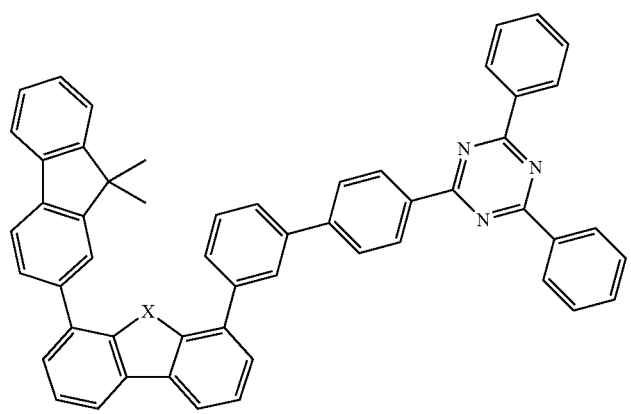
wherein in Comopund D12, X = Se,
Compound D15, represented by the formula:

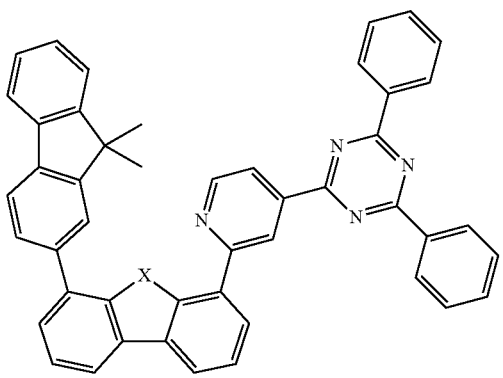
wherein in Comopund D15, X = Se,
Compound D18, represented by the formula:
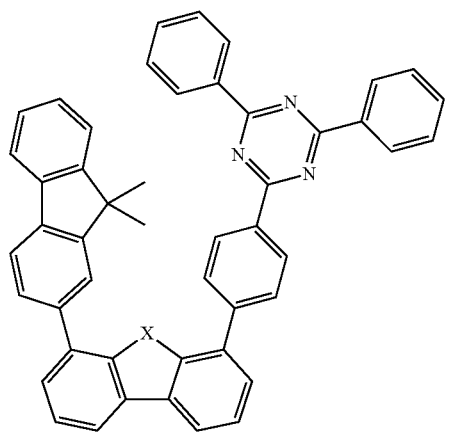
wherein in Comopund D18, X = Se,
Compound D21, represented by the formula:
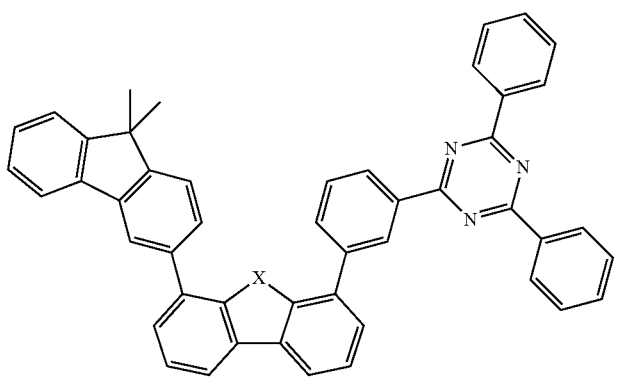
wherein in Comopund D21, X = Se,
Compound D24, represented by the fomrula:

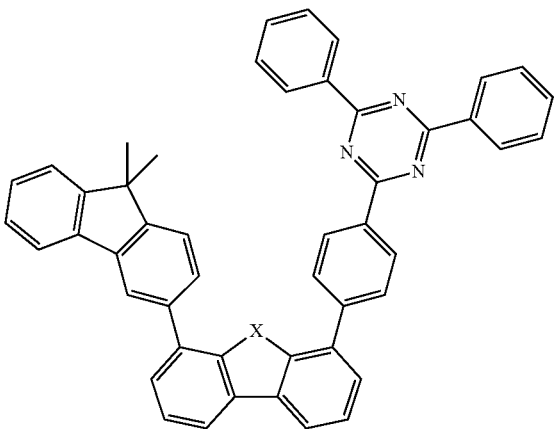
wherein in Comopund D24, X = Se,
Compound D27, represented by the formula:
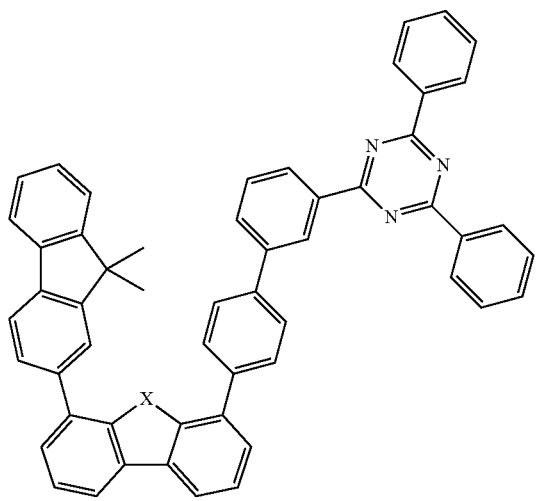
wherein in Comopund D27, X = Se,
Compound D30, represented by the formula:
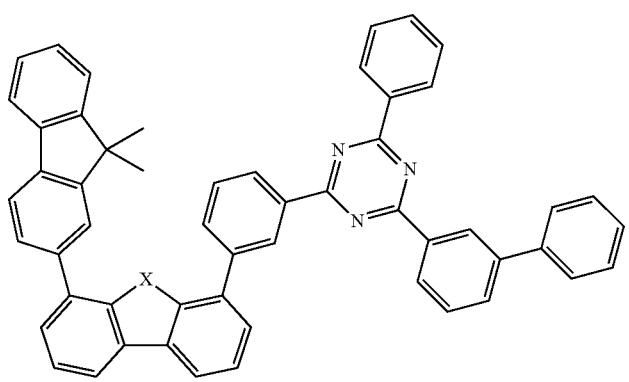
wherein in Comopund D30, X = Se,
Compound D33, represented by the formula:

-continued
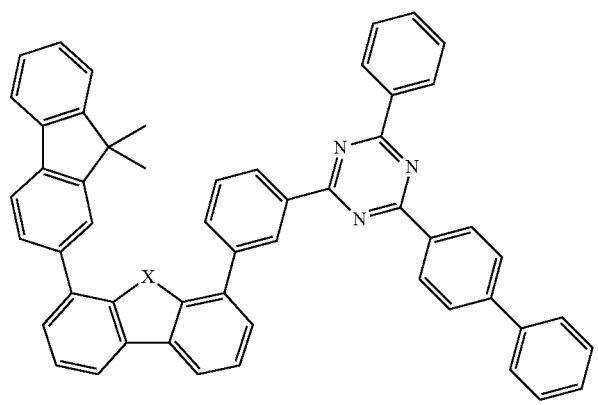
wherein in Comopund D33, X = Se,
Compound D36, represented by the formula:
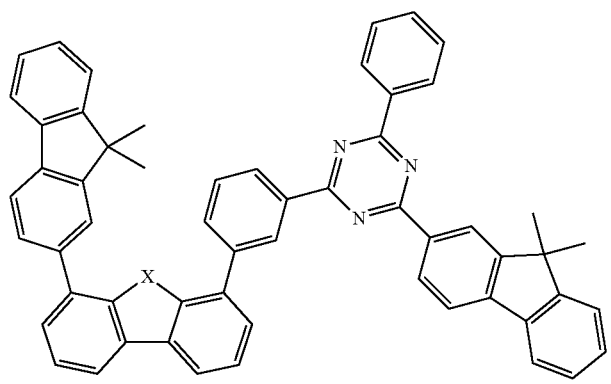
wherein in Comopund D36, X = Se,
Compound D39, represented by the formula:
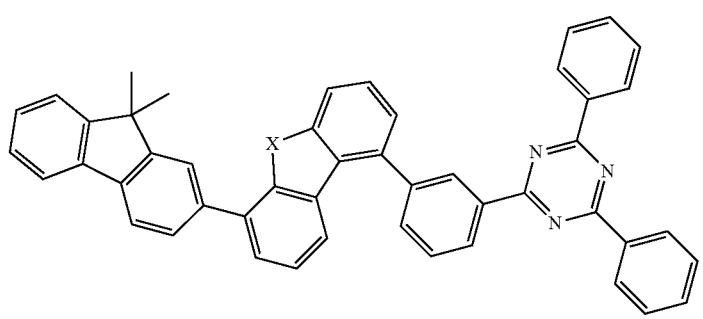
wherein in Comopund D39, X = Se,
Compound D42, represented by the formula:

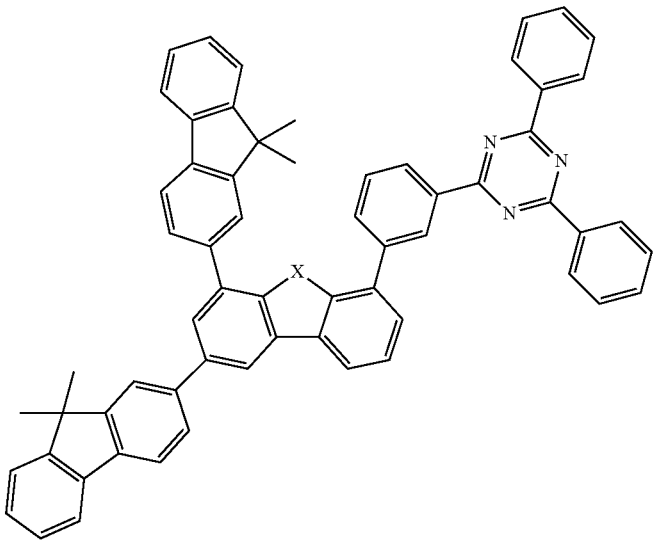
wherein in Comopund D42, X = Se,
Compound D45, represented by the formula:
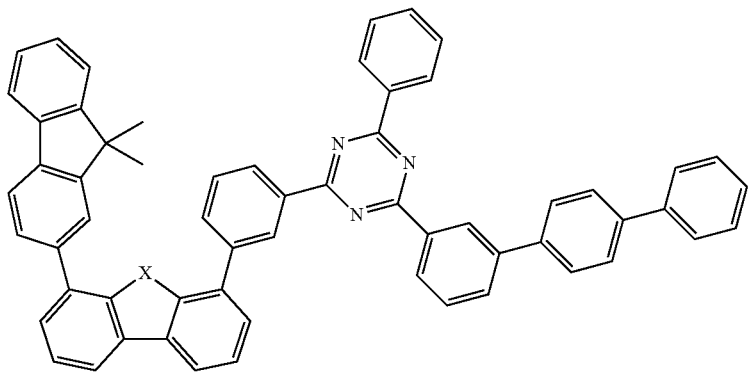
wherein in Comopund D45, X = Se,
Compound D48, represented by the formula:
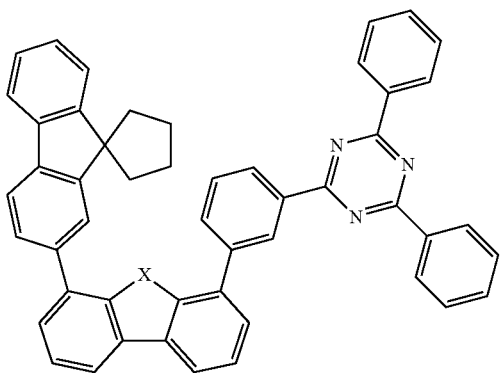
wherein in Comopund D48, X = Se,
Compound D51, represented by the formula:

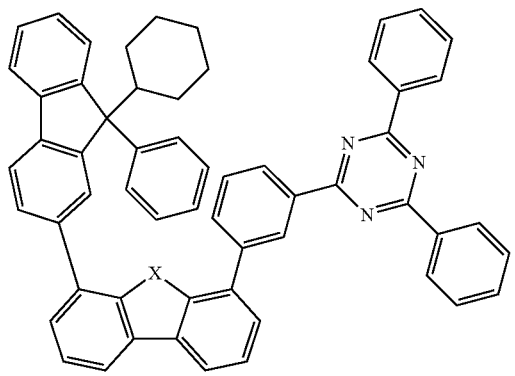
wherein in Comopund D51, X = Se,
Compound D54, represented by the formula:
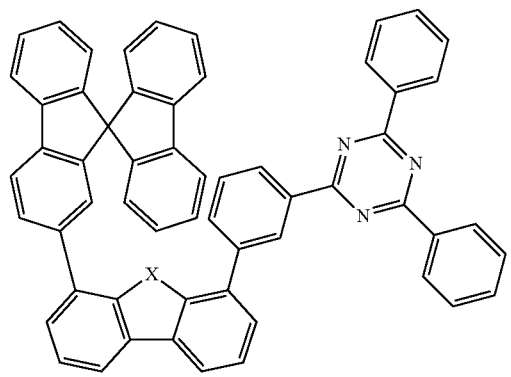
wherein in Comopund D54, X = Se,
Compound D57, represented by the formula:
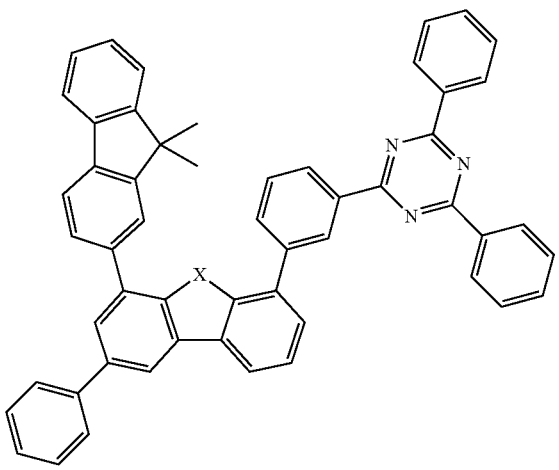
wherein in Comopund D57, X = Se,
Compound D60, represented by the formula:

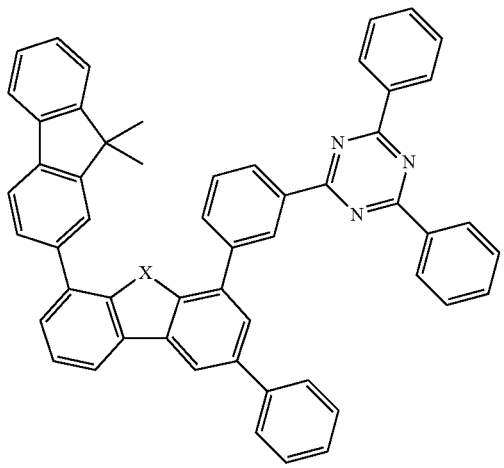
wherein in Comopund D60, X = Se,
Compound D63, represented by the formula:
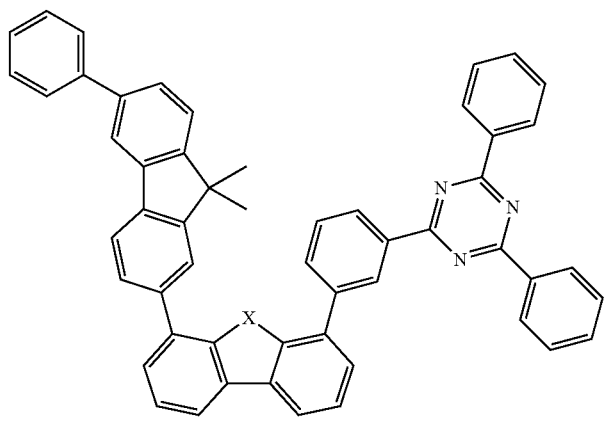
wherein in Comopund D63, X = Se,
Compound D66, represented by the formula:
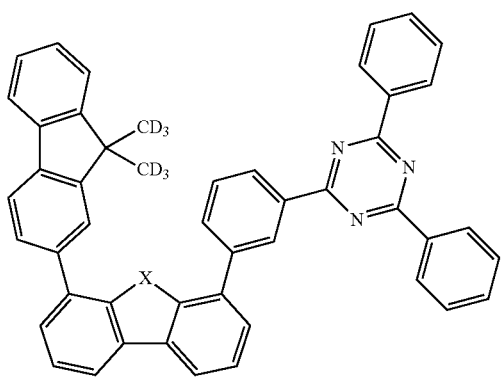
wherein in Comopund D66, X = Se,
Compound D69, represented by the formula:

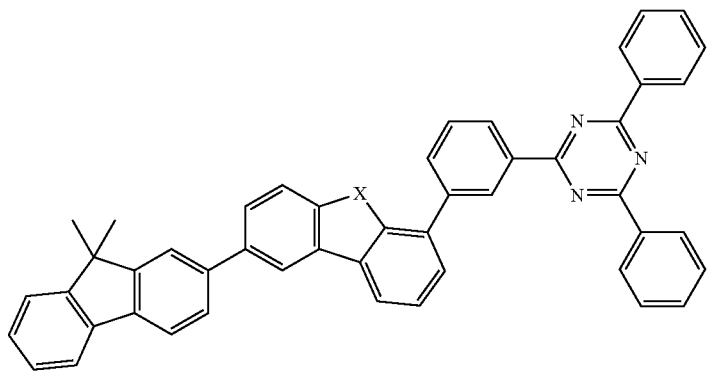
wherein in Comopund D69, X = Se,
Compound D72, represented by the formula:
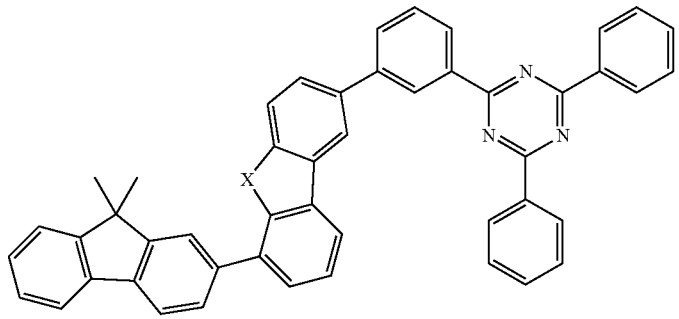
wherein in Comopund D72, X = Se,
Compound D75, represented by the formula:
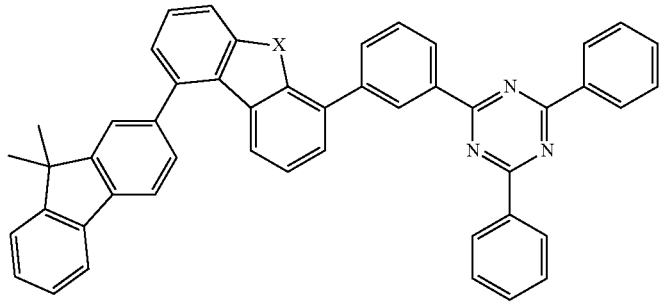
wherein in Comopund D75, X = Se,
Compound D78, represented by the formula:
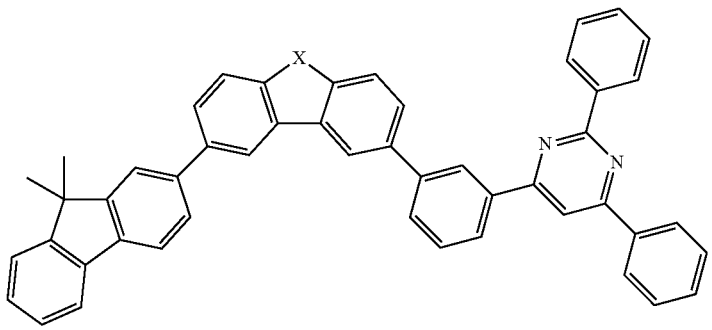
wherein in Comopund D78, X = Se,
Compound D81, represented by the formula:

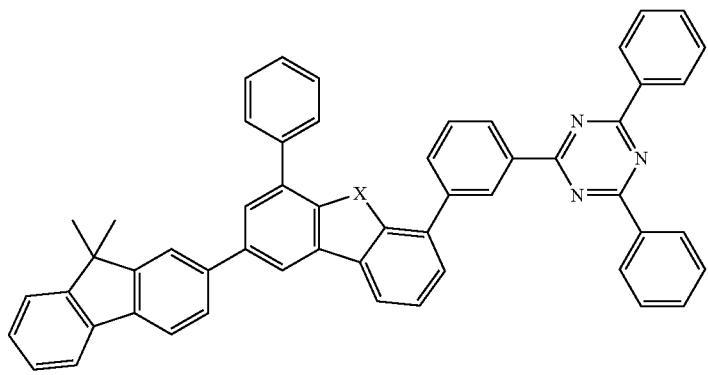
wherein in Comopund D81, X = Se,
Compound D84, represented by the formula:
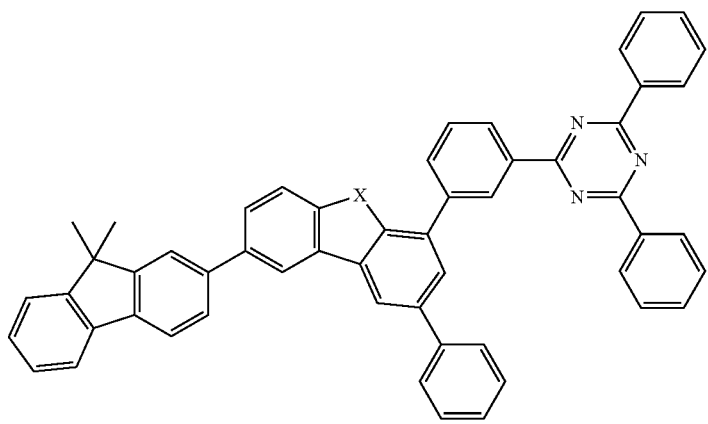
wherein in Comopund D84, X = Se,
Compound D87, represented by the fomrula:
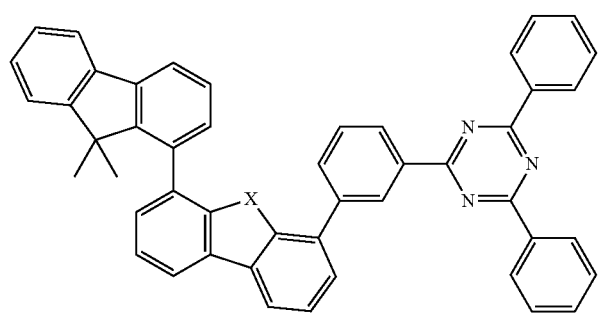
wherein in Comopund D87, X = Se,
Compound D90, represented by the formula:

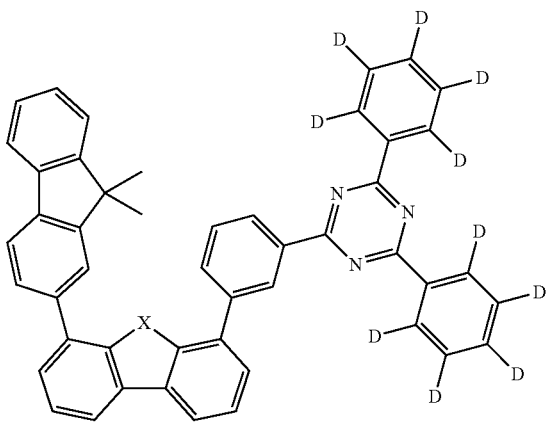
wherein in Comopund D90, X = Se,
Compound D93, represented by the formula:
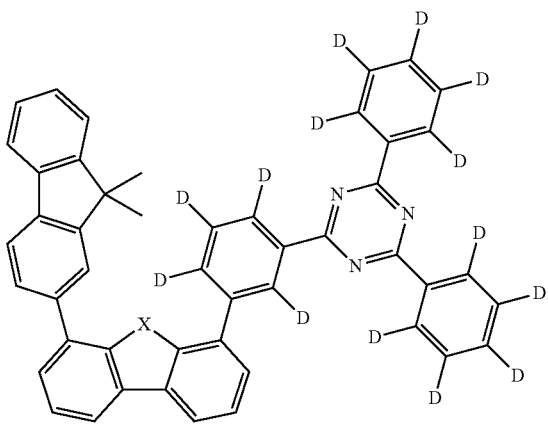
wherein in Comopund D93, X = Se,
Compound D96, represented by the formula:
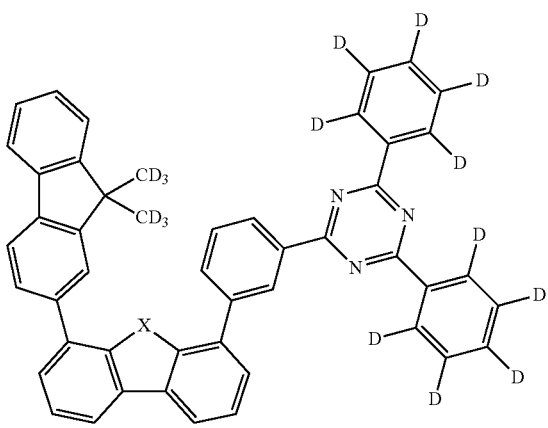
wherein in Comopund D96, X = Se, and
Compound D99, represented by the formula:

-continued
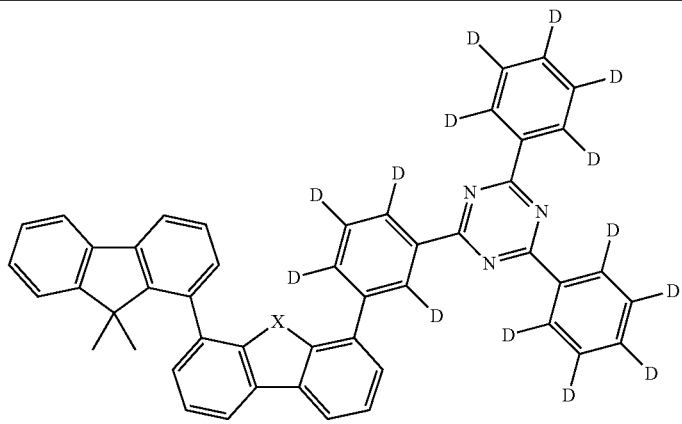
wherein in Comopund D99, X = Se.
* * * * *

UNITED STATES PATENT AND TRADEMARK OFFICE
CERTIFICATE OF CORRECTION

PATENT NO. : 11,522,140 B2
APPLICATION NO. : 15/207853
DATED : December 6, 2022
INVENTOR(S) : Lichang Zeng et al.

Page 1 of 2

It is certified that error appears in the above-identified patent and that said Letters Patent is hereby corrected as shown below:

In the Claims

In Claim 16, Column 309, please delete compound " 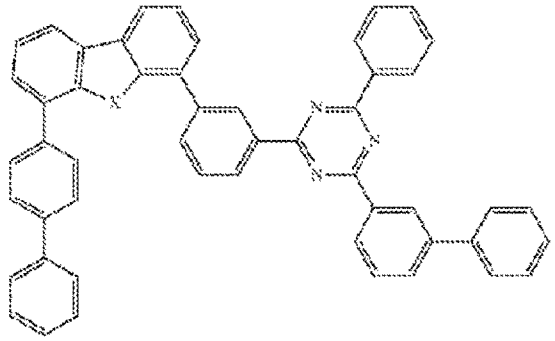 "

and insert -- 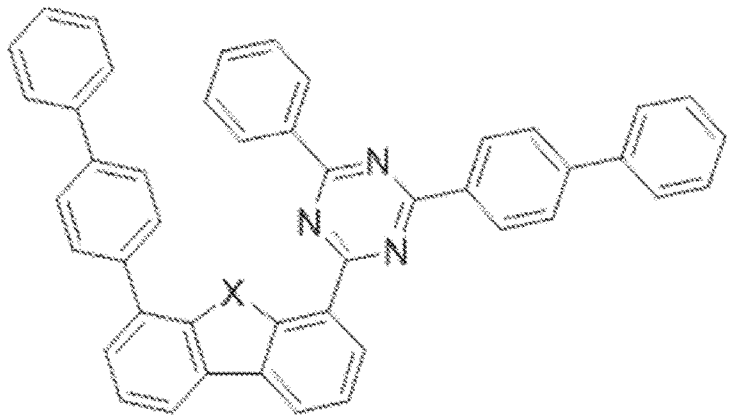 --

Signed and Sealed this
Twenty-fourth Day of January, 2023

Katherine Kelly Vidal
*Director of the United States Patent and Trademark Office*

In Claim 16, Column 347, following the text "wherein in Compound C207: X = Se, Compound C210, represented by the formula," please insert
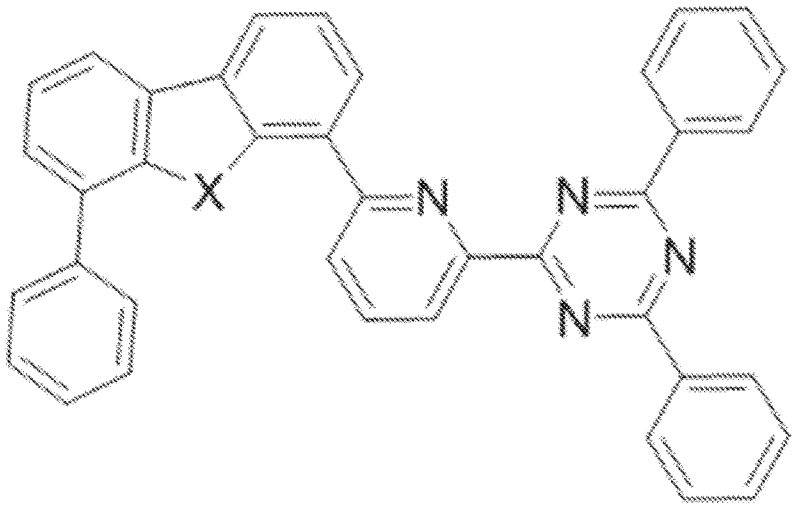
wherein in Compound C211: X = Se,
-- Compound C213, represented by the formula --
In Claim 16, Column 347, please delete the text "wherein in Compound C210: X = Se," and replace with "where in Compound C213: X= Se,"